US008293499B2

(12) United States Patent
Bongiorni et al.

(10) Patent No.: US 8,293,499 B2
(45) Date of Patent: Oct. 23, 2012

(54) BACILLUS STRAIN FOR INCREASED PROTEIN PRODUCTION

(75) Inventors: Cristina Bongiorni, Fremont, CA (US); Eugenio Ferrari, Reggiolo (IT)

(73) Assignee: Danisco US Inc., Palo Alto, CA (US)

( * ) Notice: Subject to any disclaimer, the term of this patent is extended or adjusted under 35 U.S.C. 154(b) by 0 days.

(21) Appl. No.: 13/377,529

(22) Filed: Feb. 20, 2012

(65) Prior Publication Data

US 2012/0142076 A1 Jun. 7, 2012

Related U.S. Application Data

(60) Provisional application No. 61/186,321, filed on Jun. 11, 2009.

(51) Int. Cl.
*C12P 21/06* (2006.01)
*C12N 9/20* (2006.01)
(52) U.S. Cl. ............... 435/69.1; 435/252.3; 435/252.31
(58) Field of Classification Search .................. 435/69.1, 435/252.3, 252.31
See application file for complete search history.

(56) References Cited

U.S. PATENT DOCUMENTS

| 5,387,521 | A | 2/1995 | Ferrari |
| 6,911,322 | B2 | 6/2005 | Valle et al. |
| 7,413,877 | B2 | 8/2008 | Collier et al. |
| 2003/0148461 | A1 | 8/2003 | Valle et al. |
| 2005/0202535 | A1 | 9/2005 | Collier et al. |

FOREIGN PATENT DOCUMENTS

| JP | 2006-325586 A | 12/2006 |
| JP | 2009-072154 A | 4/2009 |
| WO | WO-03/070963 A2 | 8/2003 |
| WO | WO03070963 A2 * | 8/2003 |
| WO | WO-2006/033668 A2 | 3/2006 |
| WO | WO-2008/126929 A1 | 10/2008 |
| WO | WO-2009/094084 A1 | 7/2009 |

OTHER PUBLICATIONS

Ferrari et al., "Transcription of *Bacillus subtilis* Subtilisin and Expression of Subtilisin in Sporulation Mutants," *J Bacteriol.* 170:289-295, Jan. 1988.
Gabala et al. "The *Bacillus subtilis* Iron-sparing Response is Mediated by a Fur-regulated Small RNA and Three Small, Basic Proteins," *PNAS US* 105:11927-11932, Aug. 2008.
Grossman, "Genetic Networks Controlling the Initiation of Sporulation and the Development of Genetic Competence in *Bacillus subtilis*," *Annual Reviews Genetics* 29: 477-508 (1995).
International Search Report mailed Sep. 22, 2010 for PCT/US2010/037040, 5 pages.
Kunst et al., "The DegS/DegU and ComP/ComA Two-component Systems are Part of a Network Controlling Degradative Enzyme Synthesis and Competence in *Bacillus subtilis*," *Research in Microbiology* 145:393-402, 1994.
Marahiel et al., "Regulation of Peptide Antibiotic Production in *Bacillus*," *Molecular Microbiology* 7:631-636, Mar. 1993.
McQuade et al. "Control of a Family of Phosphatase Regulatory Genes (phr) by the Alternate Sigma Factor Sigma-H of *Bacillus subtilis*," *J. Bacteriology* 183(16):4905-4909, Aug. 2001.
Perego et al., "Pentapeptide Regulation of Aspartyl-phosphate Phosphatases," *Peptides* 22:1541-1547, Oct. 2001.
Perego et al., "Multiple Protein-Aspartate Phosphatases Provide a Mechanism for the Integration of Diverse Signals in the Control of Development in *B. subtilis*," *Cell* 79: 1047-1055, Dec. 1994.
Pottathil et al., "The Extracellular Phr Peptide-Rap Phosphatase Signaling Circuit of *Bacillus subtilis*," *Front. Biosci.* 8:d32-45, Jan. 2003.
Sauter et al., "Sm-like Proteins in Eubacteria: The Crystal Structure of the Hfq Protein from *Escherichia coli*," *Nucleic Acid Res* 31:4091-4098, Jul. 2003.
Slivaggi et al., "Small Untranslated RNA Antitoxin in *Bacillus subtilis*," *J Bacteriol.* 187:6641-6650, Oct. 2005.
Tjalsma et al., "Signal Peptide-dependent Protein Transport in *Bacillus subtilis*: A Genome-based Survey of the Secretome," *Microbiol Mol Biol Rev* 64:515-547, Sep. 2000.
Westers etal. "Genome Engineering Reveals Large Dispensable Regions in *Bacillus subtilus*," *Molecular Biology and Evolution* 20:2076-2090, Dec. 2003.
Wu et al., "Engineering a *Bacillus subtilis* Expression-secretion System with a Strain Deficient in Six Extracellular Proteases," *J. Bacteriol.* 173:4952-4958, Aug. 1991.
Ye et al., "Construction of Protease Deficient *Bacillus subtilis* Strains for Expression Studies: Inactivation of Seven Extracellular Proteases and the Intracellular Lona Protease," *Proc. Internal. Symp. Rec. Adv. Bioindustry, Seoul, Korea: The Korean Society for Applied Microbiology*, pp. 160-169, Apr. 1996.

* cited by examiner

*Primary Examiner* — Maryam Monshipouri
(74) *Attorney, Agent, or Firm* — Danisco US Inc.

(57) ABSTRACT

The present invention provides host cells that have been genetically manipulated to have an enhanced capacity to produce proteins of interest. In particular, the invention relates to modified *Bacillus* sp. Host cells that have at least one inactivated phr gene. The enhanced production of proteins of interest by the modified *Bacillus* sp. Host cells is further increased in modified *Bacillus* sp. Host cells that overexpress YmaH. Methods for producing proteins of interest in the modified host cells are also provided.

37 Claims, 16 Drawing Sheets

TCATACCCTGAAAGACAAGGGAAATTGTCGGCAATGAGCCGCTCGGCAGGTAGAAGGATGTTTACCGATGCAAAAAA

GGGCAAAATGGATAGGTGGTTGTCCATGTTGAATCGTATAATGGGGGAGATTTATAAAAGAGAGTGATACATATTGAATATAC
<u>misA coding →</u>
GAAGCAGCCCGTTGTCATTTAGTCGGACCGACGGCAGTGGGAAAACCAATTTAAGTATTCAGCTAGCAAATCCTTAAACGC GGAAATTATCAGCGGAGATTCGATGCAGATTTATAAAGGGATGATATTGGAACAGCTAAAATTACCGAACAGGAGATGGAGGG AGTGCCCCATCATCTGATTGACATTTAGATCCCAAGACTCTTTCTCTACTGCCGATTATCAAAGCTTAGTAAGAAATAAAATCA GCGAGATTGCAAATAGAGGAAAAGCTTCCGATGATTGACGGCCGTACAGGGCTTTATATACAATCGAGCTTACGATTATACATT TACGGAAGAGGCAAATGATCCCGTGTTTCGAGAGAGCATGCAAATGGCTGCTGAGCGGGAAGGCGCTGACTTCTTCATGCCA AACTTGCTGCAGCAGATCCCGAGGCAGCAGCTGCGATTCATCCGAATAATACAAGAAGAGTCATTCGCCGCACTGGAAATTTAC ATACGTCCGAAAAACGATGTCTCCAGCATTTGAAGGAACAACGAGAACTTCTGTACAATCAGGCCCTTCTTCCGGAAGTGAAACGCTT GGATAGAGACACCGCTTTACGAAAAGAATTAATCAGCGGGTCGATTTGATGATGCAGTCAGGCCTGTATGCATATTTGACGGTTTGTGACA ATACGACAAGAACGTGAGAGACTGTCAATCAATACAGGCCGATAGGCGTATAAAGAGCTGCGAAACGCCCAGCTGTGGTTCGCAACAAATGCA CTTTCCGATGCTGTCGAACAGCTAAAGCAACACCGCCCTGTGTGATATGGAGCTGAAAAAAGGAAATTTCACACATATAGCAGGAAAACTCGA GGTCACATGGTTCGATAGATCGATAGAGAATCAAGGAGGACGAAACATGAAACCGATTAATATTCAGGATCAGTTTTTGAATCA
<u>ymaH coding →</u>
ACTTTAATCGAAACTGTATGATATAGAGAATCAAGGAGGACGAAACATGAAACCGATTAATATTCAGGATCAGTTTTTGAATCA AATCCGAAAGAAATACGTATGTCACTGTCTTTTTTTGCTCAACGGCTTTCAGTTGCCGGGCCAGGTGAAAGGCTTGATAACT

TTACCGTATTGTTGGAATCGGAAGCTAAGCAGCAGCTATATATAAACATGCGATCTCAACGTTTGCCGCGCAAAAACGT

CCAGCTTGAACTCGAATAGATCAAAAAATGCCATGTCAAGACATGAGGAAAGGCTGTGCGGGGGTTCCCGGCACGGTCTTTTTTATGAG (SEQ ID NO: 101)

CATGAATCCACTTTTGCTCCAAGCTTTTTGTCTCCAAGCTTTTTGTGTAAGCTGACCATGCCAAGGCCACGGTCTTTTTTATGAG

Figure 8

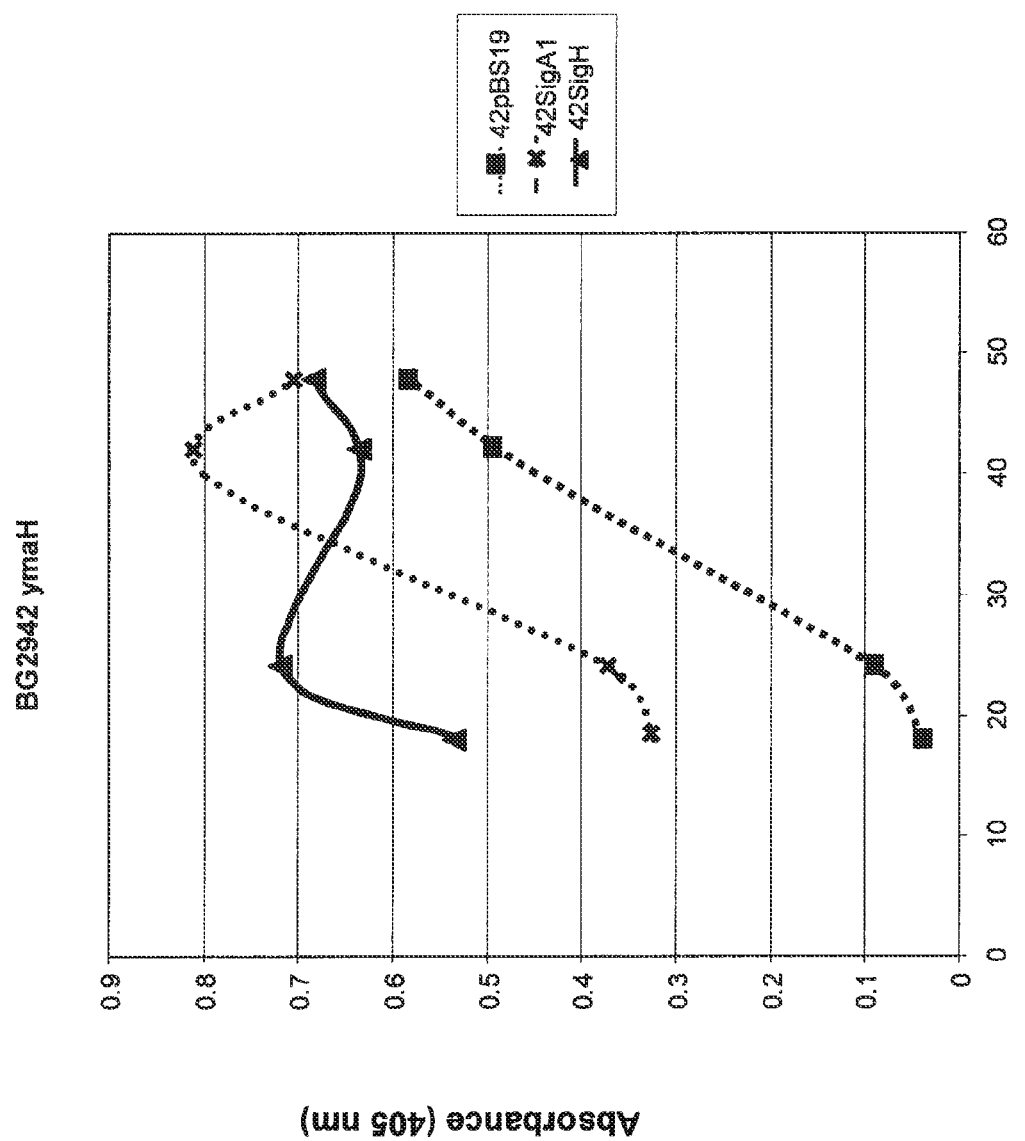

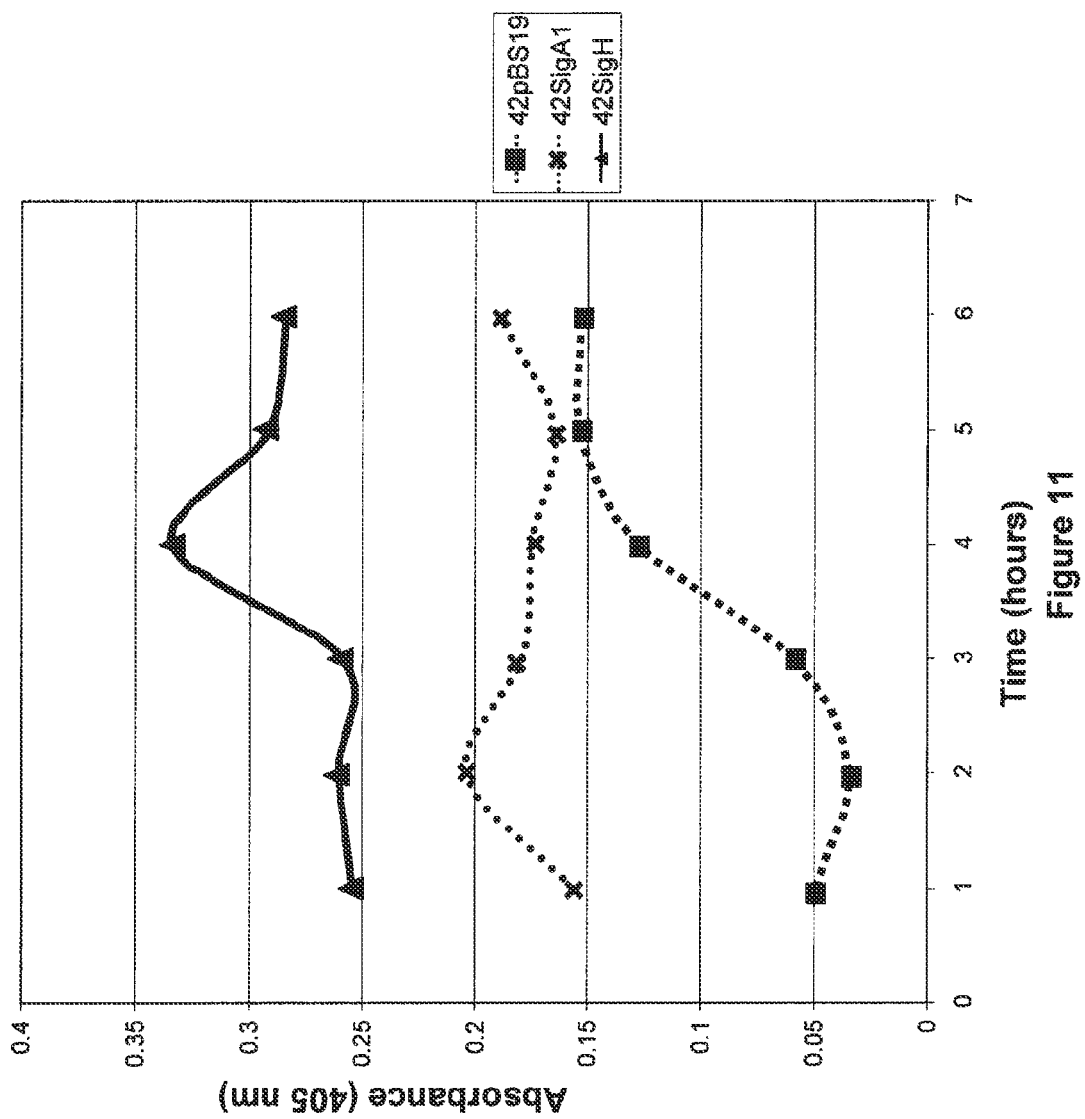

US 8,293,499 B2

BACILLUS STRAIN FOR INCREASED PROTEIN PRODUCTION

CROSS REFERENCE TO RELATED APPLICATION

This application is a National Stage under 35 U.S.C. §371 of International Application No. PCT/US2010/037040, filed Jun. 2, 2010, which claims the benefit of U.S. Provisional Application No. 61/186,321, filed Jun. 11, 2009, each of which is hereby incorporated by reference in their entirety The present invention provides host cells that have been genetically manipulated to have an enhanced capacity to produce proteins of interest. In particular, the invention relates to modified *Bacillus* sp. host cells that have at least one inactivated phr and/or rap gene. The enhanced production of proteins of interest by the modified *Bacillus* sp. host cells is further increased in modified *Bacillus* sp. host cells that over-express YmaH. Methods for producing proteins of interest in the modified host cells are also provided.

BACKGROUND

Expression and recombinant production of exogenous polypeptides is a widely used technique. It is well known that cells can be transformed with nucleic acids encoding exogenous polypeptides of interest for expression and production of large quantities of the desired polypeptides. In some applications, the methods are used to produce amounts of polypeptide over what would be produced naturally by the originating organism. Indeed, expression of exogenous nucleic acid sequences, as well as over-expression of endogenous sequences have been extensively used in modern biotechnology.

In spite of the implementation of various approaches for increasing protease yield, including screening for hyper-producing strains, cloning and over-expressing proteases, improving fed-batch and chemostat fermentations, and optimizing fermentation technologies, there remains a need for additional means for enhancing the production of proteases.

SUMMARY OF THE INVENTION

The present invention provides host cells that have been genetically manipulated to have an enhanced capacity to produce proteins of interest. In particular, the invention relates to modified *Bacillus* sp. host cells that have at least one inactivated phr and/or rap gene. The enhanced production of proteins of interest by the modified *Bacillus* sp. host cells is further increased in modified *Bacillus* sp. host cells that over-express YmaH. Methods for producing proteins of interest in the modified host cells are also provided.

In one embodiment, the invention provides a modified *Bacillus* sp. host cell that comprises a genome comprising a rap operon that has at least one inactivated phr gene, and a recombinant nucleic acid for producing a protein of interest at a level that is greater than that produced by the unmodified precursor host cell. The protein of interest is an enzyme, and preferably, a protease (e.g., a subtilisin).

In another embodiment, the invention provides a modified *Bacillus* sp. host cell that comprises a genome comprising a rap operon that has at least one inactivated phr gene, and a recombinant nucleic acid for producing a protein of interest at a level that is greater than that produced by the unmodified precursor host cell. The recombinant nucleic acid comprises a promoter that is operably linked to the polynucleotide sequence that encodes the protein of interest. Preferably the promoter is the wild-type or mutant aprE promoter. The protein of interest is an enzyme, and preferably, a protease (e.g., a subtilisin).

In another embodiment, the invention provides a modified *Bacillus* sp. host cell that comprises a genome comprising a rap operon that has at least one inactivated phr gene, and an inactivated rap gene, and a recombinant nucleic acid for producing a protein of interest at a level that is greater than that produced by the unmodified precursor host cell. Preferably, the inactivated rap gene is the rapA gene. The protein of interest is an enzyme, and preferably, a protease (e.g., a subtilisin).

In another embodiment, the invention provides a modified *Bacillus* sp. host cell that comprises a genome comprising a rap operon that has at least one inactivated phr gene, and an inactivated rap gene, (e.g., rapA gene), and a recombinant nucleic acid for producing a protein of interest at a level that is greater than that produced by the unmodified precursor host cell. The recombinant nucleic acid comprises a promoter that is operably linked to the polynucleotide sequence that encodes the protein of interest. Preferably, the promoter is the wild-type or mutant aprE promoter. The protein of interest is an enzyme, and preferably, a protease (e.g., a subtilisin).

In another embodiment, the invention provides a modified *Bacillus* sp. host cell that comprises a genome comprising a rap operon that has at least one inactivated phr gene, and a recombinant nucleic acid for producing a protein of interest at a level that is greater than that produced by the unmodified precursor host cell. The at least one inactivated phr gene is chosen from phrA, phrE, phrC, phrF, phrG, phrI, and phrK. In some embodiments, the inactivated phr gene is the inactivated phrA gene, while, other embodiments the inactivated phr gene is the phrE gene. The protein of interest is an enzyme, and preferably, a protease (e.g., a subtilisin)

In another embodiment, the invention provides a modified *Bacillus* sp. host cell that comprises a genome comprising a rap operon that has at least one inactivated phr gene, and a recombinant nucleic acid for producing a protein of interest at a level that is greater than that produced by the unmodified precursor host cell. The at least one inactivated phr gene is chosen from phrA, phrE, phrC, phrF, phrG, phrI and phrK. In some embodiments, the inactivated phr gene is the inactivated phrA gene, while, other embodiments the inactivated phr gene is the phrE gene. The recombinant nucleic acid comprises a promoter that is operably linked to the polynucleotide sequence that encodes the protein of interest. Preferably the promoter is the wild-type or mutant aprE promoter. The protein of interest is an enzyme, and preferably, a protease (e.g., a subtilisin).

In another embodiment, the invention provides a modified *Bacillus* sp. host cell that comprises a genome comprising a rap operon that has at least one inactivated phr gene, and an inactivated rap gene, and a recombinant nucleic acid for producing a protein of interest at a level that is greater than that produced by the unmodified precursor host cell. Preferably, the inactivated rap gene is the rapA gene, and the at least one inactivated phr gene is chosen from phrA, phrE, phrC, phrF, phrG, phrI and phrK. In some embodiments, the inactivated phr gene is the inactivated phrA gene, while, other embodiments the inactivated phr gene is the phrE gene. The protein of interest is an enzyme, and preferably, a protease (e.g., a subtilisin).

In another embodiment, the invention provides a modified *Bacillus* sp. host cell that comprises a genome comprising a rap operon that has at least one inactivated phr gene, and an inactivated rap gene (e.g., rapA gene), and a recombinant nucleic acid for producing a protein of interest at a level that is greater than that produced by the unmodified precursor host cell. The recombinant nucleic acid comprises a promoter that is operably linked to the polynucleotide sequence that encodes the protein of interest. Preferably, the promoter is the wild-type or mutant aprE promoter. The at least one inactivated phr gene is chosen from phrA, phrE, phrC, phrF, phrG, phrI and phrK. Preferably, the inactivated phr gene is the inactivated phrA or phrE gene. The protein of interest is an enzyme, and preferably, a protease (e.g., a subtilisin).

In another embodiment, the invention provides a modified *Bacillus* sp. host cell that comprises a genome comprising a rap operon that has an inactivated phrA gene and an inactivated phrE gene, and a recombinant nucleic acid for producing a protein of interest at a level that is greater than that produced by the unmodified precursor host cell. The protein of interest is an enzyme, and preferably, a protease (e.g., a subtilisin).

In another embodiment, the invention provides a modified *Bacillus* sp. host cell that comprises a genome comprising a rap operon that has an inactivated phrA gene and an inactivated phrE gene, and a recombinant nucleic acid for producing a protein of interest at a level that is greater than that produced by the unmodified precursor host cell. The recombinant nucleic acid comprises a promoter that is operably linked to the polynucleotide sequence that encodes the protein of interest. Preferably the promoter is the wild-type or mutant aprE promoter. The protein of interest is an enzyme, and preferably, a protease (e.g., a subtilisin).

In another embodiment, the invention provides a modified *Bacillus* sp. host cell that comprises a genome comprising a rap operon that has an inactivated phrA gene, an inactivated phrE gene, an inactivated rapA gene, and a recombinant nucleic acid for producing a protein of interest at a level that is greater than that produced by the unmodified precursor host cell. The protein of interest is an enzyme, and preferably, a protease (e.g., a subtilisin).

In another embodiment, the invention provides a modified *Bacillus* sp. host cell that comprises a genome comprising a rap operon that has an inactivated phrA gene, an inactivated phrE gene, an inactivated rapA gene, and a recombinant nucleic acid for producing a protein of interest at a level that is greater than that produced by the unmodified precursor host cell. The recombinant nucleic acid comprises a promoter that is operably linked to the polynucleotide sequence that encodes the protein of interest. Preferably the promoter is the wild-type or mutant aprE promoter. The protein of interest is an enzyme, and preferably, a protease (e.g., a subtilisin).

In another embodiment, the invention provides a modified *Bacillus* sp. host cell that over expresses YmaH and that comprises a genome comprising a rap operon that has at least one inactivated phr gene, and a recombinant nucleic acid for producing a protein of interest at a level that is greater than that produced by the unmodified precursor host cell. The protein of interest is an enzyme, and preferably, a protease (e.g., a subtilisin).

In another embodiment, the invention provides a modified *Bacillus* sp. host cell that overexpresses YmaH and that comprises a genome comprising a rap operon that has at least one inactivated phr gene, and a recombinant nucleic acid for producing a protein of interest at a level that is greater than that produced by the unmodified precursor host cell. The recombinant nucleic acid comprises a promoter that is operably linked to the polynucleotide sequence that encodes the protein of interest. Preferably the promoter is the wild-type or mutant aprE promoter. The protein of interest is an enzyme, and preferably, a protease (e.g., a subtilisin).

In another embodiment, the invention provides a modified *Bacillus* sp. host cell that overexpresses YmaH and that comprises a genome comprising a rap operon that has at least one inactivated phr gene, and an inactivated rap gene, and a recombinant nucleic acid for producing a protein of interest at a level that is greater than that produced by the unmodified precursor host cell. Preferably, the inactivated rap gene is the rapA gene. The protein of interest is an enzyme, and preferably, a protease (e.g., a subtilisin).

In another embodiment, the invention provides a modified *Bacillus* sp. host cell that overexpresses YmaH and that comprises a genome comprising a rap operon that has at least one inactivated phr gene, and an inactivated rap gene (e.g., rapA gene), and a recombinant nucleic acid for producing a protein of interest at a level that is greater than that produced by the unmodified precursor host cell. The recombinant nucleic acid comprises a promoter that is operably linked to the polynucleotide sequence that encodes the protein of interest. Preferably, the promoter is the wild-type or mutant aprE promoter. The protein of interest is an enzyme, and preferably, a protease (e.g., a subtilisin).

In another embodiment, the invention provides a modified *Bacillus* sp. host cell that overexpresses YmaH and that comprises a genome comprising a rap operon that has at least one inactivated phr gene, and a recombinant nucleic acid for producing a protein of interest at a level that is greater than that produced by the unmodified precursor host cell. The at least one inactivated phr gene is chosen from phrA, phrE, phrC, phrF, phrG, phrI, and phrK. In some embodiments, the inactivated phr gene is the inactivated phrA gene, while, other embodiments the inactivated phr gene is the phrE gene. The protein of interest is an enzyme, and preferably, a protease (e.g., a subtilisin).

In another embodiment, the invention provides a modified *Bacillus* sp. host cell that overexpresses YmaH and that comprises a genome comprising a rap operon that has at least one inactivated phr gene, and a recombinant nucleic acid for producing a protein of interest at a level that is greater than that produced by the unmodified precursor host cell. The at least one inactivated phr gene is chosen from phrA, phrE, phrC, phrF, phrG, phrI, and phrK. In some embodiments, the inactivated phr gene is the inactivated phrA gene, while, other embodiments the inactivated phr gene is the phrE gene. The recombinant nucleic acid comprises a promoter that is operably linked to the polynucleotide sequence that encodes the protein of interest. Preferably the promoter is the wild-type or mutant aprE promoter. The protein of interest is an enzyme, and preferably, a protease (e.g., a subtilisin).

In another embodiment, the invention provides a modified *Bacillus* sp. host cell that overexpresses YmaH and that comprises a genome comprising a rap operon that has at least one inactivated phr gene, and an inactivated rap gene, and a recombinant nucleic acid for producing a protein of interest at a level that is greater than that produced by the unmodified precursor host cell. Preferably, the inactivated rap gene is the rapA gene, and the at least one inactivated phr gene is chosen from phrA, phrE, phrC, phrF, phrG, phrI, and phrK. In some embodiments, the inactivated phr gene is the inactivated phrA gene, while, other embodiments the inactivated phr gene is the phrE gene. The protein of interest is an enzyme, and preferably, a protease (e.g., a subtilisin).

In another embodiment, the invention provides a modified *Bacillus* sp. host cell that overexpresses YmaH and that comprises a genome comprising a rap operon that has at least one inactivated phr gene, and an inactivated rap gene (e.g., rapA gene), and a recombinant nucleic acid for producing a protein of interest at a level that is greater than that produced by the unmodified precursor host cell. The recombinant nucleic acid comprises a promoter that is operably linked to the polynucleotide sequence that encodes the protein of interest. Preferably, the promoter is the wild-type or mutant aprE promoter. The at least one inactivated phr gene is chosen from phrA, phrE, phrC, phrF, phrG, phrI, and phrK. Preferably, the inactivated phr gene is the inactivated phrA or phrE gene. The protein of interest is an enzyme, and preferably, a protease (e.g., a subtilisin).

In another embodiment, the invention provides a modified *Bacillus* sp. host cell that overexpresses YmaH and that comprises a genome comprising a rap operon that has an inactivated phrA gene and an inactivated phrE gene, and a recombinant nucleic acid for producing a protein of interest at a level that is greater than that produced by the unmodified precursor host cell. The protein of interest is an enzyme, and preferably, a protease (e.g., a subtilisin).

In another embodiment, the invention provides a modified *Bacillus* sp. host cell that overexpresses YmaH and that comprises a genome comprising a rap operon that has an inactivated phrA gene and an inactivated phrE gene, and a recombinant nucleic acid for producing a protein of interest at a level that is greater than that produced by the unmodified precursor host cell. The recombinant nucleic acid comprises a promoter that is operably linked to the polynucleotide sequence that encodes the protein of interest. Preferably the promoter is the wild-type or mutant aprE promoter. The protein of interest is an enzyme, and preferably, a protease (e.g., a subtilisin).

In another embodiment, the invention provides a modified *Bacillus* sp. host cell that overexpresses YmaH and that comprises a genome comprising a rap operon that has an inactivated phrA gene, an inactivated phrE gene, an inactivated rapA gene, and a recombinant nucleic acid for producing a protein of interest at a level that is greater than that produced by the unmodified precursor host cell. The protein of interest is an enzyme, and preferably, a protease (e.g., a subtilisin).

In another embodiment, the invention provides a modified *Bacillus* sp. host cell that overexpresses YmaH and that comprises a genome comprising a rap operon that has an inactivated phrA gene, an inactivated phrE gene, an inactivated rapA gene, and a recombinant nucleic acid for producing a protein of interest at a level that is greater than that produced by the unmodified precursor host cell. The recombinant nucleic acid comprises a promoter that is operably linked to the polynucleotide sequence that encodes the protein of interest. Preferably the promoter is the wild-type or mutant aprE promoter. The protein of interest is an enzyme, and preferably, a protease (e.g., a subtilisin).

In another embodiment, the invention provides a method for producing a protein of interest in a host cell that comprises introducing into a precursor *Bacillus* sp. host cell an inactivating DNA construct comprising an inactivating polynucleotide that results in the inactivation of at least one indigenous phr and/or rap gene to generate a modified *Bacillus* sp. host cell; and growing said modified host cell under suitable conditions, wherein production of a protein of interest is greater in said modified host cell when compared to the production of said protein of interest in said precursor host cell. In some embodiments, the method further comprises recovering the protein of interest. The protein of interest is an enzyme, and preferably, a protease (e.g., a subtilisin). In some embodiments, the host cell comprises a mutation in at least one gene chosen from degU, degQ, degS, sco4, spoIIE, degQ and degR. Preferably, the host cell comprises a deg(Hy)32 mutation.

In another embodiment, the invention provides a method for producing a protein of interest in a host cell that comprises introducing into a precursor *Bacillus* sp. host cell an inactivating DNA construct comprising an inactivating polynucleotide that results in the inactivation of at least one indigenous phr and/or rap gene to generate a modified *Bacillus* sp. host cell; and growing said modified host cell under suitable conditions, wherein production of a protein of interest is greater in said modified host cell when compared to the production of said protein of interest in said precursor host cell. The at least one indigenous phr gene that is inactivated is chosen from phrA, phrE, phrC, phrF, phrG, phrI, and phrK. In some embodiments, the inactivated phr gene is the inactivated phrA gene, while, other embodiments the inactivated phr gene is the phrE gene. The protein of interest is an enzyme, and preferably, a protease (e.g., a subtilisin). In some embodiments, the method further comprises recovering the protein of interest. The protein of interest is an enzyme, and preferably, a protease (e.g., a subtilisin). In some embodiments, the host cell comprises a mutation in at least one gene chosen from degU, degQ, degS, sco4, spoIIE, degQ and degR. Preferably, the host cell comprises a deg(Hy)32 mutation.

In another embodiment, the invention provides a method for producing a protein of interest in a host cell that comprises introducing into a precursor *Bacillus* sp. host cell an inactivating DNA construct comprising an inactivating polynucleotide that results in the inactivation of the indigenous phrA and phrE genes and/or rap gene to generate a modified *Bacillus* sp. host cell; and growing said modified host cell under suitable conditions, wherein production of a protein of interest is greater in said modified host cell when compared to the production of said protein of interest in said precursor host cell. In some embodiments, the method further comprises recovering the protein of interest. The protein of interest is an enzyme, and preferably, a protease (e.g., a subtilisin). In some embodiments, the host cell comprises a mutation in at least one gene chosen from degU, degQ, degS, sco4, spoIIE, degQ and degR. Preferably, the host cell comprises a deg(Hy)32 mutation.

In another embodiment, the invention provides a method for producing a protein of interest in a host cell that comprises introducing into a precursor *Bacillus* sp. host cell an inactivating DNA construct comprising an inactivating polynucleotide that results in the inactivation of the indigenous phrA and rap genes to generate a modified *Bacillus* sp. host cell; and growing said modified host cell under suitable conditions, wherein production of a protein of interest is greater in said modified host cell when compared to the production of said protein of interest in said precursor host cell. In some embodiments, the method further comprises recovering the protein of interest. The protein of interest is an enzyme, and preferably, a protease (e.g., a subtilisin). In some embodiments, the host cell comprises a mutation in at least one gene chosen from degU, degQ, degS, sco4, spoIIE, degQ and degR. Preferably, the host cell comprises a deg(Hy)32 mutation.

In another embodiment, the invention provides a method for producing a protein of interest in a host cell that comprises introducing into a precursor *Bacillus* sp. host cell that overexpresses YmaH, an inactivating DNA construct comprising an inactivating polynucleotide that results in the inactivation of at least one indigenous phr and/or rap gene to generate a modified *Bacillus* sp. host cell; and growing said modified host cell under suitable conditions, wherein production of a protein of interest is greater in said modified host cell when compared to the production of said protein of interest in said precursor host cell. In some embodiments, the method further comprises recovering the protein of interest. The protein of interest is an enzyme, and preferably, a protease (e.g., a subtilisin). In some embodiments, the host cell comprises a mutation in at least one gene chosen from degU, degQ, degS, sco4, spoIIE, degQ and degR. Preferably, the host cell comprises a deg(Hy)32 mutation. Overexpression of YmaH is achieved by introducing into either the precursor or the modified host cell a SigH construct (e.g., SEQ ID NO:23), comprising a SigH promoter operably linked to a polynucleotide encoding a YmaH protein. Alternatively, overexpression of YmaH is achieved by introducing into either the precursor or the modified host cell a SigA construct (e.g., SEQ ID NOS:26 and 31), comprising a SigA promoter operably linked to a polynucleotide encoding YmaH.

In another embodiment, the invention provides a method for producing a protein of interest in a host cell that comprises introducing into a precursor Bacillus sp. host cell that overexpresses YmaH, an inactivating DNA construct comprising an inactivating polynucleotide that results in the inactivation of at least one indigenous phr and/or rap gene to generate a modified Bacillus sp. host cell; and growing said modified host cell under suitable conditions, wherein production of a protein of interest is greater in said modified host cell when compared to the production of said protein of interest in said precursor host cell. The at least one indigenous phr gene that is inactivated is chosen from phrA, phrE, phrC, phrF, phrG, phrI, and phrK. In some embodiments, the inactivated phr gene is the inactivated phrA gene, while, other embodiments the inactivated phr gene is the phrE gene. The protein of interest is an enzyme, and preferably, a protease (e.g., a subtilisin). In some embodiments, the method further comprises recovering the protein of interest. The protein of interest is an enzyme, and preferably, a protease (e.g., a subtilisin). In some embodiments, the host cell comprises a mutation in at least one gene chosen from degU, degQ, degS, sco4, spoIIE, degQ and degR. Preferably, the host cell comprises a deg(Hy)32 mutation. Overexpression of YmaH is achieved by introducing into either the precursor or the modified host cell a SigH construct (e.g., SEQ ID NO:23), comprising a SigH promoter operably linked to a polynucleotide encoding a YmaH protein. Alternatively, overexpression of YmaH is achieved by introducing into either the precursor or the modified host cell a SigA construct (e.g., SEQ ID NOS:26 and 31), comprising a SigA promoter operably linked to a polynucleotide encoding YmaH.

In another embodiment, the invention provides a method for producing a protein of interest in a host cell that comprises introducing into a precursor Bacillus sp. host cell that overexpresses YmaH, an inactivating DNA construct comprising an inactivating polynucleotide that results in the inactivation of the indigenous phrA and phrE genes and/or rap gene to generate a modified Bacillus sp. host cell; and growing said modified host cell under suitable conditions, wherein production of a protein of interest is greater in said modified host cell when compared to the production of said protein of interest in said precursor host cell. In some embodiments, the method further comprises recovering the protein of interest. The protein of interest is an enzyme, and preferably, a protease (e.g., a subtilisin). In some embodiments, the host cell comprises a mutation in at least one gene chosen from degU, degQ, degS, sco4, spoIIE, degQ and degR. Preferably, the host cell comprises a deg(Hy)32 mutation. Overexpression of YmaH is achieved by introducing into either the precursor or the modified host cell a SigH construct (e.g., SEQ ID NO:23), comprising a SigH promoter operably linked to a polynucleotide encoding a YmaH protein. Alternatively, overexpression of YmaH is achieved by introducing into either the precursor or the modified host cell a SigA construct (e.g., SEQ ID NOS:26 and 31), comprising a SigA promoter operably linked to a polynucleotide encoding YmaH.

In another embodiment, the invention provides a method for producing a protein of interest in a host cell that comprises introducing into a precursor Bacillus sp. host cell that overexpresses YmaH, an inactivating DNA construct comprising an inactivating polynucleotide that results in the inactivation of the indigenous phrA and rap genes to generate a modified Bacillus sp. host cell; and growing said modified host cell under suitable conditions, wherein production of a protein of interest is greater in said modified host cell when compared to the production of said protein of interest in said precursor host cell. In some embodiments, the method further comprises recovering the protein of interest. The protein of interest is an enzyme, and preferably, a protease (e.g., a subtilisin). In some embodiments, the host cell comprises a mutation in at least one gene chosen from degU, degQ, degS, sco4, spoIIE, degQ and degR. Preferably, the host cell comprises a deg(Hy)32 mutation. Overexpression of YmaH is achieved by introducing into either the precursor or the modified host cell a SigH construct (e.g., SEQ ID NO:23), comprising a SigH promoter operably linked to a polynucleotide encoding a YmaH protein. Alternatively, overexpression of YmaH is achieved by introducing into either the precursor or the modified host cell a SigA construct (e.g., SEQ ID NOS:26 and 31), comprising a SigA promoter operably linked to a polynucleotide encoding YmaH. protein.

The Bacillus sp. host cell of the embodiments described is a Bacillus alkalophilus, Bacillus amyloliquefaciens, Bacillus brevis, Bacillus circulans, Bacillus clausii, Bacillus coagulans, Bacillus firmus, Bacillus lautus, Bacillus lentus, Bacillus licheniformis, Bacillus megaterium, Bacillus pumilus, Bacillus stearothermophilus, Bacillus subtilis, or Bacillus thuringiensis cell. Preferably, the Bacillus sp. host cell of the embodiments described is a Bacillus subtilis host cell. In each of the present embodiments provided herein, the present invention provides isolated host cells, as well as cells in culture.

The present invention provides a host cell comprising a rap operon comprising at least one inactivated phr and/or at least one inactivated rap gene. In some embodiments, the host cell overexpresses YmaH. In some further embodiments, the host cell further comprises a recombinant nucleic acid. In still some further embodiments, the host cell further comprises a polynucleotide sequence encoding a protein of interest. In some additional embodiments, the recombinant nucleic acid comprises a promoter that is operably linked to the polynucleotide sequence encoding a protein of interest. In some further embodiments, the promoter is the wild-type or a mutant aprE promoter. In some additional embodiments, the host cell is a Bacillus sp. host cell. In still some further embodiments, the Bacillus sp. host cell is Bacillus subtilis. In some additional embodiments, the host cell produces the protein of interest at a level that is greater than that produced by a host cell that does not comprise at least one inactivated phr and/or rap gene. In some further embodiments, the protein of interest is an enzyme. In some additional embodiments, the enzyme is a protease. In still some additional embodiments, the at least one inactivated rap gene is the rapA gene. In some further embodiments, the at least one inactivated phr gene is selected from phrA, phrE, phrC, phrF, phrG, phrI, and phrK. In some embodiments, the at least one inactivated phr gene is phrA, while in some alternative embodiments, the at least one inactivated phr gene is phrE. In still some further embodiments, the host cell comprises at least one inactivated phr gene and at least one inactivated rap gene. In some further embodiments, the inactivated rap gene is the rapA gene. In still some further embodiments, there is at least one inactivated rap gene (e.g., rapA) and at least one inactivated phr gene selected from phrA, phrE, phrC, phrF, phrG, phrI, and phrK. In some embodiments, the at least one inactivated phr gene is phrA, while in some alternative embodiments, the at least one inactivated phr gene is phrE. In still some further embodiments, the host cell comprises an inactivated phrA gene, an inactivated phrE gene, an inactivated rapA gene, and a recombinant nucleic acid encoding a protein of interest. In some embodiments, the protein of interest is an enzyme. In still some further embodiments, the enzyme is a protease. In some embodiments, the host cell is a *Bacillus* sp. host cell. In some further embodiments, the *Bacillus* sp. host cell is a *Bacillus alkalophilus, Bacillus amyloliquefaciens, Bacillus brevis, Bacillus circulans, Bacillus clausii, Bacillus coagulans, Bacillus firmus, Bacillus lautus, Bacillus lentus, Bacillus licheniformis, Bacillus megaterium, Bacillus pumilus, Bacillus stearothermophilus, Bacillus subtilis*, or *Bacillus thuringiensis* cell. In some additional embodiments, the *Bacillus* sp. host cell is a *Bacillus subtilis* host cell.

The present invention also provides methods for producing at least one protein of interest comprising providing a precursor host cell and an inactivating nucleotide construct comprising an inactivating polynucleotide that inactivates at least one indigenous phr and/or rap gene; introducing said inactivating nucleotide construct into said precursor host cell to generate a modified host cell; and growing the modified host cell under suitable conditions for producing of the at least one protein of interest. In some embodiments of the present methods, the protein of interest is encoded by a recombinant nucleic acid present in the precursor host cell. In some embodiments of the present methods, the protein of interest is encoded by a recombinant nucleic acid present in the modified host cell. In some embodiments of the present methods, the protein of interest is encoded by a recombinant nucleic acid present in the precursor host cell and/or the modified host cell. In some embodiments of the present methods, the recombinant nucleic acid comprises a promoter that is operably linked to the polynucleotide sequence encoding the protein of interest. In some additional embodiments of the present methods, the protein of interest is a wild-type protein of interest. In still some additional embodiments of the present methods, the precursor host cell naturally produces the protein of interest. In some further embodiments of the present methods, the production of the protein of interest by the modified host cell is greater than the production of the protein of interest by the precursor host cell. In some embodiments of the present methods, the methods further comprise the step of recovering the protein of interest. In some embodiments of the present methods, the protein of interest is an enzyme. In some further embodiments of the present methods, the enzyme is a protease. In still some further embodiments of the present methods, the modified host cell comprises a mutation in at least one gene chosen from degU, degQ, degS, sco4, spoIIE, degQ and degR. In some embodiments of the present methods, the host cell comprises a deg (Hy)32 mutation. In some further embodiments of the present methods, the at least one indigenous phr gene that is inactivated is chosen from phrA, phrE, phrC, phrF, phrG, phrI, and phrK. In still some further embodiments of the present methods, the inactivating polynucleotide inactivates the indigenous phrA and phrE genes and/or rap gene. In some embodiments of the present methods, the at least one indigenous phr gene is phrA, while in some alternative embodiments, the at least one indigenous phr gene is phrE. In still some additional embodiments of the present methods, the indigenous rap gene is inactivated. In some further embodiments of the present methods, the indigenous rap gene is rapA. In some additional embodiments of the present methods, the precursor or modified host cell overexpresses YmaH. In some embodiments of the present methods, the overexpression of YmaH is achieved by introducing a SigH construct into the precursor or the modified host cell. In some further embodiments of the present methods, the SigH construct comprises SEQ ID NO:23, comprising a SigH promoter operably linked to a polynucleotide encoding YmaH protein. In some additional embodiments of the present methods, the overexpression of YmaH is achieved by introducing a SigA construct into the precursor or said modified host cell. In still some further embodiments of the present methods, the SigA construct comprises SEQ ID NO:26 and/or 31, comprising a SigA promoter operably linked to a polynucleotide encoding YmaH. In some embodiments of the present methods, the host cell is a *Bacillus* sp. host cell. In some further embodiments of the present methods, the *Bacillus* sp. host cell is a *Bacillus alkalophilus, Bacillus amyloliquefaciens, Bacillus brevis, Bacillus circulans, Bacillus clausii, Bacillus coagulans, Bacillus firmus, Bacillus lautus, Bacillus lentus, Bacillus licheniformis, Bacillus megaterium, Bacillus pumilus, Bacillus stearothermophilus, Bacillus subtilis*, or *Bacillus thuringiensis* cell. In some additional embodiments of the present methods, the *Bacillus* sp. host cell is a *Bacillus subtilis* cell.

BRIEF DESCRIPTION OF THE DRAWINGS

Certain aspects of the following detailed description are best understood when read in conjunction with the accompanying drawings. It is emphasized that, according to common practice, the various features of the drawings are not to-scale. On the contrary, the dimensions of the various features are arbitrarily expanded or reduced for clarity. Included in the drawings are the following figures:

FIG. 8 shows the polynucleotide sequence of a portion of the *Bacillus subtilis* genome that comprises the sequence defining a sigA promoter to the end of the sequence encoding the YmaH protein (SEQ ID NO:101). This sequence is diagrammed in FIG. 7, panel A. The beginning of the sequence encoding the miaA protein is indicated and the entire miaA coding sequence shown in bold letters; the beginning of sequence encoding the YmaH protein is indicated and the entire ymaH coding sequence shown in underlined bold letters.

FIG. 11 shows the level of production of subtilisin by *Bacillus subtilis* control host cells 42pBS19 and by *Bacillus* host cells 42SigH and 42SigA1, which overexpress ymaH.

DESCRIPTION OF THE INVENTION

Figure 1:
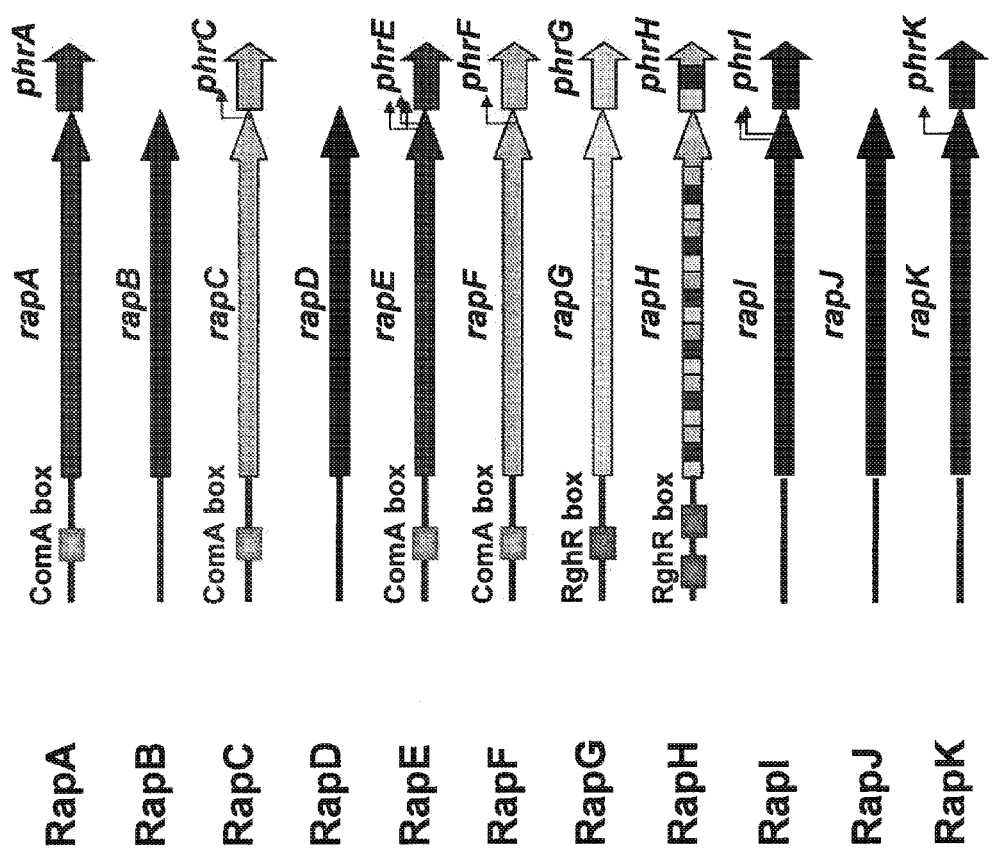
FIG. 1 illustrates the arrangement of phr and rap genes in the *Bacillus subtilis* rap operons.

The present invention provides host cells that have been genetically manipulated to have an enhanced capacity to produce proteins of interest. In particular, the invention relates to modified *Bacillus* sp. host cells that have at least one inactivated phr and/or rap gene. The enhanced production of proteins of interest by the modified *Bacillus* sp. host cells is further increased in modified *Bacillus* sp. host cells that overexpress YmaH. Methods for producing proteins of interest in the modified host cells are also provided.

Although described herein in regard to exemplary serine proteases (e.g., FNA and AprE), the compositions and methods of the present invention are not limited to serine proteases. Indeed, the present invention finds use in improving the production of various classes of enzymes as well as proteases (e.g., amylases, cellulases, oxidases, oxidoreductases, cutinases, mannanases, pectinases, amylases, lipases. etc). Indeed, it is not intended that the present invention be limited to any particular enzyme nor class of enzyme.

Unless otherwise indicated, the practice of the present invention involves conventional techniques commonly used in molecular biology, microbiology, protein purification, protein engineering, protein and DNA sequencing, and recombinant DNA fields, which are within the skill of the art. Such techniques are known to those of skill in the art and are described in numerous standard texts and reference works. All patents, patent applications, articles and publications mentioned herein, both supra and infra, are hereby expressly incorporated herein by reference.

Unless defined otherwise herein, all technical and scientific terms used herein have the same meaning as commonly understood by one of ordinary skill in the art to which this invention belongs. Various scientific dictionaries that include the terms included herein are well known and available to those in the art. Although any methods and materials similar or equivalent to those described herein find use in the practice or testing of the present invention, some preferred methods and materials are described. Accordingly, the terms defined immediately below are more fully described by reference to the Specification as a whole. It is to be understood that this invention is not limited to the particular methodology, protocols, and reagents described, as these may vary, depending upon the context they are used by those of skill in the art.

As used herein, the singular terms "a", "an," and "the" include the plural reference unless the context clearly indicates otherwise. Unless otherwise indicated, nucleic acids are written left to right in 5' to 3' orientation and amino acid sequences are written left to right in amino to carboxy orientation, respectively.

All patents, patent applications, and other publications, including all sequences disclosed within these references, referred to herein are expressly incorporated by reference, to the same extent as if each individual publication, patent or patent application was specifically and individually indicated to be incorporated by reference. All documents cited are, in relevant part, incorporated herein by reference. However, the citation of any document is not to be construed as an admission that it is prior art with respect to the present invention.

Numeric ranges are inclusive of the numbers defining the range. It is intended that every maximum numerical limitation given throughout this specification includes every lower numerical limitation, as if such lower numerical limitations were expressly written herein. Every minimum numerical limitation given throughout this specification will include every higher numerical limitation, as if such higher numerical limitations were expressly written herein. Every numerical range given throughout this specification will include every narrower numerical range that falls within such broader numerical range, as if such narrower numerical ranges were all expressly written herein.

The headings provided herein are not limitations of the various aspects or embodiments of the invention which can be had by reference to the Specification as a whole. Accordingly, as indicated above, the terms defined immediately below are more fully defined by reference to the specification as a whole.

DEFINITIONS

As used herein, a "modified host cell" is a recombinant host cell that contains at least one inactivated phr and/or a rap gene. A modified host cell is derived from a precursor host cell, which can be a wild-type or a recombinant precursor host cell comprising a phr gene that is not inactivated.

As used herein, "recombinant host cell" refers to a cell that has been modified by the introduction of at least one recombinant/heterologous nucleic acid. Thus, for example, recombinant host cells express genes that are not found in identical form within the parent form of the cell or express native genes that are otherwise abnormally expressed, under expressed or not expressed at all as a result of deliberate human intervention.

As used herein "precursor host cell" is used interchangeably with "parent host cell" to refer to a host cell that is genetically altered to generate a modified host cell.

As used herein, the term "recombinant polynucleotide" and "recombinant polypeptide" respectively refer to a polynucleotide and a polypeptide that do not naturally occur in a host cell. A recombinant polynucleotide or polypeptide molecule may contain two or more naturally-occurring sequences that are linked together in a way that does not occur naturally. "Recombination, "recombining," or generating a "recombined" or "recombinant" nucleic acid is generally the assembly of two or more nucleic acid fragments wherein the assembly gives rise to a chimeric gene.

As used herein, the term "recombinant" when used in reference to a cell means a cell that has been modified by the introduction of a heterologous nucleic acid sequence or that the cell is derived from a cell so modified. Thus, for example, recombinant cells express genes that are not found in identical form within the native (non-recombinant) form of the cell or express native genes that are otherwise abnormally expressed, under expressed or not expressed at all as a result of deliberate human intervention.

As used herein, an "analogous sequence" is a primary biological sequence, such as the amino-acid sequence or the nucleotides of DNA sequences wherein the function of the protein or encoded protein is essentially the same as that designated for Phr, Rap and YmaH proteins recited herein. Additionally, analogous proteins have at least about 60%, at least about 65%, at least about 70%, at least about 75%, at least about 80%, at least about 85%, at least about 90%, at least about 95%, at least about 97%, at least about 98%, at least about 99% or about 100% sequence identity to the sequence of variants of Phr, Rap and YmaH proteins recited herein. Analogous sequences are determined by known methods of sequence alignment. A commonly used alignment method is BLAST, although as indicated above and below, there are other methods that also find use in aligning sequences. One example of a useful algorithm is PILEUP. PILEUP creates a multiple sequence alignment from a group of related sequences using progressive, pairwise alignments. It can also plot a tree showing the clustering relationships used to create the alignment. PILEUP uses a simplification of the progressive alignment method of Feng and Doolittle (Feng and Doolittle, J. Mol. Evol., 35:351-360 [1987]). The method is similar to that described by Higgins and Sharp (Higgins and Sharp, CABIOS 5:151-153 [1989]). Useful PILEUP parameters including a default gap weight of 3.00, a default gap length weight of 0.10, and weighted end gaps. Another example of a useful algorithm is the BLAST algorithm, described by Altschul et al., (Altschul et al., J. Mol. Biol., 215:403-410, [1990]; and Karlin et al., Proc. Natl. Acad. Sci. USA 90:5873-5787 [1993]). A particularly useful BLAST program is the WU-BLAST-2 program (See, Altschul et al., Meth. Enzymol., 266:460-480 [1996]). WU-BLAST-2 uses several search parameters, most of which are set to the default values. The adjustable parameters are set with the following values: overlap span=1, overlap fraction=0.125, word threshold (T)=11. The HSP S and HSP S2 parameters are dynamic values and are established by the program itself depending upon the composition of the particular sequence and composition of the particular database against which the sequence of interest is being searched. However, the values may be adjusted to increase sensitivity. A % amino acid sequence identity value is determined by the number of matching identical residues divided by the total number of residues of the "longer" sequence in the aligned region. The "longer" sequence is the one having the most actual residues in the aligned region (gaps introduced by WU-Blast-2 to maximize the alignment score are ignored). A preferred method utilizes the BLASTN module of WU-BLAST-2 set to the default parameters, with overlap span and overlap fraction set to 1 and 0.125, respectively.

As used herein, "percent (%) sequence identity" or "percent homology" when used in reference to a polynucleotide or to a polypeptide sequence is defined as the percentage of nucleotide or amino acid residues in a candidate sequence that are identical with the nucleotide or amino acid residues of a starting sequence (i.e., the sequence of interest). The percent identity shared by polynucleotide or polypeptide sequences is determined by direct comparison of the sequence information between the molecules by aligning the sequences and determining the identity by methods known in the art. In some embodiments, the alignment includes the introduction of gaps in the sequences to be aligned. In addition, for sequences which contain either more or fewer nucleotides or amino acids than those of the candidate polynucleotide or polypeptide sequences, it is understood that the percentage of homology will be determined based on the number of homologous nucleotides or amino acids in relation to the total number of nucleotides or amino acids. As used herein "homology" refers to sequence similarity or identity, with identity being preferred. This homology is determined using standard techniques known in the art (See e.g., Smith and Waterman, Adv. Appl. Math., 2:482 [1981]; Needleman and Wunsch, J. Mol. Biol., 48:443 [1970]; Pearson and Lipman, Proc. Natl. Acad. Sci. USA 85:2444 [1988]; programs such as GAP, BESTFIT, FASTA, and TFASTA in the Wisconsin Genetics Software Package (Genetics Computer Group, Madison, Wis.); and Devereux et al., Nucl. Acid Res., 12:387-395 [1984]).

As used herein, the term "heterologous" refers to elements that are not normally associated with each other. For example, if a host cell produces a heterologous protein, that protein is a protein that is not normally produced by that host cell. Likewise, a promoter that is operably linked to a heterologous coding sequence is a promoter that is operably linked to a coding sequence that it is not a wild-type sequence.

As used herein, a "protein of interest," or "polypeptide of interest," refers to a protein that is expressed/produced by a host cell. Generally, proteins of interest are desirable proteins that have commercial significance. The protein of interest may be either homologous or heterologous to the host. In some embodiments, the protein of interest is a secreted polypeptide, particularly an enzyme, including but not limited to amylolytic enzymes, proteolytic enzymes, cellulytic enzymes, oxidoreductase enzymes and plant wall degrading enzymes. In further embodiments, these enzyme include, but are not limited to amylases, proteases, xylanases, lipases, laccases, phenol oxidases, oxidases, cutinases, cellulases, hemicellulases, esterases, peroxidases, catalases, glucose oxidases, phytases, pectinases, glucosidases, isomerases, transferases, galactosidases and chitinases. In still further embodiments, the expressed polypeptide is a hormone, cytokine, growth factor, receptor, vaccine, antibody, or the like. While it is not intended that the present invention be limited to any particular protein/polypeptide, in some most preferred embodiments, the expressed protein of interest is a protease.

As used herein, the terms "protease," and "proteolytic activity" refer to a protein or peptide exhibiting the ability to hydrolyze peptides or substrates having peptide linkages. Many well known procedures exist for measuring proteolytic activity (Kalisz, "Microbial Proteinases," In: Fiechter (ed.), *Advances in Biochemical Engineering/Biotechnology*, [1988]). For example, proteolytic activity may be ascertained by comparative assays which analyze the respective protease's ability to hydrolyze a commercial substrate. Exemplary substrates useful in the analysis of protease or proteolytic activity, include, but are not limited to di-methyl casein (Sigma C-9801), bovine collagen (Sigma C-9879), bovine elastin (Sigma E-1625), and bovine keratin (ICN Biomedical 902111). Colorimetric assays utilizing these substrates are well known in the art (See e.g., WO 99/34011; and U.S. Pat. No. 6,376,450, both of which are incorporated herein by reference). The pNA assay (See e.g., Del Mar et al., Anal. Biochem., 99:316-320 [1979]) also finds use in determining the active enzyme concentration for fractions collected during gradient elution. This assay measures the rate at which p-nitroaniline is released as the enzyme hydrolyzes the soluble synthetic substrate, succinyl-alanine-alanine-proline-phenylalanine-p-nitroanilide (sAAPF-pNA). The rate of production of yellow color from the hydrolysis reaction is measured at 410 nm on a spectrophotometer and is proportional to the active enzyme concentration. In addition, absorbance measurements at 280 nm can be used to determine the total protein concentration. The active enzyme/total-protein ratio gives the enzyme purity.

As used herein, the term "subtilisin" refers to a protease belonging to the group of serine proteases which initiate the nucleophilic attack on the peptide bond through a serine residue at the active site (serine endopeptidase). Subtilisins are secreted in large amounts from many *Bacillus* species. For example, FNA, which is subtilisin BPN' containing the Y217L substitution, is a subtilisin obtained from *Bacillus amyloliquefaciens*, and AprE is the subtilisin obtained from *Bacillus subtilis*.

As used herein, "deletion" of a gene refers to deletion of the entire coding sequence, deletion of part of the coding sequence, or deletion of the coding sequence including flanking regions. The deletion may be partial as long as the sequences left in the chromosome provides the desired loss of the biological activity of the gene. The flanking regions of the coding sequence may include from about 1 bp to about 500 bp at the 5' and 3' ends. The flanking region may be larger than 500 bp but will preferably not include other genes in the region which may be inactivated or deleted according to the invention. The end result is that the deleted gene is effectively non-functional. In simple terms, a "deletion" is defined as a change in either nucleotide or amino acid sequence in which one or more nucleotides or amino acid residues, respectively, have been removed (i.e., are absent). Thus, a "deletion mutant" has fewer nucleotides or amino acids than the respective parent host cell. In some embodiments, deletion of a phr gene provides enhanced expression of a protein of interest (e.g., a protease).

In some embodiments, deletion of one or more of genes selected from the group consisting of phrA, phrC, phrE, phrF, phrI, and phrK, provides an improved strain for the enhanced production of a protease.

As used herein, a "corresponding unmodified *Bacillus* strain" or "parent" or "precursor" *Bacillus* sp. host cell is the originating host strain from which the indigenous chromosomal region (e.g., phrA and/or phrE gene), is inactivated and from which the altered/recombinant strain is derived.

A polypeptide is "overexpressed" in a recombinant host cell if the polypeptide is expressed in the recombinant cell at a higher level that the level at which it is expressed in the precursor cell.

As used herein, the term "homologous," when used in reference to a polynucleotide or protein, refers to a polynucleotide or protein that occurs naturally in a host cell.

The term "polypeptide," as used herein, refers to a compound made up of amino acid residues linked by peptide bonds. The term "protein" as used herein, may be synonymous with the term "polypeptide" or may refer, in addition, to a complex of two or more polypeptides. Thus, the terms "protein," "peptide," and "polypeptide" are used interchangeably.

As used herein, the terms "chimeric polypeptide" and "fusion polypeptide" are used interchangeably to refer to a protein that comprises at least two separate and distinct regions that may or may not originate from the same protein. For example, a signal peptide linked to the protein of interest wherein the signal peptide is not normally associated with the protein of interest would be termed a chimeric polypeptide or chimeric protein.

As used herein, a "signal sequence" is a sequence of amino acids present at the N-terminal portion of a protein which facilitates the secretion of the mature form of the protein outside the cell. The definition of a signal sequence is a functional one. The mature form of the extracellular protein lacks the signal sequence which is cleaved off during the secretion process.

A "prosequence" is an amino acid sequence between the signal sequence and mature protease that is necessary for the secretion of the protease. Cleavage of the pro sequence results in a mature active protease.

The term "signal sequence" or "signal peptide" refers to any sequence of nucleotides and/or amino acids which may participate in the secretion of the mature or precursor forms of the protein. This definition of signal sequence is a functional one, meant to include all those amino acid sequences encoded by the N-terminal portion of the protein gene, which participate in the effectuation of the secretion of protein. They are often, but not universally, bound to the N-terminal portion of a protein or to the N-terminal portion of a precursor protein. The signal sequence may be endogenous or exogenous. The signal sequence may be that normally associated with the protein (e.g., protease), or may be from a gene encoding another secreted protein. One exemplary exogenous signal sequence comprises the first seven amino acid residues of the signal sequence from *Bacillus subtilis* subtilisin fused to the remainder of the signal sequence of the subtilisin from *Bacillus lentus* (ATCC 21536).

The term "aprE promoter" herein refers to the polynucleotide promoter sequence that naturally drives the expression of subtilisin in *B. subtilis* (Ferrari et al., J. Bacteriol. 170:289-295 [1988]). In the context of aprE promoter, "an aprE promoter" herein refers to a wild-type aprE promoter and mutants thereof. In some embodiments, the aprE promoter includes the nucleotide sequences necessary for the transcriptional regulation exerted by DegU, ScoC, AbrB and any other regulator of such promoter, and/or the aprE transcriptional leader (Hambraeus et al., Microbiology 148:1795-1803 [2002]). In some alternative embodiments, the aprE promoter does not include all of the nucleotide sequences necessary for the transcriptional regulation exerted by DegU, ScoC, AbrB and other regulators, and/or does not include the aprE transcriptional leader sequence.

As used herein, an "inactivated gene" is a locus of a genome that, prior to its inactivation, was capable of producing a protein (i.e., capable of being transcribed into an RNA that could be translated to produce a full length polypeptide). A gene encoding a polypeptide is inactivated when it not transcribed and translated into a full length protein that has biological activity (e.g., catalytic activity, in the case of an enzyme). A gene may be inactivated by altering a sequence required for its transcription, for example by altering a sequence required for RNA processing (e.g., poly-A tail addition), by altering a sequence required for translation, or by altering the amino acid sequence of the encoded polypeptide (e.g., by a nucleotide substitution, etc). Examples of inactivated genes include but are not limited to a deleted gene, a gene containing a deleted region, a gene containing a rearranged region, a gene having an inactivating point mutation or frameshift, and a gene containing an insertion. A gene may also be inactivated by altering or deleting the sequence of the adjacent gene in an operon. In addition, a gene may also be inactivated using antisense or any other method that abolishes expression of that gene.

As used herein, the term "nucleic acid" encompasses DNA, RNA, whether single stranded or double stranded, and encompasses chemically modified DNA or RNA. The terms "nucleic acid" and "polynucleotide" are used interchangeably herein.

The term "inactivation" includes any method that prevents the functional expression of one or more of the phr genes (phrA, phrC, phrE, phrF, phrI, and phrK), wherein the gene or gene product (i.e., the encoded Phr protein), is unable to exert its known function. Inactivation occurs via any suitable means, including deletions, substitutions (e.g., mutations), interruptions, and/or insertions in the nucleic acid gene sequence. In some embodiments, an altered/recombinant *Bacillus* strain comprises inactivation of one or more genes that results preferably in stable and non-reverting inactivation. In some embodiments, inactivation is achieved by deletion. In some preferred embodiments, the gene is deleted by homologous recombination. For example, in some embodiments when phrA is the gene to be deleted, an inactivating DNA construct comprising an incoming sequence having a selective marker flanked on each side by a homology box is used. The homology box comprises nucleotide sequences homologous to nucleic acids flanking regions of the chromosomal phrA gene. The inactivating DNA construct aligns with the homologous sequences of the *Bacillus* host chromosome and in a double crossover event the phrA gene is excised out of the host chromosome.

In certain embodiments, the altered/recombinant cell is a *Bacillus* sp. host cell that comprises two inactivated genes (e.g., phrA and phrE). In other embodiments, the *Bacillus* sp. host cell comprises three inactivated genes, four inactivated genes, five inactivated genes, six inactivated genes, or more. Thus, it is not intended that the number of inactivated genes be limited to any particular number of genes. In some embodiments, the inactivated genes are contiguous to each another, while in other embodiments, they are located in separate regions of the *Bacillus* chromosome. In some embodiments, an inactivated chromosomal gene has a necessary function under certain conditions, but the gene is not necessary for *Bacillus* strain viability under laboratory conditions. Preferred laboratory conditions include but are not limited to conditions such as growth in a fermenter, in a shake flask, plated media, etc., suitable for the growth of the microorganism.

As used herein, the terms "inactivating DNA construct", "inactivating polynucleotide" and "deletion cassette" are used interchangeably to refer to a DNA construct comprising a non-functional sequence that may be inserted into a gene to disrupt the function of the gene. In some embodiments, the inactivating DNA construct comprises a sequence encoding a selective marker. The inactivating DNA construct may also include two homology boxes.

As used herein, the terms "expression cassette" and "expression vector" refer to nucleic acid constructs generated recombinantly or synthetically, with a series of specified nucleic acid elements that permit transcription of a particular nucleic acid in a target cell. The recombinant expression cassette can be incorporated into a plasmid, chromosome, mitochondrial DNA, plastid DNA, virus, or nucleic acid fragment. Typically, the recombinant expression cassette portion of an expression vector includes, among other sequences, a nucleic acid sequence to be transcribed and a promoter. In preferred embodiments, expression vectors have the ability to incorporate and express heterologous DNA fragments in a host cell. Many prokaryotic and eukaryotic expression vectors are commercially available. Selection of appropriate expression vectors is within the knowledge of those of skill in the art. The term "expression cassette" is used interchangeably herein with "DNA construct," and their grammatical equivalents. Selection of appropriate expression vectors is within the knowledge of those of skill in the art.

As used herein, the terms "DNA construct" and "transforming DNA" are used interchangeably to refer to DNA used to introduce sequences into a host cell or organism. The DNA may be generated in vitro by PCR or any other suitable technique(s) known to those in the art. In particularly preferred embodiments, the DNA construct comprises a sequence of interest (e.g., as an incoming sequence). In some embodiments, the sequence is operably linked to additional elements such as control elements (e.g., promoters, etc.). The DNA construct may further comprise a selectable marker. It may further comprise an incoming sequence flanked by homology boxes. In a further embodiment, the transforming DNA comprises other non-homologous sequences, added to the ends (e.g., stuffer sequences or flanks). In some embodiments, the ends of the incoming sequence are closed such that the transforming DNA forms a closed circle. The transforming sequences may be wild-type, mutant or modified. In some embodiments, the DNA construct comprises sequences homologous to the host cell chromosome. In other embodiments, the DNA construct comprises non-homologous sequences. Once the DNA construct is assembled in vitro it may be used to: 1) insert heterologous sequences into a desired target sequence of a host cell, and/or 2) mutagenize a region of the host cell chromosome (i.e., replace an endogenous sequence with a heterologous sequence), 3) delete target genes; and/or introduce a replicating plasmid into the host.

As used herein, the term "heterologous DNA sequence" refers to a DNA sequence that does not naturally occur in a host cell. In some embodiments, a heterologous DNA sequence is a chimeric DNA sequence that is comprised of parts of different genes, including regulatory elements.

As used herein, the term "heterologous protein" refers to a protein or polypeptide that does not naturally occur in the host cell (i.e., it is encoded by a heterologous sequence).

As used herein, "homologous protein" refers to a protein or polypeptide native or naturally occurring in a cell.

The term "YmaH protein" is interchangeably used with "Hfq protein" and refers to a protein that enhances the expression of a protein of interest. In the context of YmaH, "a YmaH protein" herein refers to a wild-type YmaH protein and variants thereof, including orthologs.

As used herein, the term "vector" refers to a polynucleotide designed to introduce nucleic acids into one or more host cells. In preferred embodiments, vectors autonomously replicate in different host cells. The term is intended to encompass, but is not limited to cloning vectors, expression vectors, shuttle vectors, plasmids, phage particles, cassettes, and the like.

An "expression vector" as used herein refers to a DNA construct comprising a protein-coding region that is operably linked to a suitable control sequence capable of effecting expression of the protein in a suitable host cell. In some embodiments, such control sequences include a promoter to effect transcription, an optional operator sequence to control transcription to produce mRNA, a sequence encoding suitable ribosome binding sites on the mRNA, and enhancers and sequences which control termination of transcription and translation.

As used herein, the term "promoter" refers to a regulatory sequence that initiates transcription of a downstream nucleic acid.

As used herein, the term "operably linked" refers to an arrangement of elements that allows them to be functionally related. For example, a promoter is operably linked to a coding sequence if it controls the transcription of the sequence.

As used herein, the term "derived" encompasses the terms "originated from," "obtained," or "obtainable from," and "isolated from".

As used herein, a "non-pathogenic" organism is an organism that is not pathogenic to humans and/or other animals.

The terms "recovered," "isolated," and "separated," as used herein refer to a protein, cell, nucleic acid or amino acid that is removed from at least one component with which it is naturally associated.

As used herein in the context of introducing a nucleic acid sequence into a cell, the term "introduced" refers to any method suitable for transferring the nucleic acid sequence into the cell. Such methods for introduction include but are not limited to protoplast fusion, transfection, transformation, conjugation, and transduction (See e.g., Ferrari et al., "*Genetics*," in Hardwood et al, (eds.), *Bacillus*, Plenum Publishing Corp., pages 57-72, [1989]).

As used herein, the terms "transformed" and "stably transformed" refers to a cell that has a non-native (heterologous) polynucleotide sequence integrated into its genome or as an episomal plasmid that is maintained for at least two generations.

As used herein, the term "expression" refers to the process by which a polypeptide is produced based on the nucleic acid sequence of a gene. The process includes both transcription and translation.

As used herein, the term "selectable marker-encoding nucleotide sequence" refers to a nucleotide sequence, which is capable of expression in the host cells and where expression of the selectable marker confers to cells containing the expressed gene the ability to grow in the presence of a corresponding selective agent or lack of an essential nutrient.

As used herein, the terms "selectable marker" and "selective marker" refer to a nucleic acid (e.g., a gene) capable of expression in host cell, which allows for ease of selection of those hosts containing the vector. Examples of such selectable markers include but are not limited to antimicrobials. Thus, the term "selectable marker" refers to genes that provide an indication that a host cell has taken up an incoming DNA of interest or some other reaction has occurred. Typically, selectable markers are genes that confer antimicrobial resistance or a metabolic advantage on the host cell to allow cells containing the exogenous DNA to be distinguished from cells that have not received any exogenous sequence during the transformation. A "residing selectable marker" is one that is located on the chromosome of the microorganism to be transformed. A residing selectable marker encodes a gene that is different from the selectable marker on the transforming DNA construct. Selective markers are well known to those of skill in the art. As indicated above, preferably the marker is an antimicrobial resistant marker (e.g., $amp^R$; $phleo^R$; $spec^R$; $kan^R$; $ery^R$; $tet^R$; $cmp^R$; and $neo^R$ (See e.g., Guerot-Fleury, Gene, 167:335-337, 1995; Palmeros et al., *Gene* 247:255-264, 2000; and Trieu-Cuot et al., *Gene*, 23:331-341, 1983). Other markers useful in accordance with the invention include, but are not limited to auxotrophic markers, such as tryptophan; and detection markers, such as β-galactosidase.

As used herein, "culturing" refers to growing a population of microbial cells under suitable conditions in a liquid or solid medium. In some embodiments, culturing refers to fermentative recombinant production of an exogenous protein of interest or other desired end products (typically in a vessel or reactor).

As used herein, the term "production" when used in reference to a protein of interest encompasses the processes of transcription, and translation, and when needed, the processes of secretion and maturation, which creates the active from of the protein. For proteins that are secreted into the extracellular medium (e.g., proteases), the level of protein production is assessed as the amount of active protein secreted into the extracellular medium.

As used herein, "*Bacillus* sp." refers to all of the species within the genus "*Bacillus*," which are Gram-positive bacteria classified as members of the Family Bacillaceae, Order Bacillales, Class Bacilli. The genus "*Bacillus*" includes all species within the genus "*Bacillus*," as known to those of skill in the art, including but not limited to *Bacillus alkalophilus, Bacillus amyloliquefaciens, Bacillus brevis, Bacillus circulans, Bacillus clausii, Bacillus coagulans, Bacillus firmus, Bacillus lautus, Bacillus lentus, Bacillus licheniformis, Bacillus megaterium, Bacillus pumilus, Bacillus stearothermophilus, Bacillus subtilis,* or *Bacillus thuringiensis*. It is recognized that the genus *Bacillus* continues to undergo taxonomical reorganization. Thus, it is intended that the genus include species that have been reclassified, including but not limited to such organisms as *B. stearothermophilus*, which is now named "*Geobacillus stearothermophilus*." The production of resistant endospores in the presence of oxygen is considered the defining feature of the genus *Bacillus*, although this characteristic also applies to the recently named *Alicyclobacillus, Amphibacillus, Aneurinibacillus, Anoxybacillus, Brevibacillus, Filobacillus, Gracilibacillus, Halobacillus, Paenibacillus, Salibacillus, Thermobacillus, Ureibacillus,* and *Virgibacillus*.

Other definitions of terms may appear throughout the Specification.

Before the exemplary embodiments are described in more detail, it is to be understood that the present invention is not limited to particular embodiments described, as such may, of course, vary. It is also to be understood that the terminology used herein is for the purpose of describing particular embodiments only, and is not intended to be limiting.

Before the exemplary embodiments are described in more detail, it is to be understood that the present invention is not limited to particular embodiments described, as such may, of course, vary. It is also to be understood that the terminology used herein is for the purpose of describing particular embodiments only, and is not intended to be limiting.

Modified Host Cells

*Bacillus* sp. cells make use of two-component signal transduction systems, each containing a sensor kinase and a response regulator, to sense and respond to a wide variety of extracellular stimuli. Known two-component systems are involved in various processes, such as competence development (Dubnau, Microbiological Reviews 1991 55, 395-424), protein secretion (Kunst, Research in Microbiology 1994 145, 393-402; Darmon, Journal of Bacteriology 2002 184, 5661-5671), synthesis of peptide antibiotics and bacteriocins (Marahiel Molecular Microbiology 1993 7, 631-636; Stein, Molecular Microbiology 2002 44, 403-416) and sporulation (Grossman, Annual Reviews Genetics 1995 29, 477-508). These regulatory systems are governed by intracellular response regulators aspartyl phosphatases (Raps), and their antagonistic phosphatase regulators (Phrs). The Raps dephosphorylate response regulators, which alter gene expression thereby produce cellular responses. The Phr peptides serve as cell density-signaling molecules and inhibit the Rap phosphatases (Perego, Proceedings of the National Academy of Science USA 1997 94, 8612-8617; Perego, M. Trends in Microbiology 1998 6, 366-370; Perego, Cell 1994 79, 1047-1055).

While the Rap phosphatases remain in the cytoplasm, Phr peptides contain an amino-terminal signal peptide and are exported as pro-peptides, most likely via the Sec pathway (Perego, Molecular Microbiology 1996 19, 1151-1170; Tjalsma. Microbiological and Molecular Biology Reviews 2000 64, 515-547). Further, extracellular processing results in active Phr pentapeptides. After re-import by cells in the culture via the oligopeptide permease (Opp) system, Phr peptides specifically inhibit the activity of their cognate Rap phosphatase (Solomon, Genes and Development 1996 10, 2014-2024; Perego, Proceedings of the National Academy of Science USA 1997 94, 8612-8617; Perego, Trends in Microbiology 1998 6, 366-370). The Phr peptides act as quorum sensors in that they initiate cellular responses in response to changes in cell density. A Rap protein and the Phr peptide that inhibits the Rap protein are encoded on a single operon. There are eight rap operons transcribed with their cognate phr genes, and three other rap coding genes in the *B. subtilis* genome (Kunst, Nature 1997 390, 249-256). The rap/phr signaling systems of *Bacillus subtilis* are reviewed in Pottathil (Front Biosci. 2003 8:d32-45) and Perego (Peptides 2001 22:1541-7).

The present invention provides modified *Bacillus* sp. host cells that are genetically manipulated to have an enhanced capacity to produce proteins of interest. In particular, the present invention relates to modified *Bacillus* sp. cells that contain a genome comprising at least one rap operon that comprises an inactivated phr gene. In some embodiments, the modified *Bacillus* sp. cells contain a genome comprising at least one rap operon that comprises an inactivated phr gene and an inactivated rap gene. Inactivation of the phr and/or rap gene enhances the production of a protein of interest by the modified *Bacillus* sp. cell when compared to the production of the same protein by the unmodified precursor *Bacillus* sp. cell. Thus, the modified *Bacillus* sp. cell comprises at least one inactivated phr and/or rap gene and a polynucleotide that encodes a protein of interest. In some embodiments, the polynucleotide that encodes the protein of interest is a wild-type polynucleotide. In other embodiments, the polynucleotide that encodes the protein of interest is a recombinant polynucleotide.

The DNA sequences of several *Bacillus* sp. rap operons and the Rap and Phr proteins encoded by the operons have been determined and deposited into NCBI's Genbank database. In certain embodiments, a *Bacillus* sp. rap operon modified in the subject cell: a) may have at least about 70%, at least about 80%, at least about 90%, at least about 95%, at least about 97% or at least about 98% sequence identity to the sequence of a rap operon sequence deposited in NCBI's Genbank database; b) may hybridize under stringent conditions to a rap operon sequence deposited in NCBI's Genbank database; or c) may encode a polypeptide that has at least about 70% sequence identity (e.g., at least about 80%, at least about 90%, at least about 93%, at least about 95%, at least about 97% or at least about 98% sequence identity) to a Rap or Phr sequence deposited in NCBI's Genbank database. Exemplary phr protein and nucleotide sequences deposited in NCBI's Genbank database include those annotated in Genbank accession no. NC_000964.2; GID: 50812173 (*B. subtilis*), Genbank accession no. NC_009848.1; GID: 157690798 (*Bacillus pumilus*), Genbank accession no. NC_006270.3; GID: 163119169 (*Bacillus licheniformis*) and Genbank accession no. NC_005957.1; GID 49476684 (*Bacillus thuringiensis*) among others. Rap proteins may be identified as containing a so-called tetratricopeptide repeat domain, a pfam domain that typically contains 34 amino acids and contains the following amino acid sequence [WLF]-X(2)-[LIM]-[GAS]-X(2)-[YLF]-X(8)-[ASE]-X(3)-[FYL]-X(2)-[ASL]-X(4)-[PKE].

The above Genbank accessions are incorporated by reference in their entirety, including the nucleic acid and protein sequences therein and the annotation of those sequences, as of the earliest filing date of this patent application.

In some embodiments, the well-known *Bacillus subtilis* strain 168 finds use in the present invention. Indeed, the genome of this strain has been well-characterized (See, Kunst et al., Nature 390:249-256 [1997]; and Henner et al., Microbiol. Rev., 44:57-82 [1980]). The genome is comprised of one 4215 kb chromosome. While the coordinates used herein refer to the 168 strain, the invention encompasses analogous sequences from *Bacillus* strains other than *Bacillus subtilis* 168.

In one embodiment, a modified *Bacillus* sp. cell comprises a single inactivated phr gene (e.g., a rapA operon containing an inactive phrA gene, a rapC operon containing an inactive phrC gene; a rapE operon containing an inactive phrE gene, a rapF operon containing an inactive phrF gene, a rapI operon containing an inactive phrI gene, or a rapK operon containing an inactive phrK gene).

In one embodiment, the modified *Bacillus* sp. cell comprises an inactivated phrA gene (e.g., a rapA operon containing an inactive phrA gene). In some embodiments, inactivation results from the deletion of the entire endogenous DNA sequence that encodes the PhrA protein. In some embodiments, the entire endogenous DNA sequence of the *Bacillus subtilis* phrA gene is deleted using the inactivating DNA deletion construct of SEQ ID NO:17. In *Bacillus subtilis* 168, the DNA sequence that encodes the phrA protein MKSKW-MSGLLLVAVGFSFTQVMVHAGETANTEGKTFHIAAR-NQT; SEQ ID NO:42 (Swiss-Prot:Q00829) is atgaaatctaaatggatgtcaggtttgttgctcgttgcggtcgggttcagctttac-tcaggtgatggtcatgcaggtgaaacagcaaacacagaagggaaaacatttcat-attgcggcacgcaatcaaaca; SEQ ID NO:41 (NP_389126). Alternatively, inactivation of the phrA gene results from the deletion of a fragment of the phrA gene that prevents the functional expression of the PhrA protein. The phrA gene is located at about 1316305-1316439 bp of the *B. subtilis* 168 chromosome (Accession no. NC_000964). According to one embodiment, inactivation of the phrA gene is by insertion of a selectable marker that interrupts the phrA gene.

In another embodiment, the modified *Bacillus* sp. cell comprises an inactivated phrE gene (e.g., a rapE operon containing an inactive phrE gene). In some embodiments, inactivation results from the deletion of the entire endogenous DNA sequence that encodes the PhrE protein.

In some embodiments, the entire endogenous DNA sequence of the *Bacillus subtilis* phrE gene is deleted using the inactivating DNA deletion construct of SEQ ID NO:18. In *Bacillus subtilis* 168, the DNA sequence that encodes the phrE protein MKSKLFISLSAVLIGLAFFGSMYNGEMK-EASRNVTLAPTHEFLV; SEQ ID NO:44 (Swiss-Prot: 032025) is atgaaatctaaattgtttatcagtttatccgccgttttaattggacttg-ccttMcggatctatgtataatggcgaaatgaaggaagcatcccggaatgtaactc-tcgcacctactcatgaattccttgtt; SEQ ID NO:43 (NP_390461). Alternatively, inactivation of the phrE gene results from the deletion of a fragment of the phrE gene that prevents the functional expression of the PhrE protein. The phrE gene is located at about 2659557-2659691 bp of the *B. subtilis* 168 chromosome (Accession no. NC_000964). According to one embodiment, inactivation of the phrE gene is by insertion of a selectable marker that interrupts the phrE gene.

In yet other embodiments, the phrA and the phrE genes are deleted from the *Bacillus subtilis* chromosome using the phrA and the phrE deletion constructs set forth in SEQ ID NOS:17 and 18, respectively.

In some other embodiments, the modified *Bacillus* sp. cell comprises at least two inactivated phr genes (e.g., two rap operons each containing an inactivated phr gene), at least three inactivated phr genes (e.g., three rap operons each containing an inactivated phr gene) at least four inactivated phr genes (e.g., four rap operons each containing an inactivated phr gene), at least five inactivated phr genes (e.g., five rap operons each containing an inactivated phr gene), at least six inactivated phr genes (e.g., six rap operons each containing an inactivated phr gene), at least seven inactivated phr genes, (e.g., seven rap operons each containing an inactivated phr gene), or at least eight inactivated phr genes (e.g., eight rap operons each containing an inactivated phr gene). In one exemplary embodiment, a subject host cell may contain both a) a rapA operon containing an inactive phrA gene and b) a rapE operon containing an inactive phrE gene. In some embodiments, inactivation results from the deletion of the entire endogenous DNA sequences that encode the PhrA and the PhrE proteins, respectively. Alternatively, inactivation of the phrA and phrE gene results from the deletion of a fragment of the phrA and the phrE gene that prevents the functional expression of the PhrA and the PhrE proteins, respectively. Thus, in some embodiments, a segment of the phrA gene is deleted, and a segment of the phrE gene is deleted from the chromosome. Similarly, the inactivation of the phrA and the phrE genes results from the deletion of the entire endogenous DNA sequence that encodes the PhrA and the deletion of a DNA sequence that encodes a fragment of the PhrE protein. Alternatively, the inactivation of the phrA and the phrE genes results from the deletion of the entire endogenous DNA sequence that encodes the PhrE and the deletion of a DNA sequence that encodes a fragment of the PhrA protein. Fragments of phr genes (e.g. phrA and/or phrE), include a range of about 1% to about 99% of the indigenous chromosomal region encoding the phrA and/or phrE proteins. In other embodiments, fragments include a range of about 5% to about 95% of the indigenous chromosomal region. In yet additional embodiments, fragments comprise at least about 99%, about 98%, about 97%, about 96%, about 95%, about 94%, about 93%, about 92%, about 90%, about 88%, about 85%, about 80%, about 75%, about 70%, about 65%, about 50%, about 40%, about 30%, about 25%, about 20% and about 10% of the indigenous chromosomal region.

In some embodiments, inactivation of the phrA and/or phrE genes is achieved by deletion resulting from homologous recombination. For example, in some embodiments when phr is the gene to be deleted, an inactivating DNA construct comprising a selectable marker flanked on each side by a homology box is used. The homology box comprises nucleotide sequences homologous to nucleic acids flanking regions of the chromosomal phr gene. The DNA construct aligns with the homologous sequences of the *Bacillus* host chromosome and in a double crossover event the phr gene is excised out of the host chromosome. The inactivating DNA construct is assembled in vitro, followed by direct cloning of the construct into a competent *Bacillus* host, such that the DNA construct becomes integrated into the *Bacillus* chromosome. For example, PCR fusion and/or ligation can be employed to assemble a DNA construct in vitro. In some embodiments, the DNA construct is a non-plasmid construct, while in other embodiments it is incorporated into a vector (e.g., a plasmid).

In other embodiments, the inactivating DNA construct comprises a selectable marker flanked on the 5' and 3' ends with a fragment of the gene sequence. In some embodiments, when the DNA construct comprising the selectable marker and gene, gene fragment or homologous sequence thereto is transformed into a host cell, the location of the selectable marker renders the gene non-functional for its intended purpose. In some embodiments, the inactivating DNA construct comprises the selectable marker located in the promoter region of the gene. In other embodiments, the inactivating DNA construct comprises the selectable marker located 3' to the promoter region of gene. In yet other embodiments, the inactivating DNA construct comprises the selectable marker located in the coding region of the gene. In further embodiments, the inactivating DNA construct comprises a selectable marker flanked by a homology box on both ends. In still further embodiments, the inactivating DNA construct includes a sequence that interrupts the transcription and/or translation of the coding sequence. In yet additional embodiments, the DNA construct includes restriction sites engineered at the upstream and downstream ends of the construct.

In another embodiment, inactivation of the phrA and/or phrE gene is by insertion of a selectable marker that interrupts the phrA and/or phrE gene in a single crossover event. In some embodiments, the selectable marker is located within the gene coding sequence or on a part of the plasmid separate from the gene. The vector is integrated into the *Bacillus* chromosome, and the gene is inactivated by the insertion of the vector in the coding sequence.

Other suitable means for inactivating a phr gene include introducing mutations that result in amino acid substitutions, and truncations that accompany a corresponding loss in the biological activity of the phr protein. In some embodiments, a modified *Bacillus* sp. cell comprises inactivation of one or more phr genes that results preferably in stable and non-reverting inactivation. Methods of mutating genes are well known in the art and include but are not limited to site-directed mutation, generation of random mutations, and gapped-duplex approaches (See e.g., U.S. Pat. No. 4,760,025; Moring et al., Biotech. 2:646 [1984]; and Kramer et al., Nucleic Acids Res., 12:9441 [1984]).

Whether the inactivating DNA construct is incorporated into a vector or used without the presence of plasmid DNA, it is used to transform microorganisms. It is contemplated that any suitable method for transformation will find use with the present invention. In some embodiments, at least one copy of the inactivating DNA construct is integrated into the host *Bacillus* chromosome. In some embodiments, one or more inactivating DNA constructs of the invention are used to transform host cells. For example, one inactivating DNA construct may be used to inactivate a phrA gene and another construct may be used to inactivate a phrE gene. Of course, additional combinations are contemplated and provided by the present invention.

In some embodiments, the phrA and/or phrE gene is deleted in a precursor recombinant *Bacillus subtilis* strain in which one or more genes encoding an endogenous protease have been deleted. In some embodiments, the *Bacillus* sp. host cell comprises two or more inactivated protease genes. In some embodiments, the *Bacillus* host cell contains two inactivated protease genes (See e.g., U.S. Pat. No. 5,387,521) while in other embodiments, the *Bacillus* host cell contains 5 inactivated protease genes: nprE, aprE, epr, ispA, and bpr genes (See e.g., US20050202535). Since the sequence of the entire *B. subtilis* genome is publicly available and annotated (See e.g., Moszer, FEBS Lett., 430:28-36 [1998]), the proteases of *B. subtilis* have been identified and reviewed in detail (See e.g., He et al., Res. Microbiol., 142:797-803 [1991]). In addition, gene disruption methods for *Bacillus* cells are generally well known in the art (See e.g., Lee et al., Appl. Environ. Microbiol., 66: 476-480 [2000]; Ye et al., Proc. Internatl. Symp. Rec. Adv. Bioindustry, Seoul, Korea: The Korean Society for Applied Microbiology, pp. 160-169 [1996]; Wu et al., J. Bacteriol., 173:4952-4958 [1991]; and Sloma et al., J. Bacteriol., 173: 6889-6895 [1991]). Thus, the construction of such strains is well within the ability of one of skill in the art.

As indicated above, in some embodiments, the modified *Bacillus* sp. host cell comprises an inactivated phr gene and an inactivated rap gene. In one embodiment, the modified *Bacillus* sp. cell comprises a single rap operon that contains an inactivated phr gene and an inactivated rap gene (e.g., a rapA operon containing an inactive phrA gene and an inactivated rapA gene, a rapC operon containing an inactive phrC gene and an inactivated rapC gene; a rapE operon containing an inactive phrE gene and an inactivated rapE gene, a rapF operon containing an inactive phrF gene and an inactivated rapF gene, a rapI operon containing an inactive phrI gene and an inactivated rap/gene, or a rapK operon containing an inactive phrK gene and an inactivated rapK gene). In other embodiments, the modified *Bacillus* sp. cell comprises at least two rap operons each containing an inactivated phr gene and an inactivated rap gene. In some embodiments, inactivation results from the deletion of the entire endogenous DNA sequences that encode the Phr and the Rap proteins.

In some embodiments, the entire endogenous DNA sequence of the *Bacillus subtilis* phrA gene is deleted using the inactivating DNA deletion construct of SEQ ID NO:17. In *Bacillus subtilis* 168, the DNA sequence that encodes the PhrA protein MKSKWMSGLL LVAVGFSFTQ VMVHAG-ETAN TEGKTFHIAA RNQT; SEQ ID NO:42 (Swiss-Prot: Q00829) is:

```
                                        SEQ ID NO: 41
atgaaatctaaatggatgtcaggtttgttgctcgttgcggtcgggttcag ctttactcaggtgatggttcatgcaggtgaaacagcaaacacagaaggga aaacatttcatattgcggcacgcaatcaaaca; (NP_389126).
```

Alternatively, inactivation of the phrA gene results from the deletion of a fragment of the phrA gene that prevents the functional expression of the PhrA protein. The phrA gene is located at about 1316305-1316439 bp of the *B. subtilis* 168 chromosome (Accession no. NC_000964). According to one embodiment, inactivation of the phrA gene is by insertion of a selectable marker that interrupts the phrA gene. Alternatively, inactivation of the phrA gene results from the inactivation of the rapA gene by introducing a selectable marker comprising a terminator sequence in the rapA gene thereby preventing the functional expression of the rapA and phrA protein According to one embodiment, inactivation of the rapA gene is by insertion of a selectable marker that interrupts the rapA gene.

In one embodiment, the endogenous DNA sequence of the *Bacillus subtilis* rapA gene is deleted using the inactivating DNA deletion construct of SEQ ID NO:52. In *Bacillus subtilis* 168, the DNA sequence that encodes the rapA protein:
MRMKQTIPSSYVGLKINEWYTHIRQFH-VAEAERVKLEVEREIEDMEEDQDLLLYY SLME-FRHRVMLDYIKPFGEDTSQLEF-SELLEDIEGNQYKLTGLLEYYFNFFRGMYEFKQK MFVSAMMYYKRAEKNLALVSDDIEKAE-FAFKMAEIFYNLKQTYVSMSYAVQALETYQMY ETYTVRRIQCEFVIAGNYDDMQYPERAL-PHLELALDLAKKEGNPRLISSALYNLGNCYEK MGELQKAAEYFGKSVSICKSEKFDNL-PHSIYSLTQVLYKQKNDAEAQKKYREGLEIARQY SDELFVELFQFLHALYGKNIDTESVSHT-FQFLEEHMLYPYIEELAHDAAQFYIENGQPEKA LSFYEKMVHAQKQIQRGDCLYEI; SEQ ID NO:54 (Swiss-Prot: Q00828) is

```
                                        SEQ ID NO: 53
ttgaggatgaagcagacgattccgtcctcttatgtcgggcttaaaattaa tgaatggtatactcatatccggcagttccacgtcgctgaagccgaacggg tcaagctcgaagtagaaagagaaattgaggatatggaagaagaccaagat ttgctgctgtattattctttaatggagttcaggcaccgtgtcatgctgga ttacattaagccttttggagaggacacgtcgcagctagagttttcagaat tgttagaagacatcgaagggaatcagtacaagctgacagggcttctcgaa tattactttaatttttttcgaggaatgtatgaatttaagcagaagatgtt tgtcagtgccatgatgtattataaacgggcagaaaagaatcttgccctcg tctcggatgatattgagaaagcagagtttgcttttaaaatggctgagatt ttttacaatttaaaacaaacctatgtttcgatgagctacgccgttcaggc attagaaacataccaaatgtatgaaacgtacaccgtccgcagaatccaat gtgaattcgttattgcaggtaattatgatgatatgcagtatccagaaga gcattgccccacttagaactggctttagatcttgcaaagaaagaaggcaa tccccgcctgatcagttctgccctatataatctcggaaactgctatgaga aaatgggtgaactgcaaaaggcagccgaatactttgggaaatctgtttct atttgcaagtcggaaaagttcgataatcttccgcattctatctactcttt aacacaagttctgtataaacaaaaaaatgacgccgaagcgcaaaaaaagt atcgtgaaggattggaaatcgcccgtcaatacagtgatgaattatttgtg gagcttttcaattttacatgcgttatacggaaaaaacattgacacaga atcagtctcacacacctttcaatttcttgaagaacatatgctgtatcctt atattgaagagctggcgcatgatgctgcccaattctatatagaaaacgga cagcccgaaaaagcactttcattttatgagaaatggtgcacgcacaaaa acaaatccagagaggagattgtttatatgaaatc; (NP_389125).
```

In certain embodiments, the modified *Bacillus* sp. cell comprising the rap operon containing the inactive phr gene may contain an active or inactive rap gene. If the rap gene is active, it may have a wild-type sequence (e.g., may be endogenous to the cell) or may be modified such that it is functionally equivalent to the wild type protein of the same species.

In some embodiments, the modified *Bacillus* sp. host cell comprises an inactivated rap gene. In one embodiment, the modified *Bacillus* sp. cell comprises a single rap operon that contains an inactivated rap gene (e.g., a rapA operon containing an inactive an inactivated rapA gene, a rapB operon containing an inactive an inactivated rapB gene, a rapC operon containing an inactivated rapC gene, a rapD operon containing an inactive an inactivated rapD gene, a rapE operon containing an inactivated rapE gene, a rapF operon containing an inactivated rapF gene, a rapG operon containing an inactivated rapG, a rapI operon containing an inactivated rap/gene, a rapJ operon containing an inactivated rapJ gene, or a rapK operon containing an inactivated rapK gene). In other embodiments, the modified *Bacillus* sp. cell comprises at least two rap operons each containing an inactivated rap gene. In some embodiments, inactivation results from the deletion of the entire endogenous DNA sequences that encode the Rap proteins.

The modified *Bacillus* sp. cell is derived from a precursor host cell of a *Bacillus* sp. strain including *Bacillus alkalophilus, Bacillus amyloliquefaciens, Bacillus brevis, Bacillus circulans, Bacillus clausii, Bacillus coagulans, Bacillus firmus, Bacillus lautus, Bacillus lentus, Bacillus licheniformis, Bacillus megaterium, Bacillus pumilus, Bacillus stearothermophilus, Bacillus subtilis*, or *Bacillus thuringiensis* strains. In some embodiments, the modified *Bacillus* sp. cell is derived from an alkalophilic *Bacillus* sp. cell. Numerous alkalophilic *Bacillus* sp. are known (See e.g., U.S. Pat. No. 5,217,878; and Aunstrup et al., Proc IV IFS: Ferment. Technol. Today, 299-305 [1972]). In some particular embodiments, the *Bacillus* sp. precursor host cell is an industrial *Bacillus* sp. host cell. Examples of industrial *Bacillus* sp. host cells include, but are not limited to *Bacillus licheniformis, Bacillus lentus, Bacillus subtilis*, and *Bacillus amyloliquefaciens* host cells. In additional embodiments, the *Bacillus* sp. host cell is selected from the group consisting of *Bacillus lentus, Bacillus brevis, Bacillus stearothermophilus, Bacillus alkalophilus, Bacillus coagulans, Bacillus circulans, Bacillus pumilus, Bacillus thuringiensis, Bacillus clausii*, and *Bacillus megaterium*, as well as other organisms within the genus *Bacillus*, as discussed above. In some particularly preferred embodiments, *Bacillus subtilis* is used. For example, U.S. Pat. Nos. 5,264,366 and 4,760,025 (RE 34,606) describe various *Bacillus* host strains that find use in the present invention, although other suitable strains (e.g., industrial strains) are contemplated for use in the present invention.

An industrial strain may be a non-recombinant strain of a *Bacillus* sp., a mutant of a naturally occurring strain, or a recombinant strain. Preferably, the host strain is a recombinant host strain wherein a recombinant polynucleotide encoding a polypeptide of interest has been introduced into the host. In some embodiments, the polypeptide of interest is an enzyme (e.g., a protease). A further preferred host strain is a *Bacillus subtilis* host strain, and in particular a recombinant *Bacillus subtilis* host strain. Numerous *Bacillus subtilis* strains are known, including but not limited to 1A6 (ATCC 39085), 168 (1A01), SB19, W23, Ts85, B637, PB1753 through PB1758, PB3360, JH642, 1A243 (ATCC 39,087), ATCC 21332, ATCC 6051, MI113, DE100 (ATCC 39,094), GX4931, PBT 110, and PEP 211 strain (See e.g., Hoch et al., Genetics, 73:215-228 [1973]; U.S. Pat. No. 4,450,235; U.S. Pat. No. 4,302,544; and EP 0134048). The use of *B. subtilis* as an expression host is further described by Palva et al. and others (See, Palva et al., Gene 19:81-87 [1982]; See also, Fahnestock and Fischer, J. Bacteriol., 165:796-804 [1986]; and Wang et al, Gene 69:39-47 [1988]).

Industrial protease producing *Bacillus* sp. host cells provide particularly preferred host cells. In some preferred embodiments, use of these host cells in the present invention enhances protease production. Two general types of proteases are typically secreted by *Bacillus* sp., namely neutral (or "metalloproteases") and alkaline (or "serine") proteases. Serine proteases are enzymes which catalyze the hydrolysis of peptide bonds in which there is an essential serine residue at the active site. Serine proteases have molecular weights in the 25,000 to 30,000 range (See, Priest, Bacteriol. Rev., 41:711-753 [1977]). Subtilisin is a preferred serine protease that is produced by the modified *Bacillus* sp. host cells of the present invention. A wide variety of *Bacillus* subtilisins have been identified and sequenced, for example, GG36, subtilisin 168, subtilisin BPN', subtilisin Carlsberg, subtilisin DY, subtilisin 147 and subtilisin 309 (See e.g., EP 414279 B; WO 89/06279; and Stahl et al., J. Bacteriol., 159:811-818 [1984]). In some embodiments of the present invention, the *Bacillus* host strains produce mutant (e.g., variant) proteases. Numerous references provide examples of variant proteases and reference (See e.g., WO 99/20770; WO 99/20726; WO 99/20769; WO 89/06279; RE 34,606; U.S. Pat. No. 4,914,031; U.S. Pat. No. 4,980,288; U.S. Pat. No. 5,208,158; U.S. Pat. No. 5,310,675; U.S. Pat. No. 5,336,611; U.S. Pat. No. 5,399,283; U.S. Pat. No. 5,441,882; U.S. Pat. No. 5,482,849; U.S. Pat. No. 5,631,217; U.S. Pat. No. 5,665,587; U.S. Pat. No. 5,700,676; U.S. Pat. No. 5,741,694; U.S. Pat. No. 5,858,757; U.S. Pat. No. 5,880,080; U.S. Pat. No. 6,197,567; and U.S. Pat. No. 6,218,165).

In another embodiment, a preferred *Bacillus* sp. host is a *Bacillus* sp. that includes a mutation or deletion in at least one of the following genes, degU, degS, degR and degQ. Preferably the mutation is in a degU gene, and more preferably the mutation is degU(Hy)32 (See e.g., Msadek et al., J. Bacteriol., 172:824-834 [1990]; and Olmos et al., Mol. Gen. Genet., 253:562-567 [1997]). In one embodiment, the host cell is a *Bacillus subtilis* host cell that carries a degU32(Hy) mutation. In a further embodiment, the *Bacillus* sp. host cell comprises a mutation or deletion in scoC4, (See e.g., Caldwell et al., J. Bacteriol., 183:7329-7340 [2001]); spoIIE (See e.g., Arigoni et al, Mol. Microbiol., 31:1407-1415 [1999]); oppA or other genes of the opp operon (See e.g., Perego et al., Mol. Microbiol., 5:173-185 [1991]). Indeed, it is contemplated that any mutation in the opp operon that causes the same phenotype as a mutation in the oppA gene will find use in some embodiments of the modified *Bacillus* sp. cell of the present invention. In some embodiments, these mutations occur alone, while in other embodiments, combinations of mutations are present. In some embodiments, a modified *Bacillus* sp. cell of the invention is derived from a *Bacillus* sp. host cell that already includes a mutation to one or more of the above-mentioned genes. In alternate embodiments, a modified *Bacillus* sp. cell of the invention is further engineered to include mutation of one or more of the above-mentioned genes.

Proteins of Interest

The invention provides modified *Bacillus* sp. cells that are used to produce proteins of interest at a level that is greater than that produced by the unmodified precursor host cells. Generally, proteins of interest are desirable proteins that have commercial significance. The protein of interest may be either homologous or heterologous to the host. In some embodiments, the protein of interest is a secreted polypeptide, particularly an enzyme, including but not limited to amylolytic enzymes, proteolytic enzymes, cellulytic enzymes, oxidoreductase enzymes and plant wall degrading enzymes. In further embodiments, these enzyme include, but are not limited to amylases, proteases, xylanases, lipases, laccases, phenol oxidases, oxidases, cutinases, cellulases, hemicellulases, esterases, peroxidases, catalases, glucose oxidases, phytases, pectinases, glucosidases, isomerases, transferases, galactosidases and chitinases. In still further embodiments, the expressed polypeptide is a hormone, cytokine, growth factor, receptor, vaccine, antibody, or the like. While it is not intended that the present invention be limited to any particular protein/polypeptide, in some most preferred embodiments, the expressed protein of interest is a protease.

As noted above, in certain embodiments the host cell contains a recombinant expression cassette that comprises a polynucleotide sequence encoding a protein of interest (i.e., an expression cassette for production of a protein that is not native to the host cell). In some embodiments, the host cell comprises a recombinant nucleic acid comprising an expression cassette (i.e., a promoter, a polynucleotide encoding the protein of interest, and a transcriptional terminator), wherein the expression cassette is sufficient for the production of the protein by the Bacillus sp. host cell. In some embodiments, the recombinant nucleic acid is integrated into the genome of the host cell, while in other embodiments, the recombinant nucleic acid is present in a vector that replicates autonomously from the genome. In some embodiments, the polynucleotide encoding the protein of interest is codon optimized for expression of the protein in the Bacillus sp. host cell. While any promoter may be employed in a subject expression cassette, promoters that are regulated by the rap/phr systems (e.g., the aprE and nprE promoters) may be employed in some embodiments.

In one embodiment, the protein of interest may be, for example, an enzyme (e.g., a so-called "industrial enzyme"), or a protein having therapeutic activity such an antibody. In one particular embodiment, the protein of interest is a subtilisin, where the term "subtilisin" refers to a serine endopeptidase of the S8 family of peptidases. Subtilisin protein has an activity described as EC 3.4.21.62 (previously EC 3.4.4.16), according to IUMBM enzyme nomenclature. The activity of exemplary subtilisin proteins is generally described in Philipp et al, (Mol. Cell. Biochem. 1983 51:5-32), Siezen (Protein Sci., 1997 6:501-523); Bryan (Biochim. Biophys. Acta, 2000 1543:203-222); Maurer, 2004 Curr. Op, Biotechnol., 2004 15:330-334); and Gupta, Appl. Microbiol. Biotechnol., 2002 59:15-32).

In some embodiments, a subtilisin has an amino acid sequence that is found in a wild-type genome (i.e., the subtilisin is a naturally-occurring subtilisin), while in other embodiments, the subtilisin is a variant of a naturally-occurring subtilisin. In some embodiments, the variant subtilisin comprises an amino acid sequence that is at least about 80%, at least about 90%, at least about 95% or at least about 98% identical to a subtilisin encoded by a wild-type genome. Exemplary subtilisins include, but are not limited to: ALCANASE® (Novozymes), FNA™ (Genencor), SAVINASE® (Novozymes) PURAFECT™ (Genencor), KAP™ (Kao), EVERLASE™ (Novozymes), PURAFECT OxP™ (Genencor), FN4™ (Genencor), BLAP S™ (Henkel), BLAP X™ (Henkel), ESPERASE® (Novozymes), KANNASE™ (Novozymes) and PROPERASE™ (Genencor). In yet additional embodiments, the subtilisin includes, but is not limited to subtilisin BPN', subtilisin Carlsberg, subtilisin DY, subtilisin 147, or subtilisin 309 (See e.g., WO89/06279; and Stahl et al., J. Bacteriol., 159:811-818 [1984]). Additional subtilisins and other proteases that find use in the present invention include but are not limited to those described in WO 99/20770; WO 99/20726; WO 99/20769; WO 89/06279; RE 34,606; U.S. Pat. No. 4,914,031; U.S. Pat. No. 4,980,288; U.S. Pat. No. 5,208,158; U.S. Pat. No. 5,310,675; U.S. Pat. No. 5,336,611; U.S. Pat. No. 5,399,283; U.S. Pat. No. 5,441,882; U.S. Pat. No. 5,482,849; U.S. Pat. No. 5,631,217; U.S. Pat. No. 5,665,587; U.S. Pat. No. 5,700,676; U.S. Pat. No. 5,741,694; U.S. Pat. No. 5,858,757; U.S. Pat. No. 5,880,080; U.S. Pat. No. 6,197,567; and U.S. Pat. No. 6,218,165.

In some embodiments, the expression of the protein of interest in a host cell is driven by the aprE promoter of the aprE gene from which the B. subtilis subtilisin is naturally transcribed. The aprE gene is transcribed by sigma A ($\sigma^4$) factor and its expression is highly controlled by several regulators, such as: DegU/DegS, AbrB, Hpr and SinR (Valle and Ferrari (1989) In: Smith I, Slepecky R A, Setlow P (eds) Regulation of Procaryotic Development. American Society for Microbiology. Washington, D.C. pp 131-146), and aprE Sigma A promoter has been identified tgggtcttgacaaatattattcatctattacaataaattcacaga (SEQ ID NO:38; US 20030148461; Heiman et al., 1995, Nucleic Acid Research, Vol. 24, pp. 2351-2360). In some embodiments, the host cell comprises an aprE promoter that is the wild-type aprE promoter tgggtctactaaatattattccatctattacaataaattcacaga (SEQ ID NO:39; U.S. Patent Application Publication No. 20030148461).

In other embodiments, the expression of a protein of interest by a host cell is driven by mutant of the B. subtilis aprE promoters. In some embodiments, the invention provides for a Bacillus host cell that contains a mutant aprE promoter operably linked to a polynucleotide sequence that encodes a protein of interest. Thus, the invention encompasses host cells that express a protein of interest from a mutant aprE promoter. An example of a mutant aprE promoter is the mutant aprE promoter having the sequence:

tgggtc ttgaca aatattattccatct tacaat aaattcacaga (SEQ ID NO:40), which is described in U.S. Patent Application Publication No. 20030148461. Any one of the proteins of interest recited herein (e.g., Bacillus subtilisins) can be transcribed from an aprE promoter. In some embodiments, the invention provides for a modified Bacillus host cell that is capable of expressing a protein of interest from an aprE promoter. In some embodiments, the modified host cell is a modified B. subtilis host cell capable of expressing a protease driven by an aprE promoter. In some embodiments, the aprE promoter includes the aprE promoter regulatory elements and/or the aprE transcriptional leader, while in other embodiments, the aprE promoter does not include the aprE promoter regulatory elements and/or the aprE transcriptional leader.

In addition to the aprE promoter, the invention also encompasses compositions and methods for expressing a protein of interest by a host cell, wherein the expression is driven by any promoter suitable for driving the transcription of the gene of interest as long as the promoter comprises the transcriptional leader sequence of the aprE gene. Other suitable promoters and terminators for use in Bacillus host cells are known and include: the promoters and terminators of npr (neutral protease; i.e., NprE promoter), amy (α-amylase) and α-lactamase genes, as well as the B. subtilis levansucrase gene (sacB), B. licheniformis alpha-amylase gene (amyL), B. stearothermophilus maltogenic amylase gene (amyM), B. amyloliquefaciens alpha-amylase gene (amyQ), B. licheniformis penicillinase gene (penP), B. subtilis xylA and xylB genes, the promoters and terminators described in WO 93/10249, WO 98/07846, and WO 99/43835.

In other embodiments, the modified host cell may produce a protein of interest that is a recombinant carbohydrase, such as a liquefying and saccharifying α-amylase, an alkaline α-amylase, a α-amylase, a cellulase; a dextranase, an α-glucosidase, an α-galactosidase, a glucoamylase, a hemicellulase, a pentosanase, a xylanase, an invertase, a lactase, a naringanase, a pectinase or a pullulanase; a protease such as an acid protease, an alkali protease, bromelain, ficin, a neutral protease, papain, pepsin, a peptidase, rennet, rennin, chymosin, thermolysin, an aspartic proteinase, or trypsin; a lipase or esterase, such as a triglyceridase, a phospholipase, a pregastric esterase, a phosphatase, a phytase, an amidase, an iminoacylase, a glutaminase, a lysozyme, or a penicillin acylase; an isomerase such as glucose isomerase; an oxidoreductases (e.g., an amino acid oxidase), a catalase, a chloroperoxidase, a glucose oxidase, a hydroxysteroid dehydrogenase or a peroxidase; a lyase such as a acetolactate decarboxylase, a aspartic β-decarboxylase, a fumarase or a histadase; a transferase such as cyclodextrin glycosyltranferase; or a ligase, for example. In particular embodiments, the protein may be an aminopeptidase, a carboxypeptidase, a chitinase, a cutinase, a deoxyribonuclease, an α-galactosidase, a β-galactosidase, a β-glucosidase, a laccase, a mannosidase, a mutanase, a pectinolytic enzyme, a polyphenoloxidase, ribonuclease or transglutaminase.

In particular embodiments, the protein may be a therapeutic protein. Examples of suitable target therapeutic proteins which may be produced using a subject cell include: erythropoietin, cytokines such as interferon-α, interferon-β, interferon-γ, interferon-o, and granulocyte-CSF, GM-CSF, coagulation factors such as factor VIII, factor IX, and human protein C, antithrombin III, thrombin, soluble IgE receptor α-chain, IgG, IgG fragments, IgG fusions, IgM, IgA, interleukins, urokinase, chymase, and urea trypsin resume inhibitor, IGF-binding protein, epidermal growth factor, growth hormone-releasing factor, annexin V fusion protein, angiostatin, vascular endothelial growth factor-2, myeloid progenitor inhibitory factor-1, osteoprotegerin, α-1-antitrypsin, α-feto proteins, DNase II, kringle 3 of human plasminogen, glucocerebrosidase, TNF binding protein 1, follicle stimulating hormone, cytotoxic T lymphocyte associated antigen 4-Ig, transmembrane activator and calcium modulator and cyclophilin ligand, soluble TNF receptor Fc fusion, glucagon like protein 1 and IL-2 receptor agonist. Monoclonal antibodies may also be made.

In certain embodiments, the cell may be engineered so that the protein produced by the cell may be secreted from the cell into culture media. As such, the cell may further contain a recombinant nucleic acid encoding a fusion polypeptide containing a signal sequence, a protease cleavage site and the protein. In some embodiments, the signal sequence may be one that is naturally associated with the polypeptide to be expressed. The signal sequence may be any sequence of amino acids that is capable of directing the fusion protein into the secretory pathway of the *Bacillus* host cell. In certain cases, signal sequences that may be employed include the signal sequences of proteins that are secreted from wild-type *Bacillus* cells. Such signal sequences include the signal sequences encoded by α-amylase, protease (e.g., aprE or subtilisin E), or β-lactamase genes. Exemplary signal sequences include, but are not limited to, the signal sequences encoded by an α-amylase gene, a subtilisin gene, a β-lactamase gene, a neutral protease gene (e.g., nprT, nprS, nprM), or a prsA gene from any suitable *Bacillus* species, including, but not limited to *Bacillus alkalophilus, Bacillus amyloliquefaciens, Bacillus brevis, Bacillus circulans, Bacillus clausii, Bacillus coagulans, Bacillus firmus, Bacillus lautus, Bacillus lentus, Bacillus licheniformis, Bacillus megaterium, Bacillus pumilus, Bacillus stearothermophilus, Bacillus subtilis,* or *Bacillus thuringiensis*. In one embodiment, the signal sequence is encoded by the aprE gene of *B. subtilis* (as described in Appl. Microbiol. Biotechnol. 2003 62:369-73). Further signal peptides are described by Simonen and Palva (Microbiological Reviews 1993 57: 109-137), and other references.

The invention also provides methods for producing a protein of interest in a modified *Bacillus* sp. host cell, which comprises at least one inactivated phr gene (e.g., an inactivated phrA and/or a phrE gene), or an inactivated phr and an inactivated rap gene by culturing a modified cell that is capable of producing a protein of interest and growing the cell under suitable growth conditions for expressing the protein of interest. The methods provide for the production of any one protein of interest described above. In preferred embodiments, the protein of interest produced by the method of the invention is a protease (e.g., a subtilisin). Production of a protein of interest by a modified *Bacillus* sp. cell is greater than that obtained from a corresponding unmodified precursor host cell. In some embodiments, the improved level of protease production by a modified *Bacillus* sp. cell is further enhanced in the modified cell by overexpressing ymaH, as described below.

Modified *Bacillus* sp. Host Cells that Overexpress YmaH

In the embodiments described above, the modified *Bacillus* sp. cells, which comprise at least one inactivated phr gene and/or an inactivated rap gene, have an enhanced capacity to produce a protein of interest at a level that is greater than that reached by an unmodified precursor cell. In further embodiments described below, the enhanced level of production of a protein of interest by the modified *Bacillus* sp. cells is further increased by altering the modified cell to overexpress the RNA-binding protein ymaH. Thus, in one embodiment, the invention provides for a modified *Bacillus* sp. cell that comprises at least one inactivated phr gene (e.g., an inactivated phrA and/or phrE gene), a polynucleotide that encodes a protein of interest (e.g., a protease), and a heterologous polynucleotide that encodes a YmaH protein. In another embodiment, the modified *Bacillus* sp. cell comprises at least one inactivated phr gene (e.g. an inactivated phrA and/or phrE gene), and/or an inactivated rap gene, a polynucleotide that encodes a protein of interest (e.g., a protease), and a heterologous polynucleotide that encodes a YmaH protein.

In some embodiments, the modified *Bacillus* sp. cell comprises a polynucleotide expression construct comprising a YmaH promoter that is operably linked to a polynucleotide sequence that encodes a YmaH protein. The *Bacillus subtilis* YmaH, also known as HFQ_BACSU is an RNA-binding protein, is a member of the Hfq family of RNA-binding proteins (Sauter et al., Nucleic Acid Res 31:4091-4098, [2003]). The YmaH protein is encoded in *Bacillus subtilis* by the ymaH gene, which is an ortholog of the hfq gene of *E. coli*. (Silvaggi et al., J. Bacteriol. 187(19): 6641-6650, [2005]). YmaH is an abundant and ubiquitous RNA-binding protein that functions as a pleiotrophic regulator of RNA metabolism in prokaryotes, and is required for stabilization of some transcripts and degradation of others. YmaH binds preferentially to unstructured A/U-rich RNA sequences and is similar to the eukaryotic Sm proteins in both sequence and structure. YmaH is also known to bind small RNA molecules called riboregulators that modulate the stability or translation efficiency of RNA transcripts.

The naturally-occurring YmaH protein from *Bacillus subtilis* is a 73 amino acid protein:

(Swiss-Prot: P3756; SEQ ID NO: 45)
MKPINIQDQFLNQIRKENTYVTVFLLNGFQLRGQVKGFDNFTVLLESEGK

QQLIYKHAISTFAPQKNVQLELE that is encoded by a 219 (222 including the stop codon) base pair polynucleotide (EMBL Primary Accession Number Z99113; SEQ ID NO:46).

Thus, in some embodiments, the modified *Bacillus* sp. cell of the invention further comprises a heterologous polynucleotide sequence that encodes ymaH. In one embodiment, the ymaH protein is encoded by the naturally-occurring polynucleotide sequence found in the genome of the wild-type *Bacillus subtilis* strain 168 (SEQ ID NO:45). In some embodiments, the modified *Bacillus* sp. cell of the invention comprises a heterologous polynucleotide sequence that encodes variants of the naturally occurring ymaH. Variant YamH proteins include proteins derived from the wild-type protein by deletion (i.e., truncation), addition, or substitution of one or more amino acids at one or more sites in the native protein. Methods for such deletions, additions and substitutions are generally known in the art. For example, amino acid sequence variants of the polypeptide can be prepared by mutations in the cloned DNA sequence encoding the native protein of interest. Methods for mutagenesis and nucleotide sequence alterations are well known in the art (See e.g., Kunkel (1985) Proc. Natl. Acad. Sci. USA 82:488 492; Kunkel et al. (1987) Methods Enzymol. 154:367 382; U.S. Pat. No. 4,873,192; and the references cited therein; herein incorporated by reference. In constructing variants of the proteins of interest, modifications to the nucleotide sequences encoding the variants will be made such that variants continue to possess the desired activity. As will be understood by the skilled artisan, due to the degeneracy of the genetic code, a variety of modified polynucleotides encode a YmaH protein. In some other embodiments of the present invention, the *Bacillus* sp. cell comprises a polynucleotide encoding a YmaH protein comprising a nucleotide sequence having at least about 70% sequence identity, at least about 75% sequence identity, at least about 80% sequence identity, at least about 85% sequence identity, at least about 90% sequence identity, at least about 92% sequence identity, at least about 95% sequence identity, at least about 97% sequence identity, at least about 98% sequence identity, or at least about 99% sequence identity to the polynucleotide sequence of SEQ ID NO:46.

In other embodiments, the modified *Bacillus* sp. cell comprises polynucleotide constructs that comprise ymaH coding sequences that are analogous to the ymaH coding sequence of *Bacillus subtilis* strain 168. The genome of this strain, which is contained in one 4215 kb genome, has been well-characterized (See, Kunst et al., Nature 390:249-256 [1997]; and Henner et al., Microbiol. Rev., 44:57-82 [1980]). In some embodiments, the YmaH-encoding polynucleotide constructs encode a YmaH protein that shares at least about 65% amino acid sequence identity, at least about 70% amino acid sequence identity, at least about 75% amino acid sequence identity, at least about 80% amino acid sequence identity, at least about 85% amino acid sequence identity, at least about 90% amino acid sequence identity, at least about 92% amino acid sequence identity, at least about 95% amino acid sequence identity, at least about 97% amino acid sequence identity, at least about 98% amino acid sequence identity, and at least about 99% amino acid sequence identity with the amino acid sequence of the wild-type form of the YmaH protein and that has comparable or improved ability to enhance the production of a protein of interest in a host cell when compared to the wild-type polypeptide (SEQ ID NO:45), and that retains the ability to enhance the expression of a protein of interest in a *Bacillus* sp. (e.g., *Bacillus subtilis*) host cell. In yet other embodiments, the modified *Bacillus* sp. cell comprises YmaH-encoding polynucleotide constructs comprising polynucleotide sequences that are homologous, orthologous or paralogous to genes of the wild-type *Bacillus* sequence of SEQ ID NO:46 and that retain the ability to enhance the production of a protein of interest.

In other embodiments, the modified *Bacillus* sp. cell of the invention also encompasses polynucleotide constructs that comprise coding sequences encoding YmaH proteins that are related by being structurally and/or functionally similar. In some embodiments, these proteins are derived from a different genus and/or species, including differences between classes of organisms (e.g., a bacterial protein and a fungal protein). In some embodiments, these proteins are derived from a different genus and/or species. In additional embodiments, related proteins are provided from the same species. Indeed, it is not intended that the present invention be limited to related proteins from any particular source(s). In addition, the term "related proteins" encompasses tertiary structural homologs and primary sequence homologs (e.g., the YmaH of the present invention). For example, the present invention encompasses such homologues including but not limited to such YmaH proteins as the YmaH of *E. coli*, (HFQ_ECOLI), *Shighella flexneri* (HFQ_SHIFL), *Salmonella typhimurium* (HFQ_SALTY), *Yersinia enterocolitica* (HFQ_YEREN), *Yersinia pestis* (HFQ_YERPE), *Erwinia carotovora* (HFQ_ERWCA), *Haemophilus influenzae* (HFQ_HAEIN), *Pasteurella multocida* (HFQ_PASMU), *Vibrio cholerae* (HFQ_VIBCH), *Pseudomonas aeruginosa* (HFQ_PSEAE), *Xanthomonas axonopodis* (HFQ_XANAC), *Xanthomonas campestris* (HFQ_XANCP), *Xylella fastidiosa* (GSQ_XYLFA), *Neisseria meningitidis* (HFQ_NEIMA), *Ralstonia solanacearum* (HFQ_RALSO), *Agrobacterium tumefaciens* (HFQ_AGRTS), *Brucella melitensis* (HFQ_BRUME), *Rhizobium loti* (HFQ_RHILO), *Azorhizobium caulinodans* (HFQ_AZOCA), *Caulobacter crescentus* (HFQ_CAUCR), *Aquifex melitensis* (HFQ_AQUAE), *Thermotoga maritime* (HFQ_THEMA), *Clostridium acetobutylicum* (HFQ_CLOAB), *Clostridium perfringens* (HFQ_CLOPE), *Bacillus halodurans* (HFQ_BACHD), *Bacillus subtilis* (HFQ_BACSU), *Thermoanaerobacter tengcongensis* (HFQ_THETN), *S. aureus* (O99UG9), and *M. jannasci* (O58830) (Sauter et al., Nucleic Acids Res. 31:4091-4098 [2003]).

Related (and derivative) proteins comprise variant YmaH proteins. In some preferred embodiments, variant proteins differ from a parent protein and one another by a small number of amino acid residues. The number of differing amino acid residues may be one or more, preferably about 1, 2, 3, 4, 5, 10, 15, 20, 30, 40, 50, or more amino acid residues. In some preferred embodiments, the number of different amino acids between variants is between about 1 and about 10. In some particularly preferred embodiments, related proteins and particularly variant proteins comprise at least about 70%, about 75%, about 80%, about 85%, about 90%, about 95%, about 97%, about 98%, or about 99% amino acid sequence identity. Several methods are known in the art that are suitable for generating variants of the YmaH proteins of the present invention, including but not limited to site-saturation mutagenesis, scanning mutagenesis, insertional mutagenesis, random mutagenesis, site-directed mutagenesis, and directed-evolution, as well as various other recombinatorial approaches.

Characterization of wild-type and mutant proteins is accomplished via any means suitable and is preferably based on the assessment of properties of interest. For example, it is contemplated that YmaH proteins that are capable of further enhancing the production of a protein of interest by a modified *Bacillus* sp. cell will find use.

Overexpression of ymaH in the modified *Bacillus* sp. cell of the invention can be achieved by various means including enhancing the transcription and/or translation of the YmaH encoding polynucleotide. For example, at the transcriptional level, overexpression of ymaH can be achieved by increasing the number of polynucleotide sequences that encode ymaH in a host cell, and/or by increasing the binding strength of a ymaH promoter to enhance the activity of the cognate RNA polymerase. At the translational level, overexpression of ymaH can be achieved by enhancing the translational activity by mutating the ribosome binding site (RBS) to increase the affinity of ribosomes for the RBS. One skilled in the art will recognize that overexpression of ymaH can be effected by increasing the number of copies of the ymaH gene alone or in combination with other possible modifications made to the ymaH gene to achieve the overexpression of YmaH.

In one embodiment, the modified *Bacillus* sp. cells of the invention comprise a polynucleotide construct that comprises a polynucleotide sequence encoding ymaH operably linked to a ymaH promoter. The transcription of ymaH may be naturally driven by two promoters: a SigA promoter that is present upstream of miaA coding region, and the SigH promoter that is immediately upstream of the ymaH coding region in the miaA operon of *B. subtilis*. A ymaH promoter can be any promoter that drives the expression of yamH (e.g., a SigA and/or a SigH promoter), and may be any nucleic acid sequence which shows transcriptional activity in the host cell of choice and includes mutant, truncated and hybrid promoters, and may be obtained from genes encoding extracellular or intracellular polypeptides either homologous or heterologous to the host cell. The promoter sequence may be native or foreign to the host cell.

In one embodiment, the modified *Bacillus* sp. cells of the invention comprise a polynucleotide construct that comprises a polynucleotide sequence that encodes YmaH operably linked to a SigH promoter (e.g., SEQ ID NO:23, as shown below). SEQ ID NO:23 also exemplifies a polynucleotide construct that comprises a YmaH coding sequence that is naturally contiguous with a SigH promoter:

(SEQ ID NO: 23)
ggcaccgaattcgacgtggtttcgcaacaaaatgcaggtcacatggttcg atatgacaccgcctgttgatatggagctgaaaaaaaggaaattttcaca catatagcaggaaaactcgaactttaatcgaaactgtatgatatagagaa tcaaggaggacgaaacatgaaaccgattaatattcaggatcagttttga atcaaatccggaaagaaaatacgtatgtcactgttttttttgctgaacggc tttcagttgcggggccaggtgaaaggctttgataactttaccgtattgtt ggaatcggaaggtaagcagcagcttatatataaacatgcgatctcaacgt ttgcgccgcaaaaaacgtccagcttgaactcgaatagatcaaaaaatgc catgtcaagacatgaggaaaggctgtcggggggttcccggcggccattttt aacatgaatccacttttgctccaagcttttgtgtaagctgaccatgcca aggcacggtcttttttatgagggatccggagcc.

In another embodiment, the modified *Bacillus* sp. cells of the invention comprise a polynucleotide construct that comprises a polynucleotide sequence that encodes YmaH operably linked to a SigA promoter (e.g., SEQ ID NO:26 (SigA1) and SEQ ID NO:31 (SigA2 construct)). SEQ ID NOs:26 and 31 exemplify embodiments wherein the ymaH coding sequence is contiguous with a SigA promoter sequence to provide a chimeric polynucleotide construct. In some preferred embodiments, chimeric polynucleotide constructs thus comprise a promoter sequence that in nature is not contiguous with the ymaH coding sequence. For example, SEQ ID NOS: 26 and 31 exemplify chimeric constructs that comprise a SigA promoter that is operably linked to a polynucleotide sequence encoding YmaH, as shown below:

(SEQ ID NO: 26)
gcgccgaattctcatacccctgaaaggaaagacaagggaaattgtcggcaa tgagccgctcggcaggtagaaggatgtttaccgatgcaaaaaagggcaa aatggataggtggttgtccatgttgaatgctataatgggggagatttata aaagagagtgatacatattgaataatacgaagcagccccacacatatagc aggaaaactcgaactttaatcgaaactgtatgatatagagaatcaaggag gacgaaacatgaaaccgattaatattcaggatcagttttgaatcaaatc cggaaagaaaatacgtatgtcactgttttttttgctgaacggctttcagtt gcggggccaggtgaaaggctttgataactttaccgtattgttggaatcgg aaggtaagcagcagcttatatataaacatgcgatctcaacgtttgcgccg caaaaaacgtccagcttgaactcgaatagatcaaaaaatgccatgtcaa gacatgaggaaaggctgtcggggggttcccggcggccattttaacatgaa tccacttttgctccaagcttttgtgtaagctgaccatgccaaggcacgg tcttttttatgagggatccggtgcc (SEQ ID NO: 31)
gcgccgaattctcatacccctgaaaggaaagacaagggaaattgtcggcaa tgagccgctcggcaggtagaaggatgtttaccgatgcaaaaaagggcaa aatggataggtggttgtccatgttgaatgctataatgggggagatttata aaagagagtgctcgaactttaatcgaaactgtatgatatagagaatcaag gaggacgaaacatgaaaccgattaatattcaggatcagttttgaatcaa atccggaaagaaaatacgtatgtcactgttttttttgctgaacggctttca gttgcggggccaggtgaaaggctttgataactttaccgtattgttggaat cggaaggtaagcagcagcttatatataaacatgcgatctcaacgtttgcg ccgcaaaaaacgtccagcttgaactcgaatagatcaaaaaatgccatgt caagacatgaggaaaggctgtcggggggttcccggcggccattttaacat gaatccacttttgctccaagcttttgtgtaagctgaccatgccaaggca cggtcttttttatgagggatccggtgcc In yet another embodiment, the *Bacillus* sp. cells of invention comprise a polynucleotide construct that comprise a polynucleotide sequence that encodes YmaH and a SigA and a SigH promoter (e.g., SEQ ID NO: 22, as shown below).

(SEQ ID NO: 22)
tcatacccctgaaaggaaagacaagggaaattgtcggcaatgagccgctcg gcaggtagaaggatgtttaccgatgcaaaaaagggcaaaatggataggt -continued
ggttgtccatgttgaatgctataatggggagatttataaaagagagtga tacatattgaataatacgaagcagcccgttgtcattttagtcggaccgac ggcagtggggaaaaccaatttaagtattcagctagccaaatccttaaacg cggaaattatcagcggagattcgatgcagatttataaagggatggatatt ggaacagctaaaattaccgaacaggagatggagggagtgccccatcatct gattgacattttagatccccaagactctttctctactgccgattatcaaa gcttagtaagaaataaaatcagcgagattgcaaatagaggaaagcttccg atgattgacggcggtacagggctttatatacaatctgagcttttacgatta tacatttacggaagaggcaaatgatcccgtgtttcgagagagcatgcaaa tggctgctgagcgggaaggcgctgactttcttcatgccaaacttgctgca gcagatcccgaggcagcagctgcgattcatccgaataatacaagaagagt cattcgcgcactggaaattttacatacgtccggaaaaacgatgtcccagc atttgaaggaacaaaaacgagaacttctgtacaatgcagtgttaattggc ctgacaatggatagagacacgctttacgaaagaattaatcagcgggtcga tttgatgatgcagtcaggccttcttccggaagtgaaacgcttatacgaca agaacgtgagagactgtcaatcaatacaggcgataggctataaagagctg tatgcatattttgacggttttgtgacactttccgatgctgtcgaacagct aaagcagaactcgaggcggtatgcgaaacgccagctgacgtggtttcgca acaaaatgcaggtcacatggttcgatatgacaccgcctgttgatatggag ctgaaaaaaaggaaattttcacacatatagcaggaaaactcgaacttta atcgaaactgtatgatatagagaatcaaggaggacgaaacatgaaaccga ttaatattcaggatcagttttttgaatcaaatccggaaagaaaatacgtat gtcactgttttttttgctgaacggctttcagttgcggggccaggtgaaagg ctttgataacttttaccgtattgttggaatcggaaggtaagcagcagctta tatataaacatgcgatctcaacgtttgcgccgcaaaaaaacgtccagctt gaactcgaatagatcaaaaaatgccatgtcaagacatgaggaaaggctgt cgggggttcccggcggccatttttaacatgaatccacttttgctccaagc ttttgtgtaagctgaccatgccaaggcacggtcttttttttatgag Examples of suitable promoters for directing the expression of the ymaH gene in are the SigA and the SigH promoters from the *B. subtilis* operon that encompasses the gene encoding miaA. For example, in one embodiment, the invention provides a polynucleotide sequence defining a SigA promoter (SEQ ID NO:47, as shown below).

(SEQ ID NO: 47)
tcataccctgaaaggaaagacaagggaaattgtcggcaatgagccgctcg gcaggtagaaggatgtttaccgatgcaaaaaagggcaaaatggataggt ggttgtccatgttgaatgctataatggggagatttataaaagagagtga tacata In another embodiment, the invention provides a polynucleotide sequence defining a SigH promoter (SEQ ID NO:48, as shown below).

(SEQ ID NO: 48)
aaaggaaattttcacacatatagcaggaaaactcgaactttaatcgaaac tgtatgatatagagaatcaaggaggacgaaac Other examples of promoters that can be used for expressing the ymaH gene include Sigma A promoters that are recognized by $\sigma^A$ factor including the promoter of the *Streptomyces coelicolor* agarase gene (dagA), the promoter of the *Bacillus lentus* alkaline protease gene (aprH), the promoter of the *Bacillus licheniformis* alkaline protease gene (subtilisin Carlsberg gene), the promoter of the *Bacillus subtilis* levansucrase gene (sacB), the promoter of the *Bacillus subtilis* alpha-amylase gene (amyE), the promoter of the *Bacillus licheniformis* alpha-amylase gene (amyL), the promoter of the *Bacillus stearothermophilus* maltogenic amylase gene (amyM), and the promoter of the *Bacillus amtyloliquefacietis* alpha-amylase gene (amyQ). Examples of promoters that can be used for expressing the ymaH gene include Sigma H promoters that are recognized by $\sigma^H$ factors including spo0A, spo0F, spoVG and citG (See, Heimann, J. D. and C. P. Moran. 2002. RNA polymerase and sigma factors, pp 289-312 In A. L. Sonenshein, J. A. Hoch and R. Losick (ed), *Bacillus subtilis* and its closest relatives: from genes to cells. American Society for Microbiology, Washington, D.C.).

In some embodiments, a consensus SigA and/or SigH promoter finds use in the present invention. The construction of a consensus promoter may be accomplished by site-directed mutagenesis to create a promoter which conforms more perfectly to the established consensus sequences for the "–10" and "–35" regions of the "sigma A-type" promoters for *Bacillus subtilis* (Voskuil et al., Mol Microbiol 17: 271 279 [1995]). In other embodiments, a consensus promoter is created by site-directed mutagenesis to create a promoter which conforms more perfectly to the established consensus sequences for the "–10" and "–35" regions of the vegetative "sigma H-type" promoters for *Bacillus subtilis* (See, Heiman and Moran in *Bacillus subtilis* and its closest relatives, Ch. 21, pg 289-312; Sonenshein et al (2002 ASM Press, Washington, D.C.) The consensus sequence for the "–35" region for the sigma A-type promoter is TTGaca and for the "–10" region is tgnTATaat, and the consensus sequence for the "–35" region for the sigma H-type promoter is RnAGGAwWW and for the "–10" region is RnnGAAT. Capital letters indicate highly conserved positions; lower case letters indicate less conserved positions; abbreviation R can be A or G, and W can be A or T. The consensus promoter may be obtained from any promoter which can function in a *Bacillus* host cell.

In some embodiments, the SigA promoter, which encompasses SEQ ID NO:47 is defined by a polynucleotide sequence that is naturally present upstream of the miaA coding sequence (NP_389615; SEQ ID NO:49, shown below), while the SigH promoter, which encompasses SEQ ID NO: 48, is defined by the polynucleotide sequence that is naturally present upstream of the yamH coding region (SEQ ID NO:46, shown below).

(SEQ ID NO: 49)
ttgaataatacgaagcagcccgttgtcatttagtcggaccgacggcagt ggggaaaaccaatttaagtattcagctagccaaatccttaaacgcggaaa

```
-continued
ttatcagcggagattcgatgcagatttataaagggatggatattggaaca gctaaaattaccgaacaggagatggagggagtgccccatcatctgattga cattttagatccccaagactctttctctactgccgattatcaaagcttag taagaaataaaatcagcgagattgcaaatagaggaaagcttccgatgatt gacggcggtacagggctttatatacaatctgagctttacgattatacatt tacggaagaggcaaatgatcccgtgtttcgagagagcatgcaaatggctg ctgagcgggaaggcgctgactttcttcatgccaaacttgctgcagcagat cccgaggcagcagctgcgattcatccgaataatacaagaagagtcattcg cgcactggaaattttacatacgtccggaaaaacgatgtcccagcatttga aggaacaaaaacgagaacttctgtacaatgcagtgttaattggcctgaca atggatagagacacgctttacgaaagaattaatcagcgggtcgatttgat gatgcagtcaggccttcttccggaagtgaaacgcttatacgacaagaacg tgagagactgtcaatcaatacaggcgataggctataaagagctgtatgca tattttgacggttttgtgacactttccgatgctgtcgaacagctaaagca gaactcgaggcggtatgcgaaacgccagctgacgtggtttcgcaacaaaa tgcaggtcacatggttcgatatgacaccgcctgttgatatggagctgaaa aaaaaggaaattttcacacatatagcaggaaaactcgaactttaa (NP_389616; SEQ ID NO: 46)
atgaaaccgattaatattcaggatcagttttttgaatcaaatccggaaaga aaatacgtatgtcactgttttttttgctgaacggctttcagttgcggggcc aggtgaaaggctttgataactttaccgtattgttggaatcggaaggtaag cagcagcttatatataaacatgcgatctcaacgtttgcgccgcaaaaaaa cgtccagcttgaactcgaatag
```

In some embodiments, the SigA/SigH constructs encompass promoter sequences that have been mutated to increase the activity of the promoter when compared to the activity of the corresponding wild-type promoter resulting in the overexpression of the YmaH protein. Thus, it is understood that variants of the sequences that define the SigA and SigH promoters find use in the YmaH-expression constructs. Methods for creating promoter variants in *Bacillus* sp. are well known in the art (See e.g., Heimann et al., 2002. RNA polymerase and sigma factors, pp 289-312 In A. L. Sonenshein, J. A. Hoch and R. Losick (ed), *Bacillus subtilis* and its closest relatives: from genes to cells. American Society for Microbiology, Washington, D.C.) It is not intended that the present invention be limited to any particular promoter, as any suitable promoter known to those skilled in the art finds use with the present invention. Nonetheless, in some embodiments, the promoter is the *B. subtilis* sigH promoter, while in other embodiments the promoter is the *B. subtilis* sigA promoter. In further embodiments, the sigH and the sigA promoters serve to effect the overexpression of YmaH protein.

In some embodiments, the SigA/SigH polynucleotide constructs of the invention also comprise the requisite ribosome binding site to ensure optimal translation of the ymaH RNA transcript. In some embodiments, the polynucleotide construct comprises the ribosome bind site (RBS) sequence of the miaA gene (aagagag; SEQ ID NO:50), while in other embodiments, polynucleotide construct comprises the RBS sequence of the ymaH gene (ggagg; SEQ ID NO:51). In yet other embodiments, the polynucleotide construct comprises the ribosome binding site sequences of the miaA and the ymaH genes. In some embodiments, the invention provides constructs having the promoter and ribosome binding site sequences upstream of the ymaH coding sequence. The invention is not limited to the ribosome binding site sequences disclosed herein, as it also encompasses any suitable ribosome binding site sequences that have been mutated to increase the level of expression of the ymaH gene. Methods for obtaining mutated ribosome binding sequences that increase the expression of a gene in *Bacillus* are known in the art. For example, Band and Henner successfully increased the level of expression of Interferon in *B. subtilis* by modifying the RBS to obtain a tighter base-pairing to the 16S rRNA (Band, L. and D. J. Henner, DNA 3:17-21 [1984]).

Production of a Protein of Interest in a Modified Cell

In some embodiments, the invention provides methods for producing a protein of interest in a modified *Bacillus* sp. host cell, which comprises at least one inactivated phr gene (e.g., an inactivated phrA and/or a phrE gene), or an inactivated phr and/or rap gene by culturing a modified cell that is capable of producing a protein of interest and growing the cell under suitable growth conditions for expressing the protein of interest. The methods provide for the production of any one protein of interest described above. In some embodiments, the protein of interest produced by the method of the invention is a protease (e.g., a subtilisin).

In one embodiment, the method of the invention comprises inactivating at least one phr gene by introducing an inactivating DNA construct into a *Bacillus* sp. host cell to generate a modified *Bacillus* sp. host cell, and growing the modified cell under suitable conditions to produce a protein of interest at a level that is greater than that produced by the unmodified or precursor *Bacillus* host cell. Precursor host cells include precursor host cells of *Bacillus* sp. strains as described above, including *Bacillus alkalophilus*, *Bacillus amyloliquefaciens*, *Bacillus brevis*, *Bacillus circulans*, *Bacillus clausii*, *Bacillus coagulans*, *Bacillus firmus*, *Bacillus lautus*, *Bacillus lentus*, *Bacillus licheniformis*, *Bacillus megaterium*, *Bacillus pumilus*, *Bacillus stearothermophilus*, *Bacillus subtilis*, or *Bacillus thuringiensis* strains. In some embodiments, the precursor host cell is a *Bacillus subtilis* host cell. Preferably, the precursor host cells are recombinant cells comprising a recombinant polynucleotide that encodes a polypeptide of interest, as described above. In some embodiments, the polypeptide of interest is an enzyme (e.g., a protease, such as a subtilisin). The method of inactivating at least one phr gene (e.g. phrA and/or phrE) in a precursor *Bacillus* sp. host cell, generates a modified *Bacillus* sp. cell that produces a polypeptide of interest at a level that is greater than that achieved by the corresponding unmodified precursor host cell.

In one embodiment, the method comprises inactivating a phrA gene by introducing into the precursor *Bacillus* sp. host cell an inactivating DNA construct that deletes the indigenous phrA gene. For example the inactivating DNA construct of SEQ ID NO:17 is introduced to delete the indigenous phrA gene by homologous recombination. In another embodiment, the method comprises inactivating a phrE gene by introducing into the precursor *Bacillus* sp. host cell an inactivating DNA construct that deletes the indigenous phrE gene. For example the inactivating DNA construct of SEQ ID NO:18 is introduced to delete the indigenous phrE gene by homologous recombination. In yet another embodiment, both the phrA and phrE genes are inactivated using the inactivating constructs of SEQ ID NOs:17 and 18. The method of the invention is similarly used to inactivate other phr genes including phrC, phrF, phrG, phrH, phrI, and phrK and/or the rap genes including rapB, rapC, rapD, rapE, rapF, rapG, rapH, rapI, rapJ and rapK.

According to one embodiment, inactivation of the phrA gene is by insertion of a selectable marker that interrupts the phrA gene. Alternatively, inactivation of the phrA gene results from the inactivation of the rapA gene by introducing a selectable marker comprising a terminator sequence in the rapA gene thereby preventing the functional expression of the rapA and phrA protein According to one embodiment, inactivation of the rapA gene is by insertion of a selectable marker that interrupts the rapA gene.

Methods for inactivating phr and/or rap genes are exemplified in the experimental section below.

Production of a protein of interest (e.g., a protease), by a modified *Bacillus* sp. cell comprising at least one einactivated phr gene and/or rap gene as described above, is greater than that obtained from a corresponding unmodified precursor cell.

In some embodiments, the production of a protein of interest by a modified *Bacillus* sp. cell is further enhanced from the expression of one or more copies of a YmaH-encoding polynucleotide comprised in an expression construct that is present on a multicopy/replicating plasmid that has been introduced into the modified cell. Any one of the YmaH-encoding polynucleotide constructs described above (e.g., SigA; SigA1, SigA2, SigA3) or SigH constructs, are used to transform the modified *Bacillus* sp. cells. In some embodiments, the YmaH-encoding polynucleotide that is present on a replicating plasmid is introduced into a precursor host cell prior to the precursor host cell being modified to contain a deletion in at least one phr and/or rap gene. Thus, in some embodiments, the invention provides for modified *Bacillus* sp. cell comprising a vector comprising an expression construct comprising a YmaH-encoding polynucleotide operably linked to a YmaH promoter that is incorporated into the vector. In some embodiments, overexpression of YmaH is achieved by introducing a SigH expression construct that comprises a YmaH-encoding polynucleotide operably linked to a SigH promoter (e.g., the expression construct of SEQ ID NO:23). In embodiments, overexpression of YmaH is achieved by introducing a SigA expression construct that comprises a YmaH-encoding polynucleotide operably linked to a SigA promoter. Examples of SigA constructs include the SigA1 expression construct of SEQ ID NO:26, the SigA2 expression construct of SEQ ID NO:31, and the SigA3 construct of SEQ ID NO:22.

In some embodiments, the vector is a multicopy/replicating plasmid vector which forms an extrachromosomal self-replicating genetic element that overexpresses YmaH in the modified cell. Typically, the vector is a plasmid vector, which carries a selectable marker gene that allows for ease of selecting the host cells that contain the plasmid. Vectors that replicate autonomously in a host cell include vectors that comprise an origin of replication, which enables the vector to replicate autonomously in the *Bacillus* cell. Examples of bacterial origins of replication are the origins of replication of plasmids pBR322, pUC19, pACYC177, and pACYC184 permitting replication in *E. coli*, and pUB110, pC194, pE194, pTA1060, and pAMβ1 permitting replication in *Bacillus*. The origin of replication may be one having a mutation to make its function temperature-sensitive in the *Bacillus* cell (See e.g., Ehrlich, Proceedings of the National Academy of Sciences USA 75:1433 [1978]).

As indicated above, in some embodiments of the present invention, a polynucleotide encoding the YmaH protein is introduced into a modified cell via an expression vector capable of replicating within the host cell. Suitable replicating and integrating plasmids for *Bacillus* known in the art (See e.g., Harwood and Cutting (eds), *Molecular Biological Methods for Bacillus*, John Wiley & Sons, [1990], in particular, chapter 3; suitable replicating plasmids for *B. subtilis* include those listed on page 92).

In some embodiments, the overexpression of a YmaH polypeptide results from the expression of at least one copy of a YmaH-encoding polynucleotide that is integrated into the genome of the host cell. Thus, in some embodiments, when the vector is introduced into the host cell, it is integrated into the genome and replicated together with the genome into which it has integrated. Multiple copies of the YmaH gene can be integrated at several positions in the genome of the host cell. Alternatively, an amplifiable expression cassette carrying a sequence encoding YmaH and a selectable marker (e.g., an antimicrobial resistance marker, such as a gene coding chloramphenicol acetyl transferase) can be integrated in the genome via a single cross-over event and then amplified by challenging the transformed host cell with increasing concentrations of the appropriate antimicrobial (e.g., chloramphenicol).

In other embodiments, the invention provides a polynucleotide construct that is incorporated into an integrating vector. In some embodiments, the polynucleotide constructs of the invention that are incorporated into an integrating vector are targeted to chromosomal sequences of the *Bacillus* sp. host cell to create modified host cells that comprise stable tandem integrations of multiple vector copies. The polynucleotide construct that is incorporated into the integration vector typically comprises a selectable marker gene that provides the cell with resistance to an antimicrobial agent and allows for the amplification of the integrated ymaH construct. Tandem integration into a single site as well as single-copy and two-site integration may occur. Whether the polynucleotide construct is incorporated into a vector or used without the presence of plasmid DNA, it is used to transform modified cells using any suitable method known in the art.

Culturing Methods

The invention provides methods for producing a protein of interest in a modified *Bacillus* cell by culturing the modified cell that is capable of producing a protein of interest and growing the cell under suitable growth conditions for expressing the protein of interest. In some embodiments, the host cells and modified host cells of the present invention are cultured in conventional nutrient media. The suitable specific culture conditions, such as temperature, pH and the like are known to those skilled in the art. Additional preferred culture conditions are well known to those of skill in the art and are described in various reference publications.

In some embodiments, the protein of interest produced by the modified host cell is confined to the intracellular milieu of the host cell, while in other embodiments the protein of interest produced by the host cell is secreted into the extracellular space (i.e., the culture medium). Thus, in some embodiments, the protein of interest can be recovered from the intracellular milieu of the cell in which it is expressed by lysing the host cell and recovering the protein of interest by methods known in the art. In other embodiments, modified host cells are cultured under conditions suitable for the expression and recovery of the protein of interest from the cell culture. The protein of interest produced by a modified host cell overexpressing ymaH according to the present invention is secreted into the culture media. In some embodiments, the protein of interest (e.g., a protease), produced by the cells is recovered from the culture medium by conventional procedures, including, but not limited to separating the host cells from the medium by centrifugation or filtration, precipitating the proteinaceous components of the supernatant or filtrate by means of a salt (e.g., ammonium sulfate), chromatographic purification (e.g., ion exchange, gel filtration, affinity, etc.). Thus, any method suitable for recovering the protease(s) of the present invention finds use in the present invention. Indeed, it is not intended that the present invention be limited to any particular purification method.

In some embodiments, other recombinant constructions join the heterologous or homologous polynucleotide sequences encoding the proteins of interest to nucleotide sequence encoding a polypeptide domain which facilitates purification of soluble proteins (Kroll D J et al., DNA Cell Biol 12:441-53 [1993]). Such purification facilitating domains include, but are not limited to, metal chelating peptides such as histidine-tryptophan modules that allow purification on immobilized metals (Porath, Protein Expr Purif 3:263-281 [1992]), protein A domains that allow purification on immobilized immunoglobulin, and the domain utilized in the FLAGS extension/affinity purification system (Immunex Corp, Seattle Wash.). The inclusion of a cleavable linker sequence such as Factor XA or enterokinase (Invitrogen, San Diego Calif.) between the purification domain and the heterologous protein also find use to facilitate purification.

In some embodiments, the transformed host cells of the present invention are cultured in a suitable nutrient medium under conditions permitting the expression of a protein of interest (e.g., a protease), after which the resulting protease is recovered from the culture. The medium used to culture the cells comprises any conventional medium suitable for growing the host cells, such as minimal or complex media containing appropriate supplements. Suitable media are available from commercial suppliers or may be prepared according to published recipes (e.g., in catalogues of the American Type Culture Collection). In some embodiments, the host cells are cultured under batch, fed-batch or continuous fermentation conditions. Classical batch fermentation methods use a closed system, wherein the culture medium is made prior to the beginning of the fermentation run, the medium is inoculated with the desired organism(s), and fermentation occurs without the subsequent addition of any components to the medium. In certain cases, the pH and oxygen content, but not the carbon source content, of the growth medium are altered during batch methods. The metabolites and cell biomass of the batch system change constantly up to the time the fermentation is stopped. In a batch system, cells usually progress through a static lag phase to a high growth log phase and finally to a stationary phase where growth rate is diminished or halted. If untreated, cells in the stationary phase eventually die. In general terms, the cells in log phase produce most protein.

A variation on the standard batch system is the "fed-batch fermentation" system. In this system, nutrients (e.g., a carbon source, nitrogen source, $O_2$, and typically, other nutrients) are only added when their concentration in culture falls below a threshold. Fed-batch systems are useful when catabolite repression is apt to inhibit the metabolism of the cells and where it is desirable to have limited amounts of nutrients in the medium. Measurement of the actual nutrient concentration in fed-batch systems is estimated on the basis of the changes of measurable factors such as pH, dissolved oxygen and the partial pressure of waste gases such as $CO_2$. Batch and fed-batch fermentations are common and well known in the art.

Continuous fermentation is an open system where a defined culture medium is added continuously to a bioreactor and an equal amount of conditioned medium is removed simultaneously for processing. Continuous fermentation generally maintains the cultures at a constant high density where cells are primarily in log phase growth.

Continuous fermentation allows for the modulation of one factor or any number of factors that affect cell growth and/or end product concentration. For example, in some embodiments, a limiting nutrient such as the carbon source or nitrogen source is maintained at a fixed rate and all other parameters are allowed to moderate. In other systems, a number of factors affecting growth are altered continuously while the cell concentration, measured by media turbidity, is kept constant. Continuous systems strive to maintain steady state growth conditions. Thus, cell loss due to medium being drawn off may be balanced against the cell growth rate in the fermentation. Methods of modulating nutrients and growth factors for continuous fermentation processes as well as techniques for maximizing the rate of product formation are known to those of skill in the art and find use in the production of a protein of interest (e.g., a protease) according to the methods of the invention.

As indicated above, the modified *Bacillus* sp. of the invention produce proteins of interest at a level that is greater than that obtained from the corresponding unmodified precursor *Bacillus* sp. cells. The enhanced level of protein production by the modified cells is further increased by overexpressing YmaH. In some embodiments of the present invention, overexpression of YmaH in a *Bacillus* host cell results in an increase in the production of a protein of interest above the level obtained in the corresponding modified precursor *Bacillus* sp. cell that does not overexpress YmaH. In some embodiments, the invention provides modified *Bacillus* host cells that overexpress YmaH. In some embodiments the recombinant *Bacillus* host cell is a cell that was altered to produce greater levels of a protease than the unaltered parent/precursor *Bacillus* cell when grown under the same conditions.

The present invention also encompasses methods for producing a protein of interest in a modified cell that overexpresses YmaH in less time than that required by the precursor host cell. For example, the modified host cells of the invention are capable of producing a protein of interest at a greater level and at an earlier time than the corresponding unmodified precursor host cell. Thus, in some embodiments, the invention provides for methods of producing a protein of interest (e.g., a protease), at a level that is greater than that produced by the parent host cell and in about $\frac{1}{6}^{th}$ of the time it takes the precursor host cell to attain its maximum level of expression. In other embodiments, the modified host produces a protein of interest in about $\frac{1}{5}^{th}$, about $\frac{1}{4}^{th}$, about $\frac{1}{3}^{rd}$, or about $\frac{1}{2}$ of the time it takes the precursor host cell to attain its maximum level of expression.

Measurement of Production/Activity

EXPERIMENTAL

The following examples provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g., amounts, temperature, etc.) but some experimental errors and deviations should be accounted for. Unless indicated otherwise, parts are parts by weight, molecular weight is weight average molecular weight, temperature is in degrees Centigrade, and pressure is at or near atmospheric.

In the experimental disclosure which follows, the following abbreviations apply: ° C. (degrees Centigrade); rpm (revolutions per minute); $H_2O$ (water); aa (amino acid); by (base pair); kb (kilobase pair); kD (kilodaltons); gm (grams); μg and ug (micrograms); mg (milligrams); ng (nanograms); μl and ul (microliters); ml (milliliters); mm (millimeters); nm (nanometers); μm and um (micrometer); M (molar); mM (millimolar); μM and uM (micromolar); U (units); V (volts); MW (molecular weight); sec (seconds); min(s) (minute/minutes); h(s) and hr(s) (hour/hours); $OD_{280}$ (optical density at 280 nm); $OD_{405}$ (optical density at 405 nm); $OD_{600}$ (optical density at 600 nm); PAGE (polyacrylamide gel electrophoresis); LAS (lauryl sodium sulfonate); SDS (sodium dodecyl sulfate); and Tris (tris(hydroxymethyl)aminomethane).

Example 1 phr Gene Deletions

Figure 2:
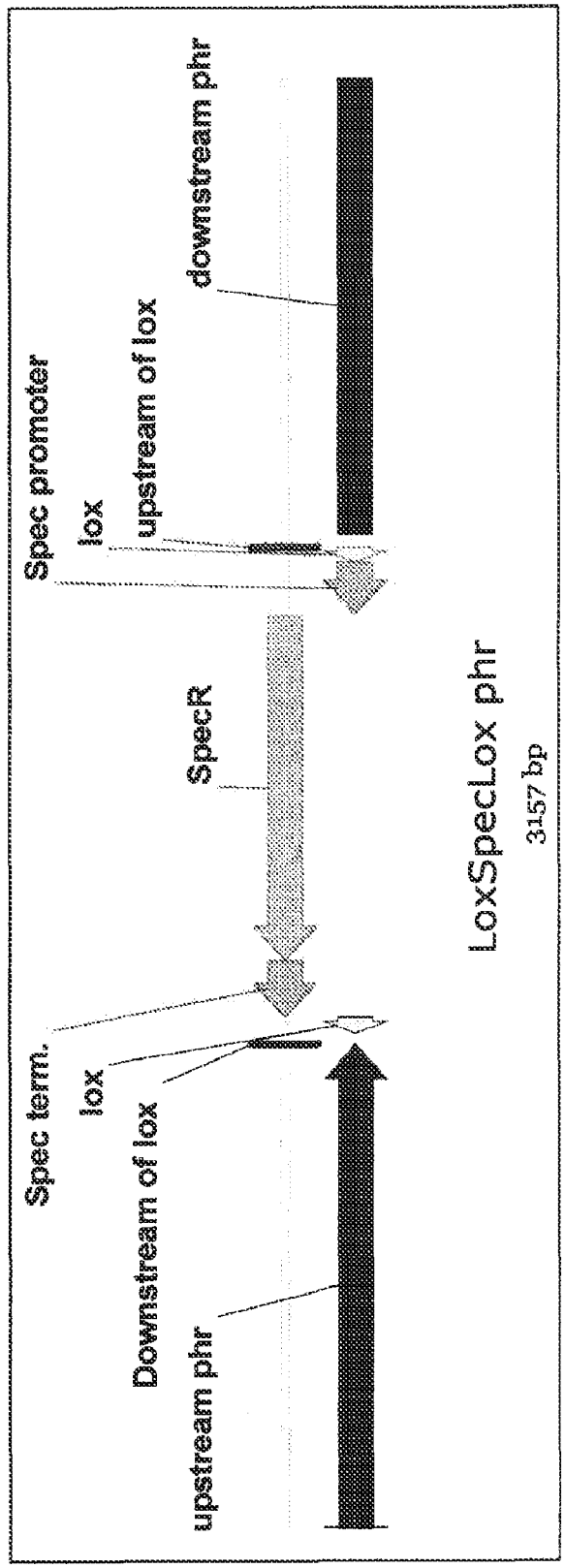
FIG. 2 schematically illustrates features common to the inactivation cassettes used to delete phr genes in *Bacillus subtilis*.

The phr genes: phrA, phrE, phrC, phrF, phrG, phrH, phrI and phrK were deleted in the *Bacillus subtilis* strain BG2942 (ΔnprE, degU(Hy)32, amyE::[PxyIRA-comK eryR]), and AprE protease expression in the resulting modified *Bacillus subtilis* strains was determined using an AAPF assay. Deletion of phr genes was performed by inserting a spectinomycin selectable marker flanked by the lox site in the phr locus of the *Bacillus* chromosome, while leaving the upstream rap gene and the downstream genes intact. The inactivation cassette used to delete the phr genes is illustrated in FIG. 2. The deletion of phrA and phrE genes was also performed in the *Bacillus subtilis* strain BG3594 (degU(Hy)32, oppA, ΔspoIIE, ΔaprE, ΔnprE), which carries the amplifiable expression construct PaprE-FNA (nucleotide sequence of aprE promoter-FNA: SEQ ID NO:19) for expressing FNA.

```
                                        (SEQ ID NO:  19)
gaattcctccatttcttctgctatcaaaataacagactcgtgatttcc aaacgagctttcaaaaaagcctctgccccttgcaaatcggatgcctgtct ataaaattcccgatattggcttaaacagcggcgcaatggcggccgcatct gatgtctttgcttggcgaatgttcatcttatttcttcctccctctcaata attttttcattctatcccttttctgtaaagtttattttttcagaatacttt tatcatcatgctttgaaaaaatatcacgataatatccattgttctcacgg aagcacacgcaggtcatttgaacgaattttttcgacaggaatttgccggg actcaggagcatttaacctaaaaaagcatgacatttcagcataatgaaca tttactcatgtctattttcgttcttttctgtatgaaaatagttatttcga gtctctacggaaatagcgagagatgatatacctaaatagagataaaatca tctcaaaaaatgggtctactaaaatattattccatctattacaataaat tcacagaatagtcttttaagtaagtctactctgaattttttaaaaggag agggtaaagagtgagaagcaaaaaattgtggatcagttgctgtttgctt tagcgttaatctttacgatggcgttcggcagcacatcctctgcccaggcg gcagggaaatcaaacggggaaaagaaatatattgtcgggtttaaacagac aatgagcacgatgagcgccgctaagaagaaagatgtcatttctgaaaaag gcgggaaagtgcaaaagcaattcaaatatgtagacgcagcttcagctaca ttaaacgaaaaagctgtaaaagaattgaaaaaagacccgagcgtcgctta cgttgaagaagatcacgtagcacatgcgtacgcgcagtccgtgccttacg gcgtatcacaaattaaagccctgctctgcactctcaaggctacactgga
```

-continued
```
tcaaatgttaaagtagcggttatcgacagcggtatcgattcttctcatcc tgatttaaaggtagcaggcggagccagcatggttccttctgaaacaaatc ctttccaagacaacaactctcacggaactcacgttgccggcacagttgcg gctcttaataactcaatcggtgtattaggcgttgcgccaagcgcatcact ttacgctgtaaaagttctcggtgctgacggttccggccaatacagctgga tcattaacggaatcgagtgggcgatcgcaaacaatatggacgttattaac atgagcctcggcggaccttctggttctgctgctttaaaagcggcagttga taaagccgttgcatccggcgtcgtagtcgttgcggcagccggtaacgaag gcacttccggcagctcaagcacagtgggctaccctggtaaataccccttct gtcattgcagtaggcgctgttgacagcagcaaccaaagagcatctttctc aagcgtaggacctgagcttgatgtcatggcacctggcgtatctatccaaa gcacgcttcctggaaacaaatacggcgcgttgaacggtacatcaatggca tctccgcacgttgccggagcggctgctttgattctttctaagcacccgaa ctggacaaacactcaagtccgcagcagtttagaaaacaccactacaaaac ttggtgattctttctactatggaaaagggctgatcaacgtacaggcggca gctcagtaa.
```

The PaprE-FNA expression construct comprises a polynucleotide sequence encoding the FNA protease operably linked to the aprE promoter of *Bacillus subtilis*. FNA (PURAFECT PRIME [Genencor]) is subtilisin BPN' from *B. amyloliquefaciens* that has the Y217N substitution (SEQ ID NO:20)

```
                                        (SEQ ID NO:  20)
VRSKKLWISLLFALALIFTMAFGSTSSAQAAGKSNGEKKYIVGFKQTMST

MSAAKKKDVISEKGGKVQKQFKYVDAASATLNEKAVKELKKDPSVAYVEE

DHVAHAYAQSVPYGVSQIKAPALHSQGYTGSNVKVAVIDSGIDSSHPDLK

VAGGASMVPSETNPFQDNNSHGTHVAGTVAALNNSIGVLGVAPSASLYAV

KVLGADGSGQYSWIINGIEWAIANNMDVINMSLGGPSGSAALKAAVDKAV

ASGVVVVAAAGNEGTSGSSSTVGYPGKYPSVIAVGAVDSSNQRASFSSVG

PELDVMAPGVSIQSTLPGNKYGALNGTSMASPHVAGAAALILSKHPNWTN

TQVRSSLENTTTKLGDSFYYGKGLINVQAAAQ.
```

A more detailed description of the construction of these strains is set forth below. The sequences of the primers used for creating the constructs used to delete the phr genes are provided in Table 1.

For the phrA deletion cassette the upstream region of the phrA gene containing the rapA sequence was amplified with the primers CB2 008-007 (SEQ ID NO:1) and CB2 008-009 (SEQ ID NO:3) and fused to the spectinomycin cassette, flanked by the loxP sequence, and amplified with the oligos CB2 008-009R (SEQ ID NO:4) and CB2 008-010R (SEQ ID NO:6). The downstream region of the phrA gene was amplified with the oligos CB2 008-010 (SEQ ID NO:5) and CB2008-008 (SEQ ID NO:2) and fused to the PCR product containing the rapA sequences and the spectinomycin cassette.

To create the phrC deletion cassette, the upstream region of the phrC gene containing the rapC sequence was amplified with the primers CB2 008-015 and CB2 008-016 and fused to the spectinomycin cassette, flanked by the loxP sequence, and amplified with the oligos CB2 008-016R and CB2 008-017R. The downstream region of the phrC gene was amplified with the oligos CB2 008-017 and CB2008-018 and fused to the PCR product containing the rapC sequences and the spectinomycin cassette.

To create the phrE deletion cassette, the upstream region of the phrE gene containing the rapE sequence was amplified with the primers CB2008-019A (SEQ ID NO:7) and CB2008-019B (SEQ ID NO:9) and fused to the spectinomycin cassette amplified with the oligos CB2008-019R (SEQ ID NO:10) and CB2008-020R (SEQ ID NO:12). The downstream region of the phrE gene was amplified with the oligos CB2008-020 (SEQ ID NO:11). and CB2008-021 (SEQ ID NO:8). and fused to the purified PCR product containing the partial rapE sequence and the spectinomycin cassette.

To create the phrF deletion cassette, the upstream region of the phrF gene containing the rapF sequence was amplified with the primers CB2008-022 and CB2008-023 and fused to the spectinomycin cassette amplified with the oligos CB2008-023R and CB2008-024R. The downstream region of the phrF gene was amplified with the oligos CB2008-024 and CB2008-025 and fused to the purified PCR product containing the rapF sequence and the spectinomycin cassette.

To create the phrG deletion cassette, the upstream region of the phrG gene containing the rapG sequence was amplified with the primers CB2008-026 and CB2008-027R and fused to the spectinomycin cassette amplified with the oligos CB2008-027 and CB2008-028R. The downstream region of the phrG gene was amplified with the oligos CB2008-028 and CB2008-029 and fused to the purified PCR product containing the rapG sequence and the spectinomycin cassette.

To create the phrH deletion cassette, the upstream region of the phrH gene containing the rapH sequence was amplified with the primers CB2008-011 and CB2008-012 and fused to the spectinomycin cassette amplified with the oligos CB2008-012R and CB2008-013R. The downstream region of the phrH gene was amplified with the oligos CB2008-013 and CB2008-014 and fused to the purified PCR product containing the rapH sequence and the spectinomycin cassette.

To create the phrI deletion cassette, the upstream region of the phrI gene containing the rapI sequence was amplified with the primers CB2008-030 and CB2008-031 and fused to the spectinomycin cassette amplified with the oligos CB2008-031R and CB2008-032R. The downstream region of the phrI gene was amplified with the oligos CB2008-032 and CB2008-033 and fused to the purified PCR product containing the rapI sequence and the spectinomycin cassette.

To create the phrK deletion cassette, the upstream region of the phrK gene containing the rapK sequence was amplified with the primers CB2008-034 and CB2008-035 and fused to the spectinomycin cassette amplified with the oligos CB2008-035R and CB2008-036R. The downstream region of the phrK gene was amplified with the oligos CB2008-036 and CB2008-037 and fused to the purified PCR product containing the rapK sequence and the spectinomycin cassette.

Two loxP sites were introduced on both sides of the spectinomycin selectable marker to facilitate the removal of the antibiotic resistance. The final PCR products were purified and transformed into *Bacillus subtilis* BG2942 (ΔnprE, degU (Hy)32, amyE::[PxyIRA-comK-eryR]).

Once the DNA constructs were stably integrated, via double cross-over, into the chromosome of a competent *Bacillus subtilis* BG2942 strain, the deletions were confirmed by PCR analysis. The phrA region was amplified with the primers CB2008-041 (SEQ ID NO:13) and CB2008-042 (SEQ ID NO:14) and the phrE region was amplified with the primers CB2008-051 (SEQ ID NO:15) and CB2008-052 (SEQ ID NO:16). The resulting PCR products were sequenced to confirm the absence of PCR errors and the insertion of the antibiotic marker in the target phr gene.

The transformation of *Bacillus subtilis* BG2942, which carries an inducible ComK construct in the amyE site, was performed as described in the patent application published as US2002182734.

The BG2942 derived strains carrying the phrA or phrE deletion were then transformed with a plasmid expressing the Cre recombinase. This was a necessary step to eliminate the spectynomycin antibiotic marker by site-specific recombination.

The sequences and the descriptions of the primers used in the above experimental procedure are set are in Table 1.

TABLE 1

| | | |
|---|---|---|
| CB2008-007: | gag gat atg gaa gaa gac caa gat ttg ctg (SEQ ID NO: 1) | upstream phrA |
| CB2008-008: | ggc aat ccc tga cag tgt gtc acc (SEQ ID NO: 2) | downstream phrA |
| CB2008-009: | gcg gcc gcc ata tgc atc cta ggc ccc cga ccg caa cga gca aca aac c (SEQ ID NO: 3) | linker up phrA down-lox |
| CB2008-009-R: | ggt ttg ttg ctc gtt gcg gtc ggg ggc cta gga tgc ata tgg cgg ccg c (SEQ ID NO: 4) | linker up phrA down-lox |
| CB2008-010: | gga tcc agc tta tcg ata ccg tcg atg cat aaa aaa aga ccc tta ggg g (SEQ ID NO: 5) | linker down phrA up-lox |
| CB2008-010R: | ccc cta agg gtc ttt ttt tat gca tcg acg gta tcg ata agc tgg atc c (SEQ ID NO: 6) | linker down phrA up-lox |
| CB2008-011: | gga ggg aag ccg ttg agt caa gcc (SEQ ID NO: 59) | upstream phrH |
| CB2008-012: | gcg gcc gcc ata tgc atc cta ggc tc atc act ttt ttt ctt aat agg c (SEQ ID NO: 60) | linker up phrH down lox |
| CB2008-012R: | gcc tat taa gaa aaa aag tga tga gcc tag gat gca tat ggc ggc cgc (SEQ ID NO: 61) | linker up phrH down lox |

TABLE 1-continued

| | | |
|---|---|---|
| CB2008-013: | gga tcc agc tta tcg ata ccg tcg agg ctt ttt ctt gct tta cgg aag acg g (SEQ ID NO: 62) | linker down phrH up lox |
| CB2008-013R: | ccg tct tcc gta aag caa gaa aaa gcc tcg acg gta tcg ata agc tgg atc c (SEQ ID NO: 63) | linker down phrH up lox |
| CB2008-014: | gcc atc att ttc atg gtg cat gct cgg (SEQ ID NO: 64) | downstream phrH |
| CB2008-015: | tca cta atg gaa ttc gga cac cag ctt atg (SEQ ID NO: 65) | upstream phrC |
| CB2008-016: | gcg gcc gcc ata tgc atc cta ggc cat cgc ggc tgc ggc caa aca aat aac (SEQ ID NO: 66) | linker up phrC down lox |
| CB2008-016R: | gtt att tgt ttg gcc gca gcc gcg atg gcc tag gat gca tat ggc ggc cgc (SEQ ID NO: 67) | linker up phrC down lox |
| CB2008-017: | gga tcc agc tta tcg ata ccg tcg aga aca agc ccc ttc tca tta gcg aga agg g (SEQ ID NO: 68) | linker down phrC up lox |
| CB2008-017R: | ccc ttc tcg cta atg aga agg ggc ttg ttc tcg acg gta tcg ata agc tgg atc c (SEQ ID NO: 69) | linker down phrC up lox |
| CB2008-018: | gca gca ttt ata tca gca agt atc tca tga ac (SEQ ID NO: 70) | downstream phrC |
| CB2008-019A: | cta atg gcc ttt cgc cat aaa att atg ttg g (SEQ ID NO: 7) | upstream phrE |
| CB2008-019B: | gcg gcc gcc ata tgc atc cta ggc cgc aag tcc aat taa aac ggc gg (SEQ ID NO: 9) | linker up phrE down lox |
| CB2008-019R: | ccg ccg ttt taa ttg gac ttg cgg cct agg atg cat atg gcg gcc gc (SEQ ID NO: 10) | linker up phrE down lox |
| CB2008-020: | gga tcc agc tta tcg ata ccg tcg att cga taa aca aca tta gtt ctg att ccc (SEQ ID NO: 11) | linker down phrE up lox |
| CB2008-020R: | ggg aat cag aac taa tgt tgt tta tcg aat cga cgg tat cga taa gct gga tcc (SEQ ID NO: 12) | linker down phrE up lox |
| CB2008-021: | tgt agg cgt tag caa gct cat gcg c (SEQ ID NO: 8) | downstream phrE |
| CB2008-022: | agt ttc ggc aca acc taa tgc ttg agt acc (SEQ ID NO: 71) | upstream phrF |
| CB2008-023: | gcg gcc gcc ata tgc atc cta ggc cag taa tag ttt aga ctt caa ttt cat ac (SEQ ID NO: 72) | linker up phrF down lox |
| CB2008-023R: | gta tga aat tga agt cta aac tat tac tgg cct agg atg cat atg gcg gcc gc (SEQ ID NO: 73) | linker up phrF down lox |
| CB2008-024: | gga tcc agc tta tcg ata ccg tcg acc gcc gtc cat cgg cgg ttt ttt cgt ccc c (SEQ ID NO: 74) | linker down phrF up lox |
| CB2008-024R: | ggg gac gaa aaa acc gcc gat gga cgg cgg tcg acg gta tcg ata agc tgg atc c (SEQ ID NO: 75) | linker down phrF up lox |
| CB2008-025: | tcg gac cgc aca atg tgt att cat tcg g (SEQ ID NO: 76) | downstream phrF |
| CB2008-026: | Aga gga tca gga ggt gct tgc cta c (SEQ ID NO: 77) | upstream phrG |
| CB2008-027: | cga acg gag gtt ata taa atg aaa agt cga cgg tat cga taa gct gga tcc (SEQ ID NO: 78) | linker up phrG and up lox |

TABLE 1-continued

| | | |
|---|---|---|
| CB2008-027R: | gga tcc agc tta tcg ata ccg tcg act ttt cat tta tat aac ctc cgt tcg (SEQ ID NO: 79) | linker up phrG and up lox |
| CB2008-028: | gcg gcc gcc ata tgc atc cta ggc cat gaa aaa ccc ccg cgg gat g (SEQ ID NO: 80) | linker down phrG and down lox |
| CB2008-028R: | cat ccc gcg ggg gtt ttt cat ggc cta gga tgc ata tgg cgg ccg c (SEQ ID NO: 81) | linker down phrG and down lox |
| CB2008-029: | tct cgg tga cat tcc gat caa tcg cg (SEQ ID NO: 82) | downstream phrG |
| CB2008-030: | gaa ttg tta aac atg gaa gaa aat caa gat gcc ctg (SEQ ID NO: 83) | upstream phrI |
| CB2008-031: | gcg gcc gcc ata tgc atc cta ggc caa tac act act taa aat cac tgc tgc c (SEQ ID NO: 84) | linker up phrI down lox |
| CB2008-031R: | ggc agc agt gat ttt aag tag tgt att ggc cta gga tgc ata tgg cgg ccg c (SEQ ID NO: 85) | linker up phrI down lox |
| CB2008-032: | gga tcc agc tta tcg ata ccg tcg act tag ata att gga aaa gag gaa aaa agc tta atc (SEQ ID NO: 86) | linker down phrI up lox |
| CB2008-032R: | gat taa gct ttt ttc ctc ttt tcc aat tat cta agt cga cgg tat cga taa gct gga tcc (SEQ ID NO: 87) | linker down phrI up lox |
| CB2008-033: | ctg tcc cta tta gtt tat ctg ctt ttt tat ctc cat cag g (SEQ ID NO: 88) | downstream phrI |
| CB2008-034: | gat gaa atg gaa gaa gat caa gaa gtt ctt gcg (SEQ ID NO: 89) | upstream phrK |
| CB2008-035: | gga tcc agc tta tcg ata ccg tcg att aaa atc aca gct aaa ata gat acg c (SEQ ID NO: 90) | linker up phrK and lox |
| CB2008-035R: | gcg tat cta ttt tag ctg tga ttt taa tcg acg gta tcg ata agc tgg atc c (SEQ ID NO:91) | linker up phrK and lox |
| CB2008-036: | gcg gcc gcc ata tgc atc cta ggc caa aag gtt gat taa tta att tag ccc (SEQ ID NO: 92) | linker down phrK and lox |
| CB2008-036R: | ggg cta aat taa tta atc aac ctt ttg gcc tag gat gca tat ggc ggc cgc (SEQ ID NO: 93) | linker down phrK and lox |
| CB2008-037: | atc gag act att tga gat acc tga aga tcc (SEQ ID NO: 94) | downstream phrK |
| CB2008-041: | actcatatccggcagttccacgtcgc (seq id no: 13) | 5' rapA |
| CB2008-042: | agatgccgtctgaggcagtttgatcacc (seq id no: 14) | 3' xlyB |
| CB2008-051: | agctgtacatgcacactcagcccctc (seq id no: 15) | 5' rapE |
| CB2008-052: | agaggcgcttttgcctttgctgtcgc (seq id no: 16) | 3' yqcG |

The nucleotide sequence of the phrA deletion construct is:

(SEQ ID NO: 17)
attcgttattgcaggtaattatgatgatatgcagtatccagaaagagcat tgccccacttagaactggctttagatcttgcaaagaaagaaggcaatccc cgcctgatcagttctgccctatataatctcggaaactgctatgagaaaat gggtgaactgcaaaaggcagccgaatactttgggaaatctgtttctattt gcaagtcggaaaagttcgataatcttccgcattctatctactctttaaca caagttctgtatataacaaaaaaatgacgccgaagcgcaaaaaaagtatcg tgaaggattggaaatcgcccgtcaatacagtgatgaattatttgtggagc tttttcaatttttacatgcgttatacggaaaaaacattgacacagaatca gtctcacacacctttcaatttcttgaagaacatatgctgtatccttatat tgaagagctggcgcatgatgctgcccaattctatatagaaaacggacagc ccgaaaaagcactttcattttatgagaaaatggtgcacgcacaaaaacaa atccagagaggagattgtttatatgaaatctaaatggatgtcaggtttgt tgctcgttgcggtcggggggcctaggatgcatatggcggccgcataacttc gtatagcatacattatacgaagttatctagacatatgcaagggtttattg -continued
ttttctaaaatctgattaccaattagaatgaatatttcccaaatattaaa
taataaaacaaaaaaattgaaaaaagtgtttccaccattttttcaattttt
tttataattttttttaatctgttatttaaatagtttatagttaaatttaca
ttttcattagtccattcaatattctctccaagataactacgaactgctaa
caaaattctctccctatgttctaatggagaagattcagccactgcatttc
ccgcaatatcttttggtatgattttacccgtgtccatagttaaaatcata
cggcataaagttaatatagagttggtttcatcatcctgataattatctat
taattcctctgacgaatccataatggctcttctcacatcagaaaatggaa
tatcaggtagtaattcctctaagtcataatttccgtatattcttttattt
tttcgttttgcttggtaaagcattatggttaaatctgaatttaattcctt
ctgaggaatgtatccttgttcataaagctcttgtaaccattctccataaa
taaattcttgtttggaggatgattccacggtaccatttcttgctgaata
ataattgttaattcaatatcgtaagttgcttttatctcctattttttt
tgaaataggtctaattttttgtataagtatttctttactttgatctgtca
atggttcagatacgacgactaaaaagtcaagatcactatttggttttagt
ccactctcaactcctgatccaaacatgtaagtaccaataaggttattttt
taaatgtttccgaagtattttttttcacttttattaatttgttcgtatgtat
tcaaatatatcctcctcactattttgattagtacctattttatatccata
gttgttaattaaataaacttaatttagtttatttatagatttcattggct
tctaaattttttatctagataacttcgtatagcatacattatacgaagtt
atggatccagcttatcgataccgtcgctcggatccactagtatgcataaa
aaaagacccttagggggtcttttttatttcttcagcttccattcttttatc
gtcagctcagaagatccacttgccaccagcggatccgcatggccgatttc
cgctgcctcttccagtgaatctgcttcgatgacatacgctccgcctgtgg
cgtcgctgaatggcccaaacatttttaaacgtttttctgcctgtaaacga
tccagaaattcatagtgcccagccacatgctcctgattaaatttctccgt
tctcattgtcagcattaaatatggtatacatattcagaccctccgtgaac
ttcagtttaacacatttatccatattacggtgatagatgatatgagctttt
tcgtcctacgaatgccacctatttatgaaaaaagaaaaggagagatgata
ggtgagcattccagtaaagaaaaatttggtttctgaggcgaaatacgcgt
tgaagtgtcctaatgcaatgtccgctgaatacattaccattcacaacacg
gcaaacgatgcatcagcggccaatgaaatcagctatatgatcgggaacac
aagctcgacaagctttcattttgcggtcgatgatcaagaggtgattcaag
gtctgccgcttaaccgaaacgcttggcacactggtgacggcacaaacggt
ccgggaaaccgcaaatcaatccggtgttgagatttgctacagcaaatcggg
aggcccgaagtatgaggcagctgaagccttggcgatttcatttgttgcac
agctgttgaaggagcgcggctggggcatcgatcgggtgagaaagcatcag
gactggagcggaaagtattgcccgcaccgcattttatcagaggggcgctg
ggatcaagtgaaggcggcgattgaaaaggaattaaacggggggcgtatcag
cgaaaaagctgcagtctcttcttcggcgtctgaatatcatgtaaaaaaa
ggtgacacactgtcagggattgccgcatcacacgggccc.

The nucleotide sequence of the phrC deletion construct is:

(SEQ ID NO: 95)
tcactaatggaattccggcaccagcttatgctggattatcttgagccgtt
agagaaattaaatatcgaagaccagccaagcctgtctgaattatcaagaa
acattgacagcaaccaggcagatctcaaagggctgctcgactattacgtg
aatttttttcgcgggatgtatgaatttgataagcgggaatttatttctgc
cattacatactataaacaggcggagaaaaagctctcctttgtcgcagacc
atattgaacgggctgaattctattttaaaatcgcggaagcttattattat
atgaagcaaacgtattttcattgattaatataaaaaacgcctatgaaat
ttacgtggagcaggaaacctataatgtgagaatcattcagtgccatttcg
tcttcggggtcaacctgatggatgaaagaaatttcgaacaagccgcacgc
catttcaaattggcgctcaacatggcccaagcagaacaaaaagcccagct
ggttggaagagcatactacaatctcgggttatgctattacaatcaagacc
ttctagaccctgccattgattactttgaaaaagcggtctccacatttgaa
agcagcaggatcgtcaattctctcccgcaagcctatttttaatcaccct
gattattataaacagggaaaacatgataaagcttcggaatatcacaagc
ggggctatgaatatgctaaagaaacagacgatgcagactatgccgtaaaa
ttcgagttttgcaatccctatatctggatcagcccaatgaagaaggaat
cgaacgatgtttccagtacttaaaaaataaaaatatgtacgctgatatag
aggatttagccctagaagtagcaaaatattactatgaacagaaatggttt
aaactgtctgcttcctactttctacaagttgaagaggcaagaaaacaaat
acaaaggagtgaaggtttgtatgaaattgaaatctaagttgtttgttatt
tgtttggccgcagccgcgatggcctaggatgcatatggcggccgcataac
ttcgtatagcatacattatacgaagttatctagacatatgcaagggttta
ttgttttctaaaatctgattaccaattagaatgaatatttcccaaatatt
aaataataaaacaaaaaaattgaaaaaagtgtttccaccatttttttcaat
ttttttataattttttttaatctgttatttaaatagtttatagttaaattt
acattttcattagtccattcaatattctctccaagataactacgaactgc
taacaaaattctctccctatgttctaatggagaagattcagccactgcat
ttcccgcaatatcttttggtatgattttacccgtgtccatagttaaaatc
atacggcataaagttaatatagagttggtttcatcatcctgataattatc
tattaattcctctgacgaatccataatggctcttctcacatcagaaaatg
gaatatcaggtagtaattcctctaagtcataatttccgtatattctttta
ttttttcgttttgcttggtaaagcattatggttaaatctgaatttaattc
cttctgaggaatgtatccttgttcataaagctcttgtaaccattctccat
aaataaattcttgtttggaggatgattccacggtaccatttcttgctga
ataataattgttaattcaatatcgtaagttgcttttatctcctattttt
ttttgaaataggtctaattttttgtataagtatttctttactttgatctg
tcaatggttcagatacgacgactaaaaagtcaagatcactatttggtttt
agtccactctcaactcctgatccaaacatgtaagtaccaataaggttatt
ttttaaatgtttccgaagtattttttttcacttttattaatttgttcgtatg -continued

```
tattcaaatatatcctcctcactattttgattagtacctattttatatcc
atagttgttaattaaataaacttaatttagtttatttatagatttcattg
gcttctaaatttttttatctagataacttcgtatagcatacattatacgaa
gttatggatccagcttatcgataccgtcgagaacaagccccttctcatta
gcgagaaggggttttttctttttcaaaaaaacaccgcaagacatagtcttgc
ggtgccgccttcatggagattacgtttatttagtagcctcctacaaatgc
agttcccacaatgatcaagaggataaataacacaacaatcaaagcgaaag
aagttccgtaacctgacattttgtgcacctccttgcgagattgcttcagc
aaatgctgcaaaactgtggcggacagggtcccgcagagacggtcagcagc
ttagaagccgccaacaaacgcagtccctacgataattaatagaataaaca
atacaacgattaaagcgaaagaactgatgccgccgtaaccgccgccgtta
gagtatcctgacataaggtttcacctccctatgaaggatactataagata
tgctgaaccgatccatttggcagggataatagtggacaagagaaaaaatg
aagaattcggctatatgaaggtgatataaaaaaatagcgggcgctgccgc
ccgctatttatgtacgattaagagatcagcacgcccgcgaaaaattcctg
gtataacgcttgaacggcttttctttcttcggcttcttttacgccaaaca
tcatgctcacttcagaagaccctgattgatcatttcgatattcacctgt
gcctctgataatgctttggcggctcttgccgttgtaccgacattgtggcg
catcgcttcccctacaaccataatcagggcgagatgatgctcgacgatga
cttcatcggcatgcaaatcctcttcgatccgtttgatgacgctgcgttca
gtggcggcatccatttgcccctgccgtaaaatgattgtcatgtcatcgat
tcccgatggaacatgctcatacgtcaaaccatgctcctccaggatttgaa
gggctctgcggccaaaaccgatttctctgttcatgagatacttgctgata
taaatgctgc
```

The nucleotide sequence of the phrE deletion construct is:

(SEQ ID NO: 18)
```
tttttctgttcagacataatggattttgatttggtgtaggcgttagcaa
gctcatgcgctaaaaggtttcttctatgtaggcatctgataagttggca
tcttctaaaaaaccaggaatactcgttaagaaagaaattttcatctcaat
taaatcaatccattggtcagcaatgccagcttgatcttcataaaatgatt
taatgttattagcgcctttgcctgaaaactcgctatcatctaaatctgca
acagctttgaacgctttctttaatttgaccatttacttttttaaatctttt
gtattcctgtgctcgcttttcagcctcggtgagcaaggttttggcttcaa
atactttcatgatcatatcctttcatttaatcgtcataacaaaatattac
catgaagaatgatgaaactaactgttatgtggatcaaatggtggaaatg
aatcattcgatctgtgtcattttacctatttgttaatcctttcaatgaaa
ggggactttccaattgtaacatcgccatcatgaaaaaattcgataacgta
gccagattcactaaacataaaagtatccgatccaacggcagttacatcat
caattacgtttaatgcatgctcaagactggtttttaatgctggctgttct
ccgtaaccccaaagaataataatgttcctatctttaaaatggtgtttagc
```

-continued
```
tagccaatcgtaaatctcttcctcgtaatctatagattgatgacaacaaa
cttcttcccacttgattcgtccccaagatgtaagggaaaactgtttgaaa
gcagttcataatattttgccgttaattcttctgataagatttctttgttt
ttccctagagcttctaagcattcatcaaataagtccaaaatgttcacctc
aaaagctttaagtatgatagatttttttcagtattagaaataagaaaaagc
cgttatgaaacggctaaagggaatcagaactaatgttgtttatcgaatcg
acggtatatcgaaaggggaatgcatgtatgaaatctaaattgtttatcag
tttatccgccgttttaattggacttgcgaaaggcgaattccagcacactg
gcggccgttactagtggatccgagctcggatccataacttcgtataatgt
atgctatacgaagttatctagataaaaaatttagaagccaatgaaatcta
taaataaactaaattaagtttatttaattaacaactatggatataaaata
ggtactaatcaaaatagtgaggaggatatatttgaatacatacgaacaaa
ttaataaagtgaaaaaaatacttcggaaacatttaaaaaataaccttatt
ggtacttacatgtttggatcaggagttgagagtggactaaaaccaaatag
tgatcttgacttttagtcgtcgtatctgaaccattgacagatcaaagta
aagaaatacttatacaaaaaattagacctatttcaaaaaaaataggagat
aaaagcaacttacgatatattgaattaacaattattattcagcaagaaat
ggtaccgtggaatcatcctcccaaacaagaatttatttatggagaatggt
tacaagagctttatgaacaaggatacattcctcagaaggaattaaattca
gatttaaccataatgctttaccaagcaaaacgaaaaaataaaagaatata
cggaaattatgacttagaggaattactacctgatattccattttctgatg
tgagaagagccattatggattcgtcagaggaattaatagataattatcag
gatgatgaaaccaactctatattaactttatgccgtatgattttaactat
ggacacgggtaaaatcataccaaaagatattgcgggaaatgcagtggctg
aatcttctccattagaacatagggagagaattttgttagcagttcgtagt
tatcttggagagaatattgaatggactaatgaaaatgtaaatttaactat
aaactatttaaataacagattaaaaaaattataaaaaaattgaaaaaatg
gtggaaacacttttttcaattttttgtttattattaatatttgggaa
atattcattctaattggtaatcagattttagaaaacaataaacccttgca
tatgtctagataacttcgtataatgtatgctatacgaagttatgcggccg
ccatatgcatcctaggccgcaagtccaattaaaacggcggataaactgat
aaacaatttagatttcatacatgcattccccttttcgatatttgcttttga
gcatataccatcttcttgaaacagatgatactatcctctattttcccatt
ataatcgaaaaggttgcctcctaacaatgccagctcttccagataagggt
atcctttgccgttctctaaacgagaaaaaatgttgagaagtttaggtgta
tcgccatttcttatataaagaacgtctaatgcttcaaataagttcataaa
tagttcgtctttaaaatctacagcacttctgattccttttgcggaagcaat
ccattgcttgtccttttttgccttgtttaaaataaatcaacgctaggtca
tgataagcttgcggaagtacgtcagagttaattttttctgtattgaaccaa
ggcttgttcgatgtaacgagcagcctatttaagttgtccattttgtgat
agcaattgccgagattgaaaaacgcagtggcatagatatgagtattttta
```

-continued
cttttaagcagctcggcacctttttaaagcttcttgaaggtggggagagc
ttttcatgattttcaaggtcatcgtagttaccggcaatgacaaaatggc
actgaatacgacgaacagagtaaagctcgtgtttcttataaatgttgtat
gaaagctcagcgtaatgcatcgaaatgtgtgtcattttcatatgataata
gacttcagacagtttaaaataaaactcagcttttttcaatcttgtcggaga
ttgtaggaattttgcgttcagcttttttgtaatatgtaatggctcttgtg
tattcaccgtttctaaactcatacatcccgcggaagaagttataataata
tgcccgcatattgtctaattttttcttatggccctcaattttatttaaat
attctgaaagttccattcggttttcatcagatggcagcgtgtattccaac
ataattttatggcgaaaggccattagttgataataaataagcaagtcttg
atcttcttccataacctc.

The nucleotide sequence of the phrF deletion construct is:

(SEQ ID NO: 96)
agtttcggcacaacctaatgcttgagtaccttgaaccgttagaaaaaatg
aggattgaggaacagccgagactgtctgatctgctgcttgagattgataa
aaaacaggctcgtttaactggtctgcttgagtactatttttaacttcttca
gaggcatgtacgagctggaccagcgggaatatctgtcggctattaaattt
ttcaaaaaggccgaaagcaagctgatattcgttaaggatcggatagagaa
agctgagttttttctttaagatgtctgaatcttattactatatgaaacaaa
cgtatttttcaatggactatgcacggcaagcatatgaaatatacaaagaa
catgaagcttataatataagattgctgcagtgtcattctttatttgccac
caattttttagatttaaaacagtatgaggatgccatctcacattttcaaa
aagcttattctatggcagaagctgaaaagcagccccaattaatggggaga
actttgtacaatatcgggctttgtaaaaacagccaaagccaatatgagga
tgccataccttatttcaaaagagcaatagctgtttttgaagaatcaaata
ttcttccttccttacctcaagcgtatttttttaattacacagatccattat
aaattaggaaaaatagataaagctcatgaatatcatagtaagggaatggc
ttattcacaaaaggccggagatgtaatatatttatcagagtttgaattttt
tgaaatctttatacttatcaggcccggatgaagaagcaattcaaggatttt
tttgattttctcgaaagtaaaatgttgtatgctgatcttgaagatttcgc
tattgatgtggcaaaatattatcatgaacgtaaaaattttcaaaaagctt
ctgcttattttttgaaggtggaacaagtaaggcaacttattcaaggagga
gtgagtttgtatgaaattgaagtctaaactattactggcctaggatgcat
atggcggccgcataacttcgtatagcatacattatacgaagttatctaga
catatgcaagggtttattgttttctaaaatctgattaccaattagaatga
atatttcccaaatatttaaataataaaacaaaaaattgaaaaagtgttt
ccaccatttttcaattttttttataattttttttaatctgttatttaaata
gtttatagttaaatttacattttcattagtccattcaatattctctccaa
gataactacgaactgctaacaaaattctctccctatgttctaatggaaa
gattcagccactgcatttcccgcaatatcttttggtatgattttacccgt -continued
gtccatagttaaaatcatacggcataaagttaatatagagttggtttcat
catcctgataattatctattaattcctctgacgaatccataatggctctt
ctcacatcagaaaatggaatatcaggtagtaattcctctaagtcataatt
tccgtatattcttttattttttcgttttgcttggtaaagcattatggtta
aatctgaatttaattccttctgaggaatgtatccttgttcataaagctct
tgtaaccattctccataaataaattcttgtttgggaggatgattccacgg
taccatttcttgctgaataataattgttaattcaatatcgtaagttgc
ttttatctcctattttttttgaaataggtctaatttttttgtataagtatt
tctttactttgatctgtcaatggttcagatacgacgactaaaaagtcaag
atcactatttggttttagtccactctcaactcctgatccaaacatgtaag
taccaataaggttattttttaaatgtttccgaagtatttttttcacttta
ttaatttgttcgtatgtattcaaatatatcctcctcactattttgattag
tacctattttatatccatagttgttaattaaataaactttaattttagttta
tttatagatttcattggcttctaaattttttatctagataacttcgtata
gcatacattatacgaagttatggatccagcttatcgataccgtcgaccgc
cgtccatcggcggttttttcgtcccctctttaccaaagtctcccaatcca
tgctatgatcttttcaataatcttgaagagagtggaaatgcagcatgtct
ctaaaaagtgtgagaacccactttactcaatggaatcgagaaaatgatgt
gacggagttcgaaacgtcgagtgcgacagttgaacaggcagctgagacaa
tcggcgtaagcctgtctagaatcgccaagtccctgtccttcagaggggaa
ggagatcaggtgattctgattgtggcagccggcgatgccaagatcgacaa
caaaaagtccaggcaaacatttggctttaaagcaagaatgctctctccta
atgaggtgctggagcagacaggccatgaaattggaggagtttgcccattt
ggattggctcatgatcctgaggtttatcttgatgtatcgctgaaacggtt
tcagactgttttccccgcatgcggcagcagaaactccgctattgaattaa
caccgaaagaattatccgaattttctttctcaaaagtgtggattgatgtt
tgtaaagactgggaataaaaaacatccagacatcgtctggatgtttact
tatttcacaaacccaagcagcatttcacggatgattttgctggctgtgtt
tgccgtttgctctgagtggtcgtataccggcgcgacttccactaaatcag
cgcccctttacgtoacctctgaacgcgcaatttcatggaccgatgcaagca
gttctttagacgtgatgccgcggcgtcaaccgttcctgtacccggtgcg
tgtgcagggtctaatacgtcaatgtcaattgtgacataaaccggacggcc
cgccagcttcggaagcacctctttcagcggttcaagcacttcaaattttg
agatgtgcatgccgttttccttcgcccattcaaactcttctttcatgccg
gaacggattccgaatgaatacacattgtgcggtccga The nucleotide sequence of the phrG deletion construct is:

(SEQ ID NO: 97)
agaggatcaggaggtgcttgcctacttctccttattggaactgcgccaca
aggttttgcttcacgaggcgagaggacagggcttcagcatgaggagcct
tctcatatgaatgctacgtctgacatgctgaaatattacttttttctgtt

```
tgaaggcatgtatgaggcctataaaaataattatgacattgccattgggc
tgtataaagatgcagagcagtatctcgacaacattcccgatccgattgaa
aaagccgaatttcacctgaaggtcggtaagctctattataagctgggaca
aaatattgtgtccctcaatcatacacggcaagcagtcaaaacattcagag
aagagacagattataaaaagaagctggcttcagccctgattaccatgtca
ggcaatatacagagatgagccagtttgaagaagctgaggcttatttggac
gaagcaattcggatcacgagtgaattagaggatcatttttttgaagccca
gcttttgcataacttcggccttctacatgcgcaaagcggcaaatcagaag
aagcggtttcgaaattagaggaggctctacagaacgatgagtatgcccgc
tccgcctattattatcattctgcctacttgctgatacgagagctgtttaa
gatcaaaagaaagaacaggccttatcttattaccaagacgtgaaggaaa
aattgactgctgagccgaatagaatatgtgaggcaaaaatagacatttta
tatgccatttatgcagaaggggtcatgcggaaacgtttcacttatgcaa
acaacatatggatgacttgttgtccgagaaagagtatgacagtgtaagag
aactttccattttggctggcgaacggtataggaacttgagctttacaaa
gaagctgcccacttttttttatgaagcattacagattgaagaactgattaa
acgaacggaggttatataaatgaaaagatggcctaggatgcatatggcgg
ccgcataacttcgtatagcatacattatacgaagttatctagacatatgc
aagggttattgttttctaaaatctgattaccaattagaatgaatatttc
ccaaatattaaataataaaacaaaaaaattgaaaaaagtgtttccaccat
ttttcaattttttttataattttttttaatctgttatttaaatagtttata
gttaaatttacattttcattagtccattcaatattctctccaagataact
acgaactgctaacaaaattctctcccctatgttctaatggagaagattcag
ccactgcatttcccgcaatatcttttggtatgattttacccgtgtccata
gttaaaatcatacggcataaagttaatatagagttggtttcatcatcctg
ataattatctattaattcctctgacgaatccataatggctcttctcacat
cagaaaatggaatatcaggtagtaattcctctaagtcataatttccgtat
attcttttattttttcgttttgcttggtaaagcattatggttaaatctga
atttaattccttctgaggaatgtatccttgttcataaagctcttgtaacc
attctccataaataaattcttgtttgggaggatgattccacggtaccatt
tcttgctgaataataattgttaattcaatatatcgtaagttgcttttatc
tcctattttttttgaaataggtctaattttttgtataagtatttctttac
tttgatctgtcaatggttcagatacgacgactaaaaagtcaagatcacta
tttggttttagtccactctcaactcctgatccaaacatgtaagtaccaat
aaggttatttttaaatgtttccgaagtatttttttcactttattaatttt
gttcgtatgtattcaaatatatcctcctcactattttgattagtacctat
tttatatccatagttgttaattaaataaacttaatttagtttatttatag
atttcattggcttctaaatttttatctagataacttcgtatagcataca
ttatacgaagttatggatccagcttatcgataccgtcgaatgaaaaccc
ccgcgggatgcggggttcaatttaacgaaagaatcctaaaacggtttgt
agttttaggattctttcatcttttcagcgtgattgaaaacccttgaagtc
```

```
taggaagaacgagcattggagcgcagcgaatgtttggaattcgtgagcac
cgaagcgcaggcctgacaacgaatgcgagggtttgtcgacacgctgaaaa
cccgcgggtgcgggggttttcttattacagcagcttcttccctaacaggg
attctacgagctctactgctgttttgcccgttttgttttttgtgatcaagg
atcgggttaacctcaacgaattcggctgaggtaatgatgcctgcgtcata
cagcatttccatagccaaatggctctcccggtagctgatgccgccgacga
caggggttccgacacccggtgcgtcgttcggatcaagtccgtccagatca
aggctcagatggacgccatcacatgctgataaataatcaagggtttcttc
aatgacctttgtcatgccaagacgatcgatttcgtgcattgtgtacacct
tcatgccgctttccttaatgtacttgcgctccccttcatcaagtgaccgg
gcgccaatgatgacgacgttttccggtttgattttaggcgcgtagccttc
aaggttaaccagtgactcgtggccaatgcctaggctgaccgcgagcggca
tgccgtgaatattgcccgatggtgaagtttcaagtgtattcaaatcgccg
tgcgcgtcataccagatgacgccgagattatcgtaatgcttcgctgtgcc
tgcaagcgtgccgatcgcaatactgtggtcaccgcccaggacaagcggga
atttttctcttcaatgactttgttgaccttttgcgcgagttttcattt
cccgccaaaacggaattcaggttttttcagttcctcgtcattttttgatttt
ttcgcgattgatcggaatgtcaccgaga
```

The nucleotide sequence of the phrH deletion construct is:

(SEQ ID NO: 98)
```
ggagggaagccgttgagtcaagccataccgtcttcgcgtgttggtgttaa
gattaatgaatggtataaaatgattcgccagttcagtgttccggatgctg
agattctgaaagcggaggttgagcaggacattcagcagatggaagaagat
caggatttactgatctattattctctgatgtgttttcggcaccagctgat
gcttgattatttggagccgggaaaaacatacgggaatcgccctacagtga
cagagcttcttgaaacgatcgagacccctcagaaaaaactcacaggtctt
ttgaaatactactctttgttttttccgcggcatgtatgaatttgaccaaaa
agaatatgtggaagcgatcggatattatcgcgaggcggagaaagaactgc
cgtttgtgtcagatgatattgagaaagcggaattccattttaaagtggca
gaagcgtattcacatgaagcaaacccatgtgtcgatgtatcatattct
tcaagccttggacatttatcaaaaccatcctctatacagcattagaacga
tacaaagcttgtttgtgatcgccggcaactatgatgatttcaaacattat
gataaagcgctcccgcatttagaggcggcgctggaattggcaatggacat
tcaaaatgacaggtttatcgccatttctctattgaacattgcaaacagct
atgacagatcaggagacgatcagatggctgtagaacattccaaaaagcg
gcgaaagtaagcagagagaaagtgcctgatctgcttccgaaagtcttgtt
tggattaagctggacattatgtaaagcgggccaaacacagaaggcgtttc
agttcatagaggaaggattagaccatatcacagcacgttctcacaaattt
tataaagaattgtttctgttcttgcaggccgtgtacaaggagactgttga
tgaacgaaaaattcatgatcttttaagctatttcgaaaaaaagaacctgc
```

-continued

```
acgcttacattgaagcatgtgcccggagtgctgccgctgttttgaaagc
agctgtcactttgaacaagcagctgcgttttatcggaaagtgctgaaagc
ccaagaagatattctaaaagggagagtgtttatatgcctattaagaaaaa
aagtgatgaggcctaggatgcatatggcggccgcataacttcgtatagca
tacattatacgaagttatctagacatatgcaagggtttattgttttctaa
aatctgattaccaattagaatgaatatttcccaaatattaaataataaaa
caaaaaaattgaaaaagtgtttccaccatttttttcaatttttttataat
ttttttaatctgttatttaaatagtttatagttaaatttacattttcatt
agtccattcaatattctctccaagataactacgaactgctaacaaaattc
tctccctatgttctaatggagaagattcagccactgcatttcccgcaata
tcttttggtatgattttacccgtgtccatagttaaaatcatacggcataa
agttaatatagagttggtttcatcatcctgataattatctattaattcct
ctgacgaatccataatggctcttctcacatcagaaaatgaatatcaggt
agtaattcctcaagtcataatttccgtatattcttttattttttcgttt
tgcttggtaaagcattatggttaaatctgaatttaattccttctgaggaa
tgtatccttgttcataaagctcttgtaaccattctccataaataaattct
tgtttgggaggatgattccacggtaccatttcttgctgaataataattgt
taattcaatatatcgtaagttgcttttatctcctatttttttgaaatag
gtctaattttttgtataagtatttctttactttgatctgtcaatggttca
gatacgacgactaaaaagtcaagatcactatttggttttagtccactctc
aactcctgatccaaacatgtaagtaccaataaggttatttttaaatgtt
tccgaagtatttttttcactttattaatttgttcgtatgtattcaaatat
atcctcctcactattttgattagtacctattttatatccatagttgttaa
ttaaataaacttaatttagtttatttatagatttcattggcttctaaatt
ttttatctagataacttcgtatagcatacattatacgaagttatggatcc
agcttatcgataccgtcgaggcttttttcttgctttacggaagacggttcc
attttccacatcgcggcattccttctattctaacgcaagacactcgaaa
caaccaaaccatttgaggtataatggataaagtgaataacagtatttaga
ttgatatatatgaaagagagtggaacatcatgggccgtaagtggaacaat
attaaagagaagaaggcgtctaaggacgcaaatacgagtcggatttatgc
gaagtttggccgtgagatttatgtggcggcgaaacagggcgagcctgatc
cggaatccaaccaggcgctgaaggttgtgcttgaacgtgcgaagacttac
agcgtgccgaaaaacatcattgaacgtgcgatcgagaaggcgaagggcgg
agcggaagagaattacgatgagcttcgttatgagggcttcgggccgaacg
gatcaatgattatcgttgatgcgctgacgaataatgtaaaccgtacggcg
ccggaagtgcgtgcggcgttcgggaaaaacggcggaaacatgggtgtgag
cggatctgttgcttacatgtttgacgcgacggctgtaatcgtggtggaag
gcaaaacggctgacgaagcgcttgaaatcctgatggaagcggatgttgat
gtacgtgacattttagaagaggatgacagcgcgatcgtgtatgccgagcc
tgatcaattccatgcggtgcaagaggcgtttaaaaacgcgggtgtcgagg
aatttacagtagcggagctgcaaatgcttgcgcaaagtgaagtaacgctt
```

-continued
```
ccggatgatgcaaaggaacagtttgaaaaattgattgatgcattagaaga
tttggaagatgttcagcaggtatatcataacgttgatttaggtgagtaag
gagtgagcaggctgttatggcctgcttttttgtcccggaaattgtttta
gctgtatgtaggcggccgcctatacgatctataagatattctcatactct
ggactgtaacctatgtgaaggagagagtaaatatgactgatacaagacat
atgtatggcggacctggttttggtcattatcagggctttggtattggcca
cccgggctatggcatgcaaagcacaggctatccgggctatggcatgtatg
gaggccacccgggctatggcatgcaaggctacccagatcacggcatacat
ggaggagtcggcggctatccgggatatggtgggtacggcggttacccaag
cggcggctatggaggctctccgggaactggaagctatccgagcatgcacc
atgaaaatgatggc
```

The nucleotide sequence of the phrI deletion construct is:

(SEQ ID NO: 99)
```
gaattgttaaacatggaagaaaatcaagatgccctgttatattatcaact
attagaatttagacatgagataatgctgagttatatgaaatctaaggaaa
tagaagatctcaataatgcttatgagactataaaagaaattgagaagcaa
gggcaattaactggcatgttggaatactattttacttttttaagggtat
gtacgagtttaggcgtaaagaattaatttcagcgataagtgcttatcgaa
tagctgaatcaaagttgtcagaagttgaggatgaaatagagaaagcagag
tttttttttcaaagtgtcctatgtatattattatatgaaacaaacatactt
ctccatgaattatgcaaatcgtgcactcaaaatatttagagagtatgaag
aatatgctgtccagactgtgcgttgtcaatttattgtagcaggaaacttg
atcgattcattggaatatgaaagagccttggaacaatttttgaagtctttt
ggaaatttccaaggaaagtaacatagagcatttaattgcaatgtcacata
tgaatattgggatttgttatgatgaattgaaagaatataagaaggcttca
caacatttaattttagcgttagaaatttttgaaaaatcaaaacatagttt
cttaacaaagactttattcactctaacctatgtagaagcaaaacaacaaa
attataatgttgctttgatatactttaggaaagggcgatttattgccgat
aaaagtgatgataaggaatactcagcgaaattcaaaatattagagggatt
atttttttctgatggtgagactcaattaataaagaatgcattttcatatc
tggcttcgagaaaaatgtttgctgatgttgaaaattttcgattgaagtc
gctgattattttcatgaacaaggaaatttaatgctctctaatgaatatta
tcgtatgagtattgaagcaagacgaaaaattaaaaaggggagattattg
atgaaaatcagccggattctattggcagcagtgatttaagtagtgtatt
ggcctaggatgcatatggcggccgcataacttcgtatagcatacattata
cgaagttatctagacatatgcaagggtttattgttttctaaaatctgatt
accaattagaatgaatatttcccaaatattaaataataaaacaaaaaaat
tgaaaaagtgtttccaccatttttttcaatttttttataatttttttaat
ctgttatttaaatagtttatagttaaatttacattttcattagtccattc
aatattctctccaagataactacgaactgctaacaaaattctctccctat
```

-continued

```
gttctaatggagaagattcagccactgcatttcccgcaatatcttttggt
atgattttacccgtgtccatagttaaaatcatacggcataaagttaatat
agagttggtttcatcatcctgataattatctattaattcctctgacgaat
ccataatggctcttctcacatcagaaaatggaatatcaggtagtaattcc
tctaagtcataatttccgtatattcttttattttttcgttttgcttggta
aagcattatggttaaatctgaatttaattccttctgaggaatgtatcctt
gttcataaagctcttgtaaccattctccataaataaattcttgtttggga
ggatgattccacggtaccatttcttgctgaataataattgttaattcaat
atatcgtaagttgcttttatctcctatttttttgaaataggtctaattt
tttgtataagtatttctttactttgatctgtcaatggttcagatacgacg
actaaaagtcaagatcactatttggttttagtccactctcaactcctga
tccaaacatgtaagtaccaataaggttattttttaaatgtttccgaagta
ttttttttcactttattaatttgttcgtatgtattcaaatatatcctcctc
actattttgattagtacctattttatatccatagttgttaattaaataaa
cttaatttagtttatttatagatttcattggcttctaaattttttatcta
gataacttcgtatagcatacattatacgaagttatggatccagcttatcg
ataccgtcgacttagataattggaaaagaggaaaaaagcttaatcttttt
tcgaaggttaagcttttttcttttatttataaaaagtgaactaactatcag
aaagaaattatattaaattttattttttgtttaaaaagtagattatata
aaggcaagctaggtggggaaaatatgtttaaaaaagaaaaagtcacaga
atacatttggactatactaataccaacaatcatcacttttatcattagtt
gggttgggtcttattacaatggtacttcgacagttagtattggacaacct
acaaaagtttccggtcagtatatcacgccaataaatataagtccctatca
tgatattaaggaattaagaataacttttccgcaaaaactagatgtaaaac
aaattagttcaaatgagcctataaatgtaaaatcagataagaacaatata
ggagttgaaagtaattccacttttgagattgcgaaaatcgttgaaaataa
tagcgttcagttgctaattacaacacaaaaaaagttaaacgataaggaaa
ttagaattgataaaaatggaaataacatttctgtaaattatgaatctcag
attgttaatcctgcaaaaaaacaattaatcaatcttataattacgtcatc
tatttattttataatgcttaatatactagcattgattatgaacaaaagat
gggataagtattatgcaaaaatgaaaaatgaaatcaaagaatttgaggat
aatgcaaagatcttgataaaaaatcaaagaagaaaagcgaggaattatc
ggagctgcgaaagaccttgaaccaagcgtttgaggaaactgataggataa
aatatcatgagaagaaaaacaaatcctcctcttagctaagttaaacgat
tataaaaagaactaaccttttggagaaatacaataagaaagttcttta
tgaacttcctgatggagataaaaaagcagataaactaatagggacag
```

The nucleotide sequence of the phrK deletion construct is:

(SEQ ID NO: 100)
```
gatgaaatggaagaagatcaagaagttcttgcgtattatagtctattaga
agaaagacataaaatgttgctgcattcttcacgaggagagcctttacaaa
agcacacctatttactgaagacaatcaaaacttcataacaaaaacaaat
gataaattagaatacaacttttattttatttgaagcaatgtacgaggcata
caacaaaaactatgatcgagcaattaacctatatggattagctgagaaaa
agcttgcagaaattccagatgaaattgaagcagctgaattttactctaaa
gtctcttacttatatactcttgttaaacaaagcattgtggcacaacatta
tataaaaaatgcaatttcaatatataagcgacaccctgattataaatgca
aactagctacatcaacaatgattgcagctgcaaactatgctgatatgaaa
cgatttgaggaagcagaacaatattacttagaagcaattgatattgcaaa
agaaacaaaagatgaattttaaaagctcaattattcacaatcttagta
tcgtttattctgattggaacaaacctgataaatgcattgaatctcttgaa
aaagcaataggaaatgaatcttggttacattcgatttattatataaattc
tttattcatgatgattaaagaactctttaaaattgacgaaaaatgaaag
ccattaattttacaataaagcacaggaaagactcatatttaatggagaat
aaagtatacgaagccaaaatcagcatcctgtataaccttattgtgggga
attaaaaaataatttcaataattgtattagtaatattgagttttaaaac
agcaaaatgaacttgaaagtgtagatgaattgtcctacatagctgcaaaa
aggtttgaatcaataggtgcttttgaagaagcaacgagcttttcaatgc
gaaaatttgggctgaacagaaaatgaatcaggtggagggaatcttatgaa
aaaacttgtgctttgcgtatctattttagctgtgattttaatcgacggta
tcgataagctggatccataacttcgtataatgtatgctatacgaagttat
ctagataaaaaatttagaagccaatgaaatctataaataaactaaattaa
gtttatttaattaacaactatggatataaaataggtactaatcaaaatag
tgaggaggatatatttgaatacatacgaacaaattaataaagtgaaaaaa
atacttcggaaacatttaaaaaataaccttattggtacttacatgtttgg
atcaggagttgagagtggactaaaaccaaatagtgatcttgacttttag
tcgtcgtatctgaaccattgacagatcaaagtaaagaaatacttatacaa
aaaattagacctatttcaaaaaaaataggagataaaagcaacttacgata
tattgaattaacaattattattcagcaagaaatggtaccgtggaatcatc
ctcccaaacaagaatttatttatggagaatggttacaagagctttatgaa
caaggatacattcctcagaaggaattaaattcagatttaaccataatgct
ttaccaagcaaaacgaaaaaataaaagaatatacgaaattatgacttag
aggaattactacctgatattccattttctgatgtgagaagagccattatg
gattcgtcagaggaattaatagataattatcaggatgatgaaaccaactc
tatattaactttatgccgtatgattttaactatggacacgggtaaaatca
taccaaaagatattgcgggaaatgcagtggctgaatcttctccattagaa
cataggggagagaattttgttagcagttcgtagttatcttggagagaatat
tgaatggactaatgaaaatgtaaatttaactataaactatttaaataaca
gattaaaaaaattataaaaaaaattgaaaaaatggtggaaacacttttttc
aattttttgttttattatttaatatttgggaaatattcattctaattgg
taatcagattttagaaaacaataaacccttgcatatgtctagataacttc
gtataatgtatgctatacgaagttatgcggccgccatatgcatcctaggc
```

-continued

```
caaaaggttgattaattaatttagccctactcaaacatttgagtgggctt ttattttatgatttatgtccaccggtcagccctgctctgtggagcgcagt acctgcaaacgtaactgagatacttctcactgtttttgcccgagtaaaa cttattaaagaacatcaagcaacacttataaatatccatcgtgatatttg tgggaaaatcaattgttttggatcgatgaaaaccaccgccaagctcatct ttactgtatccaattcctagacttattgttcgaccaactttattatatgt acgtgccettcttgcgacttcctcacaaatctccaagagcacagcttaa tctcttctctctttgtataatccctaaacaaaatctgactcttaccaaaa ctaatctgccectgcatcaatggagctcctatttcagataaatcaattcc gtgagcatgatagtacaactggtttcccattattccgaacttcttttcaa gcagctctaaaggaaatttagctaactgacctacagttgatatacccatt cgattcagatttctttccatcctccctcctatccccacattttagacaa aggtcgaactttccagagtctatttggcacatcttcatatctccaacgtg caataccactctttgttttcttactctccaggtcaagtgcaagcttacta agcaacatattgtcaccaattccaactgtgcacatcaaaccaaattctct ccacatgctgctttggattgctttggccatttcttcaggattctcttttc ctgcatctaaaaaagattaatcaattgaatacgtgtggacacattttca ggaacaaatctgtaaaacagctttgtaatctcagttgaaactctgatgaa aagcttcatttgtggatttacaatgtatattcttggatcttcaggtatct caaatagtctcgat
```

Example 2

Protease Expression in *Bacillus* sp. Cells

BG2942 precursor host cells (ΔnprE, degU(Hy)32, amyE::[PxylRA-comK eryR]) and the derived modified strains BG2942phrA::spc (CB2-1), BG2942phrE::spc (CB2-2), BG2942 phrC:spc (CB2-3), BG2942 phrF:spc (CB2-4), BG2942 phrG:spc (CB2-5), BG2942 phrI:spc (CB207) and BG2942 phrC:spc (CB2-8) were streaked onto Luria-Bertani medium-1.6% skim milk plates for overnight growth at 37° C. For each strain, single colonies were then inoculated into 10 ml of Luria-Bertani medium and grown over-night at 30° C. The pre-cultures were used to inoculate 25 ml of freshly prepared 2×SNB medium in a 250-ml flask. This medium contained the following (per liter): 16 g of Difco nutrient broth, 50 ml of 10% maltrin M150, and 40 ml of 25×SNB salts (25× salts contain [per liter] 3.7 g of CaCl$_2$.2H$_2$O, 9.6 mg of FeSO$_4$.7H$_2$O, 6 mg of MnCl$_2$.4H$_2$O, 25.0 g of KCl, and 3.26 g of MgSO$_4$.7H$_2$O). The strains were grown for nine hours and samples were taken at hourly intervals. The supernatants were tested for AprE expression and activity.

Each of the *Bacillus subtilis* cultures was assayed for the production of the native subtlisin AprE (Swiss-Prot:P37562): MRSKKLWISLLFALTLIFTMAFSNMSVQAAGKSSTE-KKYIVGFKQTMSAMSSAKKKDVISEKGGKVQKQFK-YVNAAAATLDEKAVKELKKDPSVAYVEEDHIAHEY-AQSVPYGISQIKAPALHSQGYTGSNVKVAVIDSGIDS-SHPDLNVRGGASFVPSETNPYQDGSSHGTHVAGTIA-ALNNSIGVLGVSPSASLYAVKVLDSTGSGQYSWIING-IEWAISNNMDVINMSLGGPTGSTALKTVVDKAVSSG-IVVAAAAGNEGSSGSTSTVGYPAKYPSTIAVGAVNSS-NQRASFSSAGSELDVMAPGVSIQSTLPGGTYGAYNG-TSMATPHVAGAAALILSKHPTWTNAQVRDRLESTAT-YLGNSFYYGKGLINVQAAAQ (SEQ ID NO:21) The enzyme produced was assayed for activity against the substrate, succinyl -L-Ala-L-Ala-L-Pro-L-Phe-p-nitroanalide (AAPF). The assay measured the production of protease as the increase in absorbance at 405 nm/min resulting from the hydrolysis and release of p-nitroanaline (Estell et al., J Biol. Chem., 260:6518-6521 (1985)). The measurements were made using the Sofmax Pro software, and the specified conditions were set as: Type: Kinetic; Reduction: Vmax Points (Read best 15/28 points); Lm1: 405 nm; Time: 5 minutes; and Interval: 11 Seconds. Twenty microliters of each of the *B. subtilis* supernatants were diluted in 100 ul of Tris Buffer, containing 10 mM Tris+0.005% TWEEN®-80, pH 8.6; and 25 ul of 100 mg/ml AAPF. Assays were done in microtiter plates and the Softmax Pro Software was used.

Figure 3:
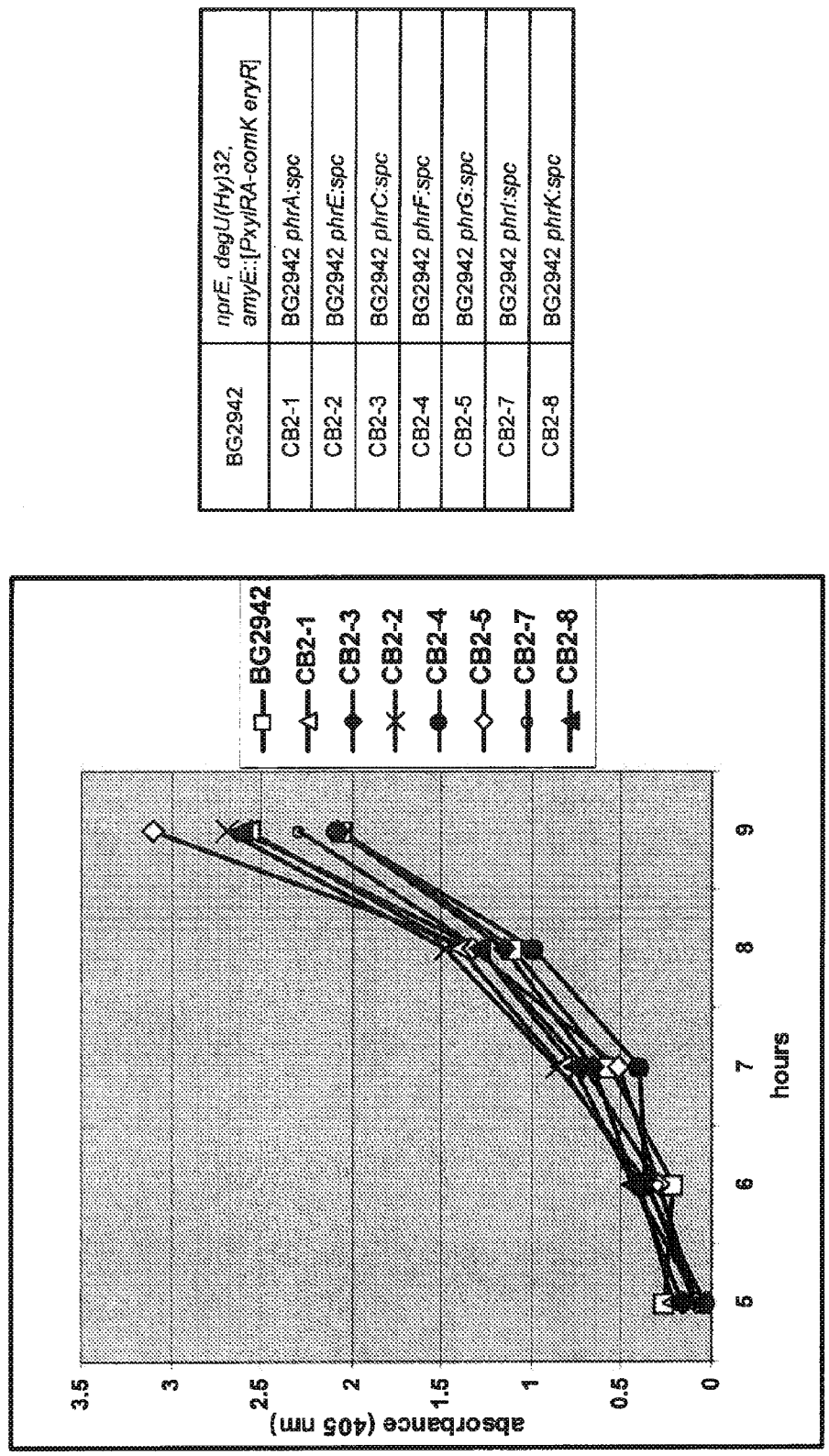
FIG. 3 shows the production of the AprE protease in the modified *Bacillus subtilis* strains that comprise a deletion of the phrA, phrE, phrC, phrF, phrG, phrI, and phrK.

The relative amounts and the activities of the AprE protease produced by the unmodified precursor strain BG2942 and from each of the modified strains CB2-1,2-2, 2-3,2-4, 2-5, 2-7, and 2-8 were determined and graphed as a function of absorbance (A405 nm) as shown in FIG. 3. The results for the BG2942 derived strains (CB2-1 and CB2-2) carrying the deletion of the phrA and phrE genes, respectively, are also shown in FIG. 4.

Figure 4:
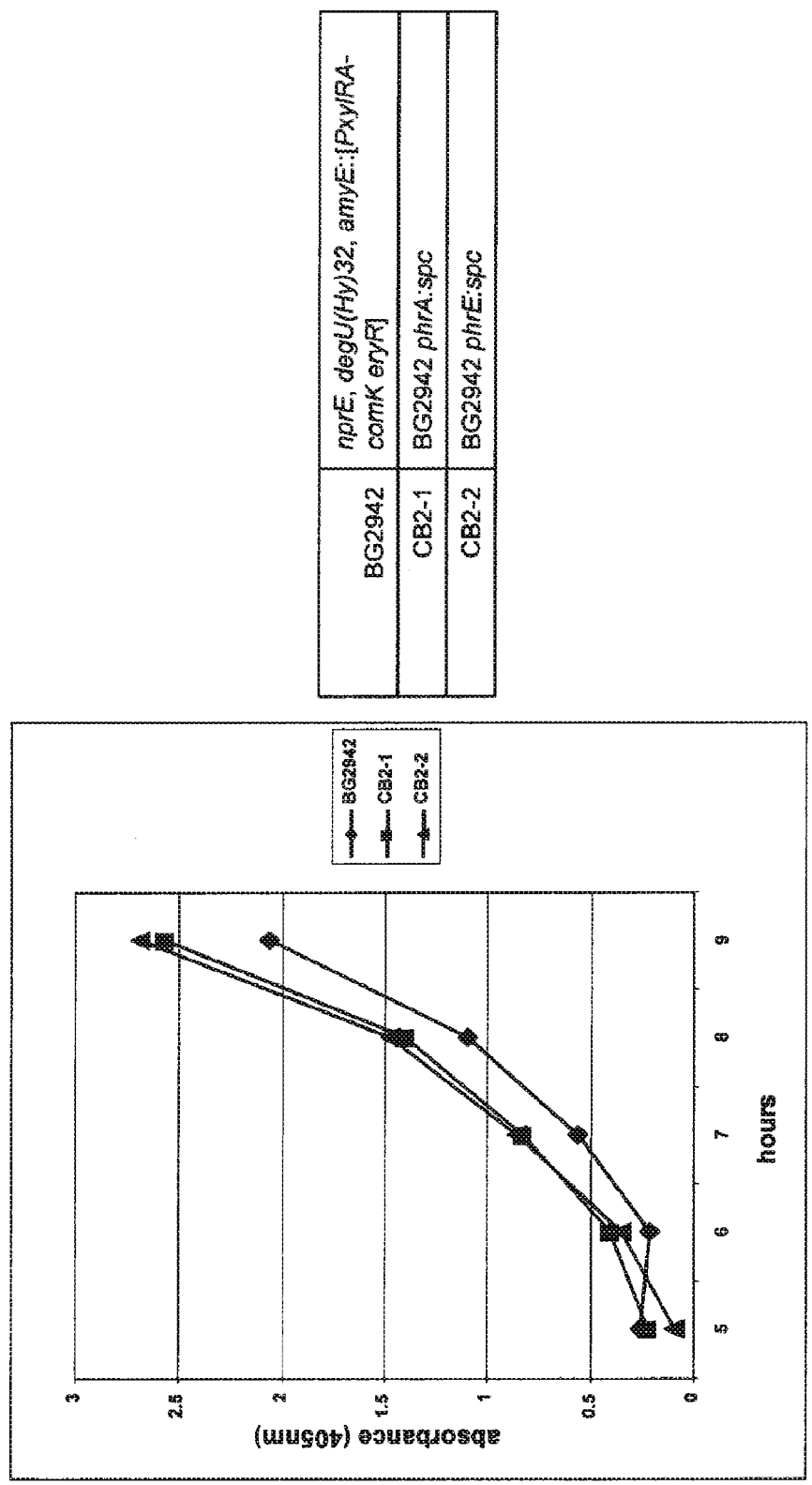
FIG. 4 is a graph showing the production of AprE in the control *Bacillus subtilis* parent strain BG2942 (diamonds) and in the modified *Bacillus subtilis* strains CB2-1 (squares) and CB2-2 (triangles), which respectively contain the deletion of the phrA and the phrE gene.

The data shown in FIGS. 3 and 4 show that that the deletion of phrA, phrE, phrC, phrG, phr I and phrK increases AprE expression in the modified CB2-1, CB2-2, CB2-3, CB2-5, CB2-7 and CB2-8 *Bacillus* sp. cells when compared to the production in the unmodified parent strain BG2942 (diamonds).

Example 3

Protease Expression in *Bacillus* sp. Cells Containing a Deletion of the phrA or the phrE Gene The inactivation constructs cassettes of phrA and phrE (SEQ ID NOS:17 and 18, respectively) were introduced into the *Bacillus subtilis* strain CF471. The CF471 strain is the BG3594 strain described above (degU(Hy)32, oppA, ΔspoIIE, ΔaprE, ΔnprE) and that further comprises the PaprE-FNA expression construct (SEQ ID NO:19), which encodes for the protease FNA (SEQ ID NO:20). The resulting modified strains CB3-47 (BG3594 phrA::spcR, aprE:[PaprE-FNA, cat]), and CB3-48 (BG3594 phrE::spcR, aprE:[PaprE-FNA, cat]) were grown in autoclaved suitable growth medium for 50 hours. Samples of the cell culture were centrifuged, and the production of protease was quantified as a function of the activity of the secreted FNA protease present in the supernatants according to the AAPF assay described above.

Figure 5:
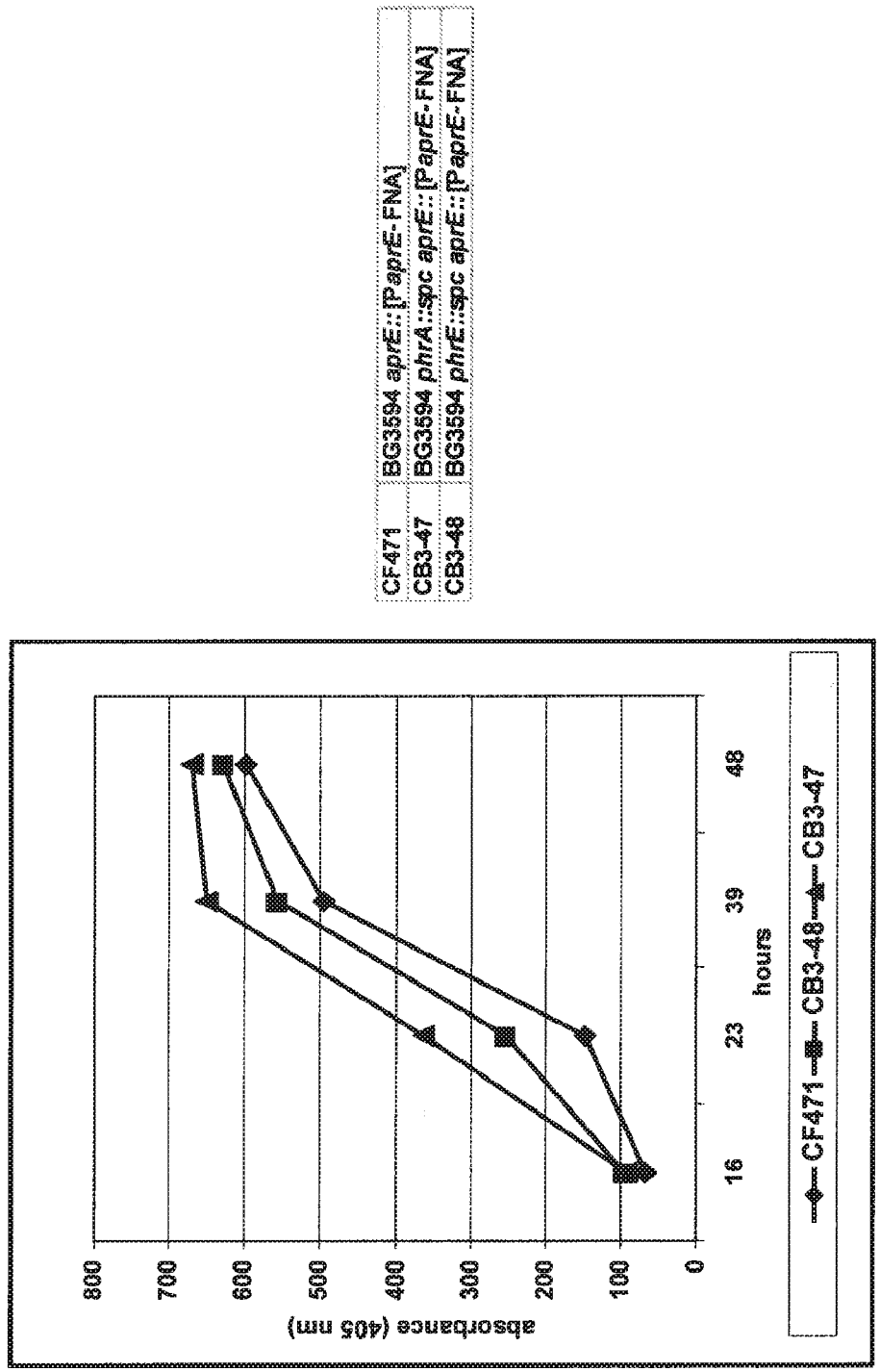
FIG. 5 is a graph showing the production of the protease FNA in the parent *B. subtilis* strain CF471 (diamonds), and in the modified *Bacillus subtilis* strains CB3-48 (squares) and CB3-47 (triangles), which respectively contain the deletion of the phrE and the phrA gene.

The results are graphed in FIG. 5, and they show that the modified cells carrying deletions of the phrA (triangles) and the phrE (squares) genes produce PaprE dependent FNA protease expression at a greater level than that produced by the unmodified parent strain CF471 (BG3594, aprE::[PaprE-FNA]; diamonds), which does not contain a deletion of either phrA and/or phrE.

Therefore, deleting phrA and phrE in a *Bacillus* sp. cell (e.g., a *Bacillus subtilis* cell), enhances the level of production of the protease FNA.

Example 4

Figure 6:
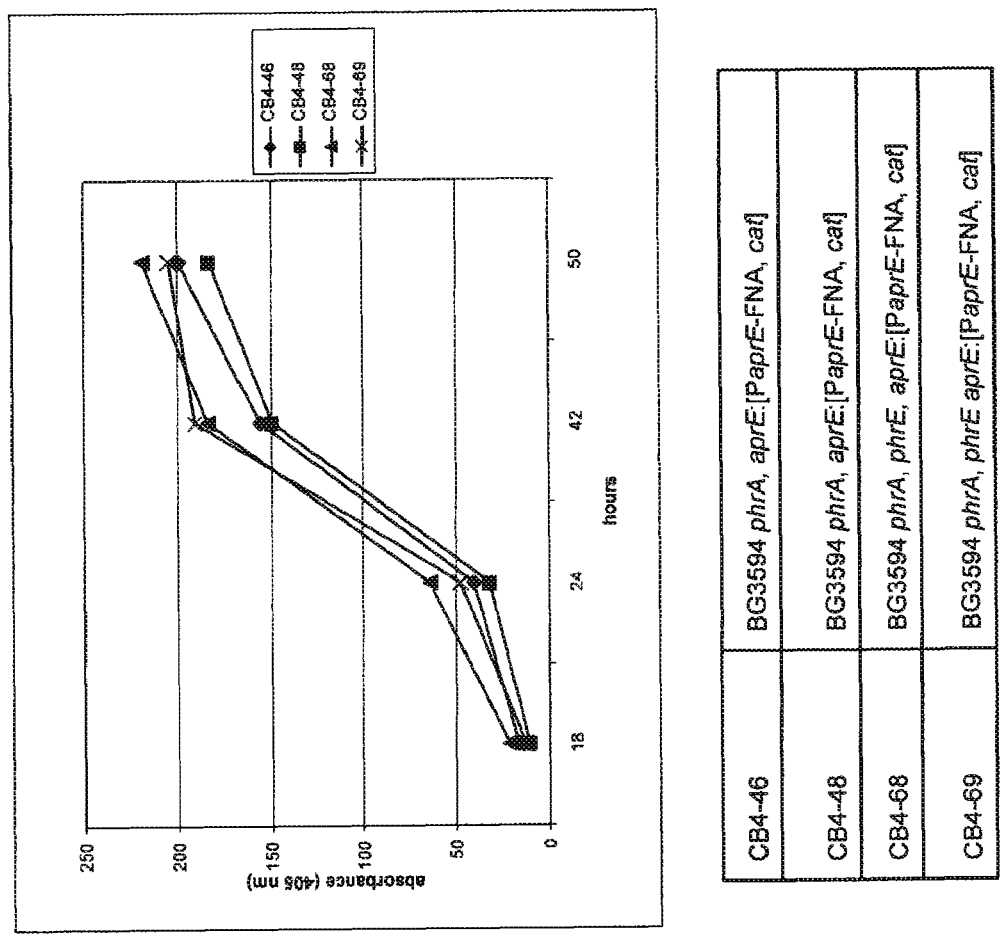
FIG. 6 is a graph showing a combined effect of deleting phrA and phrE gene on protease production in *Bacillus subtilis*.

Protease Expression in *Bacillus* sp. Cells Containing Deletions of phrA and phrE Genes The spectinomycin cassette associated with the deletion of phrA was removed through the lox recombination system in strain CF471 (BG3594, aprE::[PaprE-FNA]). The resulting strain was transformed with the construct carrying the deletion of the phrE gene. After the antibiotic resistance cassette was removed the strain was tested for PaprE dependent protease expression. FIG. 6 shows a graph of protease expression in the double phr deleted strains (CB4-68: BG3594 phrA, phrE, aprE:[PaprE-FNA, cat]; triangles, CB4-69: BG3594 phrA, phrE aprE:[PaprE-FNA, cat]; crosses) compared to the phrA deleted strains (CB4-46: BG3594 phrA, aprE:[PaprE-FNA, cat]; diamonds, CB4-48: BG3594 phrE, aprE:[PaprE-FNA, cat]; squares). The BG3594 derived strains carrying the deletion of the two phrA and phrE genes were grown in suitable growth medium for 50 hours and the supernatants were tested in an AAPF assay.

The strains carrying both deletions of the phrA and phrE genes (i.e., strains CB4-68 and CB4-69 showed an increase in FNA production when compared to the production by the strains CB4-46 and CB4-48, which both carried the deletion of only the phrA gene).

Therefore, deleting the phrA and the phrE genes from a Bacillus sp. cell (e.g., Bacillus subtilis) enhances the level of production of FNA when compared to the level of production by the Bacillus subtilis cells that were modified to contain the deletion of only the phrA gene.

Example 5

Overexpression of YmaH: Generation of SigA and SigH Polynucleotide Constructs

Polynucleotide constructs SigH, SigA1, SigA2, and SigA3 were generated to overexpress YmaH in host cells of Bacillus subtilis.

Figure 7:
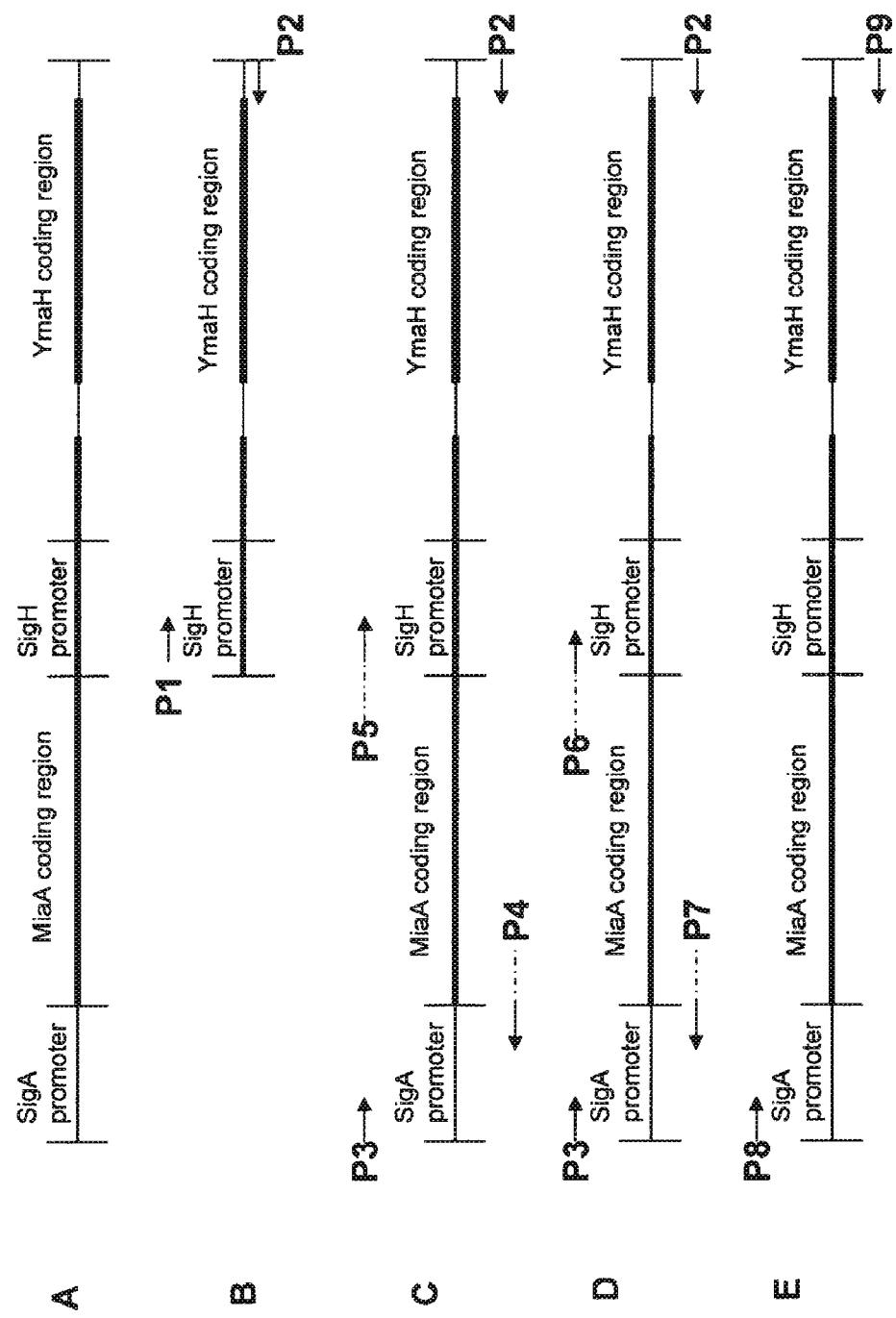
FIG. 7 illustrates the location of primers used for generating polynucleotide constructs used to overexpress YmaH in *Bacillus subtilis*. Panels B-E show the position of the primers used to generate construct SigH (panel B), and SigA constructs SigA1 (panel C), SigA2 (panel D) and SigA3 (panel E) relative to the *Bacillus* chromosomal sequence of the miaA operon of *Bacillus subtilis* (base pairs 1865428-1867019 of the *Bacillus subtilis* strain 168; NCBI accession number NC000964), which is illustrated in Panel A. Primer pairs P4-P5 and P6-P7 are fusion primers, which comprise a "tail" of base pairs at their 5' end that are homologous to the sequence being directly amplified, and are complementary to each other. The complementary tails of the fusion primers allow fusion of the amplified Sigma A promoter DNA to the amplified YmaH-encoding DNA to obtain chimeric polynucleotides containing the Sigma A promoter sequence adjacent to the YmaH-encoding sequence while deleting most, or all, of the miaA coding sequence.

PCR primers were designed to be homologous to the Bacillus subtilis genome (FIG. 7A) and to contain a 6 base pair restriction enzyme site located 6 base pairs from the 5' end of the primer. Primers were designed to engineer unique restriction sites at the upstream and downstream ends of the construct. The primary source of genome sequence (Kunst et al, Nature 390:249-256 [1997]), gene localization, and start and stop codon information was obtained from the NCBI Database: Completed Bacillus subtilis subsp. subtilis str. 168, or from the SubtiList World Wide Web Server known to those in the art (Moser, I. 1998. FEBS Lett. 430(1-2):28-36). The sequence considered is reported as SEQ ID NO:22 with coordinates 1 865428-1867019 in the NCBI database, ACC No NC000964 is shown in FIG. 7A.

(SEQ ID NO: 22)
tcatacctgaaaggaaagacaagggaaattgtcggcaatgagccgctcg gcaggtagaaggatgtttaccgatgcaaaaaagggcaaaatggataggt ggttgtccatgttgaatgctataatggggagatttataaaagagagtga tacatattgaataatacgaagcagcccgttgtcattttagtcggaccgac ggcagtggggaaaaccaatttaagtattcagctagccaaatccttaaacg cggaaattatcagcggagattcgatgcagatttataaagggatggatatt ggaacagctaaaattaccgaacaggagatggagggagtgccccatcatct gattgacattttagatcccaagactcttttctctactgccgattatcaaa gcttagtaagaaataaaatcagcgagattgcaaatagaggaaagcttccg atgattgacggcggtacagggctttatatacaatctgagctttacgatta -continued
tacatttacggaagaggcaaatgatcccgtgtttcgagagagcatgcaaa tggctgctgagcgggaaggcgctgactttcttcatgccaaacttgctgca gcagatcccgaggcagcagctgcgattcatccgaataatacaagaagagt cattcgcgcactggaaatttacatacgtccggaaaaacgatgtcccagc atttgaaggaacaaaaacgagaacttctgtacaatgcagtgttaattggc ctgacaatggatagagacacgctttacgaaagaattaatcagcgggtcga tttgatgatgcagtcaggccttcttccggaagtgaaacgcttatacgaca agaacgtgagagactgtcaatcaatacaggcgataggctataaagagctg tatgcatattttgacggttttgtgacactttccgatgctgtcgaacagct aaagcagaactcgaggcggtatgcgaaacgccagctgacgtggtttcgca acaaaatgcaggtcacatggttcgatatgacaccgcctgttgatatggag ctgaaaaaaaggaaattttcacacatatagcaggaaaactcgaacttta atcgaaactgtatgatatagagaatcaaggaggacgaaacatgaaaccga ttaatattcaggatcagttttgaatcaaatccggaaagaaaatacgtat gtcactgttttttgctgaacggctttcagttgcggggccaggtgaaagg ctttgataactttaccgtattgttggaatcggaaggtaagcagcagctta tatataaacatgcgatctcaacgtttgcgccgcaaaaaaacgtccagctt gaactcgaatagatcaaaaaatgccatgtcaagacatgaggaaaggctgt cgggggttcccggcggccattttaacatgaatccacttttgctccaagc tttttgtgtaagctgaccatgccaaggcacggtctttttttatgag.

The SigH construct (FIG. 5B; SEQ ID NO:23)

(SEQ ID NO: 23)
ggcaccgaattcgacgtggtttcgcaacaaaatgcaggtcacatggttcg atatgacaccgcctgttgatatggagctgaaaaaaaggaaattttcaca catatagcaggaaaactcgaactttaatcgaaactgtatgatatagagaa tcaaggaggacgaaacatgaaaccgattaatattcaggatcagttttga atcaaatccggaaagaaaatacgtatgtcactgttttttgctgaacggc tttcagttgcggggccaggtgaaaggctttgataactttaccgtattgtt ggaatcggaaggtaagcagcagcttatatataaacatgcgatctcaacgt ttgcgccgcaaaaaaacgtccagcttgaactcgaatagatcaaaaaatgc catgtcaagacatgaggaaaggctgtcgggggttcccggcggccattttt aacatgaatccacttttgctccaagcttttgtgtaagctgaccatgcca aggcacggtctttttttatgagggatccggagcc was generated to comprise the polynucleotide sequence encompassing the Sigma H promoter aaaggaaattttcacacatatagcaggaaaactcgaactttaatcgaaactgtatgatatagagaatcaaggaggacgaaac; SEQ ID NO:48, and the adjacent sequence atgaaaccgattaatattcaggatcagttttgaatcaaatccggaaagaaaatacgtatgtcactgttttttgctgaacggctttcagttgcggggccaggtgaaaggctttgataactttaccgtattgttggaatcggaaggtaagcagcagcttatatataaacatgcgatctcaacgtttgcgccgcaaaaaaacgtccagcttgaactcgaatag; SEQ ID NO:46 (NP_389616), encoding the YmaH protein MKPINIQDQFLNQIRKENTYVTVFLLNGFQLRGQVKGFDNFTVLLESEGKQQLIYKHAISTFAPQKNVQLELE; SEQ ID NO: 45 (Swiss-Prot:P3756). The Sigma H promoter is naturally located within the polynucleotide sequence encoding the miaA gene, close to the 3' end of the gene, and immediately upstream of the ymaH gene. The entire Sigma H promoter and adjacent ymaH coding sequence was amplified by PCR using the forward primer P1: ggcaccgaattcgacgtggtttcgcaa-caaaatgcag (SEQ ID NO:24; position 987 to 1011 of SEQ ID N0:22), with an EcoRI restriction site added at the 5' end, and a reverse primer P2: ggcaccggatccctcataaaaaaagaccgtgccttgg (SEQ ID NO:25, at position 1472 to 1496 of SEQ ID NO:22), with and added BamHI restriction site (FIG. 7B).

The SigA1 and SigA2 constructs were generated in a three step process by 1) amplifying individual fragments of *Bacillus subtilis* chromosomal DNA, 2) purifying and assembling the fragments; and 3) amplifying the assembled product by PCR.

The SigA1 construct (FIG. 7C; SEQ ID NO:26)

```
                                          (SEQ ID NO: 26)
gcgccgaattctcatacccctgaaaggaaagacaagggaaattgtcggcaa tgagccgctcggcaggtagaaggatgtttaccgatgcaaaaaagggcaa aatggataggtggttgtccatgttgaatgctataatgggggagatttata aaagagagtgatacatattgaataatacgaagcagccccacacatatagc aggaaaactcgaactttaatcgaaactgtatgatatagagaatcaaggag gacgaaacatgaaaccgattaatattcaggatcagtttttgaatcaaatc cggaaagaaaatacgtatgtcactgtttttttgctgaacggctttcagtt gcggggccaggtgaaaggctttgataaacttaccgtattgttggaatcgg aaggtaagcagcagcttatatataaacatgcgatctcaacgtttgccg caaaaaaacgtccagcttgaactcgaatagatcaaaaatgccatgtcaa gacatgaggaaaggctgtcggggttcccggcggccatttttaacatgaa tccacttttgctccaagcttttgtgtaagctgaccatgccaaggcacgg tcttttttatgagggatccggtgcc
``` was generated using two sets of primers. A first set of primers: forward primer P3: gcgccgaattctcatacccctgaaaggaaagacaagg (SEQ ID NO:27) located at the 5' end of SEQ ID NO:22; and reverse primer P4: ttcgagttttcctgctatatgt-gtggggctgcttcgtattattcaatatg (SEQ ID NO:28) located from bp 153 to bp 177 on the SEQ ID NO:22, was used to amplify a first fragment containing the SigA promoter, Ribosome Binding Site, start codon and the first few codons of the miaA gene

```
                                         SEQ ID NO: 49
ttgaataatacgaagcagcccgttgtcattttagtcggaccgacggcagt ggggaaaaccaatttaagtattcagctagccaaatccttaaacgcggaaa ttatcagcggagattcgatgcagatttataaagggatggatattggaaca gctaaaattaccgaacaggagatggagggagtgccccatcatctgattga catttagatccccaagactctttctctactgccgattatcaaagcttag taagaaataaaatcagcgagattgcaaatagaggaaagcttccgatgatt gacggcggtacagggctttatatacaatctgagctttacgattatacatt tacggaagaggcaaatgatcccgtgtttcgagagagcatgcaaatggctg ctgagcgggaaggcgctgactttcttcatgccaaacttgctgcagcagat cccgaggcagcagctgcgattcatccgaataatacaagaagagtcattcg
```

```
                                         -continued
cgcactggaaattttacatacgtccggaaaaacgatgtcccagcatttga aggaacaaaaacgagaacttctgtacaatgcagtgttaattggcctgaca atggatagagacacgctttacgaaagaattaatcagcgggtcgatttgat gatgcagtcaggccttcttccggaagtgaaacgcttatacgacaagaacg tgagagactgtcaatcaatacaggcgataggctataaagagctgtatgca tattttgacggttttgtgacactttccgatgctgtcgaacagctaaagca gaactcgaggcggtatgcgaaacgccagctgacgtggtttcgcaacaaaa tgcaggtcacatggttcgatatgacaccgcctgttgatatggagctgaaa aaaaggaaattttcacacatatagcaggaaaactcgaacttttaa;.
```

A second set of primers, forward primer P5: catattgaataatac-gaagcagcccacacatatagcaggaaaactcgaa (SEQ ID NO:29) located from bp 1071 to bp 1095 on the SEQ ID NO:22 and reverse primer P2 (SEQ ID NO:25), were used to amplify a second fragment containing the DNA sequence encoding the YmaH protein. Reverse primer P4 and forward primer P5 are fusion primers that were designed to contain tails that are complementary to each other but that are not homologous to the sequence that is being amplified to eliminate the intervening miaA coding sequence. The two fragments were annealed, and the resulting SigA1 construct contained the SigA promoter (SEQ ID NO:47) tcatacccctgaaaggaaaga-caagggaaattgtcggcaatgagc-cgctcggcaggtagaaggatgtttaccgatgcaaaaaag ggcaaaatggatag-gtggttgtccatgttgaatgctataatgggggagatttataaaagagagtgatacata; (SEQ ID NO:47), the ribosome binding site aagagag; SEQ ID NO:50, and the transcription start site of the miaA gene. The SigA1 construct was amplified using forward primer P3 (SEQ ID NO:27) and reverse primer P2 (SEQ ID NO:25), which respectively contain an EcoRI and a BamHI restriction site, and ligated into the polylinker of replicating plasmid pBS19. The polynucleotide sequence of pBS19 is shown below (SEQ ID NO:30). The pBS19 plasmid can replicate in *E. coli* and *Bacillus subtilis*, and carries the chloamphenicol resistance selection marker gene.

```
                                         (SEQ ID NO: 30)
gaattcgagctcggtaccggggatcctctagagtcgacctgcaggcatg caagcttggcgatcctgcctcgcgcgtttcggtgatgacggtgaaaacct ctgacacatgcagctcccggagacggtcacagcttgtctgtaagcggatg ccgggagcagacaagcccgtcagggcgcgtcagcgggtgttggcgggtgt cggggcgcagccatgacccagtcacgtagcgatagcggagtgtatactgg cttaactatgcggcatcagagcagattgtactgagagtgcaccatatgcg gtgtgaaataccgcacagatgcgtaaggagaaaataccgcatcaggcgct cttccgcttcctcgctcactgactcgctgcgctcggtcgttcggctgcgg cgagcggtatcagctcactcaaaggcggtaatacggttatccacagaatc aggggataacgcaggaaagaacatgtgagcaaaaggccagcaaaaggcca ggaaccgtaaaaaggccgcgttgctggcgtttttccataggctccgccc cctgacgagcatcacaaaaatcgacgctcaagtcagaggtggcgaaaccc gacaggactataaagataccaggcgtttccccctggaagctccctcgtgc gctctcctgttccgaccctgccgcttaccggatacctgtccgcctttctc
```

-continued

```
ccttcgggaagcgtggcgctttctcatagctcacgctgtaggtatctcag ttcggtgtaggtcgttcgctccaagctgggctgtgtgcacgaacccccg ttcagcccgaccgctgcgccttatccggtaactatcgtcttgagtccaac ccggtaagacacgacttatcgccactggcagcagccactggtaacaggat tagcagagcgaggtatgtaggcggtgctacagagttcttgaagtggtggc ctaactacggctacactagaaggacagtatttggtatctgcgctctgctg aagccagttaccttcggaaaaagagttggtagctcttgatccggcaaaca aaccaccgctggtagcggtggttttttgtttgcaagcagcagattacgc gcagaaaaaaggatctcaagaagatcctttgatcttttctacggggtct gacgctcagtggaacgaaaactcacgttaagggattttggtcatgagatt atcaaaaggatctggagctgtaatatataaaccttcttcaactaacggg gcaggttagtgacattagaaaaccgactgtaaaaagtacagtcggcatta tctcatattataaaagccagtcattaggcctatctgacaattcctgaata gagttcataaacaatcctgcatgataaccatcacaaacagaatgatgtac ctgtaaagatagcggtaaatatattgaattacctttattaatgaattttc ctgctgtaataatgggtagaaggtaattactattattattgatatttaag ttaaacccagtaaatgaagtccatggaataatagaaagagaaaaagcatt ttcaggtataggtgttttgggaaacaatttccccgaaccattatatttct ctacatcagaaaggtataaatcataaaactctttgaagtcattcttttaca ggagtccaaataccagagaatgttttagatacaccatcaaaaattgtata aagtggctctaacttatcccaataacctaactctccgtcgctattgtaac cagttctaaaagctgtatttgagtttatcacccttgtcactaagaaaata aatgcagggtaaaatttatatccttcttgttttatgtttcggtataaaac actaatatcaatttctgtggttatactaaaagtcgtttgttggttcaaat aatgattaaatatctcttttctcttccaattgtctaaatcaattttatta aagttcatttgatatgcctcctaaattttatctaaagtgaatttaggag gcttacttgtctgctttcttcattagaatcaatcctttttaaaagtcaa tattactgtaacataaatatatattttaaaaatatcccactttatccaat tttcgtttgttgaactaatgggtgctttagttgaagaataaaagaccaca ttaaaaaatgtggtcttttgtgttttttaaaggatttgagcgtagcgaa aaatccttttctttcttatcttgataataagggtaactattgccggttgt ccattcatggctgaactctgcttcctctgttgacatgacacacatcatct caatatccgaatagggcccatcagtctgacgaccaagagagccataaaca ccaatagccttaacatcatccccatatttatccaatattcgttccttaat ttcatgaacaatcttcattcttcttctctagtcattattattggtccat tcactattctcattcccttttcagataattttagatttgcttttctaaat aagaatatttggagagcaccgttcttattcagctattaataactcgtctt cctaagcatccttcaatccttttaataacaattatagcatctaatcttca acaaactggccgtttgttgaactactctttaataaaataattttttccgt tcccaattccacattgcaataatagaaaatccatcttcatcggcttttc gtcatcatctgtatgaatcaaatcgccttcttctgtgtcatcaaggttta atttttatgtatttcttttaacaaaccaccataggagattaacctttta cggtgtaaaccttcctccaaatcagacaaacgtttcaaattcttttcttc atcatcggtcataaaatccgtatcctttacaggatattttgcagtttcgt caattgccgattgtatatccgatttatatttatttttcggtcgaatcatt tgaacttttacatttggatcatagtctaatttcattgccttttccaaaa ttgaatccattgttttgattcacgtagttttctgtattcttaaaataag ttggttccacacataccaatacatgcatgtgctgattataagaattatct ttattatttattgtcacttccgttgcacgcataaaaccaacaagatttttt attaattttttttatattgcatcattcggcgaaatccttgagccatatctg acaaactcttatttaattcttcgccatcataaacattttttaactgttaat gtgagaaacaaccaacgaactgttggcttttgtttaataacttcagcaac aaccttttgtgactgaatgccatgtttcattgctctcctccagttgcaca ttggacaaagcctggatttacaaaaccacactcgatacaactttctttcg cctgtttcacgattttgtttatactctaatatttcagcacaatctttac tctttcagcctttttaaattcaagaatatgcagaagttcaaagtaatcaa cattagcgattttcttttctctccatggtctcacttttccacttttttgtc ttgtccactaaaacccttgattttttcatctgaataaatgctactattagg acacataatattaaaagaaacccccatctatttagttatttgtttagtca cttataactttaacagatggggttttttctgtgcaaccaattttaagggtt ttcaatacttttaaaacacatacataccaacacttcaacgcacctttcagc aactaaaataaaaatgacgttatttctatatgtatcaagataagaaagaa caagttcaaaaccatcaaaaaaagacaccttttcaggtgcttttttttatt ttataaactcattccctgatctcgacttcgttcttttttttacctctcggt tatgagttagttcaaattcgttcttttaggttctaaatcgtgttttct tggaattgtgctgttttatccttacctttgtctacaaacccttaaaaac gttttaaaggcttttaagccgtctgtacgttccttaag
```

The SigA2 construct (FIG. 7C; SEQ ID NO:31)

(SEQ ID NO: 31)
```
gcgccgaattctcatacccctgaaaggaaagacaagggaaattgtcggcaa tgagccgctcggcaggtagaaggatgtttaccgatgcaaaaaagggcaa aatggataggtggttgtccatgttgaatgctataatgggggagatttata aaagagagtgctcgaactttaatcgaaactgtatgatatagagaatcaag gaggacgaaacatgaaaccgattaatattcaggatcagttttttgaatcaa atccggaaagaaaatacgtatgtcactgtttttttgctgaacggctttca gttgcggggccaggtgaaaggctttgataactttaccgtattgttggaat cggaaggtaagcagcagcttatatataaacatgcgatctcaacgtttgcg ccgcaaaaaaacgtccagcttgaactcgaatagatcaaaaaatgccatgt caagacatgaggaaaggctgtcggggggttcccggcggccatttttaacat
```

-continued
gaatccacttttgctccaagcttttgtgtaagctgaccatgccaaggca cggtctttttttatgagggatccggtgcc was generated according to the method described for the construction of the SigA1 construct using the following primers (FIG. 7D). The first fragment containing the SigA promoter was amplified using forward primer P3 (SEQ ID NO:27) and reverse fusion primer P7:

(SEQ ID NO: 33)
catacagtttcgattaaagttcgagcactctcttttataaatctccccca located from bp 125 to bp 149 on the SEQ ID NO:22. The second fragment containing the DNA sequence encoding the YmaH protein was amplified using the forward fusion primer P6:

tggggagatttataaaagagagtgctcgaactttaatcgaaactgtatg (SEQ ID NO:32) located from bp 1090 to bp 1114 on the SEQ ID NO:22 and the reverse primer P2 (SEQ ID NO:25). The two fragments were annealed, and the resulting SigA2 construct contained the SigA promoter, the ribosome binding site GGAGG; SEQ ID NO:51) and the transcription start site of the ymaH gene.

The invention also encompasses a fourth SigA construct (SigA3; SEQ ID NO:22; FIG. 7E), which is generated by amplifying the miaA ymaH region of the *Bacillus* chromosomal DNA that includes a SigA promoter, the region encoding the MiaA protein, the a YmaH promoter and the region encoding the YmaH protein.

The SigA3 construct was generated using forward primer P8 gcgcgcgaattcagggaaattgtcggcaatgagccgctcggc (SEQ ID NO:34) and reverse primer P9 gcgcgccatggctgattcgtctcagt-tctgcttcactttca (SEQ ID NO:35). SEQ ID NO:34 places an EcoRI restriction site at the 5' end of the fragment, while SEQ ID NO:35 places a NcoI site at the 3' end. This allows to clone the fragment in the pBN3 vector reported as SEQ ID NO:36, shown below:

(SEQ ID NO: 36)
gacgtctaagaaaccattattatcatgacattaacctataaaaataggcg tatcacgaggccctttcgtcttcaagaattaattctcatgtttgacagct tatcatcgataagcttgcatgcctgcaggtcgactctagaggatccccgg gtaccgagctcgaattccttaaggaacgtacagacggcttaaaagccttt aaaaacgttttaaggggtttgtagacaaggtaaaggataaaacagcaca attccaagaaaacacgatttagaacctaaaaagaacgaatttgaactaa ctcataaccgagaggtaaaaaagaacgaagtcgagatcagggaatgagt ttataaaataaaaaaagcacctgaaaaggtgtctttttttgatggttttg aacttgttctttcttatcttgatacatatagaaataacgtcattttatt ttagttgctgaaaggtgcgttgaagtgttggtatgtatgtgttttaaagt attgaaaacccttaaaattggttgcacagaaaaacccccatctgttaaagt tataagtgactaaacaaataactaaatagatgggggtttcttttaatatt atgtgtcctaatagtagcatttattcagatgaaaaatcaagggttttagt ggacaagacaaaagtggaaagtgagaccatggagagaaaagaaaatcg ctaatgttgattactttgaacttctgcatattcttgaatttaaaaaggct gaaagagtaaaagattgtgctgaaatattagagtataaacaaaatcgtga aacaggcgaaagaaagttgtatcgagtgtggttttgtaaatccaggctttt gtccaatgtgcaactggaggagagcaatgaaacatggcattcagtcacaa aaggttgttgctgaagttattaaacaaaagccaacagttcgttggttgtt tctcacattaacagttaaaaatgtttatgatggcgaagaattaaataaga gtttgtcagatatggctcaaggatttcgccgaatgatgcaatataaaaaa attaataaaaatcttgttggttttatgcgtgcaacggaagtgacaataaa taataaagataattcttataatcagcacatgcatgtattggtatgtgtgg aaccaacttattttaagaatacagaaaactacgtgaatcaaaaacaatgg attcaattttggaaaaaggcaatgaaattagactatgatccaaatgtaaa agttcaaatgattcgaccgaaaaataaatataaatcggatatacaatcgg caattgacgaaactgcaaaatatcctgtaaaggatacggattttatgacc gatgatgaagaaaagaatttgaaacgtttgtctgatttggaggaaggttt acaccgtaaaaggttaatctcctatggtggtttgttaaaagaaatacata aaaaattaaaccttgatgacacagaagaaggcgatttgattcatacagat gatgacgaaaaagccgatgaagatggattttctattattgcaatgtggaa ttgggaacggaaaaattatttttattaaagagtagttcaacaaacgggcca gtttgttgaagattagatgctataattgttattaaaaggattgaaggatg cttaggaagacgagttattaatagctgaataagaacggtgctctccaaat attcttatttagaaaagcaaatctaaaattatctgaaaagggaatgagaa tagtgaatggaccaataataatgactagagaagaaagaatgaagattgtt catgaaattaaggaacgaatattggataaatatggggatgatgttaaggc tattggtgtttatggctctcttggtcgtcagactgatgggccctattcgg atattgagatgatgtgtgtcatgtcaacagaggaagcagagttcagccat gaatggacaaccggtgagtggaaggtggaagtgaattttgatagcgaaga gattctactagattatgcatctcaggtggaatcagattggccgcttacac atggtcaattttttctctattttgccgatttatgattcaggtggatactta gagaaagtgtatcaaactgctaaatcggtagaagcccaaacgttccacga tgcgatttgtgcccttatcgtagaagagctgtttgaatatgcaggcaaat ggcgtaatattcgtgtgcaaggaccgacaacatttctaccatccttgact gtacaggtagcaatggcaggtgccatgttgattggtctgcatcatcgcat ctgttatacgacgagcgcttcggtcttaactgaagcagttaagcaatcag atcttccttcaggttatgaccatctgtgccagttcgtaatgtctggtcaa ctttccgactctgagaaacttctggaatcgctagagaatttctggaatgg gattcaggagtggacagaacgacacggatatatagtggatgtgtcaaaac gcataccattttgaacgatgacctctaataattgttaatcatgttggtta cctgcctcgcgcgtttcggtgatgacggtgaaaacctctgacacatgcag ctcccggagacggtcacagcttgtctgtaagcggatgccgggagcagaca agcccgtcagggcgcgtcagcgggtgttggcgggtgtcggggcgcagcca tgacccagtcacgtagcgatagcggagtgtatactggcttaactatgcgg catcagagcagattgtactgagagtgcaccatatgcggtgtgaaataccg cacagatgcgtaaggagaaaataccgcatcaggcgctcttccgcttcctc -continued
```
gctcactgactcgctgcgctcggtcgttcggctgcggcgagcggtatcag ctcactcaaaggcggtaatacggttatccacagaatcaggggataacgca ggaaagaacatgtgagcaaaaggccagcaaaaggccaggaaccgtaaaaa ggccgcgttgctggcgttttccataggctccgcccccctgacgagcatc acaaaaatcgacgctcaagtcagaggtggcgaaacccgacaggactataa agataccaggcgtttccccctggaagctccctcgtgcgctctcctgttcc gaccctgccgcttaccggatacctgtccgcctttctcccttcgggaagcg tggcgctttctcatagctcacgctgtaggtatctcagttcggtgtaggtc gttcgctccaagctgggctgtgtgcacgaaccccccgttcagcccgaccg ctgcgccttatccggtaactatcgtcttgagtccaacccggtaagacacg acttatcgccactggcagcagccactggtaacaggattagcagagcgagg tatgtaggcggtgctacagagttcttgaagtggtggcctaactacggcta cactagaaggacagtatttggtatctgcgctctgctgaagccagttacct tcggaaaagagttggtagctcttgatccggcaaacaaaccaccgctggt agcggtggtttttttgtttgcaagcagcagattacgcgcagaaaaaagg atctcaagaagatcctttgatcttttctacgtgggtctgacgctcagtgg aacgaaaactcacgttaagggattttggtcatgagattatcaaaaaggat cttcacctagatccttttaaattaaaaatgaagttttaaatcaatctaaa gtatatatgagtaaacttggtctgacagttaccaatgcttaatcagtgag gcacctatctcagcgatctgtctatttcgttcatccatagttgcctgact ccccgtcgtgtagataactacgatacgggagggcttaccatctggcccca gtgctgcaatgataccgcgagacccacgctcaccggctccagatttatca gcaataaaccagccagccggaagggccgagcgcagaagtggtcctgcaac taatccgcctccatccagtctattaattgttgccgggaagctagagtaag tagttcgccagttaatagtttgcgcaacgttgttgccattgctacaggca tcgtggtgtcacgctcgtcgtttggtatggcttcattcagctccggttcc caacgatcaaggcgagttacatgatcccccatgttgtgcaaaaaagcggt tagctccttcggtcctccgatcgttgtcagaagtaagttggccgcagtgt tatcactcatggttatggcagcactgcataattctcttactgtcatgcca tccgtaagatgcttttctgtgactggtgagtactcaaccaagtcattctg agaatagtgtatgcggcgaccgagttgctcttgcccggcgtcaatacggg ataataccgcgccacatagcagaactttaaaagtgctcatcattggaaaa cgttcttcggggcgaaaactctcaaggatcttaccgctgttgagatccag ttcgatgtaaccactcgtgcacccaactgatcttcagcatcttttactt tcaccagcgtttctgggtgagcaaaaacaggaaggcaaaatgccgcaaaa aagggaataagggcgacacggaaatgttgaatactcatactcttcctttt tcaatattattgaagcatttatcagggttattgtctcatgagcggataca tatttgaatgtatttagaaaaataaacaaatagggggttccgcgcacattt ccccgaaaagtgccacct
```

All PCR reactions were performed in 50 ul volume containing 1-2 ul DNA or from a colony resuspension, 5 ul of 10×Pfu Ultra buffer (Stratagene), 1 uL of 10 mM dNTP blend (Roche), 0.5 uL of 0.2 uM primers, 1 ul Pfu Ultra High Fidelity Polymerase, and the volume adjusted with water to have a total volume of 50 ul. The PCR conditions were: 95° C. for 2 min, 30 cycles of 95° C. for 30 sec, 62° C. for 30 sec, 72° C. for 1 min, followed by 1 cycle of 72° C. for 10 min.

The obtained PCR fragments were gel purified using Qiagen Gel Purification Kit according to the manufacturers instructions.

Fusion constructs were obtained by annealing 0.25 ul aliquots of purified PCR fragments that were mixed together and added into fresh PCR mix following the above recipe using primers P3 and P2. The total volume of the PCR mixture was 50 µl. The PCR conditions were the same as above adjusting the annealing temperature according to the Tm of the primers.

The desired SigH, SigA1, and SigA2 constructs were ligated into pBS19 plasmids that had been digested with EcoRI and BamHI to generate SigA and SigH expression vectors that were used to transform host cells as described in Example 4.

The transformation mixture was plated on LB+1.6% skim milk+5 ug/ml cmp plates. The next day, halo-forming colonies were picked and plated for single colonies. The colony purification was performed twice. Five individual clones were analyzed by sequencing of aprE promoter region. All of them had consensus sequence at −35 region of aprE promoter.

Example 6

Host Cell Transformation and Expression of AprE Protease

Five microliters of the ligation mixture containing either the SigA1 or SigH constructs were used to transform *E. coli*Top10 cells (Invitrogen) by electroporation. The transformed cells were plated onto LB agar plates containing 5 ppm/ml chloramphenicol (Cm), and colonies were allowed to grow overnight at 37 C. Individual colonies were picked and transferred to tubes containing 5 ml of LB+5 ppm/ml Cm. Cultures were grown overnight at 37° C. while shaking at 250 rpm. Plasmid DNA was prepared from the *E. coli* cultures, and a portion of the plasmid DNA preparation was sequenced (Sequetech). Automated sequence analysis was performed using Phrep, Phrap, Consed, Custal W software.

The plasmid bearing the right construct from each of the expression vectors was used to transform *Bacillus subtilis* host cells. The expression vectors containing the SigH (SEQ ID NO:23) and SigA1 (SEQ ID NO:26) and SigA2 (SEQ ID NO:31) constructs were named pBS19 ymaH-H and pBS19 ymaH-A1 and pBS19 ymaH-A2 were transformed into *B. subtilis* strains BG2941 and BG2942 as follows. Two microliters of the plasmid DNA carrying the appropriate constructs were used to transform 100 µl of *B. subtilis* cells BG 2941 (ΔnprE, amyE::PxylRA-comK-phleoR) and BG2942 (ΔnprE, degU(Hy)32, amyE::PxylRA-comK-eryR). The BG2941 and BG2942 transformants carrying the SigH constructs were named 41SigH and 42SigH, respectively; and the BG2941 and BG2942 transformants carrying the SigA1 constructs were named 41SigA1 and 42SigA1, respectively. Some BG2941 and BG2942 host cells were also transformed with a control (empty) pBS19 plasmid, and were named 41pBS19 and 42pBS19. Both BG2941 and BG2942 host cells carry the deletion of the nprE gene, which abolishes most of the non-aprE background proteolytic activity, thus facilitating the measurement of the alkaline protease (AprE) produced. The BG2941 and BG2942 host cells also carry the cassette amyE::PxylRA-comK-phleoR, which allows to make competent cells by inducing a growing culture with xylose (Hahn et al., Mol. Microbiol. 18:755-67 [1995]). The BG2942 host cells also carry a mutation in the degU gene (degU(Hy)32 mutation), which alone increases the level of subtilisin secreted by the host cells by several fold relative to that secreted by host cells that do not carry the degU(Hy) mutation (Msadek et al. J Bacteriol, 172:824-834 [1990]).

The effect of overexpressing YmaH in *Bacillus* host cells was determined qualitatively and quantitatively in assays described in Example 7.

Example 7

Effect of Overexpressing YmaH on the Production of Protease

Casein assay:—The effect of overexpressing YmaH on the production of endogenous AprE subtilisin protease by *Bacillus* host cells was determined first by a qualitative assay that compares the size of the halos produced by the colonies grown on agar plates containing casein in the form of skim milk. As protease enzyme is secreted by the *Bacillus* cells, it digests the casein in the skim milk, and forms regions of clearing, or halos around the growing colony. Host cells which have an inactive protease will exhibit little or no halo around the colonies. Thus, the size of the halo provides a qualitative assessment of the amount of protease that is produced by the secreting colony (Wells, T. A. et al. Nucleic Acids Res., 11, 7911-7925: [1983]).

BG2941 and BG2942 *Bacillus subtilis* host cells transformed with SigH or SigA1 expression vectors were plated onto LB agar plates containing 1.6% skim milk and 5 ppm Cm, and incubated overnight in at 3° C. The following day, colonies from some of the transfomants were single colony isolated on LB agar plates with 5 ppm Cm, and the plates were incubated overnight at 37 C. Single colony isolates were picked and patched on the same type of plates and incubated again at 3° C. overnight.

The largest halos were produced by the 42SigH host cells. The 42SigH cells are BG2942 *Bacillus subtilis* host cells that carry the degU(Hy)32 mutation and the SigH construct that enables the overexpression of YmaH protein. In particular, the size of the halos of the 42SigH cells evidences that overexpressing ymaH further enhances the production of subtilisin in host cells that already produce levels of the enzyme that are greater than those produced by wild-type cells. For example, 42SigH cells produce halos that are bigger than those produced by the 42pBS19 cells, which carry the degU (Hy) mutation but do not carry a construct that enables overexpression of ymaH, but which in turn produce halos that are bigger than the halos produced by the 41pBS19 cells, which are BG2941 *Bacillus subtilis* host cells that do not carry the degU(Hy)32 mutation and do not carry a construct that enables overexpression of ymaH. The halos produced by the 42SigH cells were also greater than the halos produced by the 41SigH cells, which do not carry the degU(Hy) mutation but carry the SigH construct to enable overexpression of YmaH.

AAPF assay—The production of subtilisin by transformed *Bacillus* host cells 42SigH, 42SigA1, 41SigA2, which overexpress ymaH, and their respective controls 42pBS19, and 41pBS19 was quantified as a function of the activity of the secreted AprE protease. The proteolytic activity of the secreted protease was determined as the rate of hydrolysis of the substrate succinyl -L-Ala-L-Ala-L-Pro-L-Phe-p-nitroanalide (AAPF from Sigma Chemical Co). The assay measured the level of production of protease as the absorbance at 405 nm/min resulting from the hydrolysis and release of p-nitroanaline (Estell et al., J Biol. Chem., 260:6518-6521 [1985]). The measurements were made using the Sofmax Pro software, and the specified conditions were set as: Type: Kinetic; Reduction: Vmax Points (Read best 15/28 points); Lm1: 405 nm; Time: 5 minutes; and Interval: 11 Seconds.

Liquid cultures of *B. subtilis* control host cells 41pBS19 and 42pBS19, and host cells overexpressing YmaH were obtained by inoculating 5 ml of LB containing 5 pmm of chloramphenicol (Cm) with single colonies of transformed cells 41SigH and 42SigA1 and 42SigH, and allowing the cells to grow while shaking at 37 C until growth reached mid-logarithmic phase. Each of the cultures was diluted 1:100 with fresh complex medium containing 5 ppm Cm, and allowed to grow at 3° C. while shaking at 250 rpm. Samples of the cultures were taken at the times indicated in the figures. The samples were centrifuged and the supernatants were tested for production of subtilisin.

Ten microliters of each of the *B. subtilis* cultures supernatants were diluted 100 ul of Tris Buffer, containing 10 mM Tris+0.005% TWEEN®-80, pH 8.6; and 25 ul of 100 mg/ml AAPF. The activity of each of the protease was calculated, and the effect of overexpressing YmaH on the production of the protease is shown in FIGS. 10A-B and FIG. 11.

Figure 10B:
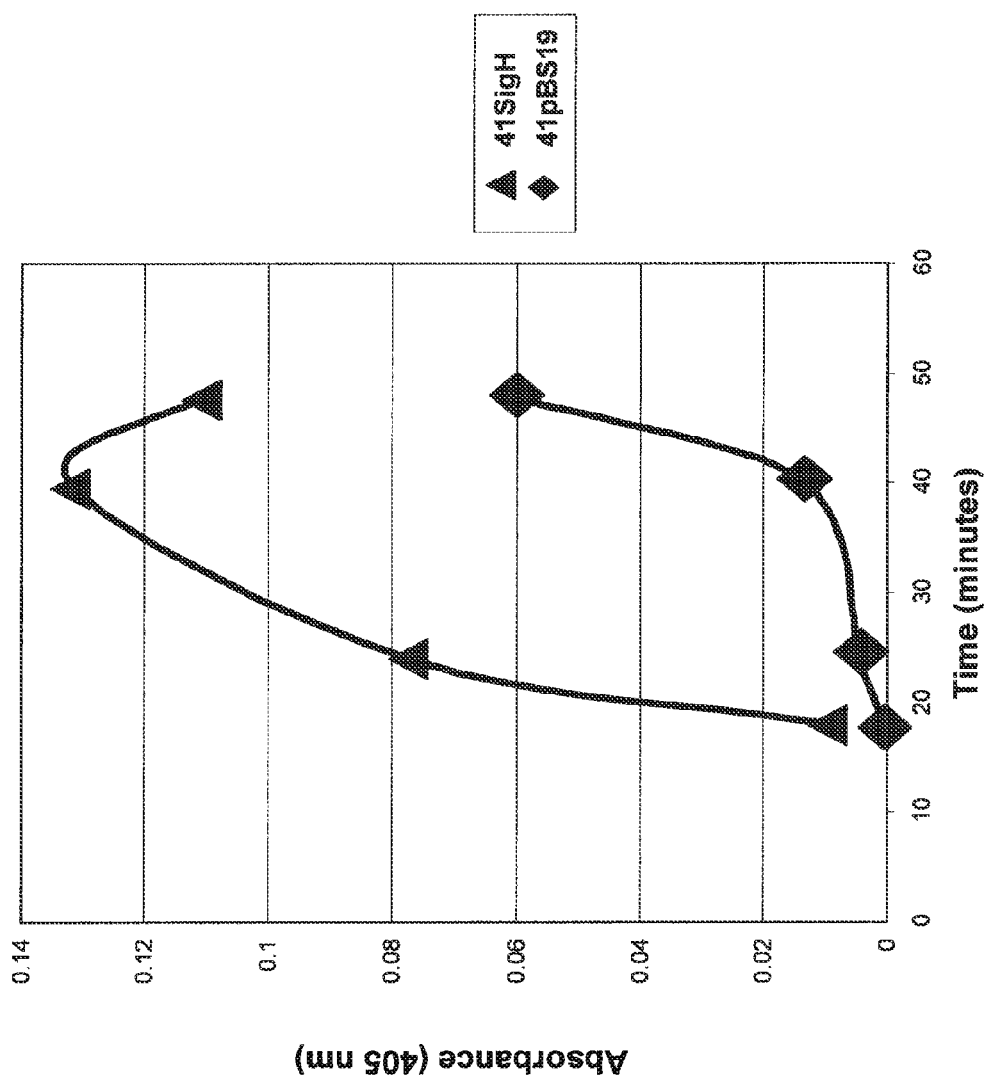
FIG. 10 (A-B) Panel A shows a graph of the proteolytic activity of subtilisin produced by *Bacillus* control host cells (42pBS) and by *Bacillus subtilis* host cells that overexpress ymaH (42SigA1 and 42SigH). Panel B shows the subtilisin activity produced by *Bacillus* control host cells (41 pBS) and by *Bacillus subtilis* host cells that overexpress ymaH (41SigH). The proteolytic activity was measured as the increase in absorbance at 405 nm due to the hydrolysis and release of p-nitroanaline. The level of enzymatic activity is indicative of the effect of overexpressing ymaH on the production of subtilisin by *Bacillus* host cells.

FIGS. 10A and 10B show that overexpressing YmaH in *Bacillus* host cells, whether in presence (42SigA and 42SigH; FIG. 10A) or absence (41SigH; FIG. 10B) of the degU(Hy) mutation, enhances the production of the AprE subtilisin by several fold when compared to the level produces by the respective control cells 41 pBS19 and 42pBS19. In addition, cells that overexpress YmaH produce elevated levels of the AprE subtilisin earlier than cells that do not overexpress YmaH. For example, FIG. 10A shows that 42sigH cells produce almost as much subtilisin at 20 hours of growth as the parent control cells produce at 48 hours. Similarly, FIG. 10B shows that 41SigH cells produce more subtilisin at 25 hours than the 41 pBS control cells produce at 48 hours. The graph shown in FIG. 11 shows that cells that the expression of YmaH when driven by the SigH promoter (42SigH) results in the production of subtilisin that is greater than that produced by cells in which YmaH expression is driven by the Sigma A promoter (42SigA). FIG. 11 also shows that overexpression of YmaH whether driven by the SigH or SigA promoter results in enhanced production of AprE subtilisin as early as after only one hour of cell growth.

Example 8

Effect of YmaH Overexpression on Protease Expression in Modified *Bacillus* sp. Host Cells Containing an Inactivated PhrA or PhrE Gene The effect of overexpressing YmaH protein on the enhanced ability of *Bacillus* cells that lack phrA or phrE to produce protease was tested.

The expression construct SigH, which comprises the ymaH gene operably linked to its native promoter (SigH promoter), was amplified by PCR using the primers ymaH 1F EcoRI (P1; SEQ ID NO:24) and ymaH 3'R BamHI (P2; SEQ ID NO:25) and cloned in the multicopy plasmid pBS19 using EcoRI and BamHI restriction sites to generate plasmid pBS19 ymaH sigH (SEQ ID NO:37).

The sequence of the primers used for the amplification is set forth below:

| Primer | Sequence | Description |
| --- | --- | --- |
| ymaH 1F EcoRI (P1) | ggcaccgaattcgacgtggtttcg caacaaaatgca g (SEQ ID NO: 24) | 5' ymaH |
| ymaH 3'R BamHI (P2) | ggcaccggatcctcataaaaaaag accgtgccttgg (SEQ ID NO: 25 | 3' ymaH |

Figure 9:
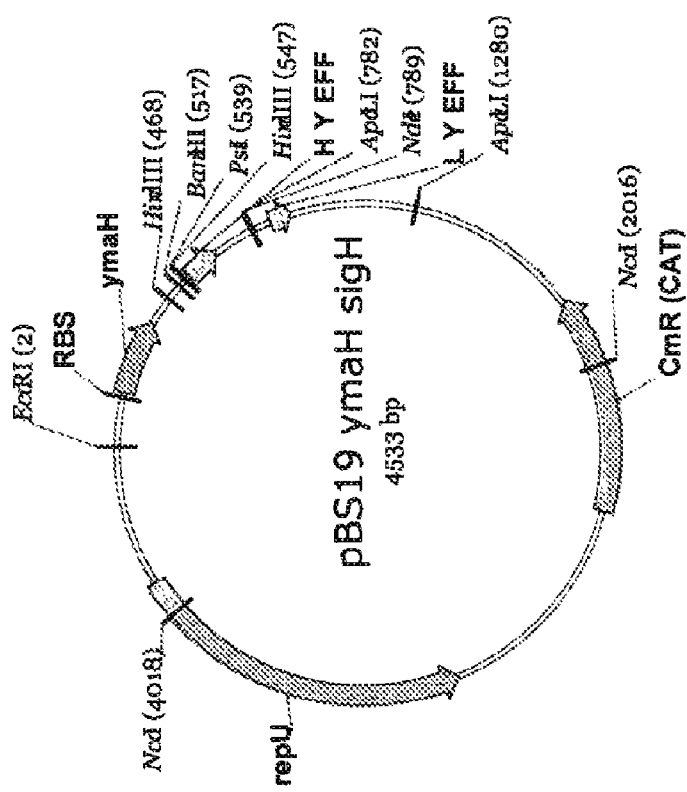
FIG. 9 shows a map of the plasmid pBS19-ymaH sigH.

The map of the plasmid pBS19 ymaH sigH is set forth in FIG. 9, and the sequence of the plasmid pBS19 ymaH sigH is set forth below:

(SEQ ID NO: 37)
gaattcgacgtggtttcgcaacaaaatgcaggtcacatggttcgatatga
caccgcctgttgatatggagctgaaaaaaaaggaaattttcacacatata
gcaggaaaactcgaactttaatcgaaactgtatgatatagagaatcaagg
aggacgaaacatgaaaccgattaatattcaggatcagttttttgaatcaaa
tccgaaagaaaatacgtatgtcactgttttttttgctgaacggctttcag
ttgcggggccaggtgaaaggctttgataactttaccgtattgttggaatc
ggaaggtaagcagcagcttatatataaacatgcgatctcaacgtttgcgc
cgcaaaaaaacgtccagcttgaactcgaatagatcaaaaaatgccatgtc
aagacatgaggaaaggctgtcgggggttcccggcggccatttttaacatg
aatccacttttgctccaagctttttgtgtaagctgaccatgccaaggcac
ggtctttttttatgaggatcctctagagtcgacctgcaggcatgcaagct
tggcgatcctgcctcgcgcgtttcggtgatgacggtgaaaacctctgaca
catgcagctcccggagacggtcacagcttgtctgtaagcggatgccggga
gcagacaagcccgtcagggcgcgtcagcgggtgttggcgggtgtcgggc
gcagccatgacccagtcacgtagcgatagcggagtgtatactggcttaac
tatgcggcatcagagcagattgtactgagagtgcaccatatgcggtgtga
ataccgcacagatgcgtaaggagaaaataccgcatcaggcgctcttccg
cttcctcgctcactgactcgctgcgctcggtcgttcggctgcggcgagcg
gtatcagctcactcaaaggcggtaatacggttatccacagaatcaggggga
taacgcaggaaagaacatgtgagcaaaaggccagcaaaaggccaggaacc
gtaaaaaggccgcgttgctggcgtttttccataggctccgccccctgac
gagcatcacaaaaatcgacgctcaagtcagaggtggcgaaacccgacagg
actataaagataccaggcgtttccccctggaagctccctcgtgcgctctc
ctgttccgaccctgccgcttaccggatacctgtccgcctttctcccttcg
ggaagcgtggcgctttctcatagctcacgctgtaggtatctcagttcggt
gtaggtcgttcgctccaagctgggctgtgtgcacgaaccccccgttcagc
ccgaccgctgcgccttatccggtaactatcgtcttgagtccaacccggta
agacacgacttatcgccactggcagcagccactggtaacaggattagcag
agcgaggtatgtaggcggtgctacagagttcttgaagtggtggcctaact
acggctacactagaaggacagtatttggtatctgcgctctgctgaagcca
gttaccttcggaaaaagagttggtagctcttgatccggcaaacaaaccac cgctggtagcggtggtttttatgtttgcaagcagcagattacgcgcagaaa
aaaaggatctcaagaagatcctttgatcttttctacggggtctgacgctc
agtggaacgaaaactcacgttaagggattttggtcatgagattatcaaaa
aggatctgtgagctgtaatataaaaacttcttcaactaacggggcaggtt
agtgacattagaaaaccgactgtaaaaagtacagtcggcattatctcata
ttataaaagccagtcattaggcctatctgacaattcctgaatagagttca
taaacaatcctgcatgataaccatcacaaacagaatgatgtacctgtaaa
gatagcggtaaatatattgaattcctttattaatgaatttcctgctgt
aataatgggtagaaggtaattactattattattgatatttaagttaaacc
cagtaaatgaagtccatggaataatagaaagagaaaagcattttcaggt
ataggtgtttgggaaacaatttccccgaaccattatatttctctacatc
agaaaggtataaatcataaaactctttgaagtcattctttacaggagtcc
aaataccagagaatgttttagatacaccatcaaaaattgtataaagtggc
tctaacttatcccaataacctaactctccgtcgctattgtaaccagttct
aaaagctgtatttgagtttatcacccttgtcactaagaaaataaatgcag
ggtaaaatttatatccttcttgttttatgtttcggtataaaacactaata
tcaatttctgtggttatactaaaagtcgtttgttggttcaaataatgatt
aaatatctcttttctcttccaattgtctaaatcaattttattaaagttca
tttgatatgcctcctaaatttttatctaaagtgaatttaggaggcttact
tgtctgctttcttcattagaatcaatcctttttttaaaagtcaatattact
gtaacataaatatatattttaaaaatatcccactttatccaattttcgtt
tgttgaactaatgggtgatttagttgaagaataaaaagaccacattaaaa
atgtggtattttgtgtttttttaaaggatttgagcgtagcgaaaaatcct
tttatttattatcttgataataagggtaactattgccggttgtccattca
tggctgaactctgattcctctgttgacatgacacacatcatctcaatatc
cgaatagggcccatcagtctgacgaccaagagagccataaacaccaatag
ccttaacatcatcccatatttatccaatattcgttccttaatttcatga
acaatcttcattatttcttctctagtcattattattggtccattcactat
tctcattcccttttcagataattttagatttgcttttctaaataagaata
tttggagagcaccgttattattcagctattaataactcgtattcctaagc
atccttcaatccttttaataacaattatagcatctaatcttcaacaaact
ggcccgtttgttgaactactatttaataaaataattttttccgttcccaat
tccacattgcaataatagaaaatccatcttcatcggcttttttcgtcatca
tctgtatgaatcaaatcgccttcttctgtgtcatcaaggtttaatttttt
atgtatttcttttaacaaaccaccataggagattaaccttttacggtgta
aaccttcctccaaatcagacaaacgtttcaaattattttattcatcatcg
gtcataaaatccgtatcctttacaggatattttgcagtttcgtcaattgc
cgattgtatatccgatttatatttattttaggtcgaatcatttgaactt
ttacatttggatcatagtctaatttcattgccttttttccaaaattgaatc
cattgttttgattcacgtagttttctgtattcttaaaataagttggttc
cacacataccaatacatgcatgtgctgattataagaattatctttattat -continued
```
ttattgtcacttccgttgcacgcataaaaccaacaagattttttattaatt tttttatattgcatcattcggcgaaatcattgagccatatctgacaaact cttatttaattcttcgccatcataaacattttttaactgttaatgtgagaa acaaccaacgaactgttggcttttgtttaataacttcagcaacaaccttt tgtgactgaatgccatgtttcattgctctcctccagttgcacattggaca aagcctggatttacaaaaccacactcgatacaactttatttcgcctgttt cacgatttttgtttatactctaatatttcagcacaatctttttactctttca gcctttttaaattcaagaatatgcagaagttcaaagtaatcaacattagc gattttatttctctccatggtatcactttttccactttttgtcttgtcca ctaaaaccattgattttttcatctgaataaatgctactattaggacacata atattaaaagaaaccccccatctatttagttatttgtttagtcacttataa ctttaacagatggggttttctgtgcaaccaattttaagggttttcaata ctttaaaacacatacataccaacacttcaacgcacctttcagcaactaaa ataaaaatgacgttatttctatatgtatcaagataagaaagaacaagttc aaaaccatcaaaaaaagacaccttttcaggtgattttttttattttataaa ctcattccctgatctcgacttcgttcttttttacctctcggttatgagt tagttcaaattcgttcttttaggttctaaatcgtgttttttattggaatt gtgctgttttatccttaccttgtctacaaacccattaaaaacgtttta aaggcttttaagccgtctgtacgttccttaaa.
```

The strain BG2942 deleted for the phrA (CB2-1) and the strain BG2942 deleted for the phrE gene (CB 2-2) were each transformed with the multicopy plasmid pBS19 ymaH sigH (SEQ ID NO:37) to generate strains CB2-11 (BG2942 phrA: spc, pBS19 ymaH sigH) and CB2-12 (BG2942 phrE:spc, pBS19 ymaH sigH), respectively, and tested for the expression of aprE. BG2942 cells that do not carry a deletion of either the phrA or the phrE gene were transformed with the pBS19 ymaH sigH plasmid to generate the control strain 42SigH (BG2942 pBS19 ymaH sigH). All BG2942 derived strains (42SigH, CB2-11 and CB2-12) were grown for nine hours in 2×SNB media and the supernatants were utilized for assaying the activity of AprE using the AAPF assay.

Figure 12:
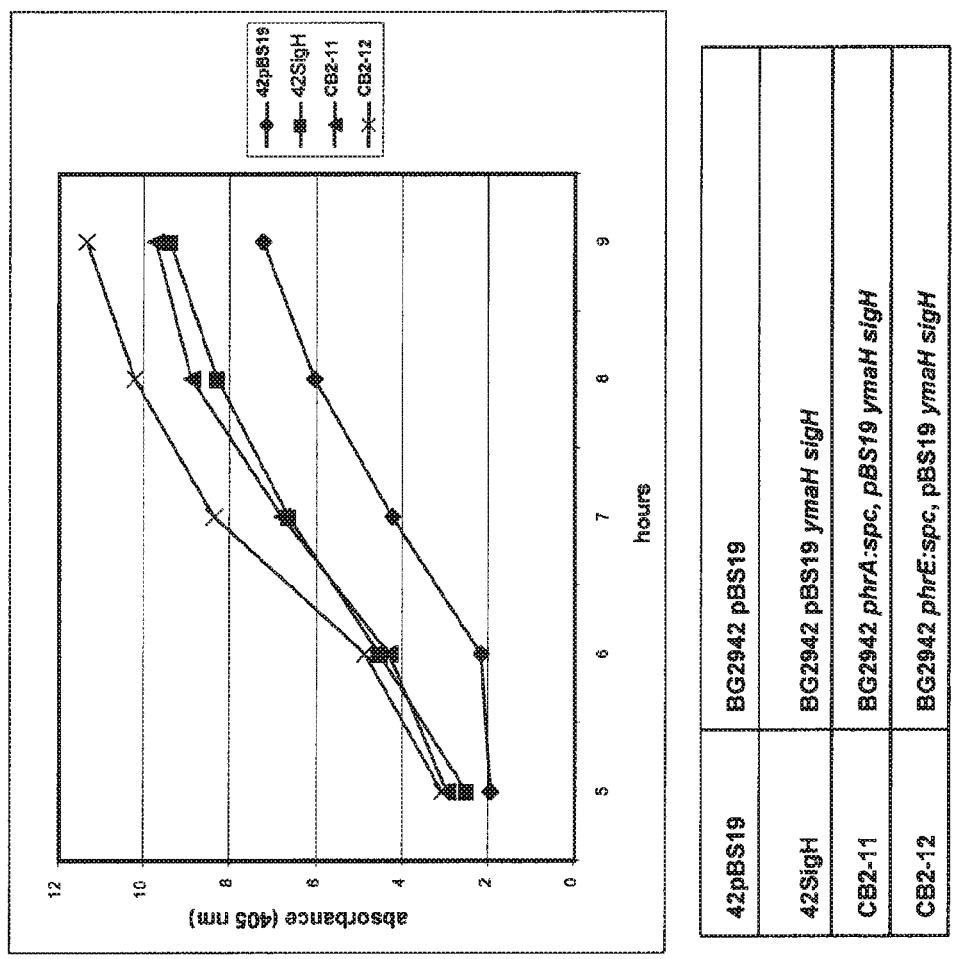
FIG. 12 is a graph showing a synergistic effect of phr deletion and YamH over-expression (using multicopy plasmid pBS19-ymaH sigH) on AprE expression. The effect of overexpression of YmaH is shown in the *Bacillus subtilis* strain named YmaH (squares), and in the modified strains CB2-11 (triangles) and CB2-12 (crosses), which respectively contain a deletion of the phrA and phrE gene, and is compared to the production of AprE in the control strain 42pBS19.

FIG. 12 shows the effect of overexpressing YmaH on the production of protease by strains carrying the deletion of either the phrA or phrE gene. The strains carrying the multicopy plasmid pBS19 ymaH sigH (i.e., 42SigH), CB2-11 and CB2-12, showed a higher protease expression when compared to the BG2942 strain that was transformed only with a control pBS19 plasmid (42pBS19). In particular, the results show that overexpression of YmaH in the 42SigH strain (BG2942 pBS19 ymaH sigH) (squares) enhances the production of the AprE protease obtained in the control BG2942 pBS19 (diamonds). In addition, the results also show that deletion of phrE in combination with overexpression of ymaH (CB2-12; crosses) further enhances the production of protease by the BG2942 pBS19 ymaH sigH strain (42SigH; squares) when compared to the production by the modified *Bacillus subtilis* strain CB2-2 (BG2942 phrE:spc) or to the 42SigH (BG2942 ymaH sigH) strain.

Thus, while overexpression of YmaH enhances the production of a protein of interest (e.g., a subtilisin), combining the overexpression of YmaH with the deletion of a phr gene, in particular, the phrE gene, further enhances the production of a protein of interest.

Example 9

Protease Expression in *Bacillus* sp. Cells Containing a Deletion of the rapA/phrA Genes Transcription of the rapA/phrA operon was abolished in *Bacillus subtilis* strain BG3594 (degU(Hy)32, oppA, ΔspoIIE, ΔaprE, ΔnprE) that carries the PaprE-FNA expression construct to generate strain JS1121 according to the following.

Figure 13:
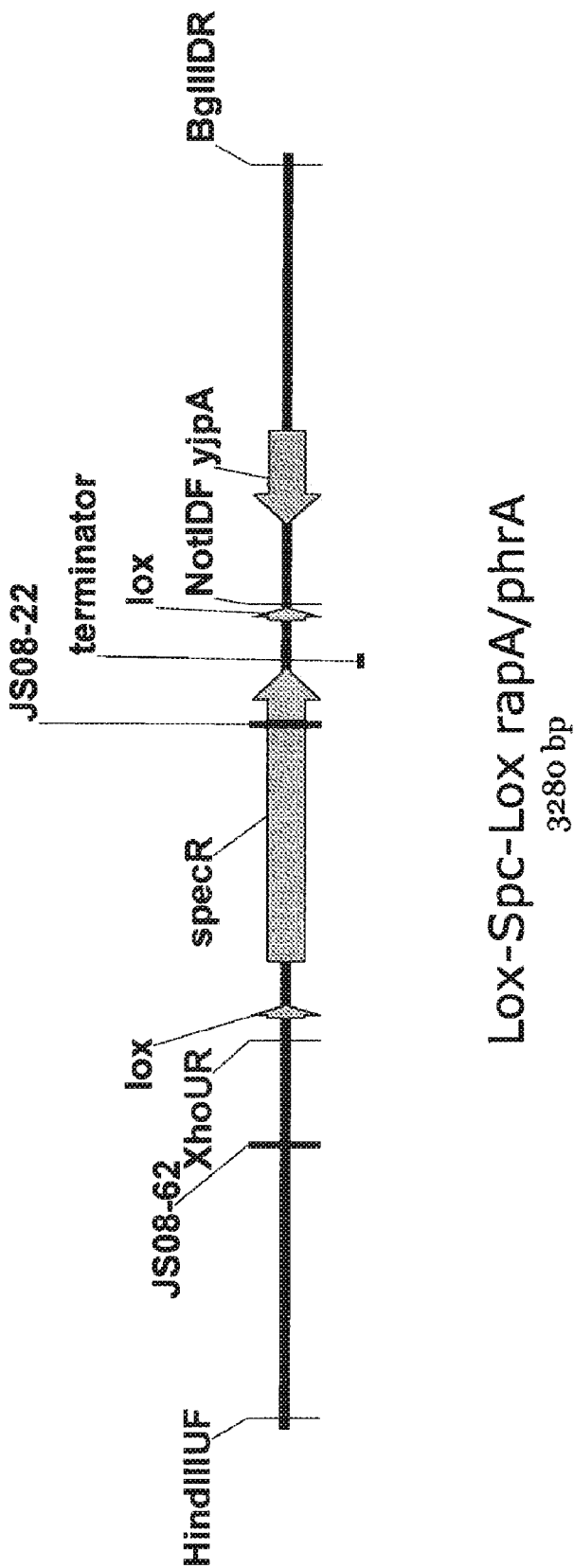
FIG. 13 schematically illustrates the DNA construct used to delete the rapA gene.

The deletion cassette of the rapA/phrA operon is diagramed in FIG. 13, and the polynucleotide sequence is:
```
tggagggagtcagaccgcgtctttgg-
gaaaaaagcaagcggaaagtgaccgtgtttacggatggagatggagggacttca
agagagcaggaagccattgtcagagag-
gttcagcggagtcaagtcatcatgaatccgctattgaaaaaagagatatacag
atcaattgatcagttttttcatagt-
gataaatcgttttatcaaacatatga-
catcccttacaagcgcggcattctgttatatggacctc   ctggaaacggaaagac-
gacgttagtgaagtcgatcgcaggcagtatcgatgcacctgttgcttattggcaaat
tactgaattta                  cgtcgagcgagacaatagaa-
gaagtctttcaggcagcgagacgc-
ctcgctcctgcagttctggtcatcgaggatatagattc gatgccggaagatgtgcg-
gtccttttttctcaatacgctggacggcgcgacatcaaaagagggctatttctcat
cggtacgac                        aaactatcccgaagagatcgatccag-
gtttgatgaatcgtgcaggacgatttgaccgtgcctatgaaatcgggcttccggatg
aagagctgcggctggaatatatgaaaat-
gagaggctttggcatctttttgagtgaaggagaaataaaaaacgccgcaaaac tta-
cagaaggcttttcctttgcacagctgg-
gagaattatatgtatcttcagcccttcaatggcaccaagaagggaatcaccatatt
gaaaccatggtgaaagacatgacag-
gagagcaaagaaaaagccagcggggaagctggatggaaagaaacaaagtc
ggttttcactaaaagaaagcacgggt-
gtttgaaaaacccgtgcttttttgt-
tgcggttagccgaaattcgacaattgcggttattttg cgttcttcttttttcttgtaaatat-
gataaaatatgacatatctcgggtaattcaaaaggggggattaattgaggatgaag
cagacg              ctcgaggtcgacggtatcgataagctg-
gatccataacttcgtataatgtatgctatacgaagttatctagataaaaaatttagaa
gccaatgaaatctataaataaactaaat-
taagtttatttaattaacaactatggatataaaataggtactaatcaaaatagtgag
gaggatatatttgaatacatacgaa-
caaattaataaagtgaaaaaaatacttcggaaacatttaaaaaataaaccttattggtac
ttacatgtttggatcaggagt-
tgagagtggactaaaaccaaatagt-
gatcttgactttttagtcgtcgtatctgaaccattgacaga             tcaaagtaaa-
gaaatacttatacaaaaaattagacctatttcaaaaaaaaataggagataaaagcaac
ttacgatatattgaat                  taacaattattattcagcaagaaatgg-
taccgtggaatcatcctcccaaacaagaatttatttatggagaatggttacaagagct
ttatgaacaaggatacattcctcagaag-
gaattaaattcagatttaaccataatgcttaccaagcaaaacgaaaaaataaaa
gaatatacggaaattatgacttagag-
gaattactacctgatattccattttct-
gatgtgagaagagccattatggattcgtcagag gaattaatagataattatcaggat-
gatgaaaccaactctatattaactttatgccgtatgattttaactatggacacgggta
aaat                        cataccaaaagatattgcgggaaatg-
cagtggctgaatcttctccattagaacatagggagagaattttgttagcagttcgtagt
tatcttggagagaatattgaatggac-
taatgaaaatgtaaatttaactataaactatttaaataacagattaaaaaaattataaa
aaaattgaaaaaatggtggaaa-
cactttttcaattttttgttttat-
tatttaatatttgggaaatattcattctaattggtaatcagatttt agaaaacaataaac-
ccttgcatatgtctagataacttcgtataatgtatgctatacgaagttatgcggccgcc
acgcacaaaa                    acaaatccagagaggagattgtttatat-
gaaatctaaatggatgtcaggtttgttgctcgttgcggtcgggttcagctttactcagg
tgatggttcatcgcaggtgaaacagcaaa-
cacagaagggaaaacatttcatattgcggcacgcaatcaaacatgatgcataa
aaaaagacccttaggggtctttt-
``` tatttcttcagcttccattctttatcgtcagctcagaagatccacttgccaccagcggatccgcatggccgatttccgctgcctcttccagtgaatctgcttcgatgacatacgctccgcctgtggcgtcgctgaatggcccaaacatt tttaaacgtttnctgcctgtaaacgatccagaaattcatagtgcccagccacatgctcctgattaaatttctccgttctcattgtcag cattaaatatggtatacatattcagaccctccgtgaacttcagtttaacacatttatccatattacggtgatagatgatatgagctttt cgtcctacgaatgccacctatttatgaaaaagaaaaggagagatgataggtgagcattccagtaaagaaaaatttggtttct gaggcgaaatacgcgttgaagtgtcctaatgcaatgtccgctgaatacattaccattcacaacacggcaaacgatgcatcag cggccaatgaaatcagctatatgatcgggaacacaagctcgacaagctttcattttgcggtcgatgatcaagaggtgattcaaggtctgccgcttaaccgaaacgcttggcacactggtgacggcacaaacggtccgggaaaccgcaaatcaatcggtgttgagatttgctacagcaaatcgggaggcccgaagtatgaggcagctgaagccttggcgatttcatttgttgcacagctgttgaagg agcgcggctggggcatcgatcgggtgagaaagcatcaggactggagcggaaagtattgcccgcaccgcatt ttatcagag gggcgctgggatcaagtgaaggcggcgattgaaaaggaattaaacgggggcgtatcagcgaaaaaagctgcagtctcttcttcggcgtctgaatatcatgtaaaaaaggtgacacactgtcagggattgccgcatca; SEQ ID NO:52, was made by PCR amplification of the two partial yjo nucleotide sequences and ligation of the amplified fragments to the lox-Spectinomycin-lox cassette. The partial yjoB gene sequence located upstream the rapA sequence was amplified using the oligos HindIIIUF gcgtgcaagctt ggagggagtcagaccgcgtctttgg; SEQ ID NO:56, and XhoUR agagga ctcgagcgtctgcttcatcctcaattaatc; SEQ ID NO:55, and the sequence located downstream the rapA gene containing the phrA and yjpA gene sequences was amplified using oligos NotIDF ttatgaga gcggccgc cacgcacaaaaacaaatccagagag; SEQ ID NO:57, and BglIIDR ccccgtagatctcggcaatccctgacagtgtgtcacc; SEQ ID NO:58.

Since the phrA gene is transcribed by the rapA promoter (McQuade et al. J. Bacteriology 2001 August; 183(16):4905-9) both the rapA (NP_389125) and the phrA (NP_389126) sequences are not transcribed in this construct.

*Bacillus* sp. strains CF471, CB3-47, JS1121, which contain the PaprE-FNA expression cassette, were grown in a suitable growth medium for 50 hours in shake flasks, and the supernatants were sampled at 18, 24, 42, 48 hours and tested in an AAPF assay as described above.

Figure 14:
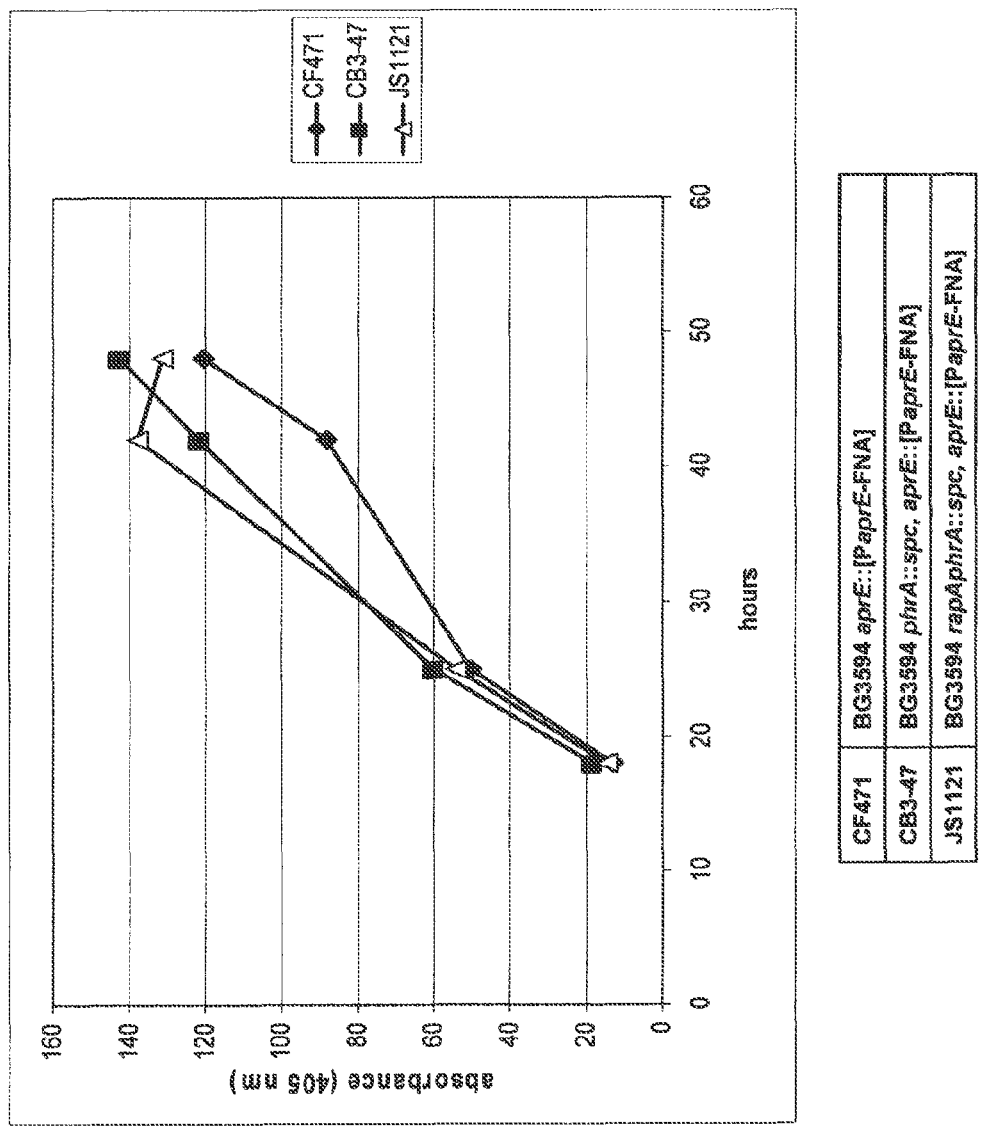
FIG. 14 shows the level of production of subtilisin FNA by *Bacillus subtilis* control host cells CF471 (filled diamond), the modified *Bacillus subtilis* cells CB3-47 (filled square) comprising an inactivated phrA gene, and the modified *Bacillus subtilis* cells JS1121 (open triangle) comprising an inactivated rapA gene and an inactivated phrA gene.
Figure 15:
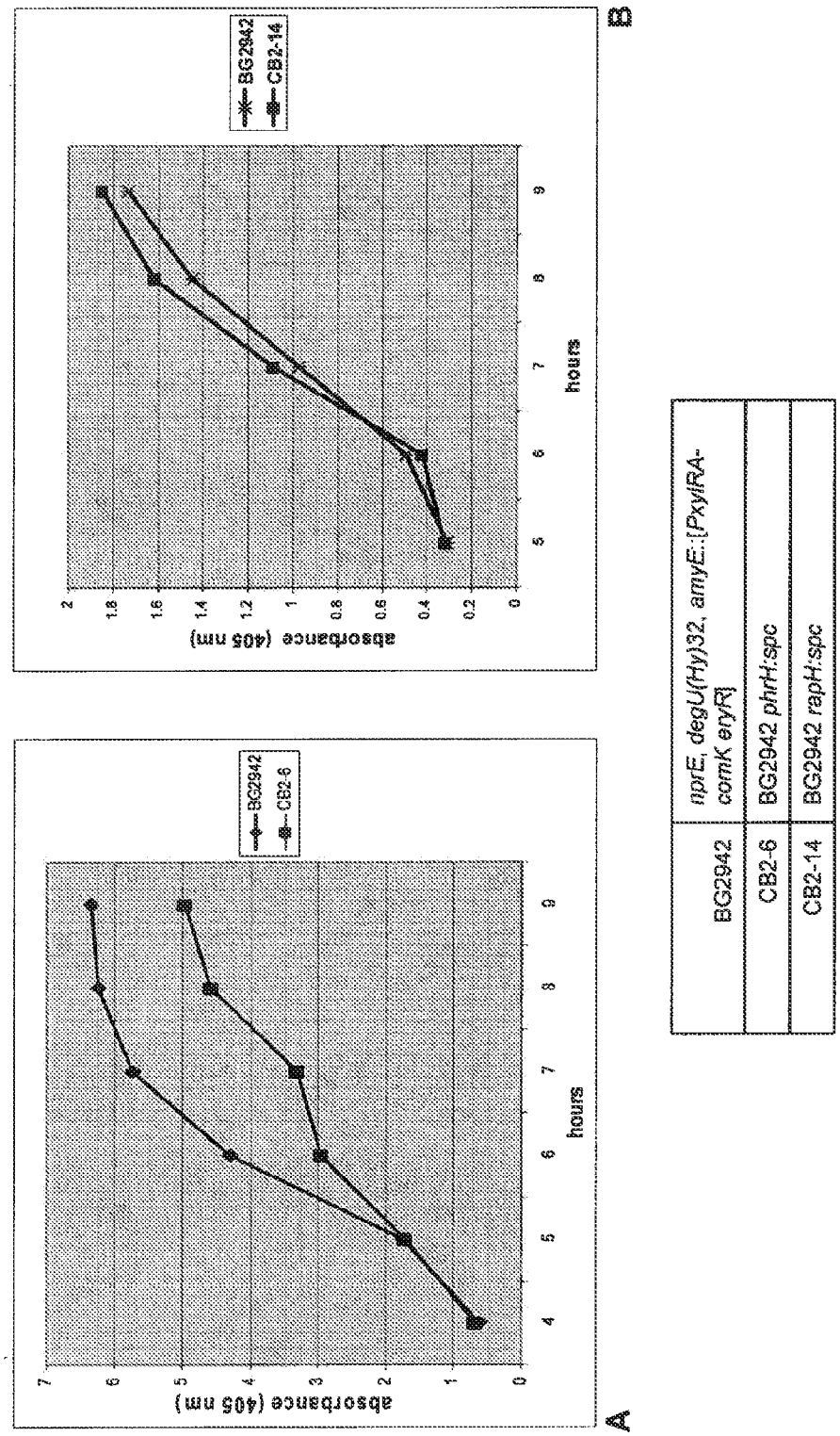
FIG. 15 (A-B) shows the effect of deleting the phrH gene (filled square, panel A) or the rapH gene (filled square, panel B) genes on the production of AprE by *Bacillus subtilis*.

The results (FIG. 14) showed that the strain carrying the deletion of phrA (CB3-47; closed squares), and the strain carrying the deletion of rapA and phrA genes (JS1121; open triangles) exhibit increased FNA expression when compared to the control strain CF471 (closed diamonds).

Therefore, inactivation of the phrA and/or the rapA genes increases the production of the heterologous subtilisin FNA when compared to the production of the same enzyme by the unmodified precursor host cell.

While particular embodiments of the present invention have been illustrated and described, it will be apparent to those skilled in the art that various other changes and modifications can be made without departing from the spirit and scope of the invention. It is therefore intended to cover in the appended claims all such changes and modifications that are within the scope of this invention.

All patents and publications mentioned in the specification are indicative of the levels of those skilled in the art to which the invention pertains. All patents and publications are herein incorporated by reference to the same extent as if each individual publication was specifically and individually indicated to be incorporated by reference.

Having described the preferred embodiments of the present invention, it will appear to those ordinarily skilled in the art that various modifications may be made to the disclosed embodiments, and that such modifications are intended to be within the scope of the present invention.

Those of skill in the art readily appreciate that the present invention is well adapted to carry out the objects and obtain the ends and advantages mentioned, as well as those inherent therein. The compositions and methods described herein are representative of preferred embodiments, are exemplary, and are not intended as limitations on the scope of the invention. It is readily apparent to one skilled in the art that varying substitutions and modifications may be made to the invention disclosed herein without departing from the scope and spirit of the invention.

The invention illustratively described herein suitably may be practiced in the absence of any element or elements, limitation or limitations which is not specifically disclosed herein. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims.

The invention has been described broadly and generically herein. Each of the narrower species and subgeneric groupings falling within the generic disclosure also form part of the invention. This includes the generic description of the invention with a proviso or negative limitation removing any subject matter from the genus, regardless of whether or not the excised material is specifically recited herein.

What is claimed is:

1. A host cell comprising a rap operon comprising at least one inactivated phr gene, wherein said host cell further overexpresses YmaH.

2. The host cell of claim 1, wherein said host cell further comprises a recombinant nucleic acid.

3. The host cell of claim 1, wherein said host cell further comprises a polynucleotide sequence encoding a protein of interest.

4. The host cell of claim 2, wherein said recombinant nucleic acid comprises a promoter that is operably linked to said polynucleotide sequence encoding a protein of interest.

5. The host cell of claim 4, wherein said promoter is the wild-type or a mutant aprE promoter.

6. The host cell of claim 3, wherein said host cell produces said protein of interest at a level that is greater than that produced by a host cell that does not comprise at least one inactivated phr gene and does not overexpress YmaH.

7. The host cell of claim 6, wherein said protein of interest is an enzyme.

8. The host cell of claim 7, wherein said enzyme is a protease.

9. The host cell of claim 1, wherein said at least one inactivated phr gene is selected from phrA, phrE, phrC, phrF, phrG, phrI, and phrK.

10. The host cell of claim 9, wherein said at least one inactivated phr gene is phrA.

11. The host cell of claim 9, wherein said at least one inactivated phr gene is phrE.

12. The host cell of claim 1, wherein said host cell further comprises at least one inactivated rap gene.

13. The host cell of claim 12, wherein said inactivated rap gene is the rapA gene.

14. The host cell of claim 12, wherein said at least one inactivated phr gene is selected from phrA, phrE, phrC, phrF, phrG, phrI, and phrK.

15. The host cell of claim 14, wherein said at least one inactivated phr gene is phrA.

16. The host cell of claim 14, wherein said at least one inactivated phr gene is phrE.

17. The host cell of claim 12, comprising an inactivated phrA gene, an inactivated phrE gene, an inactivated rapA gene, and a recombinant nucleic acid encoding a protein of interest.

18. The host cell of claim 17, wherein said protein of interest is an enzyme.

19. The host cell of claim 18, wherein said enzyme is a protease.

20. The host cell of claim 1, wherein said host cell is a *Bacillus* sp. host cell.

21. The host cell of claim 20, wherein said *Bacillus* sp. host cell is a *Bacillus alkalophilus, Bacillus amyloliquefaciens, Bacillus brevis, Bacillus circulans, Bacillus clausii, Bacillus coagulans, Bacillus firmus, Bacillus lautus, Bacillus lentus, Bacillus licheniformis, Bacillus megaterium, Bacillus pumilus, Bacillus stearothermophilus, Bacillus subtilis,* or *Bacillus thuringiensis* cell.

22. The host cell of claim 20, wherein said *Bacillus* sp. host cell is a *Bacillus subtilis* host cell.

23. A method for producing at least one protein of interest comprising providing a host cell comprising a rap operon comprising at least one inactivated phr gene, wherein said host cell further overexpresses YmaH; and growing said host cell under suitable conditions for producing said at least one protein of interest.

24. The method of claim 23, wherein said protein of interest is encoded by a recombinant nucleic acid present in said host cell.

25. The method of claim 24, wherein said recombinant nucleic acid comprises a promoter that is operably linked to the polynucleotide sequence encoding said protein of interest.

26. The method of claim 23, wherein production of said protein of interest by said host cell is greater than the production of said protein of interest by a host cell that does not comprise at least one inactivated phr gene and does not overexpress YmaH.

27. The method of claim 23, wherein the protein of interest is an enzyme.

28. The method of claim 27, wherein said enzyme is a protease.

29. The method of claim 23, wherein said at least one phr gene that is inactivated is chosen from phrA, phrE, phrC, phrF, phrG, phrI, and phrK.

30. The method of claim 29, wherein said at least one phr gene is phrA.

31. The method of claim 29, wherein said at least one phr gene is phrE.

32. The method of claim 23, wherein said host cell further comprises at least one inactivated rap gene.

33. The method of claim 32, wherein said inactivated rap gene is rapA.

34. The method of claim 23, wherein said host cell is a *Bacillus* sp. host cell.

35. The method of claim 34, wherein said *Bacillus* sp. host cell is a *Bacillus alkalophilus, Bacillus amyloliquefaciens, Bacillus brevis, Bacillus circulans, Bacillus clausii, Bacillus coagulans, Bacillus firmus, Bacillus lautus, Bacillus lentus, Bacillus licheniformis, Bacillus megaterium, Bacillus pumilus, Bacillus stearothermophilus, Bacillus subtilis,* or *Bacillus thuringiensis* cell.

36. The method of claim 34, wherein said *Bacillus* sp. host cell is a *Bacillus subtilis* cell.

37. The method of claim 23, wherein said host cell comprises an inactivated phrA gene, an inactivated phrE gene, an inactivated rapA gene, and a recombinant nucleic acid encoding said protein of interest.

* * * * *

SEQUENCE LISTING

<160> NUMBER OF SEQ ID NOS: 101

<210> SEQ ID NO 1
<211> LENGTH: 30
<212> TYPE: DNA
<213> ORGANISM: Artificial Sequence
<220> FEATURE:
<223> OTHER INFORMATION: Synthetic primer CB2008-007: upstream phrA

<400> SEQUENCE: 1
gaggatatgg aagaagacca agatttgctg                              30

<210> SEQ ID NO 2
<211> LENGTH: 24
<212> TYPE: DNA
<213> ORGANISM: Artificial Sequence
<220> FEATURE:
<223> OTHER INFORMATION: Synthetic primer CB2008-008: downstream phrA

<400> SEQUENCE: 2
ggcaatccct gacagtgtgt cacc                                    24

<210> SEQ ID NO 3
<211> LENGTH: 49
<212> TYPE: DNA
<213> ORGANISM: Artificial Sequence
<220> FEATURE:
<223> OTHER INFORMATION: Synthetic primer CB2008-009: linker up phrA
      down-lox

<400> SEQUENCE: 3
gcggccgcca tatgcatcct aggcccccga ccgcaacgag caacaaacc          49

<210> SEQ ID NO 4
<211> LENGTH: 49
<212> TYPE: DNA
<213> ORGANISM: Artificial Sequence
<220> FEATURE:
<223> OTHER INFORMATION: Synthetic primer CB2008-009-R: linker up phrA
      down-lox

<400> SEQUENCE: 4
ggtttgttgc tcgttgcggt cggggggccta ggatgcatat ggcggccgc         49

<210> SEQ ID NO 5
<211> LENGTH: 49
<212> TYPE: DNA
<213> ORGANISM: Artificial Sequence
<220> FEATURE:
<223> OTHER INFORMATION: Synthetic primer CB2008-010: linker down phrA
      up-lox

<400> SEQUENCE: 5
ggatccagct tatcgatacc gtcgatgcat aaaaaaagac ccttagggg          49

<210> SEQ ID NO 6
<211> LENGTH: 49
<212> TYPE: DNA
<213> ORGANISM: Artificial Sequence
<220> FEATURE:
<223> OTHER INFORMATION: Synthetic primer CB2008-010R: linker down phrA
      up-lox

<400> SEQUENCE: 6
cccctaaggg tcttttttta tgcatcgacg gtatcgataa gctggatcc          49

<210> SEQ ID NO 7
<211> LENGTH: 31
<212> TYPE: DNA
<213> ORGANISM: Artificial Sequence
<220> FEATURE:
<223> OTHER INFORMATION: Synthetic primer CB2008-019A: upstream phrE

<400> SEQUENCE: 7
ctaatggcct ttcgccataa aattatgttg g                             31

```
<210> SEQ ID NO 8
<211> LENGTH: 25
<212> TYPE: DNA
<213> ORGANISM: Artificial Sequence
<220> FEATURE:
<223> OTHER INFORMATION: Synthetic primer CB2008-021:  downstream phrE

<400> SEQUENCE: 8
tgtaggcgtt agcaagctca tgcgc                                          25

<210> SEQ ID NO 9
<211> LENGTH: 47
<212> TYPE: DNA
<213> ORGANISM: Artificial Sequence
<220> FEATURE:
<223> OTHER INFORMATION: Synthetic primer CB2008-019B:  linker up phrE
      down lox

<400> SEQUENCE: 9
gcggccgcca tatgcatcct aggccgcaag tccaattaaa acggcgg                  47

<210> SEQ ID NO 10
<211> LENGTH: 47
<212> TYPE: DNA
<213> ORGANISM: Artificial Sequence
<220> FEATURE:
<223> OTHER INFORMATION: Synthetic primer CB2008-019R:  linker up phrE
      down lox

<400> SEQUENCE: 10
ccgccgtttt aattggactt gcggcctagg atgcatatgg cggccgc                  47

<210> SEQ ID NO 11
<211> LENGTH: 54
<212> TYPE: DNA
<213> ORGANISM: Artificial Sequence
<220> FEATURE:
<223> OTHER INFORMATION: Synthetic primer CB2008-020:  linker down phrE
      up lox

<400> SEQUENCE: 11
ggatccagct tatcgatacc gtcgattcga taaacaacat tagttctgat tccc         54

<210> SEQ ID NO 12
<211> LENGTH: 54
<212> TYPE: DNA
<213> ORGANISM: Artificial Sequence
<220> FEATURE:
<223> OTHER INFORMATION: Synthetic primer CB2008-020R:  linker down phrE
      up lox

<400> SEQUENCE: 12
gggaatcaga actaatgttg tttatcgaat cgacggtatc gataagctgg atcc         54

<210> SEQ ID NO 13
<211> LENGTH: 26
<212> TYPE: DNA
<213> ORGANISM: Artificial Sequence
<220> FEATURE:
<223> OTHER INFORMATION: Synthetic primer CB2008-041:  5' rapA

<400> SEQUENCE: 13
actcatatcc ggcagttcca cgtcgc                                         26

<210> SEQ ID NO 14
<211> LENGTH: 28
<212> TYPE: DNA
```

```
<213> ORGANISM: Artificial Sequence
<220> FEATURE:
<223> OTHER INFORMATION: Synthetic primer CB2008-042: 3' xlyB

<400> SEQUENCE: 14
agatgccgtc tgaggcagtt tgatcacc                                          28

<210> SEQ ID NO 15
<211> LENGTH: 26
<212> TYPE: DNA
<213> ORGANISM: Artificial Sequence
<220> FEATURE:
<223> OTHER INFORMATION: Synthetic primer CB2008-051: 5' rapE

<400> SEQUENCE: 15
agctgtacat gcacactcag cccctc                                            26

<210> SEQ ID NO 16
<211> LENGTH: 27
<212> TYPE: DNA
<213> ORGANISM: Artificial Sequence
<220> FEATURE:
<223> OTHER INFORMATION: Synthetic primer CB2008-052: 3' yqcG

<400> SEQUENCE: 16
agaggcgctt ttgcctttg ctgtcgc                                            27

<210> SEQ ID NO 17
<211> LENGTH: 2739
<212> TYPE: DNA
<213> ORGANISM: Artificial Sequence
<220> FEATURE:
<223> OTHER INFORMATION: Synthetic construct: nucleotide sequence of
      the phrA deletion construct

<400> SEQUENCE: 17
attcgttatt gcaggtaatt atgatgatat gcagtatcca gaaagagcat tgccccactt        60
agaactggct ttagatcttg caaagaaaga aggcaatccc cgcctgatca gttctgccct       120
atataatctc ggaaactgct atgagaaaat gggtgaactg caaaaggcag ccgaatactt       180
tgggaaatct gttttctatt gcaagtcgga aaagttcgat aatcttccgc attctatcta       240
ctctttaaca caagttctgt ataaacaaaa aaatgacgcc gaagcgcaaa aaaagtatcg       300
tgaaggattg gaaatcgccc gtcaatacag tgatgaatta tttgtggagc tttttcaatt       360
tttacatgcg ttatacggaa aaaacattga cacagaatca gtctcacaca cctttcaatt       420
tcttgaagaa catatgctgt atccttatat tgaagagctg gcgcatgatg ctgcccaatt       480
ctatatagaa aacggacagc ccgaaaaagc actttcattt tatgagaaaa tggtgcacgc       540
acaaaaacaa atccagagag gagattgttt atatgaaatc taaatggatg tcaggtttgt       600
tgctcgttgc ggtcgggggc ctaggatgca tatggcggcc gcataacttc gtatagcata       660
cattatacga agttatctag acatatgcaa gggtttattg ttttctaaaa tctgattacc       720
aattagaatg aatatttccc aaatattaaa taataaaaca aaaaaattga aaaagtgtt       780 tccaccattt tttcaattt tttataattt ttttaatctg ttatttaaat agtttatagt       840
taaatttaca ttttcattag tccattcaat attctctcca agataactac gaactgctaa       900
caaaattctc tccctatgtt ctaatggaga agattcagcc actgcatttc cgcaatatc       960 ttttggtatg attttacccg tgtccatagt taaatcata cggcataaag ttaatataga      1020
gttggtttca tcatcctgat aattatctat taattcctct gacgaatcca taatggctct      1080
tctcacatca gaaaatggaa tatcaggtag taattcctct aagtcataat ttccgtatat      1140
```

```
tcttttattt tttcgttttg cttggtaaag cattatggtt aaatctgaat ttaattcctt    1200
ctgaggaatg tatccttgtt cataaagctc ttgtaaccat tctccataaa taaattcttg    1260
tttgggagga tgattccacg gtaccatttc ttgctgaata ataattgtta attcaatata    1320
tcgtaagttg cttttatctc ctatttttt tgaataggt ctaattttt gtataagtat    1380 ttctttactt tgatctgtca atggttcaga tacgacgact aaaaagtcaa gatcactatt    1440
tggttttagt ccactctcaa ctcctgatcc aaacatgtaa gtaccaataa ggttattttt    1500
taaatgtttc cgaagtattt ttttcacttt attaatttgt tcgtatgtat tcaaatatat    1560
cctcctcact attttgatta gtacctattt tatatccata gttgttaatt aaataaactt    1620
aatttagttt atttatagat ttcattggct tctaaatttt ttatctagat aacttcgtat    1680
agcatacatt atacgaagtt atggatccag cttatcgata ccgtcgctcg gatccactag    1740
tatgcataaa aaaagaccct taggggtctt ttttatttct tcagcttcca ttcttttatc    1800
gtcagctcag aagatccact tgccaccagc ggatccgcat ggccgatttc cgctgcctct    1860
tccagtgaat ctgcttcgat gacatacgct ccgcctgtgg cgtcgctgaa tggcccaaac    1920
atttttaaac gttttctgc ctgtaaacga tccagaaatt catagtgccc agccacatgc    1980
tcctgattaa atttctccgt tctcattgtc agcattaaat atggtataca tattcagacc    2040
ctccgtgaac ttcagtttaa cacatttatc catattacgg tgatagatga tatgagcttt    2100
tcgtcctacg aatgccacct atttatgaaa aagaaaagg agagatgata ggtgagcatt    2160
ccagtaaaga aaaatttggt ttctgaggcg aaatacgcgt tgaagtgtcc taatgcaatg    2220
tccgctgaat acattaccat tcacaacacg gcaaacgatg catcagcggc caatgaaatc    2280
agctatatga tcgggaacac aagctcgaca agctttcatt ttgcggtcga tgatcaagag    2340
gtgattcaag gtctgccgct taaccgaaac gcttggcaca ctggtgacgg cacaaacggt    2400
ccgggaaacc gcaaatcaat cggtgttgag atttgctaca gcaaatcggg aggcccgaag    2460
tatgaggcag ctgaagcctt ggcgatttca tttgttgcac agctgttgaa ggagcgcggc    2520
tggggcatcg atcgggtgag aaagcatcag gactggagcg gaaagtattg cccgcaccgc    2580
attttatcag agggggcgctg ggatcaagtg aaggcggcga ttgaaaagga attaaacggg    2640
ggcgtatcag cgaaaaaagc tgcagtctct tcttcggcgt ctgaatatca tgtaaaaaaa    2700
ggtgacacac tgtcagggat tgccgcatca cacgggcc                           2739
```

<210> SEQ ID NO 18
<211> LENGTH: 3268
<212> TYPE: DNA
<213> ORGANISM: Artificial Sequence
<220> FEATURE:
<223> OTHER INFORMATION: Synthetic construct: nucleotide sequence of the
      phrE deletion construct

<400> SEQUENCE: 18

```
ttttttctgt tcagacataa tggatttga tttggtgtag gcgttagcaa gctcatgcgc      60 taaaaggtt tcttctatgt aggcatctga taagttggca tcttctaaaa aaccaggaat     120
actcgttaag aaagaaattt tcatctcaat taaatcaatc cattggtcag caatgccagc    180
ttgatcttca taaatgatt taatgttatt agcgcctttg cctgaaaact cgctatcatc    240
taaatctgca acagctttga acgctttctt taatttgacc attttacttt ttaaatcttt    300
gtattcctgt gctcgctttt cagcctcggt gagcaaggtt ttggcttcaa atactttcat    360
gatcatatcc tttcatttaa tcgtcataac aaaatattac catggaagaa tgatgaaact    420
```

```
aactgttatg tggatcaaat ggtggaaatg aatcattcga tctgtgtcat tttacctatt    480
tgttaatcct ttcaatgaaa ggggactttc caattgtaac atcgccatca tgaaaaaatt    540
cgataacgta gccagattca ctaaacataa aagtatccga tccaacggca gttacatcat    600
caattacgtt taatgcatgc tcaagactgg tttttaatgc tggctgttct ccgtaacccc    660
aaagaataat aatgttccta tctttaaaat ggtgtttagc tagccaatcg taaatctctt    720
cctcgtaatc tatagattga tgacaacaaa cttcttccca cttgattcgt ccccaagatg    780
taagggaaaa ctgttgtaaa gcagttcata atattttgcc gttaattctt ctgataagat    840
ttctttgttt ttccctagag cttctaagca ttcatcaaat aagtccaaaa tgttcacctc    900
aaaagcttta agtatgatag atttttttcag tattagaaat aagaaaaagc cgttatgaaa    960
cggctaaagg gaatcagaac taatgttgtt tatcgaatcg acggtatatc gaaaggggaa   1020
tgcatgtatg aaatctaaat tgtttatcag tttatccgcc gttttaattg gacttgcgaa   1080
aggcgaattc cagcacactg gcggccgtta ctagtggatc cgagctcgga tccataactt   1140
cgtataatgt atgctatacg aagttatcta gataaaaaat ttagaagcca atgaaatcta   1200
taaataaact aaattaagtt tatttaatta acaactatgg atataaaata ggtactaatc   1260
aaaatagtga ggaggatata tttgaataca tacgaacaaa ttaataaagt gaaaaaaata   1320
cttcggaaac atttaaaaaa taaccttatt ggtacttaca tgtttggatc aggagttgag   1380
agtggactaa aaccaaatag tgatcttgac ttttagtcg tcgtatctga accattgaca   1440
gatcaaagta aagaaatact tatacaaaaa attagaccta tttcaaaaaa ataggagat   1500 aaaagcaact tacgatatat tgaattaaca attattattc agcaagaaat ggtaccgtgg   1560
aatcatcctc ccaaacaaga atttatttat ggagaatggt tacaagagct ttatgaacaa   1620
ggatacattc ctcagaagga attaaattca gatttaacca taatgctta ccaagcaaaa   1680 cgaaaaata aaagaatata cggaaattat gacttagagg aattactacc tgatattcca   1740 tttttctgatg tgagaagagc cattatggat tcgtcagagg aattaataga taattatcag   1800
gatgatgaaa ccaactctat attaactta tgccgtatga ttttaactat ggacacgggt   1860
aaaatcatac caaaagatat tgcgggaaat gcagtggctg aatcttctcc attagaacat   1920
agggagagaa ttttgttagc agttcgtagt tatcttggag agaatattga atggactaat   1980
gaaaatgtaa atttaactat aaactattta aataacagat taaaaaatt ataaaaaaat   2040 tgaaaaaatg gtggaaacac ttttttcaat tttttgtttt tattatttaa tatttgggaa   2100
atattcattc taattggtaa tcagatttta gaaaacaata aacccttgca tatgtctaga   2160
taacttcgta taatgtatgc tatacgaagt tatgcggccg ccatatgcat cctaggccgc   2220
aagtccaatt aaaacggcgg ataaactgat aaacaattta gatttcatac atgcattccc   2280
ctttcgatat ttgcttttga gcatatacca tcttcttgaa acagatgata ctatcctcta   2340
tttccccatt ataatcgaaa aggttgcctc taacaatgc cagctcttcc agataagggt   2400
atcctttgcc gttctctaaa cgagaaaaaa tgttgagaag tttaggtgta tcgccatttc   2460
ttatataaag aacgtctaat gcttcaaata agttcataaa tagttcgtct ttaaaatcta   2520
cagcacttct gattcctttg cggaagcaat ccattgcttg tcctttttg ccttgtttaa   2580 aataaatcaa cgctaggtca tgataagctt gcggaagtac gtcagagtta attttttctgt   2640 attgaaccaa ggcttgttcg atgtaacgag cagcctatt taagttgtcc attttgtgat   2700
agcaattgcc gagattgaaa aacgcagtgg catagatatg agtattttta cttttaagca   2760
gctcggcacc ttttaaagct tcttgaaggt gggggagagc ttttcatga ttttcaaggt   2820
```

| catcgtagtt accggcaatg acaaaatggc actgaatacg acgaacagag taaagctcgt | 2880 |
| gtttcttata aatgttgtat gaaagctcag cgtaatgcat cgaaatgtgt gtcattttca | 2940 |
| tatgataata gacttcagac agtttaaaat aaaactcagc tttttcaatc ttgtcggaga | 3000 |
| ttgtaggaat tttgcgttca gcttttttgt aatatgtaat ggctcttgtg tattcaccgt | 3060 |
| ttctaaactc atacatcccg cggaagaagt tataataata tgcccgcata ttgtctaatt | 3120 |
| ttttcttatg gccctcaatt ttatttaaat attctgaaag ttccattcgg ttttcatcag | 3180 |
| atggcagcgt gtattccaac ataattttat ggcgaaaggc cattagttga taataaataa | 3240 |
| gcaagtcttg atcttcttcc ataacctc | 3268 |

<210> SEQ ID NO 19
<211> LENGTH: 1759
<212> TYPE: DNA
<213> ORGANISM: Artificial Sequence
<220> FEATURE:
<223> OTHER INFORMATION: Synthetic construct: nucleotide sequence of
      aprE promoter-FNA

<400> SEQUENCE: 19

| gaattcctcc attttcttct gctatcaaaa taacagactc gtgattttcc aaacgagctt | 60 |
| tcaaaaaagc ctctgcccct tgcaaatcgg atgcctgtct ataaaattcc cgatattggc | 120 |
| ttaaacagcg gcgcaatggc ggccgcatct gatgtctttg cttggcgaat gttcatctta | 180 |
| tttcttcctc cctctcaata atttttcat tctatccctt ttctgtaaag tttattttc | 240 |
| agaatacttt tatcatcatg ctttgaaaaa atatcacgat aatatccatt gttctcacgg | 300 |
| aagcacacgc aggtcatttg aacgaatttt ttcgacagga atttgccggg actcaggagc | 360 |
| atttaaccta aaaagcatg acatttcagc ataatgaaca tttactcatg tctattttcg | 420 |
| ttcttttctg tatgaaaata gttatttcga gtctctacgg aaatagcgag agatgatata | 480 |
| cctaaataga gataaaatca tctcaaaaaa atgggtctac taaaatatta ttccatctat | 540 |
| tacaataaat tcacagaata gtcttttaag taagtctact ctgaattttt ttaaaaggag | 600 |
| agggtaaaga gtgagaagca aaaaattgtg gatcagtttg ctgtttgctt tagcgttaat | 660 |
| ctttacgatg gcgttcggca gcacatcctc tgcccaggcg gcagggaaat caaacgggga | 720 |
| aaagaaatat attgtcgggt ttaaacagac aatgagcacg atgagcgccg ctaagaagaa | 780 |
| agatgtcatt tctgaaaaag gcgggaaagt gcaaaagcaa ttcaaatatg tagacgcagc | 840 |
| ttcagctaca ttaaacgaaa aagctgtaaa agaattgaaa aaagacccga gcgtcgctta | 900 |
| cgttgaagaa gatcacgtag cacatgcgta cgcgcagtcc gtgccttacg gcgtatcaca | 960 |
| aattaaagcc cctgctctgc actctcaagg ctacactgga tcaaatgtta agtagcggt | 1020 |
| tatcgacagc ggtatcgatt cttctcatcc tgatttaaag gtagcaggcg gagccagcat | 1080 |
| ggttccttct gaaacaaatc cttttccaaga caacaactct cacgaactc acgttgccgg | 1140 |
| cacagttgcg gctcttaata actcaatcgg tgtattaggc gttgcgccaa gcgcatcact | 1200 |
| ttacgctgta aaagttctcg gtgctgacgg ttcggccaa tacagctgga tcattaacgg | 1260 |
| aatcgagtgg gcgatcgcaa acaatatgga cgttattaac atgagcctcg gcggaccttc | 1320 |
| tggttctgct gctttaaaag cggcagttga taaagccgtt gcatccggcg tcgtagtcgt | 1380 |
| tgcggcagcc ggtaacgaag gcacttccgg cagctcaagc acagtgggct accctggtaa | 1440 |
| ataccctct gtcattgcag taggcgctgt tgacagcagc aaccaaagag catctttctc | 1500 |
| aagcgtagga cctgagcttg atgtcatggc acctggcgta tctatccaaa gcacgcttcc | 1560 |
| tggaaacaaa tacggcgcgt tgaacggtac atcaatggca tctccgcacg ttgccggagc | 1620 |

```
ggctgctttg attctttcta agcacccgaa ctggacaaac actcaagtcc gcagcagttt   1680
agaaaacacc actacaaaac ttggtgattc tttctactat ggaaaagggc tgatcaacgt   1740
acaggcggca gctcagtaa                                                1759
```

```
<210> SEQ ID NO 20
<211> LENGTH: 382
<212> TYPE: PRT
<213> ORGANISM: B. amyloliquefaciens

<400> SEQUENCE: 20
```

| | | | | | | | | | | | | | | | |
|---|---|---|---|---|---|---|---|---|---|---|---|---|---|---|---|
| Val | Arg | Ser | Lys | Lys | Leu | Trp | Ile | Ser | Leu | Leu | Phe | Ala | Leu | Ala | Leu |
| 1 | | | | 5 | | | | | 10 | | | | | 15 | |
| Ile | Phe | Thr | Met | Ala | Phe | Gly | Ser | Thr | Ser | Ser | Ala | Gln | Ala | Ala | Gly |
| | | | 20 | | | | | 25 | | | | | 30 | | |
| Lys | Ser | Asn | Gly | Glu | Lys | Lys | Tyr | Ile | Val | Gly | Phe | Lys | Gln | Thr | Met |
| | | | 35 | | | | | 40 | | | | | 45 | | |
| Ser | Thr | Met | Ser | Ala | Ala | Lys | Lys | Asp | Val | Ile | Ser | Glu | Lys | Gly | |
| | 50 | | | | | 55 | | | | | 60 | | | | |
| Gly | Lys | Val | Gln | Lys | Gln | Phe | Lys | Tyr | Val | Asp | Ala | Ala | Ser | Ala | Thr |
| 65 | | | | | 70 | | | | | 75 | | | | | 80 |
| Leu | Asn | Glu | Lys | Ala | Val | Lys | Glu | Leu | Lys | Lys | Asp | Pro | Ser | Val | Ala |
| | | | | 85 | | | | | 90 | | | | | 95 | |
| Tyr | Val | Glu | Glu | Asp | His | Val | Ala | His | Ala | Tyr | Ala | Gln | Ser | Val | Pro |
| | | | 100 | | | | | 105 | | | | | 110 | | |
| Tyr | Gly | Val | Ser | Gln | Ile | Lys | Ala | Pro | Ala | Leu | His | Ser | Gln | Gly | Tyr |
| | | | 115 | | | | | 120 | | | | | 125 | | |
| Thr | Gly | Ser | Asn | Val | Lys | Val | Ala | Val | Ile | Asp | Ser | Gly | Ile | Asp | Ser |
| | 130 | | | | | 135 | | | | | 140 | | | | |
| Ser | His | Pro | Asp | Leu | Lys | Val | Ala | Gly | Gly | Ala | Ser | Met | Val | Pro | Ser |
| 145 | | | | | 150 | | | | | 155 | | | | | 160 |
| Glu | Thr | Asn | Pro | Phe | Gln | Asp | Asn | Asn | Ser | His | Gly | Thr | His | Val | Ala |
| | | | | 165 | | | | | 170 | | | | | 175 | |
| Gly | Thr | Val | Ala | Ala | Leu | Asn | Asn | Ser | Ile | Gly | Val | Leu | Gly | Val | Ala |
| | | | 180 | | | | | 185 | | | | | 190 | | |
| Pro | Ser | Ala | Ser | Leu | Tyr | Ala | Val | Lys | Val | Leu | Gly | Ala | Asp | Gly | Ser |
| | | | 195 | | | | | 200 | | | | | 205 | | |
| Gly | Gln | Tyr | Ser | Trp | Ile | Ile | Asn | Gly | Ile | Glu | Trp | Ala | Ile | Ala | Asn |
| | 210 | | | | | 215 | | | | | 220 | | | | |
| Asn | Met | Asp | Val | Ile | Asn | Met | Ser | Leu | Gly | Gly | Pro | Ser | Gly | Ser | Ala |
| 225 | | | | | 230 | | | | | 235 | | | | | 240 |
| Ala | Leu | Lys | Ala | Ala | Val | Asp | Lys | Ala | Val | Ala | Ser | Gly | Val | Val | Val |
| | | | | 245 | | | | | 250 | | | | | 255 | |
| Val | Ala | Ala | Ala | Gly | Asn | Glu | Gly | Thr | Ser | Gly | Ser | Ser | Ser | Thr | Val |
| | | | 260 | | | | | 265 | | | | | 270 | | |
| Gly | Tyr | Pro | Gly | Lys | Tyr | Pro | Ser | Val | Ile | Ala | Val | Gly | Ala | Val | Asp |
| | | | 275 | | | | | 280 | | | | | 285 | | |
| Ser | Ser | Asn | Gln | Arg | Ala | Ser | Phe | Ser | Ser | Val | Gly | Pro | Glu | Leu | Asp |
| | 290 | | | | | 295 | | | | | 300 | | | | |
| Val | Met | Ala | Pro | Gly | Val | Ser | Ile | Gln | Ser | Thr | Leu | Pro | Gly | Asn | Lys |
| 305 | | | | | 310 | | | | | 315 | | | | | 320 |
| Tyr | Gly | Ala | Leu | Asn | Gly | Thr | Ser | Met | Ala | Ser | Pro | His | Val | Ala | Gly |
| | | | | 325 | | | | | 330 | | | | | 335 | |
| Ala | Ala | Ala | Leu | Ile | Leu | Ser | Lys | His | Pro | Asn | Trp | Thr | Asn | Thr | Gln |
| | | | 340 | | | | | 345 | | | | | 350 | | |

```
Val Arg Ser Ser Leu Glu Asn Thr Thr Thr Lys Leu Gly Asp Ser Phe
            355                 360                 365

Tyr Tyr Gly Lys Gly Leu Ile Asn Val Gln Ala Ala Ala Gln
            370                 375                 380

<210> SEQ ID NO 21
<211> LENGTH: 381
<212> TYPE: PRT
<213> ORGANISM: Bacillus subtilis

<400> SEQUENCE: 21

Met Arg Ser Lys Lys Leu Trp Ile Ser Leu Leu Phe Ala Leu Thr Leu
1               5                   10                  15

Ile Phe Thr Met Ala Phe Ser Asn Met Ser Val Gln Ala Ala Gly Lys
            20                  25                  30

Ser Ser Thr Glu Lys Lys Tyr Ile Val Gly Phe Lys Gln Thr Met Ser
            35                  40                  45

Ala Met Ser Ser Ala Lys Lys Lys Asp Val Ile Ser Glu Lys Gly Gly
    50                  55                  60

Lys Val Gln Lys Gln Phe Lys Tyr Val Asn Ala Ala Ala Ala Thr Leu
65              70                  75                  80

Asp Glu Lys Ala Val Lys Glu Leu Lys Lys Asp Pro Ser Val Ala Tyr
                85                  90                  95

Val Glu Glu Asp His Ile Ala His Glu Tyr Ala Gln Ser Val Pro Tyr
            100                 105                 110

Gly Ile Ser Gln Ile Lys Ala Pro Ala Leu His Ser Gln Gly Tyr Thr
            115                 120                 125

Gly Ser Asn Val Lys Val Ala Val Ile Asp Ser Gly Ile Asp Ser Ser
130                 135                 140

His Pro Asp Leu Asn Val Arg Gly Gly Ala Ser Phe Val Pro Ser Glu
145                 150                 155                 160

Thr Asn Pro Tyr Gln Asp Gly Ser Ser His Gly Thr His Val Ala Gly
                165                 170                 175

Thr Ile Ala Ala Leu Asn Asn Ser Ile Gly Val Leu Gly Val Ser Pro
            180                 185                 190

Ser Ala Ser Leu Tyr Ala Val Lys Val Leu Asp Ser Thr Gly Ser Gly
            195                 200                 205

Gln Tyr Ser Trp Ile Ile Asn Gly Ile Glu Trp Ala Ile Ser Asn Asn
        210                 215                 220

Met Asp Val Ile Asn Met Ser Leu Gly Gly Pro Thr Gly Ser Thr Ala
225                 230                 235                 240

Leu Lys Thr Val Val Asp Lys Ala Val Ser Ser Gly Ile Val Val Ala
                245                 250                 255

Ala Ala Ala Gly Asn Glu Gly Ser Ser Gly Ser Thr Ser Thr Val Gly
            260                 265                 270

Tyr Pro Ala Lys Tyr Pro Ser Thr Ile Ala Val Gly Ala Val Asn Ser
            275                 280                 285

Ser Asn Gln Arg Ala Ser Phe Ser Ser Ala Gly Ser Glu Leu Asp Val
        290                 295                 300

Met Ala Pro Gly Val Ser Ile Gln Ser Thr Leu Pro Gly Gly Thr Tyr
305                 310                 315                 320

Gly Ala Tyr Asn Gly Thr Ser Met Ala Thr Pro His Val Ala Gly Ala
                325                 330                 335

Ala Ala Leu Ile Leu Ser Lys His Pro Thr Trp Thr Asn Ala Gln Val
            340                 345                 350
```

Arg Asp Arg Leu Glu Ser Thr Ala Thr Tyr Leu Gly Asn Ser Phe Tyr
            355                 360                 365

Tyr Gly Lys Gly Leu Ile Asn Val Gln Ala Ala Ala Gln
    370                 375                 380

<210> SEQ ID NO 22
<211> LENGTH: 1496
<212> TYPE: DNA
<213> ORGANISM: Artificial Sequence
<220> FEATURE:
<223> OTHER INFORMATION: Synthetic polynucleotide construct that
      comprise a polynucleotide sequence that encodes YmaH and a SigA
      and a SigH promoter

<400> SEQUENCE: 22
tcataccctg aaaggaaaga caagggaaat tgtcggcaat gagccgctcg gcaggtagaa     60
ggatgtttac cgatgcaaaa aaagggcaaa atggataggt ggttgtccat gttgaatgct    120
ataatggggg agatttataa aagagagtga tacatattga ataatacgaa gcagcccgtt    180
gtcattttag tcggaccgac ggcagtgggg aaaaccaatt taagtattca gctagccaaa    240
tccttaaacg cggaaattat cagcggagat tcgatgcaga tttataaagg gatggatatt    300
ggaacagcta aaattaccga acaggagatg gagggagtgc cccatcatct gattgacatt    360
ttagatcccc aagactcttt ctctactgcc gattatcaaa gcttagtaag aaataaaatc    420
agcgagattg caaatagagg aaagcttccg atgattgacg gcggtacagg gctttatata    480
caatctgagc tttacgatta tacatttacg gaagaggcaa atgatcccgt gtttcgagag    540
agcatgcaaa tggctgctga gcgggaaggc gctgactttc ttcatgccaa acttgctgca    600
gcagatcccg aggcagcagc tgcgattcat ccgaataata caagaagagt cattcgcgca    660
ctggaaattt tacatacgtc cggaaaaacg atgtcccagc atttgaagga acaaaaacga    720
gaacttctgt acaatgcagt gttaattggc ctgacaatgg atagagacac gctttacgaa    780
agaattaatc agcgggtcga tttgatgatg cagtcaggcc ttcttccgga agtgaaacgc    840
ttatacgaca gaacgtgag agactgtcaa tcaatacagg cgataggcta taaagagctg    900
tatgcatatt ttgacggttt tgtgacactt tccgatgctg tcgaacagct aaagcagaac    960
tcgaggcggt atgcgaaacg ccagctgacg tggtttcgca acaaaatgca ggtcacatgg   1020
ttcgatatga caccgcctgt tgatatggag ctgaaaaaaa aggaaatttt cacacatata   1080
gcaggaaaac tcgaacttta atcgaaactg tatgatatag agaatcaagg aggacgaaac   1140
atgaaaccga ttaatattca ggatcagttt ttgaatcaaa tccggaaaga aaatacgtat   1200
gtcactgttt ttttgctgaa cggctttcag ttgcggggcc aggtgaaagg ctttgataac   1260
tttaccgtat tgttggaatc ggaaggtaag cagcagctta tatataaaca tgcgatctca   1320
acgtttgcgc cgcaaaaaaa cgtccagctt gaactcgaat agatcaaaaa atgccatgtc   1380
aagacatgag gaaaggctgt cggggggttcc cggcggccat ttttaacatg aatccacttt   1440
tgctccaagc ttttttgtgta agctgaccat gccaaggcac ggtcttttttt tatgag      1496

<210> SEQ ID NO 23
<211> LENGTH: 534
<212> TYPE: DNA
<213> ORGANISM: Artificial Sequence
<220> FEATURE:
<223> OTHER INFORMATION: Synthetic SigH construct

<400> SEQUENCE: 23
ggcaccgaat tcgacgtggt ttcgcaacaa aatgcaggtc acatggttcg atatgacacc     60

```
gcctgttgat atggagctga aaaaaaagga aatttcaca catatagcag gaaaactcga    120
actttaatcg aaactgtatg atatagagaa tcaaggagga cgaaacatga accgattaa    180 tattcaggat cagtttttga atcaaatccg gaaagaaaat acgtatgtca ctgttttttt    240
gctgaacggc tttcagttgc ggggccaggt gaaaggcttt gataacttta ccgtattgtt    300
ggaatcggaa ggtaagcagc agcttatata taaacatgcg atctcaacgt ttgcgccgca    360
aaaaaacgtc cagcttgaac tcgaatagat caaaaaatgc catgtcaaga catgaggaaa    420
ggctgtcggg ggttcccggc ggccattttt aacatgaatc cacttttgct ccaagctttt    480
tgtgtaagct gaccatgcca aggcacggtc ttttttatg agggatccgg agcc           534

<210> SEQ ID NO 24
<211> LENGTH: 37
<212> TYPE: DNA
<213> ORGANISM: Artificial Sequence
<220> FEATURE:
<223> OTHER INFORMATION: Synthetic primer: ymaH 1F EcoRI (P1)

<400> SEQUENCE: 24
ggcaccgaat tcgacgtggt ttcgcaacaa aatgcag                              37

<210> SEQ ID NO 25
<211> LENGTH: 37
<212> TYPE: DNA
<213> ORGANISM: Artificial Sequence
<220> FEATURE:
<223> OTHER INFORMATION: Synthetic primer: reverse primer P2

<400> SEQUENCE: 25
ggcaccggat ccctcataaa aaaagaccgt gccttgg                              37

<210> SEQ ID NO 26
<211> LENGTH: 626
<212> TYPE: DNA
<213> ORGANISM: Artificial Sequence
<220> FEATURE:
<223> OTHER INFORMATION: Synthetic SigA1 construct

<400> SEQUENCE: 26
gcgccgaatt ctcatacccct gaaaggaaag acaagggaaa ttgtcggcaa tgagccgctc    60
ggcaggtaga aggatgttta ccgatgcaaa aaaagggcaa atggataggg tggttgtcca    120
tgttgaatgc tataatgggg gagatttata aagagagtg atacatattg aataatacga    180
agcagcccca cacatatagc aggaaaactc gaactttaat cgaaactgta tgatatagag    240
aatcaaggag gacgaaacat gaaaccgatt aatattcagg atcagttttt gaatcaaatc    300
cggaaagaaa atacgtatgt cactgttttt ttgctgaacg gctttcagtt gcggggccag    360
gtgaaaggct ttgataactt taccgtattg ttggaatcgg aaggtaagca gcagcttata    420
tataaacatg cgatctcaac gtttgcgccg caaaaaaacg tccagcttga actcgaatag    480
atcaaaaaat gccatgtcaa gacatgagga aaggctgtcg ggggttcccg gcggccattt    540
ttaacatgaa tccactttg ctccaagctt tttgtgtaag ctgaccatgc caaggcacgg    600
tcttttttta tgagggatcc ggtgcc                                          626

<210> SEQ ID NO 27
<211> LENGTH: 36
<212> TYPE: DNA
<213> ORGANISM: Artificial Sequence
<220> FEATURE:
<223> OTHER INFORMATION: Synthetic forward primer P3
```

<400> SEQUENCE: 27
gcgccgaatt ctcataccct gaaaggaaag acaagg                                    36

<210> SEQ ID NO 28
<211> LENGTH: 50
<212> TYPE: DNA
<213> ORGANISM: Artificial Sequence
<220> FEATURE:
<223> OTHER INFORMATION: Synthetic reverse primer P4

<400> SEQUENCE: 28
ttcgagtttt cctgctatat gtgtggggct gcttcgtatt attcaatatg                     50

<210> SEQ ID NO 29
<211> LENGTH: 50
<212> TYPE: DNA
<213> ORGANISM: Artificial Sequence
<220> FEATURE:
<223> OTHER INFORMATION: Synthetic forward primer P5

<400> SEQUENCE: 29
catattgaat aatacgaagc agccccacac atatagcagg aaaactcgaa                     50

<210> SEQ ID NO 30
<211> LENGTH: 4039
<212> TYPE: DNA
<213> ORGANISM: Artificial Sequence
<220> FEATURE:
<223> OTHER INFORMATION: Synthetic polynucleotide sequence of pBS19

<400> SEQUENCE: 30
gaattcgagc tcggtacccg ggatcctct agagtcgacc tgcaggcatg caagcttggc          60
gatcctgcct cgcgcgtttc ggtgatgacg gtgaaaacct ctgacacatg cagctcccgg        120
agacggtcac agcttgtctg taagcggatg ccgggagcag acaagcccgt cagggcgcgt        180
cagcgggtgt tggcgggtgt cggggcgcag ccatgaccca gtcacgtagc gatagcggag        240
tgtatactgg cttaactatg cggcatcaga gcagattgta ctgagagtgc accatatgcg        300
gtgtgaaata ccgcacagat gcgtaaggag aaaataccgc atcaggcgct cttccgcttc        360
ctcgctcact gactcgctgc gctcggtcgt tcggctgcgg cgagcggtat cagctcactc        420
aaaggcggta atacggttat ccacagaatc aggggataac gcaggaaaga acatgtgagc        480
aaaaggccag caaaaggcca ggaaccgtaa aaaggccgcg ttgctggcgt ttttccatag        540
gctccgcccc cctgacgagc atcacaaaaa tcgacgctca agtcagaggt ggcgaaaccc        600
gacaggacta taaagatacc aggcgtttcc ccctggaagc tccctcgtgc gctctcctgt        660
tccgaccctg ccgcttaccg gatacctgtc cgcctttctc ccttcgggaa gcgtggcgct        720
ttctcatagc tcacgctgta ggtatctcag ttcggtgtag tcgttcgct ccaagctggg         780
ctgtgtgcac gaacccccg ttcagcccga ccgctgcgcc ttatccggta actatcgtct         840
tgagtccaac ccggtaagac acgacttatc gccactggca gcagccactg gtaacaggat        900
tagcagagcg aggtatgtag gcggtgctac agagttcttg aagtggtggc ctaactacgg        960
ctacactaga aggacagtat ttggtatctg cgctctgctg aagccagtta ccttcggaaa       1020
aagagttggt agctcttgat ccggcaaaca aaccaccgct ggtagcggtg gtttttttgt       1080
ttgcaagcag cagattacgc gcagaaaaaa aggatctcaa gaagatcctt tgatcttttc       1140
tacgggtct gacgctcagt ggaacgaaaa ctcacgttaa gggattttgg tcatgagatt        1200
atcaaaaagg atctggagct gtaatataaa aaccttcttc aactaacggg gcaggttagt       1260

```
gacattagaa aaccgactgt aaaaagtaca gtcggcatta tctcatatta taaaagccag   1320
tcattaggcc tatctgacaa ttcctgaata gagttcataa acaatcctgc atgataacca   1380
tcacaaacag aatgatgtac ctgtaaagat agcggtaaat atattgaatt acctttatta   1440
atgaattttc ctgctgtaat aatgggtaga aggtaattac tattattatt gatatttaag   1500
ttaaacccag taaatgaagt ccatggaata atagaaagag aaaaagcatt ttcaggtata   1560
ggtgttttgg gaaacaattt ccccgaacca ttatatttct ctacatcaga aaggtataaa   1620
tcataaaact ctttgaagtc attcttttaca ggagtccaaa taccagagaa tgttttagat   1680
acaccatcaa aaattgtata aagtggctct aacttatccc aataacctaa ctctccgtcg   1740
ctattgtaac cagttctaaa agctgtattt gagtttatca cccttgtcac taagaaaata   1800
aatgcagggt aaaatttata tccttcttgt tttatgtttc ggtataaaac actaatatca   1860
atttctgtgg ttatactaaa agtcgtttgt tggttcaaat aatgattaaa tatctctttt   1920
ctcttccaat tgtctaaatc aattttatta aagttcattt gatatgcctc ctaaattttt   1980
atctaaagtg aatttaggag cttacttgt ctgctttctt cattagaatc aatccttttt    2040
taaaagtcaa tattactgta acataaatat atattttaaa aatatcccac tttatccaat   2100
tttcgtttgt tgaactaatg ggtgctttag ttgaagaata aaagaccaca ttaaaaaatg   2160
tggtcttttg tgtttttta aaggatttga gcgtagcgaa aaatccttt ctttcttatc     2220 ttgataataa gggtaactat tgccggttgt ccattcatgg ctgaactctg cttcctctgt   2280
tgacatgaca cacatcatct caatatccga atagggccca tcagtctgac gaccaagaga   2340
gccataaaca ccaatagcct aacatcatc cccatattta tccaatattc gttccttaat    2400
ttcatgaaca atcttcattc tttcttctct agtcattatt attggtccat tcactattct   2460
cattcccttt tcagataatt ttagatttgc ttttctaaat aagaatattt ggagagcacc   2520
gttcttattc agctattaat aactcgtctt cctaagcatc cttcaatcct tttaataaca   2580
attatagcat ctaatcttca acaaactggc ccgtttgttg aactactctt taataaaata   2640 attttccgt tcccaattcc acattgcaat aatagaaaat ccatcttcat cggcttttc     2700 gtcatcatct gtatgaatca aatcgccttc ttctgtgtca tcaaggttta atttttatg    2760 tatttctttt aacaaaccac cataggagat taaccttta cggtgtaaac cttcctccaa    2820
atcagacaaa cgtttcaaat tcttttcttc atcatcggtc ataaaatccg tatcctttac   2880
aggatatttt gcagtttcgt caattgccga ttgtatatcc gatttatatt tatttttcgg   2940
tcgaatcatt tgaactttta catttggatc atagtctaat ttcattgcct ttttccaaaa   3000
ttgaatccat tgttttgat tcacgtagtt ttctgtattc ttaaaataag ttggttccac    3060
acataccaat acatgcatgt gctgattata agaattatct ttattattta ttgtcacttc   3120
cgttgcacgc ataaaaccaa caagattttt attaattttt ttatattgca tcattcggcg   3180
aaatccttga gccatatctg acaaactctt atttaattct tcgccatcat aaacattttt   3240
aactgttaat gtgagaaaca accaacgaac tgttggcttt tgtttaataa cttcagcaac   3300
aaccttttgt gactgaatgc catgtttcat tgctctcctc cagttgcaca ttggacaaag   3360
cctggattta caaaccaca ctcgatacaa ctttctttcg cctgtttcac gattttgttt    3420
atactctaat atttcagcac aatctttac tctttcagcc ttttaaatt caagaatatg     3480 cagaagttca aagtaatcaa cattagcgat tttcttttct ctccatggtc tcacttttcc   3540 acttttgtc ttgtccacta aaaccctga ttttcatct gaataaatgc tactattagg      3600
acacataata ttaaaagaaa ccccccatcta tttagttatt tgtttagtca cttataactt  3660
```

```
taacagatgg ggttttttctg tgcaaccaat tttaagggtt ttcaatactt taaaacacat    3720
acataccaac acttcaacgc acctttcagc aactaaaata aaaatgacgt tatttctata    3780
tgtatcaaga taagaaagaa caagttcaaa accatcaaaa aaagacacct tttcaggtgc    3840
tttttttatt ttataaactc attccctgat ctcgacttcg ttcttttttt acctctcggt    3900
tatgagttag ttcaaattcg ttcttttag gttctaaatc gtgttttttct tggaattgtg    3960 ctgttttatc ctttaccttg tctacaaacc ccttaaaaac gtttttaaag gcttttaagc    4020
cgtctgtacg ttccttaag                                                 4039
```

<210> SEQ ID NO 31
<211> LENGTH: 579
<212> TYPE: DNA
<213> ORGANISM: Artificial Sequence
<220> FEATURE:
<223> OTHER INFORMATION: Synthetic SigA2 construct

<400> SEQUENCE: 31

```
gcgccgaatt ctcatacccct gaaaggaaag acaagggaaa ttgtcggcaa tgagccgctc     60
ggcaggtaga aggatgttta ccgatgcaaa aaaagggcaa aatggatagg tggttgtcca    120
tgttgaatgc tataatgggg gagatttata aaagagagtg ctcgaacttt aatcgaaact    180
gtatgatata gagaatcaag gaggacgaaa catgaaaccg attaatattc aggatcagtt    240
tttgaatcaa atccggaaag aaaatacgta tgtcactgtt ttttgctga acggctttca     300 gttgcggggc caggtaaaag ctttgataa ctttaccgta ttgttggaat cggaaggtaa     360
gcagcagctt atatataaac atgcgatctc aacgtttgcg ccgcaaaaaa acgtccagct    420
tgaactcgaa tagatcaaaa aatgccatgt caagacatga ggaaaggctg tcggggggttc    480 ccggcggcca ttttttaacat gaatccactt ttgctccaag ctttttgtgt aagctgacca    540
tgccaaggca cggtctttttt ttatgaggga tccggtgcc                            579
```

<210> SEQ ID NO 32
<211> LENGTH: 50
<212> TYPE: DNA
<213> ORGANISM: Artificial Sequence
<220> FEATURE:
<223> OTHER INFORMATION: Synthetic forward fusion primer P6

<400> SEQUENCE: 32

```
tgggggagat ttataaaaga gagtgctcga actttaatcg aaactgtatg                 50
```

<210> SEQ ID NO 33
<211> LENGTH: 50
<212> TYPE: DNA
<213> ORGANISM: Artificial Sequence
<220> FEATURE:
<223> OTHER INFORMATION: Synthetic reverse fusion primer P7

<400> SEQUENCE: 33

```
catacagttt cgattaaagt tcgagcactc tcttttataa atctccccca                 50
```

<210> SEQ ID NO 34
<211> LENGTH: 42
<212> TYPE: DNA
<213> ORGANISM: Artificial Sequence
<220> FEATURE:
<223> OTHER INFORMATION: Synthetic forward primer P8

<400> SEQUENCE: 34

```
gcgcgcgaat tcagggaaat tgtcggcaat gagccgctcg gc                         42
```

<210> SEQ ID NO 35
<211> LENGTH: 41
<212> TYPE: DNA
<213> ORGANISM: Artificial Sequence
<220> FEATURE:
<223> OTHER INFORMATION: Synthetic reverse primer P9

<400> SEQUENCE: 35
gcgcgccatg gctgattcgt ctcagttctg cttcactttc a                          41

<210> SEQ ID NO 36
<211> LENGTH: 4768
<212> TYPE: DNA
<213> ORGANISM: Artificial Sequence
<220> FEATURE:
<223> OTHER INFORMATION: Synthetic pBN3 vector

<400> SEQUENCE: 36

| | |
|---|---|
| gacgtctaag aaaccattat tatcatgaca ttaacctata aaaataggcg tatcacgagg | 60 |
| cccttcgtc ttcaagaatt aattctcatg tttgacagct tatcatcgat aagcttgcat | 120 |
| gcctgcaggt cgactctaga ggatccccgg gtaccgagct cgaattcctt aaggaacgta | 180 |
| cagacggctt aaaagccttt aaaaacgttt ttaaggggtt tgtagacaag gtaaaggata | 240 |
| aaacagcaca attccaagaa aaacacgatt tagaacctaa aaagaacgaa tttgaactaa | 300 |
| ctcataaccg agaggtaaaa aagaacgaa gtcgagatca gggaatgagt ttataaaata | 360 |
| aaaaaagcac ctgaaaaggt gtcttttttt gatggttttg aacttgttct ttcttatctt | 420 |
| gatacatata gaaataacgt cattttatt ttagttgctg aaaggtgcgt tgaagtgttg | 480 |
| gtatgtatgt gttttaaagt attgaaaacc cttaaaattg gttgcacaga aaaccccat | 540 |
| ctgttaaagt tataagtgac taaacaaata actaaataga tgggggtttc ttttaatatt | 600 |
| atgtgtccta atagtagcat ttattcagat gaaaaatcaa gggttttagt ggacaagaca | 660 |
| aaaagtggaa aagtgagacc atggagagaa agaaaatcg ctaatgttga ttactttgaa | 720 |
| cttctgcata ttcttgaatt taaaaaggct gaaagagtaa aagattgtgc tgaaatatta | 780 |
| gagtataaac aaaatcgtga acaggcgaaa agaaagttgt atcgagtgtg gttttgtaaa | 840 |
| tccaggcttt gtccaatgtg caactggagg agagcaatga acatggcat tcagtcacaa | 900 |
| aaggttgttg ctgaagttat taaacaaaag ccaacagttc gttggttgtt tctcacatta | 960 |
| acagttaaaa atgtttatga tggcgaagaa ttaaataaga gtttgtcaga tatggctcaa | 1020 |
| ggatttcgcc gaatgatgca atataaaaaa attaataaaa atcttgttgg ttttatgcgt | 1080 |
| gcaacggaag tgacaataaa taataagat aattcttata atcagcacat gcatgtattg | 1140 |
| gtatgtgtgg aaccaactta ttttaagaat acagaaaact acgtgaatca aaacaatgg | 1200 |
| attcaatttt ggaaaaaggc aatgaaatta gactatgatc aaatgtaaa agttcaaatg | 1260 |
| attcgaccga aaaataaata taatcggat atacaatcgg caattgacga aactgcaaaa | 1320 |
| tatcctgtaa aggatacgga ttttatgacc gatgatgaag aaagaattt gaacgtttg | 1380 |
| tctgatttgg aggaaggttt acaccgtaaa aggttaatct cctatggtgg tttgttaaaa | 1440 |
| gaaatacata aaaattaaa ccttgatgac acagaagaag gcgatttgat tcatacagat | 1500 |
| gatgacgaaa agccgatga agatggattt tctattattg caatgtggaa ttgggaacgg | 1560 |
| aaaaattatt ttattaaaga gtagttcaac aaacgggcca gtttgttgaa gattagatgc | 1620 |
| tataattgtt attaaaagga ttgaaggatg cttaggaaga cgagttatta atagctgaat | 1680 |
| aagaacggtg ctctccaaat attcttatt agaaaagcaa atctaaaatt atctgaaaag | 1740 |

```
ggaatgagaa tagtgaatgg accaataata atgactagag aagaaagaat gaagattgtt    1800
catgaaatta aggaacgaat attggataaa tatggggatg atgttaaggc tattggtgtt    1860
tatggctctc ttggtcgtca gactgatggg ccctattcgg atattgagat gatgtgtgtc    1920
atgtcaacag aggaagcaga gttcagccat gaatggacaa ccggtgagtg aaggtggaa     1980 gtgaattttg atagcgaaga gattctacta gattatgcat ctcaggtgga atcagattgg    2040
ccgcttacac atggtcaatt tttctctatt ttgccgattt atgattcagg tggatactta    2100
gagaaagtgt atcaaactgc taaatcggta gaagcccaaa cgttccacga tgcgatttgt    2160
gcccttatcg tagaagagct gttttgaatat gcaggcaaat ggcgtaatat tcgtgtgcaa    2220
ggaccgacaa catttctacc atccttgact gtacaggtag caatggcagg tgccatgttg    2280
attggtctgc atcatcgcat ctgttatacg acgagcgctt cggtcttaac tgaagcagtt    2340
aagcaatcag atcttccttc aggttatgac catctgtgcc agttcgtaat gtctggtcaa    2400
ctttccgact ctgagaaact tctggaatcg ctagagaatt tctggaatgg gattcaggag    2460
tggacagaac gacacggata tatagtggat gtgtcaaaac gcataccatt ttgaacgatg    2520
acctctaata attgttaatc atgttggtta cctgcctcgc gcgtttcggt gatgacggtg    2580
aaaacctctg acacatgcag ctcccggaga cggtcacagc ttgtctgtaa gcggatgccg    2640
ggagcagaca agcccgtcag ggcgcgtcag cgggtgttgg cgggtgtcgg ggcgcagcca    2700
tgacccagtc acgtagcgat agcggagtgt atactggctt aactatgcgg catcagagca    2760
gattgtactg agagtgcacc atatgcgtg tgaaataccg cacagatgcg taaggagaaa     2820
ataccgcatc aggcgctctt ccgcttcctc gctcactgac tcgctgcgct cggtcgttcg    2880
gctgcggcga gcggtatcag ctcactcaaa ggcggtaata cggttatcca cagaatcagg    2940
ggataacgca ggaaagaaca tgtgagcaaa aggccagcaa aaggccagga accgtaaaaa    3000
ggccgcgttg ctggcgtttt tccataggct ccgcccccct gacgagcatc acaaaaatcg    3060
acgctcaagt cagaggtggc gaaacccgac aggactataa agataccagg cgtttccccc    3120
tggaagctcc ctcgtgcgct ctcctgttcc gaccctgccg cttaccggat acctgtccgc    3180 cttctccct tcgggaagcg tggcgctttc tcatagctca cgctgtaggt atctcagttc     3240
ggtgtaggtc gttcgctcca agctgggctg tgtgcacgaa ccccccgttc agcccgaccg    3300
ctgcgcctta tccggtaact atcgtcttga gtccaacccg gtaagacacg acttatcgcc    3360
actggcagca gccactggta acaggattag cagagcgagg tatgtaggcg gtgctacaga    3420
gttcttgaag tggtggccta actacggcta cactagaagg acagtatttg gtatctgcgc    3480
tctgctgaag ccagttacct tcggaaaaag agttggtagc tcttgatccg gcaaacaaac    3540
caccgctggt agcggtggtt ttttgtttg caagcagcag attacgcgca gaaaaaagg      3600 atctcaagaa gatcctttga tcttttctac ggggtctgac gctcagtgga acgaaaactc    3660
acgttaaggg attttggtca tgagattatc aaaaaggatc ttcacctaga tccttttaaa    3720
ttaaaaatga agttttaaat caatctaaag tatatatgag taaacttggt ctgacagtta    3780
ccaatgctta atcagtgagg cacctatctc agcgatctgt ctatttcgtt catccatagt    3840
tgcctgactc cccgtcgtgt agataactac gatacgggag ggcttaccat ctggccccag    3900
tgctgcaatg ataccgcgag acccacgctc accggctcca gatttatcag caataaacca    3960
gccagccgga agggccgagc gcagaagtgg tcctgcaact ttatccgcct ccatccagtc    4020
tattaattgt tgccgggaag ctagagtaag tagttcgcca gttaatagtt tgcgcaacgt    4080
tgttgccatt gctacaggca tcgtggtgtc acgctcgtcg tttggtatgg cttcattcag    4140
```

```
ctccggttcc caacgatcaa ggcgagttac atgatccccc atgttgtgca aaaaagcggt   4200
tagctccttc ggtcctccga tcgttgtcag aagtaagttg gccgcagtgt tatcactcat   4260
ggttatggca gcactgcata attctcttac tgtcatgcca tccgtaagat gcttttctgt   4320
gactggtgag tactcaacca agtcattctg agaatagtgt atgcggcgac cgagttgctc   4380
ttgcccggcg tcaatacggg ataataccgc gccacatagc agaactttaa aagtgctcat   4440
cattggaaaa cgttcttcgg ggcgaaaact ctcaaggatc ttaccgctgt tgagatccag   4500
ttcgatgtaa cccactcgtg cacccaactg atcttcagca tcttttactt tcaccagcgt   4560
ttctgggtga gcaaaaacag gaaggcaaaa tgccgcaaaa aagggaataa gggcgacacg   4620
gaaatgttga atactcatac tcttcctttt tcaatattat tgaagcattt atcagggtta   4680
ttgtctcatg agcggataca tatttgaatg tatttagaaa aataaacaaa tagggggttcc   4740 gcgcacattt ccccgaaaag tgccacct                                     4768

<210> SEQ ID NO 37
<211> LENGTH: 4533
<212> TYPE: DNA
<213> ORGANISM: Artificial Sequence
<220> FEATURE:
<223> OTHER INFORMATION: Synthetic sequence of the plasmid pBS19 ymaH
      sigH

<400> SEQUENCE: 37
gaattcgacg tggtttcgca acaaaatgca ggtcacatgg ttcgatatga caccgcctgt     60
tgatatggag ctgaaaaaaa aggaaatttt cacacatata gcaggaaaac tcgaacttta    120
atcgaaactg tatgtatag agaatcaagg aggacgaaac atgaaaccga ttaatattca    180
ggatcagttt ttgaatcaaa tccggaaaga aaatacgtat gtcactgttt ttttgctgaa    240
cggctttcag ttgcggggcc aggtgaaagg ctttgataac tttaccgtat tgttggaatc    300
ggaaggtaag cagcagctta tatataaaca tgcgatctca acgtttgcgc cgcaaaaaaa    360
cgtccagctt gaactcgaat agatcaaaaa atgccatgtc aagacatgag gaaaggctgt    420
cgggggttcc cggcggccat ttttaacatg aatccacttt tgctccaagc tttttgtgta    480
agctgaccat gccaaggcac ggtcttttt tatgaggatc ctctagagtc gacctgcagg    540
catgcaagct tggcgatcct gcctcgcgcg tttcggtgat gacggtgaaa acctctgaca    600
catgcagctc ccggagacgg tcacagcttg tctgtaagcg gatgccggga gcagacaagc    660
ccgtcagggc gcgtcagcgg gtgttggcgg gtgtcgggc gcagccatga cccagtcacg    720
tagcgatagc ggagtgtata ctggcttaac tatgcggcat cagagcagat tgtactgaga    780
gtgcaccata tgcggtgtga ataccgcac agatgcgtaa ggagaaaata ccgcatcagg    840
cgctcttccg cttcctcgct cactgactcg ctgcgctcgg tcgttcggct gcggcgagcg    900
gtatcagctc actcaaaggc ggtaatacgg ttatccacag aatcagggga taacgcagga    960
aagaacatgt gagcaaaagg ccagcaaaag gccaggaacc gtaaaaaggc cgcgttgctg   1020
gcgtttttcc ataggctccg cccccctgac gagcatcaca aaaatcgacg ctcaagtcag   1080
aggtggcgaa acccgacagg actataaaga taccaggcgt ttccccctgg aagctccctc   1140
gtgcgctctc ctgttccgac cctgccgctt accggatacc tgtccgcctt tctcccttcg   1200
ggaagcgtgg cgctttctca tagctcacgc tgtaggtatc tcagttcggt gtaggtcgtt   1260
cgctccaagc tgggctgtgt gcacgaaccc ccgttcagc ccgaccgctg cgccttatcc   1320
ggtaactatc gtcttgagtc caacccggta agacacgact tatcgccact ggcagcagcc   1380
```

```
actggtaaca ggattagcag agcgaggtat gtaggcggtg ctacagagtt cttgaagtgg    1440
tggcctaact acggctacac tagaaggaca gtatttggta tctgcgctct gctgaagcca    1500
gttaccttcg gaaaaagagt tggtagctct tgatccggca acaaaccac cgctggtagc     1560
ggtggttttt ttgtttgcaa gcagcagatt acgcgcagaa aaaaggatc tcaagaagat     1620
cctttgatct tttctacggg gtctgacgct cagtggaacg aaaactcacg ttaagggatt    1680
ttggtcatga gattatcaaa aaggatctgg agctgtaata taaaaccctt cttcaactaa    1740
cggggcaggt tagtgacatt agaaaaccga ctgtaaaaag tacagtcggc attatctcat    1800
attataaaag ccagtcatta ggcctatctg acaattcctg aatagagttc ataaacaatc    1860
ctgcatgata accatcacaa acagaatgat gtacctgtaa agatagcggt aaatatattg    1920
aattaccttt attaatgaat tttcctgctg taataatggg tagaaggtaa ttactattat    1980
tattgatatt taagttaaac ccagtaaatg aagtccatgg aataatagaa agagaaaaag    2040
cattttcagg tataggtgtt tgggaaaca atttccccga accattatat ttctctacat     2100
cagaaaggta taaatcataa aactctttga agtcattctt tacaggagtc caaataccag    2160
agaatgtttt agatacacca tcaaaaattg tataaagtgg ctctaactta tcccaataac    2220
ctaactctcc gtcgctattg taaccagttc taaaagctgt atttgagttt atcacccttg    2280
tcactaagaa aataaatgca gggtaaaatt tatatccttc ttgttttatg tttcggtata    2340
aaacactaat atcaatttct gtggttatac taaaagtcgt tgttggttc aaataatgat     2400
taaatatctc ttttctcttc caattgtcta aatcaatttt attaaagttc atttgatatg    2460
cctcctaaat ttttatctaa agtgaattta ggaggcttac ttgtctgctt tcttcattag    2520
aatcaatcct tttttaaaag tcaatattac tgtaacataa atatatattt taaaaatatc    2580
ccactttatc caattttcgt tgttgaact aatgggtgct ttagttgaag aataaaagac      2640
cacattaaaa aatgtggtct tttgtgtttt tttaaaggat ttgagcgtag cgaaaaatcc    2700
ttttcttttct tatcttgata ataagggtaa ctattgccgg ttgtccattc atggctgaac   2760
tctgcttcct ctgttgacat gacacacatc atctcaatat ccgaataggg cccatcagtc    2820
tgacgaccaa gagagccata acaccaata gccttaacat catccccata tttatccaat     2880
attcgttcct taattcatg aacaatcttc attcttttctt ctctagtcat tattattggt    2940
ccattcacta ttctcattcc ctttttcagat aattttagat ttgcttttct aaataagaat   3000
atttggagag caccgttctt attcagctat taataactcg tcttcctaag catccttcaa    3060
tccttttaat aacaattata gcatctaatc ttcaacaaac tggcccgttt gttgaactac    3120
tcttaataa aataattttt ccgttcccaa ttccacattg caataataga aaatccatct     3180
tcatcggctt tttcgtcatc atctgtatga atcaaatcgc cttcttctgt gtcatcaagg    3240
tttaattttt tatgtatttc ttttaacaaa ccaccatagg agattaaccct tttacggtgt   3300
aaaccttcct ccaaatcaga caaacgtttc aaattctttt cttcatcatc ggtcataaaa    3360
tccgtatcct ttacaggata ttttgcagtt tcgtcaattg ccgattgtat atccgattta    3420
tatttatttt tcggtcgaat catttgaact tttacatttg gatcatagtc taatttcatt    3480
gcctttttcc aaaattgaat ccattgtttt tgattcacgt agttttctgt attcttaaaa    3540
taagttggtt ccacacatac caatacatgc atgtgctgat tataagaatt atctttatta    3600
tttattgtca cttccgttgc acgcataaaa ccaacaagat tttattaat tttttatat      3660
tgcatcattc ggcgaaatcc ttgagccata tctgacaaac tcttatttaa ttcttcgcca    3720
tcataaacat tttttaactgt taatgtgaga aacaaccaac gaactgttgg cttttgttta   3780
```

```
ataacttcag caacaacctt ttgtgactga atgccatgtt tcattgctct cctccagttg    3840
cacattggac aaagcctgga tttacaaaac cacactcgat acaactttct ttcgcctgtt    3900
tcacgatttt gtttatactc taatatttca gcacaatctt ttactctttc agccttttta    3960
aattcaagaa tatgcagaag ttcaaagtaa tcaacattag cgattttctt ttctctccat    4020
ggtctcactt ttccactttt tgtcttgtcc actaaaaccc ttgattttttc atctgaataa    4080 atgctactat taggacacat aatattaaaa gaaaccccca tctatttagt tatttgttta    4140
gtcacttata actttaacag atggggtttt tctgtgcaac caattttaag ggttttcaat    4200
actttaaaac acatacatac caacacttca acgcaccttt cagcaactaa aataaaaatg    4260
acgttatttc tatatgtatc aagataagaa agaacaagtt caaaaccatc aaaaaaagac    4320
accttttcag gtgctttttt tattttataa actcattccc tgatctcgac ttcgttcttt    4380
ttttacctct cggttatgag ttagttcaaa ttcgttcttt ttaggttcta aatcgtgttt    4440
ttcttggaat tgtgctgttt tatcctttac cttgtctaca aaccccttaa aaacgttttt    4500
aaaggctttt aagccgtctg tacgttcctt aag                                4533

<210> SEQ ID NO 38
<211> LENGTH: 46
<212> TYPE: DNA
<213> ORGANISM: Bacillus subtilis

<400> SEQUENCE: 38
tgggtcttga caaatattat tccatctatt acaataaatt cacaga                   46

<210> SEQ ID NO 39
<211> LENGTH: 46
<212> TYPE: DNA
<213> ORGANISM: Bacillus subtilis

<400> SEQUENCE: 39
tgggtctact aaaatattat tccatctatt acaataaatt cacaga                   46

<210> SEQ ID NO 40
<211> LENGTH: 46
<212> TYPE: DNA
<213> ORGANISM: Bacillus subtilis

<400> SEQUENCE: 40
tgggtcttga caaatattat tccatctatt acaataaatt cacaga                   46

<210> SEQ ID NO 41
<211> LENGTH: 132
<212> TYPE: DNA
<213> ORGANISM: Bacillus subtilis

<400> SEQUENCE: 41
atgaaatcta aatggatgtc aggtttgttg ctcgttgcgg tcgggttcag ctttactcag    60
gtgatggttc atgcaggtga acagcaaac acagaaggga aacatttca tattgcggca    120 cgcaatcaaa ca                                                       132

<210> SEQ ID NO 42
<211> LENGTH: 44
<212> TYPE: PRT
<213> ORGANISM: Bacillus subtilis

<400> SEQUENCE: 42

Met Lys Ser Lys Trp Met Ser Gly Leu Leu Leu Val Ala Val Gly Phe
1               5                   10                  15
```

Ser Phe Thr Gln Val Met Val His Ala Gly Glu Thr Ala Asn Thr Glu
            20                  25                  30

Gly Lys Thr Phe His Ile Ala Ala Arg Asn Gln Thr
            35                  40

<210> SEQ ID NO 43
<211> LENGTH: 132
<212> TYPE: DNA
<213> ORGANISM: Bacillus subtilis

<400> SEQUENCE: 43
atgaaatcta aattgtttat cagtttatcc gccgttttaa ttggacttgc cttttttcgga      60 tctatgtata atggcgaaat gaaggaagca tcccggaatg taactctcgc acctactcat     120
gaattccttg tt                                                         132

<210> SEQ ID NO 44
<211> LENGTH: 44
<212> TYPE: PRT
<213> ORGANISM: Bacillus subtilis

<400> SEQUENCE: 44

Met Lys Ser Lys Leu Phe Ile Ser Leu Ser Ala Val Leu Ile Gly Leu
1               5                   10                  15

Ala Phe Phe Gly Ser Met Tyr Asn Gly Glu Met Lys Glu Ala Ser Arg
            20                  25                  30

Asn Val Thr Leu Ala Pro Thr His Glu Phe Leu Val
            35                  40

<210> SEQ ID NO 45
<211> LENGTH: 73
<212> TYPE: PRT
<213> ORGANISM: Bacillus subtilis

<400> SEQUENCE: 45

Met Lys Pro Ile Asn Ile Gln Asp Gln Phe Leu Asn Gln Ile Arg Lys
1               5                   10                  15

Glu Asn Thr Tyr Val Thr Val Phe Leu Leu Asn Gly Phe Gln Leu Arg
            20                  25                  30

Gly Gln Val Lys Gly Phe Asp Asn Phe Thr Val Leu Leu Glu Ser Glu
            35                  40                  45

Gly Lys Gln Gln Leu Ile Tyr Lys His Ala Ile Ser Thr Phe Ala Pro
        50                  55                  60

Gln Lys Asn Val Gln Leu Glu Leu Glu
65                  70

<210> SEQ ID NO 46
<211> LENGTH: 222
<212> TYPE: DNA
<213> ORGANISM: Bacillus subtilis

<400> SEQUENCE: 46
atgaaaccga ttaatattca ggatcagttt ttgaatcaaa tccggaaaga aaatacgtat      60
gtcactgttt ttttgctgaa cggctttcag ttgcggggcc aggtgaaagg ctttgataac     120
tttaccgtat tgttggaatc ggaagtaag cagcagctta tatataaaca tgcgatctca     180
acgtttgcgc cgcaaaaaaa cgtccagctt gaactcgaat ag                        222

<210> SEQ ID NO 47
<211> LENGTH: 156

```
<212> TYPE: DNA
<213> ORGANISM: Artificial Sequence
<220> FEATURE:
<223> OTHER INFORMATION: Synthetic SigA1construct containing the SigA
      promoter

<400> SEQUENCE: 47 tcatacccctg aaaggaaaga caagggaaat tgtcggcaat gagccgctcg gcaggtagaa    60
ggatgtttac cgatgcaaaa aaagggcaaa atggataggt ggttgtccat gttgaatgct   120
ataatggggg agatttataa aagagagtga tacata                             156

<210> SEQ ID NO 48
<211> LENGTH: 82
<212> TYPE: DNA
<213> ORGANISM: Bacillus subtilis

<400> SEQUENCE: 48
aaaggaaatt ttcacacata tagcaggaaa actcgaactt taatcgaaac tgtatgatat    60
agagaatcaa ggaggacgaa ac                                             82

<210> SEQ ID NO 49
<211> LENGTH: 945
<212> TYPE: DNA
<213> ORGANISM: Bacillus subtilis

<400> SEQUENCE: 49
ttgaataata cgaagcagcc cgttgtcatt ttagtcggac cgacggcagt ggggaaaacc    60
aatttaagta ttcagctagc caaatcctta acgcggaaa ttatcagcgg agattcgatg    120
cagatttata aagggatgga tattggaaca gctaaaatta ccgaacagga gatggaggga   180 gtgcccatc atctgattga catttagat ccccaagact ctttctctac tgccgattat    240
caaagcttag taagaaataa atcagcgag attgcaaata gaggaaagct tccgatgatt   300
gacggcggta cagggcttta tatacaatct gagctttacg attatacatt tacggaagag   360
gcaaatgatc ccgtgtttcg agagagcatg caaatggctg ctgagcggga aggcgctgac   420
tttcttcatg ccaaacttgc tgcagcagat cccgaggcag cagctgcgat tcatccgaat   480
aatacaagaa gagtcattcg cgcactggaa attttacata cgtccggaaa aacgatgtcc   540
cagcatttga aggaacaaaa acgagaactt ctgtacaatg cagtgttaat tggcctgaca   600
atggatagag acacgcttta cgaaagaatt aatcagcggg tcgatttgat gatgcagtca   660
ggccttcttc cggaagtgaa acgcttatac gacaagaacg tgagagactg tcaatcaata   720
caggcgatag gctataaaga gctgtatgca tattttgacg gttttgtgac actttccgat   780
gctgtcgaac agctaaagca gaactcgagg cggtatgcga aacgccagct gacgtggttt   840
cgcaacaaaa tgcaggtcac atggttcgat atgacaccgc tgttgatat ggagctgaaa    900 aaaaaggaa ttttcacaca tatagcagga aaactcgaac tttaa                    945

<210> SEQ ID NO 50
<211> LENGTH: 7
<212> TYPE: DNA
<213> ORGANISM: Bacillus subtilis

<400> SEQUENCE: 50 aagagag                                                               7

<210> SEQ ID NO 51
<211> LENGTH: 5
<212> TYPE: DNA
```

<213> ORGANISM: Bacillus subtilis

<400> SEQUENCE: 51 ggagg    5

<210> SEQ ID NO 52
<211> LENGTH: 3258
<212> TYPE: DNA
<213> ORGANISM: Artificial Sequence
<220> FEATURE:
<223> OTHER INFORMATION: Chemically synthesized deletion cassette of the rapA/phrA operon

<400> SEQUENCE: 52

```
tgggggagt cagaccgcgt ctttgggaaa aaagcaagcg gaaagtgacc gtgtttacgg      60
atggagatgg agggacttca agagagcagg aagccattgt cagagaggtt cagcggagtc    120
aagtcatcat gaatccgcta ttgaaaaaag agatatacag atcaattgat cagttttttc    180
atagtgataa atcgttttat caaacatatg acatccctta caagcgcggc attctgttat    240
atggacctcc tggaaacgga aagacgacgt tagtgaagtc gatcgcaggc agtatcgatg    300
cacctgttgc ttattggcaa attactgaat ttacgtcgag cgacacaata gaagaagtct    360
ttcaggcagc gagacgcctc gctcctgcag ttctggtcat cgaggatata gattcgatgc    420
cggaagatgt gcggtccttt tttctcaata cgctggacgg cgcgacatca aaagagggggc   480
tatttctcat cggtacgaca aactatcccg aagagatcga tccaggtttg atgaatcgtg    540
caggacgatt tgaccgtgcc tatgaaatcg gcttccgga tgaagagctg cggctggaat     600
atatgaaaat gagaggcttt ggcatctttt tgagtgaagg agaaataaaa aacgccgcaa    660
aacttacaga aggcttttcc tttgcacagc tgggagaatt atatgtatct tcagcccttc    720
aatggcacca agaagggaat caccatattg aaaccatggt gaaagacatg acaggagagc    780
aaagaaaaag ccagcgggga agctggatgg aaagaaacaa agtcggtttt cactaaaaga    840
aagcacgggt gtttgaaaaa cccgtgcttt tttgttgcgg ttagccgaaa ttcgacaatt    900
gcggttattt tgcgttcttc ttttttcttgt aaatatgata aaatatgaca tatctcgggt    960
aattcaaaag gggggattaa ttgaggatga agcagacgct cgaggtcgac ggtatcgata   1020
agctggatcc ataacttcgt ataatgtatg ctatacgaag ttatctagat aaaaaattta   1080
gaagccaatg aaatctataa ataaactaaa ttaagtttat ttaattaaca actatggata   1140
taaaataggt actaatcaaa atagtgagga ggatatattt gaatacatac gaacaaatta   1200
ataaagtgaa aaaaatactt cggaaacatt taaaaaataa ccttattggt acttacatgt   1260
ttggatcagg agttgagagt ggactaaaac caaatagtga tcttgacttt ttagtcgtcg   1320
tatctgaacc attgacagat caaagtaaag aaatacttat acaaaaaatt agacctattt   1380
caaaaaaaat aggagataaa agcaacttac gatatattga attaacaatt attattcagc   1440
aagaaatggt accgtggaat catcctccca aacaagaatt tatttatgga gaatggttac   1500
aagagcttta tgaacaagga tacattcctc agaaggaatt aaattcagat ttaaccataa   1560
tgctttacca agcaaaacga aaaaataaaa gaatatacgg aaattatgac ttagaggaat   1620
tactacctga tattccattt tctgatgtga gaagagccat tatggattcg tcagaggaat   1680
taatagataa ttatcaggat gatgaaacca actctatatt aactttatgc cgtatgattt   1740
taactatgga cacgggtaaa atcataccaa aagatattgc gggaaatgca gtggctgaat   1800
cttctccatt agaacatagg gagagaaatt tgttagcagt tcgtagttat cttgagagga   1860
atattgaatg gactaatgaa aatgtaaatt taactataaa ctatttaaat aacagattaa   1920
```

| | | | |
|---|---|---|---|
| aaaaattata | aaaaaattga | aaaaatggtg | gaaacactttt tttcaatttt tttgttttat | 1980 |
| tatttaatat | ttgggaaata | ttcattctaa | ttggtaatca gattttagaa aacaataaac | 2040 |
| ccttgcatat | gtctagataa | cttcgtataa | tgtatgctat acgaagttat gcggccgcca | 2100 |
| cgcacaaaaa | caaatccaga | gaggagattg | tttatatgaa atctaaatgg atgtcaggtt | 2160 |
| tgttgctcgt | tgcggtcggg | ttcagcttta | ctcaggtgat ggttcatgca ggtgaaacag | 2220 |
| caaacacaga | agggaaaaca | tttcatattg | cggcacgcaa tcaaacatga tgcataaaaa | 2280 |
| aagacccta | ggggtctttt | ttatttcttc | agcttccatt cttttatcgt cagctcagaa | 2340 |
| gatccacttg | ccaccagcgg | atccgcatgg | ccgatttccg ctgcctcttc cagtgaatct | 2400 |
| gcttcgatga | catacgctcc | gcctgtggcg | tcgctgaatg gcccaaacat ttttaaacgt | 2460 |
| ttttctgcct | gtaaacgatc | cagaaattca | tagtgcccag ccacatgctc ctgattaaat | 2520 |
| ttctccgttc | tcattgtcag | cattaaatat | ggtatacata ttcagaccct ccgtgaactt | 2580 |
| cagtttaaca | catttatcca | tattacggtg | atagatgata tgagcttttc gtcctacgaa | 2640 |
| tgccacctat | ttatgaaaaa | agaaaaggag | agatgatagg tgagcattcc agtaaagaaa | 2700 |
| aatttggttt | ctgaggcgaa | atacgcgttg | aagtgtccta atgcaatgtc cgctgaatac | 2760 |
| attaccattc | acaacacggc | aaacgatgca | tcagcggcca atgaaatcag ctatatgatc | 2820 |
| gggaacacaa | gctcgacaag | ctttcatttt | gcggtcgatg atcaagaggt gattcaaggt | 2880 |
| ctgccgctta | accgaaacgc | ttggcacact | ggtgacggca caaacggtcc gggaaaccgc | 2940 |
| aaatcaatcg | gtgttgagat | ttgctacagc | aaatcgggag gcccgaagta tgaggcagct | 3000 |
| gaagccttgg | cgatttcatt | tgttgcacag | ctgttgaagg agcgcggctg gggcatcgat | 3060 |
| cgggtgagaa | agcatcagga | ctggagcgga | aagtattgcc cgcaccgcat tttatcagag | 3120 |
| gggcgctggg | atcaagtgaa | ggcggcgatt | gaaaaggaat taaacggggg cgtatcagcg | 3180 |
| aaaaaagctg | cagtctcttc | ttcggcgtct | gaatatcatg taaaaaaagg tgacacactg | 3240 |
| tcagggattg | ccgcatca | | | 3258 |

<210> SEQ ID NO 53
<211> LENGTH: 1134
<212> TYPE: DNA
<213> ORGANISM: Bacillus subtilis

<400> SEQUENCE: 53

| | | | |
|---|---|---|---|
| ttgaggatga | agcagacgat | tccgtcctct | tatgtcgggc ttaaaattaa tgaatggtat | 60 |
| actcatatcc | ggcagttcca | cgtcgctgaa | gccgaacggg tcaagctcga agtagaaaga | 120 |
| gaaattgagg | atatggaaga | agaccaagat | ttgctgctgt attattcttt aatggagttc | 180 |
| aggcaccgtg | tcatgctgga | ttacattaag | ccttttggag aggacacgtc gcagctagag | 240 |
| ttttcagaat | tgttagaaga | catcgaaggg | aatcagtaca agctgacagg gcttctcgaa | 300 |
| tattacttta | attttttcg | aggaatgtat | gaatttaagc agaagatgtt tgtcagtgcc | 360 |
| atgatgtatt | ataaacgggc | agaaaagaat | cttgccctcg tctcggatga tattgagaaa | 420 |
| gcagagtttg | cttttaaaat | ggctgagatt | ttttacaatt taaaacaaac ctatgtttcg | 480 |
| atgagctacg | ccgttcaggc | attagaaaca | taccaaatgt atgaaacgta caccgtccgc | 540 |
| agaatccaat | gtgaattcgt | tattgcaggt | aattatgatg atatgcagta tccagaaaga | 600 |
| gcattgcccc | acttagaact | ggctttagat | cttgcaaaga aagaaggcaa tccccgcctg | 660 |
| atcagttctg | ccctatataa | tctcggaaac | tgctatgaga aatgggtga actgcaaaag | 720 |
| gcagccgaat | actttgggaa | atctgtttct | atttgcaagt cggaaaagtt cgataatctt | 780 |

```
ccgcattcta tctactcttt aacacaagtt ctgtataaac aaaaaaatga cgccgaagcg    840
caaaaaaagt atcgtgaagg attggaaatc gcccgtcaat acagtgatga attatttgtg    900 gagcttttc aattttaca tgcgttatac ggaaaaaaca ttgacacaga atcagtctca      960
cacacctttc aatttcttga agaacatatg ctgtatcctt atattgaaga gctggcgcat   1020
gatgctgccc aattctatat agaaaacgga cagcccgaaa aagcacttc attttatgag    1080 aaaatggtgc acgcacaaaa acaaatccag agaggagatt gtttatatga aatc         1134
```

<210> SEQ ID NO 54
<211> LENGTH: 378
<212> TYPE: PRT
<213> ORGANISM: Bacillus subtilis

<400> SEQUENCE: 54

```
Met Arg Met Lys Gln Thr Ile Pro Ser Ser Tyr Val Gly Leu Lys Ile
1               5                   10                  15

Asn Glu Trp Tyr Thr His Ile Arg Gln Phe His Val Ala Glu Ala Glu
            20                  25                  30

Arg Val Lys Leu Glu Val Glu Arg Glu Ile Glu Asp Met Glu Glu Asp
        35                  40                  45

Gln Asp Leu Leu Leu Tyr Tyr Ser Leu Met Glu Phe Arg His Arg Val
    50                  55                  60

Met Leu Asp Tyr Ile Lys Pro Phe Gly Glu Asp Thr Ser Gln Leu Glu
65                  70                  75                  80

Phe Ser Glu Leu Leu Glu Asp Ile Glu Gly Asn Gln Tyr Lys Leu Thr
                85                  90                  95

Gly Leu Leu Glu Tyr Tyr Phe Asn Phe Phe Arg Gly Met Tyr Glu Phe
            100                 105                 110

Lys Gln Lys Met Phe Val Ser Ala Met Met Tyr Tyr Lys Arg Ala Glu
        115                 120                 125

Lys Asn Leu Ala Leu Val Ser Asp Asp Ile Glu Lys Ala Glu Phe Ala
    130                 135                 140

Phe Lys Met Ala Glu Ile Phe Tyr Asn Leu Lys Gln Thr Tyr Val Ser
145                 150                 155                 160

Met Ser Tyr Ala Val Gln Ala Leu Glu Thr Tyr Gln Met Tyr Glu Thr
                165                 170                 175

Tyr Thr Val Arg Arg Ile Gln Cys Glu Phe Val Ile Ala Gly Asn Tyr
            180                 185                 190

Asp Asp Met Gln Tyr Pro Glu Arg Ala Leu Pro His Leu Glu Leu Ala
        195                 200                 205

Leu Asp Leu Ala Lys Lys Glu Gly Asn Pro Arg Leu Ile Ser Ser Ala
    210                 215                 220

Leu Tyr Asn Leu Gly Asn Cys Tyr Glu Lys Met Gly Glu Leu Gln Lys
225                 230                 235                 240

Ala Ala Glu Tyr Phe Gly Lys Ser Val Ser Ile Cys Lys Ser Glu Lys
                245                 250                 255

Phe Asp Asn Leu Pro His Ser Ile Tyr Ser Leu Thr Gln Val Leu Tyr
            260                 265                 270

Lys Gln Lys Asn Asp Ala Glu Ala Gln Lys Lys Tyr Arg Glu Gly Leu
        275                 280                 285

Glu Ile Ala Arg Gln Tyr Ser Asp Glu Leu Phe Val Glu Leu Phe Gln
    290                 295                 300

Phe Leu His Ala Leu Tyr Gly Lys Asn Ile Asp Thr Glu Ser Val Ser
305                 310                 315                 320
```

His Thr Phe Gln Phe Leu Glu Glu His Met Leu Tyr Pro Tyr Ile Glu
                325                 330                 335

Glu Leu Ala His Asp Ala Ala Gln Phe Tyr Ile Glu Asn Gly Gln Pro
            340                 345                 350

Glu Lys Ala Leu Ser Phe Tyr Glu Lys Met Val His Ala Gln Lys Gln
        355                 360                 365

Ile Gln Arg Gly Asp Cys Leu Tyr Glu Ile
    370                 375

<210> SEQ ID NO 55
<211> LENGTH: 36
<212> TYPE: DNA
<213> ORGANISM: Artificial Sequence
<220> FEATURE:
<223> OTHER INFORMATION: Synthetic oligonucleotide: XhoUR

<400> SEQUENCE: 55
agaggactcg agcgtctgct tcatcctcaa ttaatc                        36

<210> SEQ ID NO 56
<211> LENGTH: 37
<212> TYPE: DNA
<213> ORGANISM: Artificial Sequence
<220> FEATURE:
<223> OTHER INFORMATION: Synthetic oligonucleotide: HindIIIUF

<400> SEQUENCE: 56
gcgtgcaagc ttggagggag tcagaccgcg tctttgg                       37

<210> SEQ ID NO 57
<211> LENGTH: 41
<212> TYPE: DNA
<213> ORGANISM: Artificial Sequence
<220> FEATURE:
<223> OTHER INFORMATION: Synthetic oligonucleotide: NotIDF

<400> SEQUENCE: 57
ttatgagagc ggccgccacg cacaaaaaca aatccagaga g                  41

<210> SEQ ID NO 58
<211> LENGTH: 37
<212> TYPE: DNA
<213> ORGANISM: Artificial Sequence
<220> FEATURE:
<223> OTHER INFORMATION: Synthetic oligonucleotide: BglIIDR

<400> SEQUENCE: 58
ccccgtagat ctcggcaatc cctgacagtg tgtcacc                       37

<210> SEQ ID NO 59
<211> LENGTH: 24
<212> TYPE: DNA
<213> ORGANISM: Artificial Sequence
<220> FEATURE:
<223> OTHER INFORMATION: Synthetic primer CB2008-011: upstream phrH

<400> SEQUENCE: 59
ggagggaagc cgttgagtca agcc                                     24

<210> SEQ ID NO 60
<211> LENGTH: 49
<212> TYPE: DNA
<213> ORGANISM: Artificial Sequence
<220> FEATURE:
<223> OTHER INFORMATION: Synthetic primer CB2008-012: linker up phrH down lox

<400> SEQUENCE: 60
gcggccgcca tatgcatcct aggcctcatc acttttttc ttaataggc                49

<210> SEQ ID NO 61
<211> LENGTH: 49
<212> TYPE: DNA
<213> ORGANISM: Artificial Sequence
<220> FEATURE:
<223> OTHER INFORMATION: Synthetic primer CB2008-012R: linker up phrH
      down lox

<400> SEQUENCE: 61
gcctattaag aaaaaaagtg atgaggccta ggatgcatat ggcggccgc                 49

<210> SEQ ID NO 62
<211> LENGTH: 52
<212> TYPE: DNA
<213> ORGANISM: Artificial Sequence
<220> FEATURE:
<223> OTHER INFORMATION: Synthetic primer CB2008-013: linker down phrH
      up lox

<400> SEQUENCE: 62
ggatccagct tatcgatacc gtcgaggctt tttcttgctt tacggaagac gg             52

<210> SEQ ID NO 63
<211> LENGTH: 52
<212> TYPE: DNA
<213> ORGANISM: Artificial Sequence
<220> FEATURE:
<223> OTHER INFORMATION: Synthetic primer CB2008-013R: linker down phrH
      up lox

<400> SEQUENCE: 63
ccgtcttccg taaagcaaga aaagcctcg acggtatcga taagctggat cc              52

<210> SEQ ID NO 64
<211> LENGTH: 27
<212> TYPE: DNA
<213> ORGANISM: Artificial Sequence
<220> FEATURE:
<223> OTHER INFORMATION: Synthetic primer CB2008-014: downstream phrH

<400> SEQUENCE: 64
gccatcattt tcatggtgca tgctcgg                                          27

<210> SEQ ID NO 65
<211> LENGTH: 30
<212> TYPE: DNA
<213> ORGANISM: Artificial Sequence
<220> FEATURE:
<223> OTHER INFORMATION: Synthetic primer CB2008-015: upstream phrC

<400> SEQUENCE: 65
tcactaatgg aattccggca ccagcttatg                                       30

<210> SEQ ID NO 66
<211> LENGTH: 51
<212> TYPE: DNA
<213> ORGANISM: Artificial Sequence
<220> FEATURE:
<223> OTHER INFORMATION: Synthetic primer CB2008-016: linker up phrC
      down lox

<400> SEQUENCE: 66

```
gcggccgcca tatgcatcct aggccatcgc ggctgcggcc aaacaaataa c            51
```

<210> SEQ ID NO 67
<211> LENGTH: 51
<212> TYPE: DNA
<213> ORGANISM: Artificial Sequence
<220> FEATURE:
<223> OTHER INFORMATION: Synthetic primer CB2008-016R: linker up phrC down lox

<400> SEQUENCE: 67

```
gttatttgtt tggccgcagc cgcgatggcc taggatgcat atggcggccg c            51
```

<210> SEQ ID NO 68
<211> LENGTH: 55
<212> TYPE: DNA
<213> ORGANISM: Artificial Sequence
<220> FEATURE:
<223> OTHER INFORMATION: Synthetic primer CB2008-017: linker down phrC up lox

<400> SEQUENCE: 68

```
ggatccagct tatcgatacc gtcgagaaca agccccttct cattagcgag aaggg        55
```

<210> SEQ ID NO 69
<211> LENGTH: 55
<212> TYPE: DNA
<213> ORGANISM: Artificial Sequence
<220> FEATURE:
<223> OTHER INFORMATION: Synthetic primer CB2008-017R: linker down phrC up lox

<400> SEQUENCE: 69

```
cccttctcgc taatgagaag gggcttgttc tcgacggtat cgataagctg gatcc        55
```

<210> SEQ ID NO 70
<211> LENGTH: 32
<212> TYPE: DNA
<213> ORGANISM: Artificial Sequence
<220> FEATURE:
<223> OTHER INFORMATION: Synthetic primer CB2008-018: downstream phrC

<400> SEQUENCE: 70

```
gcagcattta tatcgcaag tatctcatga ac                                   32
```

<210> SEQ ID NO 71
<211> LENGTH: 30
<212> TYPE: DNA
<213> ORGANISM: Artificial Sequence
<220> FEATURE:
<223> OTHER INFORMATION: Synthetic primer CB2008-022: upstream phrF

<400> SEQUENCE: 71

```
agtttcggca caacctaatg cttgagtacc                                     30
```

<210> SEQ ID NO 72
<211> LENGTH: 53
<212> TYPE: DNA
<213> ORGANISM: Artificial Sequence
<220> FEATURE:
<223> OTHER INFORMATION: Synthetic primer CB2008-023: linker up phrF down lox

<400> SEQUENCE: 72

```
gcggccgcca tatgcatcct aggccagtaa tagtttagac ttcaatttca tac           53
```

<210> SEQ ID NO 73

```
<211> LENGTH: 53
<212> TYPE: DNA
<213> ORGANISM: Artificial Sequence
<220> FEATURE:
<223> OTHER INFORMATION: Synthetic primer CB2008-023R: linker up phrF
      down lox

<400> SEQUENCE: 73
gtatgaaatt gaagtctaaa ctattactgg cctaggatgc atatggcggc cgc         53

<210> SEQ ID NO 74
<211> LENGTH: 55
<212> TYPE: DNA
<213> ORGANISM: Artificial Sequence
<220> FEATURE:
<223> OTHER INFORMATION: Synthetic primer CB2008-024: linker down phrF
      up lox

<400> SEQUENCE: 74
ggatccagct tatcgatacc gtcgaccgcc gtccatcggc ggttttttcg tcccc       55

<210> SEQ ID NO 75
<211> LENGTH: 55
<212> TYPE: DNA
<213> ORGANISM: Artificial Sequence
<220> FEATURE:
<223> OTHER INFORMATION: Synthetic primer CB2008-024R: linker down phrF
      up lox

<400> SEQUENCE: 75
ggggacgaaa aaccgccga tggacggcgg tcgacggtat cgataagctg gatcc        55

<210> SEQ ID NO 76
<211> LENGTH: 28
<212> TYPE: DNA
<213> ORGANISM: Artificial Sequence
<220> FEATURE:
<223> OTHER INFORMATION: Synthetic primer CB2008-025: downstream phrF

<400> SEQUENCE: 76
tcggaccgca caatgtgtat tcattcgg                                    28

<210> SEQ ID NO 77
<211> LENGTH: 25
<212> TYPE: DNA
<213> ORGANISM: Artificial Sequence
<220> FEATURE:
<223> OTHER INFORMATION: Synthetic primer CB2008-026: upstream phrG

<400> SEQUENCE: 77
agaggatcag gaggtgcttg cctac                                       25

<210> SEQ ID NO 78
<211> LENGTH: 51
<212> TYPE: DNA
<213> ORGANISM: Artificial Sequence
<220> FEATURE:
<223> OTHER INFORMATION: Synthetic primer CB2008-027: linker up phrG
      and up lox

<400> SEQUENCE: 78
cgaacggagg ttatataaat gaaaagtcga cggtatcgat aagctggatc c          51

<210> SEQ ID NO 79
<211> LENGTH: 51
<212> TYPE: DNA
<213> ORGANISM: Artificial Sequence
<220> FEATURE:
```

<223> OTHER INFORMATION: Synthetic primer CB2008-027R: linker up phrG
and up lox

<400> SEQUENCE: 79
ggatccagct tatcgatacc gtcgactttt catttatata acctccgttc g     51

<210> SEQ ID NO 80
<211> LENGTH: 46
<212> TYPE: DNA
<213> ORGANISM: Artificial Sequence
<220> FEATURE:
<223> OTHER INFORMATION: Synthetic primer CB2008-028: linker down phrG
and down lox

<400> SEQUENCE: 80
gcggccgcca tatgcatcct aggccatgaa aaccccgc gggatg     46

<210> SEQ ID NO 81
<211> LENGTH: 46
<212> TYPE: DNA
<213> ORGANISM: Artificial Sequence
<220> FEATURE:
<223> OTHER INFORMATION: Synthetic primer CB2008-028R: linker down phrG
and down lox

<400> SEQUENCE: 81
catcccgcgg gggtttttca tggcctagga tgcatatggc ggccgc     46

<210> SEQ ID NO 82
<211> LENGTH: 26
<212> TYPE: DNA
<213> ORGANISM: Artificial Sequence
<220> FEATURE:
<223> OTHER INFORMATION: Synthetic primer CB2008-029: downstream phrG

<400> SEQUENCE: 82
tctcggtgac attccgatca atcgcg     26

<210> SEQ ID NO 83
<211> LENGTH: 36
<212> TYPE: DNA
<213> ORGANISM: Artificial Sequence
<220> FEATURE:
<223> OTHER INFORMATION: Synthetic primer CB2008-030: upstream phrI

<400> SEQUENCE: 83
gaattgttaa acatggaaga aaatcaagat gccctg     36

<210> SEQ ID NO 84
<211> LENGTH: 52
<212> TYPE: DNA
<213> ORGANISM: Artificial Sequence
<220> FEATURE:
<223> OTHER INFORMATION: Synthetic primer CB2008-031: linker up phrI
down lox

<400> SEQUENCE: 84
gcggccgcca tatgcatcct aggccaatac actacttaaa atcactgctg cc     52

<210> SEQ ID NO 85
<211> LENGTH: 52
<212> TYPE: DNA
<213> ORGANISM: Artificial Sequence
<220> FEATURE:
<223> OTHER INFORMATION: Synthetic primer CB2008-031R: linker up phrI
down lox

<400> SEQUENCE: 85

```
ggcagcagtg attttaagta gtgtattggc ctaggatgca tatggcggcc gc            52
```

<210> SEQ ID NO 86
<211> LENGTH: 60
<212> TYPE: DNA
<213> ORGANISM: Artificial Sequence
<220> FEATURE:
<223> OTHER INFORMATION: Synthetic primer CB2008-032:  linker down phrI
      up lox

<400> SEQUENCE: 86

```
ggatccagct tatcgatacc gtcgacttag ataattggaa aagaggaaaa aagcttaatc    60
```

<210> SEQ ID NO 87
<211> LENGTH: 60
<212> TYPE: DNA
<213> ORGANISM: Artificial Sequence
<220> FEATURE:
<223> OTHER INFORMATION: Synthetic primer CB2008-032R:  linker down phrI
      up lox

<400> SEQUENCE: 87

```
gattaagctt ttttcctctt ttccaattat ctaagtcgac ggtatcgata agctggatcc    60
```

<210> SEQ ID NO 88
<211> LENGTH: 40
<212> TYPE: DNA
<213> ORGANISM: Artificial Sequence
<220> FEATURE:
<223> OTHER INFORMATION: Synthetic primer CB2008-033:  downstream phrI

<400> SEQUENCE: 88

```
ctgtccctat tagtttatct gcttttttat ctccatcagg                          40
```

<210> SEQ ID NO 89
<211> LENGTH: 33
<212> TYPE: DNA
<213> ORGANISM: Artificial Sequence
<220> FEATURE:
<223> OTHER INFORMATION: Synthetic primer CB2008-034:  upstream phrK

<400> SEQUENCE: 89

```
gatgaaatgg aagaagatca agaagttctt gcg                                 33
```

<210> SEQ ID NO 90
<211> LENGTH: 52
<212> TYPE: DNA
<213> ORGANISM: Artificial Sequence
<220> FEATURE:
<223> OTHER INFORMATION: Synthetic primer CB2008-035:  linker up phrK
      and lox

<400> SEQUENCE: 90

```
ggatccagct tatcgatacc gtcgattaaa atcacagcta aaatagatac gc            52
```

<210> SEQ ID NO 91
<211> LENGTH: 52
<212> TYPE: DNA
<213> ORGANISM: Artificial Sequence
<220> FEATURE:
<223> OTHER INFORMATION: Synthetic primer CB2008-035R:  linker up phrK
      and lox

<400> SEQUENCE: 91

```
gcgtatctat tttagctgtg attttaatcg acggtatcga taagctggat cc            52
```

```
<210> SEQ ID NO 92
<211> LENGTH: 51
<212> TYPE: DNA
<213> ORGANISM: Artificial Sequence
<220> FEATURE:
<223> OTHER INFORMATION: Synthetic primer CB2008-036:  linker down phrK
      and lox

<400> SEQUENCE: 92
gcggccgcca tatgcatcct aggccaaaag gttgattaat taatttagcc c          51

<210> SEQ ID NO 93
<211> LENGTH: 51
<212> TYPE: DNA
<213> ORGANISM: Artificial Sequence
<220> FEATURE:
<223> OTHER INFORMATION: Synthetic primer CB2008-036R:  linker down phrK
      and lox

<400> SEQUENCE: 93
gggctaaatt aattaatcaa cctttggcc taggatgcat atggcggccg c           51

<210> SEQ ID NO 94
<211> LENGTH: 30
<212> TYPE: DNA
<213> ORGANISM: Artificial Sequence
<220> FEATURE:
<223> OTHER INFORMATION: Synthetic primer CB2008-037:  downstream phrK

<400> SEQUENCE: 94
atcgagacta tttgagatac ctgaagatcc                                  30

<210> SEQ ID NO 95
<211> LENGTH: 3110
<212> TYPE: DNA
<213> ORGANISM: Artificial Sequence
<220> FEATURE:
<223> OTHER INFORMATION: Synthetic construct: nucleotide sequence of the
      phrC deletion construct

<400> SEQUENCE: 95
tcactaatgg aattccggca ccagcttatg ctggattatc ttgagccgtt agagaaatta   60
aatatcgaag accagccaag cctgtctgaa ttatcaagaa acattgacag caaccaggca  120
gatctcaaag gctgctcga ctattacgtg aatttttttc gcgggatgta tgaatttgat    180
aagcgggaat ttatttctgc cattacatac tataaacagg cggagaaaaa gctctccttt   240
gtcgcagacc atattgaacg ggctgaattc tattttaaaa tcgcggaagc ttattattat   300
atgaagcaaa cgtatttttc attgattaat ataaaaaacg cctatgaaat ttacgtggag   360
caggaaacct ataatgtgag aatcattcag tgccatttcg tcttcggggt caacctgatg   420
gatgaaagaa atttcgaaca agccgcacgc catttcaaat tggcgctcaa catggcccaa   480
gcagaacaaa aagcccagct ggttggaaga gcatactaca atctcgggtt atgctattac   540
aatcaagacc ttctagaccc tgccattgat tactttgaaa aagcggtctc cacatttgaa   600
agcagcagga tcgtcaattc tctcccgcaa gcctattttt taatcaccct gatttattat   660
aaacagggaa acatgataa agcttcggaa tatcacaagc ggggctatga atatgctaaa   720
gaaacagacg atgcagacta tgccgtaaaa ttcgagtttt tgcaatccct atatctggat   780
cagcccaatg aagaaggaat cgaacgatgt ttccagtact aaaaaataa aaatatgtac   840 gctgatatag aggatttagc cctagaagta gcaaaatatt actatgaaca gaatggtttt   900
aaactgtctg cttcctactt tctacaagtt gaagaggcaa gaaaacaaat acaaggagt   960
```

```
gaaggtttgt atgaaattga aatctaagtt gtttgttatt tgtttggccg cagccgcgat   1020
ggcctaggat gcatatggcg gccgcataac ttcgtatagc atacattata cgaagttatc   1080
tagacatatg caagggttta ttgttttcta aatctgatt accaattaga atgaatattt    1140
cccaaatatt aaataataaa acaaaaaaat tgaaaaagt gtttccacca ttttttcaat    1200
ttttttataa ttttttttaat ctgttattta aatagtttat agttaaattt acattttcat  1260
tagtccattc aatattctct ccaagataac tacgaactgc taacaaaatt ctctccctat   1320
gttctaatgg agaagattca gccactgcat ttcccgcaat atcttttggt atgattttac   1380
ccgtgtccat agttaaaatc atacggcata aagttaatat agagttggtt tcatcatcct   1440
gataattatc tattaattcc tctgacgaat ccataatggc tcttctcaca tcagaaaatg   1500
gaatatcagg tagtaattcc tctaagtcat aatttccgta tattctttta ttttttcgtt   1560
ttgcttggta aagcattatg gttaaatctg aatttaattc cttctgagga atgtatcctt   1620
gttcataaag ctcttgtaac cattctccat aaataaattc ttgtttggga ggatgattcc   1680
acggtaccat ttcttgctga ataataattg ttaattcaat atatcgtaag ttgcttttat   1740
ctcctatttt ttttgaaata ggtctaattt tttgtataag tatttctta ctttgatctg    1800 tcaatggttc agatacgacg actaaaaagt caagatcact atttggtttt agtccactct   1860
caactcctga tccaaacatg taagtaccaa taaggttatt ttttaaatgt ttccgaagta   1920 ttttttttcac tttattaatt tgttcgtatg tattcaaata tatcctcctc actattttga   1980
ttagtaccta ttttatatcc atagttgtta attaaataaa cttaatttag tttatttata   2040
gatttcattg gcttctaaat tttttatcta gataacttcg tatagcatac attatacgaa   2100
gttatggatc cagcttatcg ataccgtcga gaacaagccc cttctcatta gcgagaaggg   2160 gttttttcttt tcaaaaaaac accgcaagac atagtcttgc ggtgccgcct tcatggagat   2220
tacgtttatt tagtagcctc ctacaaatgc agttcccaca atgatcaaga ggataaataa   2280
cacaacaatc aaagcgaaag aagttccgta acctgacatt ttgtgcacct ccttgcgaga   2340
ttgcttcagc aaatgctgca aaactgtggc ggacagggtc ccgcagagac ggtcagcagc   2400
ttagaagccg ccaacaaacg cagtccctac gataattaat agaataaaca atacaacgat   2460
taaagcgaaa gaactgatgc cgccgtaacc gccgccgtta gagtatcctg acataaggtt   2520
tcacctccct atgaaggata ctataagata tgctgaaccg atccatttgg cagggataat   2580
agtggacaag agaaaaaatg aagaattcgg ctatatgaag gtgatataaa aaaatagcgg   2640
gcgctgccgc ccgctatta tgtacgatta agagatcagc acgcccgcga aaaattcctg    2700
gtataacgct tgaacggctt ttcttctctc ggcttctttt acgccaaaca tcatgctcac   2760
ttcagaagac ccctgattga tcatttcgat attcacctgt gcctctgata atgctttggc   2820
ggctcttgcc gttgtaccga cattgtggcg catcgcttcc cctacaacca taatcagggc   2880
gagatgatgc tcgacgatga cttcatcggc atgcaaatcc tcttcgatcc gtttgatgac   2940
gctgcgttca gtggcggcat ccatttgccc ctgccgtaaa atgattgtca tgtcatcgat   3000
tcccgatgga acatgctcat acgtcaaacc atgctcctcc aggatttgaa gggctctgcg   3060
gccaaaaccg atttctctgt tcatgagata cttgctgata taaatgctgc                 3110
```

<210> SEQ ID NO 96
<211> LENGTH: 3088
<212> TYPE: DNA
<213> ORGANISM: Artificial Sequence
<220> FEATURE:
<223> OTHER INFORMATION: Synthetic construct: nucleotide sequence of the
      phrF deletion construct

<400> SEQUENCE: 96

```
agtttcggca caacctaatg cttgagtacc ttgaaccgtt agaaaaaatg aggattgagg      60
aacagccgag actgtctgat ctgctgcttg agattgataa aaaacaggct cgtttaactg     120
gtctgcttga gtactatttt aacttcttca gaggcatgta cgagctggac cagcgggaat     180
atctgtcggc tattaaattt ttcaaaaagg ccgaaagcaa gctgatattc gttaaggatc     240
ggatagagaa agctgagttt ttctttaaga tgtctgaatc ttattactat atgaaacaaa     300
cgtattttc aatggactat gcacggcaag catatgaaat atacaaagaa catgaagctt      360
ataatataag attgctgcag tgtcattctt tatttgccac caatttttta gatttaaaac     420
agtatgagga tgccatctca cattttcaaa aagcttattc tatggcagaa gctgaaaagc     480
agccccaatt aatggggaga actttgtaca atatcgggct tgtaaaaaac agccaaagcc     540
aatatgagga tgccatacct tatttcaaaa gagcaatagc tgttttttgaa gaatcaaata    600
ttcttccttc cttacctcaa gcgtattttt taattacaca gatccattat aaattaggaa     660
aaatagataa agctcatgaa tatcatagta agggaatggc ttattcacaa aaggccggag     720
atgtaatata tttatcagag tttgaatttt tgaaatcttt tacttatca ggcccggatg      780
aagaagcaat tcaaggattt tttgattttc tcgaaagtaa atgttgtat gctgatcttg      840
aagatttcgc tattgatgtg gcaaaatatt atcatgaacg taaaaatttt caaaaagctt     900
ctgcttattt tttgaaggtg gaacaagtaa ggcaacttat tcaaggagga gtgagtttgt     960
atgaaattga gtctaaaact attactggcc taggatgcat atggcggccg cataacttcg    1020
tatagcatac attatacgaa gttatctaga catatgcaag ggtttattgt tttctaaaat    1080
ctgattacca attagaatga atatttccca aatattaaat aataaaacaa aaaaattgaa    1140
aaaagtgttt ccaccatttt ttcaatttt ttataatttt tttaatctgt tatttaaata     1200
gtttatagtt aaatttacat tttcattagt ccattcaata ttctctccaa gataactacg    1260
aactgctaac aaaattctct ccctatgttc taatggagaa gattcagcca ctgcatttcc    1320
cgcaatatct tttggtatga ttttacccgt gtccatagtt aaaatcatac ggcataaagt    1380
taatatagag ttggtttcat catcctgata attatctatt aattcctctg acgaatccat    1440
aatggctctt ctcacatcag aaaatggaat atcaggtagt aattcctcta agtcataatt    1500
tccgtatatt ctttattttt ttcgttttgc ttggtaaagc attatggtta aatctgaatt    1560
taattccttc tgaggaatgt atccttgttc ataaagctct tgtaaccatt ctccataaat    1620
aaattcttgt ttgggaggat gattccacgg taccattct tgctgaataa taattgttaa     1680
ttcaatatat cgtaagttgc ttttatctcc tattttttt gaaataggtc taattttttg     1740
tataagtatt tctttacttt gatctgtcaa tggttcagat acgacgacta aaaagtcaag    1800
atcactattt ggttttagtc cactctcaac tcctgatcca aacatgtaag taccaataag    1860
gttatttttt aaatgtttcc gaagtatttt tttcactta ttaatttgtt cgtatgtatt      1920
caaatatatc ctcctcacta ttttgattag tacctatttt atatccatag ttgttaatta    1980
aataaactta atttagttta tttatagatt tcattggctt ctaaattttt tatctagata    2040
acttcgtata gcatacatta tacgaagtta tggatccagc ttatcgatac cgtcgaccgc    2100
cgtccatcgg cggttttttc gtcccctctt taccaaagtc tcccaatcca tgctatgatc    2160
ttttcaataa tcttgaagag agtggaaatg cagcatgtct ctaaaaagtg tgagaaccca    2220
ctttactcaa tggaatcgag aaaatgatgt gacggagttc gaaacgtcga gtgcgacagt    2280
tgaacaggca gctgagacaa tcggcgtaag cctgtctaga atcgccaagt ccctgtcctt    2340
```

```
cagaggggaa ggagatcagg tgattctgat tgtggcagcc ggcgatgcca agatcgacaa    2400
caaaaagtcc aggcaaacat ttggctttaa agcaagaatg ctctctccta atgaggtgct    2460
ggagcagaca ggccatgaaa ttggaggagt ttgcccattt ggattggctc atgatcctga    2520
ggtttatctt gatgtatcgc tgaaacggtt tcagactgtt ttccccgcat gcggcagcag    2580
aaactccgct attgaattaa caccgaaaga attatccgaa ttttctttct caaaagtgtg    2640
gattgatgtt tgtaaagact gggaataaaa aaacatccag acatcgtctg gatgtttact    2700
tatttcacaa acccaagcag catttcacgg atgattttgc tggctgtgtt tgccgtttgc    2760
tctgagtggt cgtataccgg cgcgacttcc actaaatcag cgccctttac gtttacctct    2820
gaacgcgcaa tttcatggac cgatgcaagc agttctttag acgtgatgcc gccggcgtca    2880
accgttcctg tacccggtgc gtgtgcaggg tctaatacgt caatgtcaat tgtgacataa    2940
accggacggc ccgccagctt cggaagcacc tctttcagcg gttcaagcac ttcaaatttt    3000
gagatgtgca tgccgttttc cttcgcccat tcaaactctt ctttcatgcc ggaacggatt    3060
ccgaatgaat acacattgtg cggtccga                                       3088
```

<210> SEQ ID NO 97  
<211> LENGTH: 3079  
<212> TYPE: DNA  
<213> ORGANISM: Artificial Sequence  
<220> FEATURE:  
<223> OTHER INFORMATION: Synthetic construct: nucleotide sequence of the phrG deletion construct

<400> SEQUENCE: 97

```
agaggatcag gaggtgcttg cctacttctc cttattggaa ctgcgccaca aggttttgct     60
tcacgaggcg agaggacagg gctttcagca tgaggagcct tctcatatga atgctacgtc    120
tgacatgctg aaatattact ttttctgtt tgaaggcatg tatgaggcct ataaaaataa    180
ttatgacatt gccattgggc tgtataaaga tgcagagcag tatctcgaca acattcccga    240
tccgattgaa aaagccgaat tcacctgaa ggtcggtaag ctctattata agctgggaca    300
aaatattgtg tccctcaatc atacacggca agcagtcaaa acattcagag aagagacaga    360
ttataaaaag aagctggctt cagccctgat taccatgtca ggcaattta cagagatgag    420 ccagtttgaa gaagctgagg cttatttgga cgaagcaatt cggatcacga gtgaattaga    480
ggatcatttt tttgaagccc agcttttgca taacttcggc cttctacatg cgcaaagcgg    540
caaatcagaa gaagcggttt cgaaattaga ggaggctcta cagaacgatg agtatgcccg    600
ctccgcctat tattatcatt ctgcctactt gctgatacga gagctgttta agatcaaaaa    660
gaaagaacag gccttatctt attaccaaga cgtgaaggaa aaattgactg ctgagccgaa    720
tagaatatgt gaggcaaaaa tagacatttt atatgccatt tatgcagaag ggggtcatgc    780
ggaaacgttt cacttatgca acaacatat ggatgacttg ttgtccgaga agagtatga    840 cagtgtaaga gaactttcca ttttggctgg cgaacggtat agggaacttg agctttacaa    900
agaagctgcc cactttttt atgaagcatt acagattgaa gaactgatta acgaacgga    960 ggttatataa atgaaaagat ggcctaggat gcatatggcg gccgcataac ttcgtatagc    1020
atacattata cgaagttatc tagacatatg caagggttta ttgttttcta aaatctgatt    1080
accaattaga atgaatattt cccaaatatt aataataaa acaaaaaaat tgaaaaagt    1140 gtttccacca ttttttcaat tttttttata ttttttttaat ctgttattta aatagtttat    1200
agttaaattt acatttcat tagtccattc aatattctct ccaagataac tacgaactgc    1260
```

-continued

```
taacaaaatt ctctccctat gttctaatgg agaagattca gccactgcat ttcccgcaat    1320
atcttttggt atgattttac ccgtgtccat agttaaaatc atacggcata aagttaatat    1380
agagttggtt tcatcatcct gataattatc tattaattcc tctgacgaat ccataatggc    1440
tcttctcaca tcagaaaatg gaatatcagg tagtaattcc tctaagtcat aatttccgta    1500
tattctttta ttttttcgtt ttgcttggta aagcattatg gttaaatctg aatttaattc    1560
cttctgagga atgtatcctt gttcataaag ctcttgtaac cattctccat aaataaattc    1620
ttgtttggga ggatgattcc acggtaccat tcttgctga  ataataattg ttaattcaat    1680
atatcgtaag ttgcttttat ctcctatttt ttttgaaata ggtctaattt tttgtataag    1740
tatttcttta ctttgatctg tcaatggttc agatacgacg actaaaaagt caagatcact    1800
atttggtttt agtccactct caactcctga tccaaacatg taagtaccaa taaggttatt    1860
ttttaaatgt ttccgaagta ttttttttcac tttattaatt tgttcgtatg tattcaaata    1920
tatcctcctc actattttga ttagtaccta ttttatatcc atagttgtta attaaataaa    1980
cttaatttag tttatttata gatttcattg gcttctaaat ttttttatcta gataacttcg    2040 tatagcatac attatacgaa gttatggatc cagcttatcg ataccgtcga atgaaaaacc    2100
cccgcgggat gcggggttc aatttaacga aagaatccta aaacggtttg tagttttagg    2160
attctttcat cttttcagcg tgattgaaaa cccttgaagt ctaggaagaa cgagcattgg    2220
agcgcagcga atgtttggaa ttcgtgagca ccgaagcgca ggcctgacaa cgaatgcgag    2280
ggtttgtcga cacgctgaaa acccgcgggt gcggggtttt tcttattaca gcagcttctt    2340
ccctaacagg gattctacga gctctactgc tgttttgccc gttttgtttt tgtgatcaag    2400
gatcgggtta acctcaacga attcggctga ggtaatgatg cctgcgtcat acagcatttc    2460
catagccaaa tggctctccc ggtagctgat gccgccgacg acaggggttc cgacacccgg    2520
tgcgtcgttc ggatcaagtc cgtccagatc aaggctcaga tggacgccat cacatgctga    2580
taaataatca agggtttctt caatgacctt tgtcatgcca agacgatcga tttcgtgcat    2640
tgtgtacacc ttcatgccgc tttccttaat gtacttgcgc tccccttcat caagtgaccg    2700
ggcgccaatg atgacgacgt tttccggttt gattttaggc gcgtagcctt caaggttaac    2760
cagtgactcg tggccaatgc ctaggctgac cgcgagcggc atgccgtgaa tattgcccga    2820
tggtgaagtt tcaagtgtat tcaaatcgcc gtgcgcgtca taccagatga cgccgagatt    2880
atcgtaatgc ttcgctgtgc ctgcaagcgt gccgatcgca atactgtggt caccgcccag    2940
gacaagcggg aatttttct cttcaatgac tttgttgacc ttttgcgcga gttttcatt     3000 tcccgccaaa acggaattca ggttttcag ttcctcgtca tttttgattt tttcgcgatt    3060
gatcggaatg tcaccgaga                                                 3079
```

<210> SEQ ID NO 98
<211> LENGTH: 3564
<212> TYPE: DNA
<213> ORGANISM: Artificial Sequence
<220> FEATURE:
<223> OTHER INFORMATION: Synthetic construct: nucleotide sequence of the phrH deletion construct

<400> SEQUENCE: 98

```
ggagggaagc cgttgagtca agccataccg tcttcgcgtg ttggtgttaa gattaatgaa      60
tggtataaaa tgattcgcca gttcagtgtt ccggatgctg agattctgaa agcggaggtt     120
gagcaggaca ttcagcagat ggaagaagat caggatttac tgatctatta ttctctgatg     180
tgttttcggc accagctgat gcttgattat ttggagccgg gaaaaacata cgggaatcgc     240
```

```
cctacagtga cagagcttct tgaaacgatc gagacccctc agaaaaaact cacaggtctt    300
ttgaaatact actctttgtt tttccgcggc atgtatgaat ttgaccaaaa agaatatgtg    360
gaagcgatcg gatattatcg cgaggcggag aaagaactgc cgtttgtgtc agatgatatt    420
gagaaagcgg aattccattt taaagtggca gaagcgtatt atcacatgaa gcaaacccat    480
gtgtcgatgt atcatattct tcaagccttg gacatttatc aaaaccatcc tctatacagc    540
attagaacga tacaaagctt gtttgtgatc gccggcaact atgatgattt caaacattat    600
gataaagcgc tcccgcattt agaggcggcg ctggaattgg caatggacat tcaaaatgac    660
aggtttatcg ccatttctct attgaacatt gcaaacagct atgacagatc aggagacgat    720
cagatggctg tagaacattt ccaaaaagcg cgaaagtaa gcagagagaa agtgcctgat    780
ctgcttccga aagtcttgtt tggattaagc tggacattat gtaaagcggg ccaaacacag    840
aaggcgtttc agttcataga ggaaggatta gaccatatca cagcacgttc tcacaaattt    900
tataaagaat tgtttctgtt cttgcaggcc gtgtacaagg agactgttga tgaacgaaaa    960
attcatgatc ttttaagcta tttcgaaaaa aagaacctgc acgcttacat tgaagcatgt   1020
gcccggagtg ctgccgctgt ttttgaaagc agctgtcact ttgaacaagc agctgcgttt   1080
tatcggaaag tgctgaaagc ccaagaagat attctaaaag ggagagtgtt tatatgccta   1140
ttaagaaaaa aagtgatgag gcctaggatg catatggcgg ccgcataact tcgtatagca   1200
tacattatac gaagttatct agacatatgc aagggtttat tgttttctaa aatctgatta   1260
ccaattagaa tgaatatttc ccaaatatta aataataaaa caaaaaaatt gaaaaagtg   1320 tttccaccat ttttttcaatt ttttttataat tttttttaatc tgttatttaa atagtttata   1380
gttaaattta catttttcatt agtccattca atattctctc caagataact acgaactgct   1440
aacaaaattc tctccctatg ttctaatgga gaagattcag ccactgcatt tcccgcaata   1500
tcttttggta tgattttacc cgtgtccata gttaaaatca tacggcataa agttaatata   1560
gagttggttt catcatcctg ataattatct attaattcct ctgacgaatc cataatggct   1620
cttctcacat cagaaaatgg aatatcaggt agtaattcct ctaagtcata atttccgtat   1680
attcttttat tttttcgttt tgcttggtaa agcattatgg ttaaatctga atttaattcc   1740
ttctgaggaa tgtatccttg ttcataaagc tcttgtaacc attctccata ataaattct   1800 tgtttgggag gatgattcca cggtaccatt tcttgctgaa taataattgt taattcaata   1860
tatcgtaagt tgcttttatc tcctattttt tttgaaatag gtctaatttt ttgtataagt   1920
atttctttac tttgatctgt caatggttca gatacgacga ctaaaaagtc aagatcacta   1980
tttggtttta gtccactctc aactcctgat ccaaacatgt aagtaccaat aaggttattt   2040
tttaaatgtt tccgaagtat tttttcact ttattaattt gttcgtatgt attcaaatat   2100
atcctcctca ctattttgat tagtacctat tttatatcca tagttgttaa ttaaataaac   2160
ttaatttagt ttatttatag atttcattgg cttctaaatt ttttatctag ataacttcgt   2220
atagcataca ttatacgaag ttatggatcc agcttatcga taccgtcgag cttttctt   2280 gctttacgga agacggttcc attttccaca tcgcggcatt ccttctattt ctaacgcaag   2340
acactcgaaa caaccaaacc atttgaggta taatggataa agtgaataac agtatttaga   2400
ttgatatata tgaaagagag tggaacatca tgggccgtaa gtggaacaat attaaagaga   2460
agaaggcgtc taaggacgca aatacgagtc ggatttatgc gaagtttggc cgtgagattt   2520
atgtggcggc gaaacagggc gagcctgatc cggaatccaa ccaggcgctg aaggttgtgc   2580
ttgaacgtgc gaagacttac agcgtgccga aaaacatcat tgaacgtgcg atcgagaagg   2640
```

-continued

```
cgaagggcgg agcggaagag aattacgatg agcttcgtta tgagggcttc gggccgaacg    2700
gatcaatgat tatcgttgat gcgctgacga ataatgtaaa ccgtacggcg ccggaagtgc    2760
gtgcggcgtt cgggaaaaac ggcggaaaca tgggtgtgag cggatctgtt gcttacatgt    2820
ttgacgcgac ggctgtaatc gtggtggaag gcaaaacggc tgacgaagcg cttgaaatcc    2880
tgatggaagc ggatgttgat gtacgtgaca ttttagaaga ggatgacagc gcgatcgtgt    2940
atgccgagcc tgatcaattc catgcggtgc aagaggcgtt taaaaacgcg ggtgtcgagg    3000
aatttacagt agcggagctg caaatgcttg cgcaaagtga agtaacgctt ccggatgatg    3060
caaaggaaca gtttgaaaaa ttgattgatg cattagaaga tttggaagat gttcagcagg    3120
tatatcataa cgttgattta ggtgagtaag gagtgagcag gctgttatgg cctgcttttt    3180
ttgtcccgga aattgtttta gctgtatgta ggcggccgcc tatacgatct ataagatatt    3240
ctcatactct ggactgtaac ctatgtgaag gagagagtaa atatgactga tacaagacat    3300
atgtatggcg gacctggttt tggtcattat cagggctttg gtattggcca cccgggctat    3360
ggcatgcaaa gcacaggcta tccgggctat ggcatgtatg gaggccaccc gggctatggc    3420
atgcaaggct acccagatca cggcatacat ggaggagtcg gcggctatcc gggatatggt    3480
gggtacggcg gttacccaag cggcggctat ggaggctctc cgggaactgg aagctatccg    3540
agcatgcacc atgaaaatga tggc    3564
```

<210> SEQ ID NO 99
<211> LENGTH: 3147
<212> TYPE: DNA
<213> ORGANISM: Artificial Sequence
<220> FEATURE:
<223> OTHER INFORMATION: Synthetic construct: nucleotide sequence of the phrI deletion construct

<400> SEQUENCE: 99

```
gaattgttaa acatggaaga aaatcaagat gccctgttat attatcaact attagaattt      60
agacatgaga taatgctgag ttatatgaaa tctaaggaaa tagaagatct caataatgct     120
tatgagacta taaagaaat tgagaagcaa gggcaattaa ctggcatgtt ggaatactat     180
ttttactttt ttaagggtat gtacgagttt aggcgtaaag aattaatttc agcgataagt     240
gcttatcgaa tagctgaatc aaagttgtca gaagttgagg atgaaataga gaaagcagag     300
ttttttttca agtgtcccta tgtatattat tatatgaaac aaacatactt ctccatgaat     360
tatgcaaatc gtgcactcaa aatatttaga gagtatgaag aatatgctgt ccagactgtg     420
cgttgtcaat ttattgtagc aggaaacttg atcgattcat ggaatatga agagccttg      480 gaacaatttt tgaagtcttt ggaaatttcc aaggaaagta acatagagca tttaattgca     540
atgtcacata tgaatattgg gatttgttat gatgaattga agaatataa gaaggcttca     600 caacatttaa tttagcgtt agaaattttt gaaaatcaa acatagttt cttaacaaag      660 actttattca ctctaaccta tgtagaagca aaacaacaaa attataatgt gcttttgata     720
tactttagga aagggcgatt tattgccgat aaaagtgatg ataaggaata ctcagcgaaa     780
ttcaaaatat tagagggatt attttttttct gatggtgaga ctcaattaat aaagaatgca     840
ttttcatatc tggcttcgag aaaaatgttt gctgatgttg aaaatttttc gattgaagtc     900
gctgattatt ttcatgaaca aggaaattta atgctctcta atgaatatta tcgtatgagt     960
attgaagcaa gacgaaaaat taaaaagggg gagattattg atgaaaatca gccggattct    1020
attggcagca gtgattttaa gtagtgtatt ggcctaggat gcatatggcg gccgcataac    1080
```

```
ttcgtatagc atacattata cgaagttatc tagacatatg caagggttta ttgttttcta    1140
aaatctgatt accaattaga atgaatattt cccaaatatt aaataataaa acaaaaaaat    1200
tgaaaaaagt gtttccacca ttttttcaat tttttttataa tttttttaat ctgttattta   1260
aatagtttat agttaaattt acattttcat tagtccattc aatattctct ccaagataac    1320
tacgaactgc taacaaaatt ctctccctat gttctaatgg agaagattca gccactgcat    1380
ttcccgcaat atcttttggt atgattttac ccgtgtccat agttaaaatc atacggcata    1440
aagttaatat agagttggtt tcatcatcct gataattatc tattaattcc tctgacgaat    1500
ccataatggc tcttctcaca tcagaaaatg gaatatcagg tagtaattcc tctaagtcat    1560
aatttccgta tattctttta ttttttcgtt ttgcttggta aagcattatg gttaaatctg    1620
aatttaattc cttctgagga atgtatcctt gttcataaag ctcttgtaac cattctccat    1680
aaataaattc ttgtttggga ggatgattcc acggtaccat ttcttgctga ataataattg    1740
ttaattcaat atatcgtaag ttgctttat  ctcctatttt ttttgaaata ggtctaattt    1800
tttgtataag tatttcttta ctttgatctg tcaatggttc agatacgacg actaaaaagt    1860
caagatcact atttggtttt agtccactct caactcctga tccaaacatg taagtaccaa    1920
taaggttatt ttttaaatgt ttccgaagta ttttttttcac tttattaatt tgttcgtatg    1980
tattcaaata tatcctcctc actatttga  ttagtaccta ttttatatcc atagttgtta    2040
attaaataaa cttaatttag tttatttata gatttcattg gcttctaaat tttttatcta    2100
gataacttcg tatagcatac attatacgaa gttatggatc cagcttatcg ataccgtcga    2160
cttagataat tggaaaagag gaaaaaagct taatcttttt tcgaaggtta agcttttttct   2220
tttatttata aaaagtgaac taactatcag aaagaaatta tattaaattt tatttttttg    2280
tttaaaaagt agattatata aaggcaagct aggtggggga aaatatgttt aaaaaagaaa    2340
aagtcacaga atacatttgg actatactaa taccaacaat catcactttt atcattagtt    2400
gggttgggtc ttattacaat ggtacttcga cagttagtat tggacaacct acaaaagttt    2460
ccggtcagta tatcacgcca ataatataa  gtccctatca tgatattaag gaattaagaa    2520
taacttttcc gcaaaaacta gatgtaaaac aaattagttc aaatgagcct ataaatgtaa    2580
aatcagataa gaacaatata ggagttgaaa gtaattccac ttttgagatt gcgaaaatcg    2640
ttgaaaataa tagcgttcag ttgctaatta caacacaaaa aaagttaaac gataaggaaa    2700
ttagaattga taaaaatgga aataacattt ctgtaaatta tgaatctcag attgttaatc    2760
ctgcaaaaaa acaattaatc aatcttataa ttacgtcatc tatttatttt ataatgctta    2820
atatactagc attgattatg aacaaaagat gggataagta ttatgcaaaa atgaaaaatg    2880
aaatcaaaga atttgaggat aatgcaaaag atcttgataa aaaatcaaag aagaaaagcg    2940
aggaattatc ggagctgcga aagaccttga accaagcgtt tgaggaaact gataggataa    3000
aatatcatga gaagaaaaaa caaatcctcc tcttagctaa gttaaacgat tataaaaaag    3060
aactaacctt ttggagaaat acaataagaa aagttcttta tgaacttcct gatggagata    3120
aaaaagcaga taaactaata gggacag                                        3147
```

<210> SEQ ID NO 100  
<211> LENGTH: 3114  
<212> TYPE: DNA  
<213> ORGANISM: Artificial Sequence  
<220> FEATURE:  
<223> OTHER INFORMATION: Synthetic construct: nucleotide sequence of the phrK deletion construct

<400> SEQUENCE: 100

```
gatgaaatgg aagaagatca agaagttctt gcgtattata gtctattaga agaaagacat      60
aaaatgttgc tgcattcttc acgaggagag cctttacaaa agcacaccta ttttactgaa     120
gacaatcaaa acttcataac aaaaacaaat gataaattag aatacaactt ttatttattt     180
gaagcaatgt acgaggcata caacaaaaac tatgatcgag caattaacct atatggatta     240
gctgagaaaa agcttgcaga aattccagat gaaattgaag cagctgaatt ttactctaaa     300
gtctcttact tatatactct tgttaaacaa agcattgtgg cacaacatta tataaaaaat     360
gcaatttcaa tatataagcg acaccctgat tataaatgca aactagctac atcaacaatg     420
attgcagctg caaactatgc tgatatgaaa cgatttgagg aagcagaaca atattactta     480
gaagcaattg atattgcaaa agaaacaaaa gatgaatttt taaaagctca attatttcac     540
aatcttagta tcgtttattc tgattggaac aaacctgata aatgcattga atctcttgaa     600
aaagcaatag gaaatgaatc ttggttacat tcgatttatt atataaattc tttattcatg     660
atgattaaag aactctttaa aattgacgaa aaaatgaaag ccattaattt ttacaataaa     720
gcacaggaaa gactcatatt aatggagaat aaagtatacg aagccaaaat cagcatcctg     780
tataacettt attgtgggga attaaaaaat aatttcaata attgtattag taatattgag     840
tttttaaaac agcaaaatga acttgaaagt gtagatgaat tgtcctacat agctgcaaaa     900
aggtttgaat caataggtgc ttttgaagaa gcaacgagct ttttcaatgc gaaaatttgg     960
gctgaacaga aaatgaatca ggtggaggga atcttatgaa aaaacttgtg ctttgcgtat    1020
ctattttagc tgtgatttta atcgacggta tcgataagct ggatccataa cttcgtataa    1080
tgtatgctat acgaagttat ctagataaaa aatttagaag ccaatgaaat ctataaataa    1140
actaaattaa gtttatttaa ttaacaacta tggatataaa ataggtacta atcaaaatag    1200
tgaggaggat atatttgaat acatacgaac aaattaataa agtgaaaaaa atacttcgga    1260
aacatttaaa aaataaccett attggtactt acatgtttgg atcaggagtt gagagtggac    1320
taaaaccaaa tagtgatctt gactttttag tcgtcgtatc tgaaccattg acagatcaaa    1380
gtaaagaaat acttatacaa aaaattagac ctatttcaaa aaaaatagga gataaaagca    1440
acttacgata tattgaatta acaattatta ttcagcaaga aatggtaccg tggaatcatc    1500
ctcccaaaca agaatttatt tatggagaat ggttacaaga gctttatgaa caaggataca    1560
ttcctcagaa ggaattaaat tcagatttaa ccataatgct ttaccaagca aaacgaaaaa    1620
ataaaagaat atacgaaat tatgacttag aggaattact acctgatatt ccattttctg    1680
atgtgagaag agccattatg gattcgtcag aggaattaat agataattat caggatgatg    1740
aaaccaactc tatattaact ttatgccgta tgatttttaac tatggacacg ggtaaaatca    1800
taccaaaaga tattgcggga aatgcagtgg ctgaatcttc tccattagaa catagggaga    1860
gaattttgtt agcagttcgt agttatcttg gagagaatat tgaatggact aatgaaaatg    1920
taaatttaac tataaactat ttaaataaca gattaaaaaa attataaaaa aattgaaaaa    1980
atggtggaaa cactttttc aattttttg ttttattatt taatatttgg gaaatattca    2040
ttctaattgg taatcagatt ttagaaaaca ataaaccctt gcatatgtct agataacttc    2100
gtataatgta tgctatacga agttatgcgg ccgccatatg catcctaggc caaaaggttg    2160
attaattaat ttagccctac tcaaacattt gagtgggctt ttatttatg atttatgtcc    2220
accggtcagc cctgctctgt ggagcgcagt acctgcaaac gtaactgaga tacttctcac    2280
tgttttttgc ccgagtaaaa cttattaaag aacatcaagc aacacttata aatatccatc    2340
```

-continued

| | | | |
|---|---|---|---|
| gtgatatttg | tgggaaaatc | aattgttttg gatcgatgaa | aaccaccgcc aagctcatct | 2400 |
| ttactgtatc | caattcctag | acttattgtt cgaccaactt | tattatatgt acgtgccctt | 2460 |
| cttgcgactt | cctcacaaat | ctccaagagc acagctttaa | tctcttctct ctttgtataa | 2520 |
| tccctaaaca | aaatctgact | cttaccaaaa ctaatctgcc | cctgcatcaa tggagctcct | 2580 |
| atttcagata | aatcaattcc | gtgagcatga tagtacaact | ggtttcccat tattccgaac | 2640 |
| ttcttttcaa | gcagctctaa | aggaaattta gctaactgac | ctacagttga tatacccatt | 2700 |
| cgattcagat | ttcttttccat | cctccctcct atcccccaca | ttttagacaa aggtcgaact | 2760 |
| ttccagagtc | tatttggcac | atcttcatat ctccaacgtg | caataccact ctttgttttc | 2820 |
| ttactctcca | ggtcaagtgc | aagcttacta agcaacatat | tgtcaccaat tccaactgtg | 2880 |
| cacatcaaac | caaattctct | ccacatgctg ctttggattg | ctttggccat tcttcagga | 2940 |
| ttctcttttc | ctgcatctaa | aaaagattaa tcaattgaat | acgtgtggac acattttca | 3000 |
| ggaacaaatc | tgtaaaacag | ctttgtaatc tcagttgaaa | ctctgatgaa aagcttcatt | 3060 |
| tgtggattta | caatgtatat | tcttggatct tcaggtatct | caaatagtct cgat | 3114 |

<210> SEQ ID NO 101
<211> LENGTH: 1496
<212> TYPE: DNA
<213> ORGANISM: Bacillus subtilis

<400> SEQUENCE: 101

| | | | |
|---|---|---|---|
| tcataccctg | aaaggaaaga | caagggaaat tgtcggcaat | gagccgctcg gcaggtagaa | 60 |
| ggatgtttac | cgatgcaaaa | aaagggcaaa atggataggt | ggttgtccat gttgaatgct | 120 |
| ataatggggg | agatttataa | aagagagtga tacatattga | ataatacgaa gcagcccgtt | 180 |
| gtcattttag | tcggaccgac | ggcagtgggg aaaaccaatt | taagtattca gctagccaaa | 240 |
| tccttaaacg | cggaaattat | cagcggagat tcgatgcaga | tttataaagg gatggatatt | 300 |
| ggaacagcta | aaattaccga | acaggagatg gagggagtgc | cccatcatct gattgacatt | 360 |
| ttagatcccc | aagactcttt | ctctactgcc gattatcaaa | gcttagtaag aaataaaatc | 420 |
| agcgagattg | caaatagagg | aaagcttccg atgattgacg | gcggtacagg gctttatata | 480 |
| caatctgagc | tttacgatta | tacatttacg gaagaggcaa | atgatcccgt gtttcgagag | 540 |
| agcatgcaaa | tggctgctga | gcgggaaggc gctgactttc | ttcatgccaa acttgctgca | 600 |
| gcagatcccg | aggcagcagc | tgcgattcat ccgaataata | caagaagagt cattcgcgca | 660 |
| ctggaaattt | tacatacgtc | cggaaaaacg atgtcccagc | atttgaagga caaaaacga | 720 |
| gaacttctgt | acaatgcagt | gttaattggc ctgacaatgg | atagagacac gctttacgaa | 780 |
| agaattaatc | agcgggtcga | tttgatgatg cagtcaggcc | ttcttccgga agtgaaacgc | 840 |
| ttatacgaca | agaacgtgag | agactgtcaa tcaatacagg | cgataggcta taaagagctg | 900 |
| tatgcatatt | ttgacggttt | tgtgacactt tccgatgctg | tcgaacagct aaagcagaac | 960 |
| tcgaggcggt | atgcgaaacg | ccagctgacg tggtttcgca | acaaaatgca ggtcacatgg | 1020 |
| ttcgatatga | caccgcctgt | tgatatggag ctgaaaaaaa | aggaaatttt cacacatata | 1080 |
| gcaggaaaac | tcgaacttta | atcgaaactg tatgatatag | agaatcaagg aggacgaaac | 1140 |
| atgaaaccga | ttaatattca | ggatcagttt ttgaatcaaa | tccggaaaga aaatacgtat | 1200 |
| gtcactgttt | ttttgctgaa | cggctttcag ttgcggggcc | aggtgaaagg ctttgataac | 1260 |
| tttaccgtat | tgttggaatc | ggaaggtaag cagcagctta | tatataaaca tgcgatctca | 1320 |
| acgtttgcgc | cgcaaaaaaa | cgtccagctt gaactcgaat | agatcaaaaa atgccatgtc | 1380 |

```
aagacatgag gaaaggctgt cggggttcc cggcggccat ttttaacatg aatccacttt    1440
tgctccaagc tttttgtgta agctgaccat gccaaggcac ggtcttttt tatgag         1496
```